United States Patent
Facchini et al.

(10) Patent No.: US 12,416,029 B2
(45) Date of Patent: **\*Sep. 16, 2025**

(54) COMPOSITIONS AND METHODS FOR MAKING BENZYLISOQUINOLINE ALKALOIDS, MORPHINAN ALKALOIDS, THEBAINE, AND DERIVATIVES THEREOF

(71) Applicant: Antheia, Inc., Menlo Park, CA (US)

(72) Inventors: Peter James Facchini, Calgary (CA); Xue Chen, Calgary (CA); Jeffrey C. Colbeck, Davis, CA (US); Joseph E. Tucker, Strathmore (CA)

(73) Assignee: Antheia Inc., Menlo Park, CA (US)

( * ) Notice: Subject to any disclaimer, the term of this patent is extended or adjusted under 35 U.S.C. 154(b) by 9 days.

This patent is subject to a terminal disclaimer.

(21) Appl. No.: 17/496,540

(22) Filed: Oct. 7, 2021

(65) Prior Publication Data

US 2022/0205004 A1 Jun. 30, 2022

Related U.S. Application Data

(63) Continuation of application No. 16/312,776, filed as application No. PCT/US2017/039589 on Jun. 27, 2017, now Pat. No. 11,142,780.

(60) Provisional application No. 62/514,104, filed on Jun. 2, 2017, provisional application No. 62/469,006, filed on Mar. 9, 2017, provisional application No. 62/438,540, filed on Dec. 23, 2016, provisional application No. 62/438,702, filed on Dec. 23, 2016, provisional application No. 62/438,601, filed on Dec. 23, 2016, provisional application No. 62/438,588, filed on Dec. 23, 2016, provisional application No. 62/438,695, filed on Dec. 23, 2016, provisional application No. 62/433,431, filed on Dec. 13, 2016, provisional application No. 62/355,022, filed on Jun. 27, 2016.

(51) Int. Cl.
| | | |
|---|---|---|
| *C12N 9/70* | (2006.01) | |
| *C12N 9/88* | (2006.01) | |
| *C12P 17/18* | (2006.01) | |
| *C12N 15/70* | (2006.01) | |
| *C12P 13/22* | (2006.01) | |
| *C12P 17/12* | (2006.01) | |

(52) U.S. Cl.
CPC .............. *C12P 17/182* (2013.01); *C12N 9/88* (2013.01); *C12N 15/70* (2013.01); *C12P 13/22* (2013.01); *C12P 17/12* (2013.01); *C12Y 114/16002* (2013.01); *C12Y 201/01128* (2013.01)

(58) Field of Classification Search
CPC ......... C12P 17/12; C12P 17/188; C12P 13/22; C12P 7/22; C12N 9/0071; C12N 15/70; C12N 9/0006; C12N 15/8243; C12N 5/04; C12N 9/10; C12Y 114/11031; C12Y 114/21004
USPC ....................................... 435/252.3
See application file for complete search history.

(56) References Cited

U.S. PATENT DOCUMENTS

| | | | |
|---|---|---|---|
| 6,573,428 | B1 | 6/2003 | Vodkin et al. |
| 11,142,780 | B2 | 10/2021 | Facchini et al. |
| 2009/0156815 | A1 | 6/2009 | Wang et al. |
| 2016/0208269 | A1 | 7/2016 | Smolke et al. |

FOREIGN PATENT DOCUMENTS

| | | |
|---|---|---|
| WO | WO-2011/058446 A2 | 5/2011 |
| WO | WO-2015/081437 A1 | 6/2015 |
| WO | WO-2015/173590 A1 | 11/2015 |
| WO | WO-2018/005553 A1 | 1/2018 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Kisselev L., (Structure, 2002, vol. 10: 8-9.*
Witkowski et al., (Biochemistry 38:11643-11650, 1999.*
Fossati et al. PLOS 2015, pp. 1-15.*
Zulka et al. Planta 2007, 225, pp. 1085-1106.*
U.S. Office Action dated Apr. 23, 2021 in U.S. Appl. No. 16/312,895.
Facchini, P.J. "GenBank Accession No. FE967184" Mar. 31, 2008, [online] [retrieved on Sep. 19, 2017]. Retrieved from the internet: <https://www.ncbi.nlm.nih.gov/nucest/FE967184>.
Shitan et al. "Alkaloid Transporters in Plants", Plant Biotechnology, 31:453-463 (2014).
Fossati et al. (2015). "Synthesis of Morphinan Alkaloids in Saccharomyces cerevisiae", PLoS One 10(4):e0124459.
U.S. Non-Final Office Action dated May 20, 2020 in U.S. Appl. No. 16/312,895.
Fisinger et al. "Thebaine synthase: A new enzyme in the morphine pathway in Papaver somniferum", Natural Product Communications, 2:249-253 (2007).
Beaudoin et al., "Benzylisoquinoline alkaloid biosynthesis in opium poppy", Planta, 240: 19-32 (2014).

(Continued)

*Primary Examiner* — Robert B Mondesi
*Assistant Examiner* — Mohammad Y Meah
(74) *Attorney, Agent, or Firm* — Mintz, Levin, Cohn, Ferris, Glovsky and Popeo, P.C.

(57) ABSTRACT

Disclosed herein are methods that may be used for the synthesis of benzylisoquinoline alkaloids ("BIAs") such as alkaloid morphinan. The methods disclosed can be used to produce thebaine, oripavine, codeine, morphine, oxycodone, hydrocodone, oxymorphone, hydromorphone, naltrexone, naloxone, hydroxycodeinone, neopinone, and/or buprenorphine. Compositions and organisms useful for the synthesis of BIAs, including thebaine synthesis polypeptides, purine permeases, and polynucleotides encoding the same, are provided.

6 Claims, 58 Drawing Sheets

Specification includes a Sequence Listing.

(56) References Cited

OTHER PUBLICATIONS

Database EMBL [Online] Jul. 2, 2015 (Jul. 2, 2015), "Papaver somniferum (opium poppy) reticuline epimerase ID-AKO60181; SV 1; linearl; genomic DNA; STD; PLN; 2703 BP.", retrieved from EBI accession No. Em_CDS: AKO60181.
Database Geneseq [Online] Apr. 9, 2015 (Apr. 9, 2015), "Papaver somniferum OMT protein, SEQ ID 543.", retrieved from EBI accession No. GSP:BBU80692 Database accession No. BBU80692.
Winzer et al., "A Papaver somnifarum 10-Gene Cluster for Synthesis of the Anticancer Alkaloid Noscapine", Science, 336:1704-1708 (2012).
Hagel et al., "Dioxygenases catalyze the O-demethylation steps of morphine biosynthesis in opium poppy", Nature Chemical Biology, 6:273-275 (2010).
Morris et al., "Plug-and-Play Benzylisoquinoline Alkaloid Biosynthetic Gene Discovery in Engineered Yeast" in Methods in Enzymology, 144-178 (Elsevier 2016).
Galanie et al., "Complete biosynthesis of opioids in yeast", Science, 349:1095-1100 (2015).
Glenn, W.S. et al.' "Recent progress in the metabolic engineering of alkaloids in plant 1-49 systems", Curr. Opin. Biotechnol. Apr. 2013 (Apr. 2013), vol. 24(2), pp. 354-365.
Chen et al., "A pathogenesis-related 10 protein catalyzes the final step in thebaine biosynthesis", 2018, Nature Chemical Biology, 14:738-743.
U.S. Final Office Action dated Nov. 25, 2020 in U.S. Appl. No. 16/312,895.
Dastmalchi et al., "Purine Permease-Type Benzylisoquinoline Alkaloid Transporters in Opium Poppy", 2019, Plant Psychology, 181:916-933.
Grothe et al., "Melocular Characterization of the Salutaridinol 7-O-Acetyltransferase Involved in Morphine Biosynthesis in Opium Poppy Papaver somniferum", 2001, The Journal of Biological Chemistry, 276:30717-30723.
Farrow et al. "Stereochemical Inversion of (S)-reticuline by a cytochrome P450 fusion in opium poppy" Nature Chemical Biology, vol. 11, Sep. 2015, p. 728-732.
Zulak et al., "Gene transcript and metabolite profiling of elicitor-induced opium poppy cell cultures reveals the coordinate regulation of primary and secondary metabolism," Planta, 225:1085-1106 (2007).
Kisselev L.," Polypeptide release factors in prokaryotes and eukaryotes: same function, different structure," Structure, 2002, vol. 10: 8-9.
Witkowski et al., "Conversion of a beta-ketoacyl synthase to a malonyl decarboxylase by replacement of the active-site cysteine with glutamine," Biochemistry 38:11643-11650, 1999.
Whisstock et al., "Prediction of protein function from protein sequence and structure," Quarterly Reviews of Biophysics 2003, vol. 36 (3): 307-340.
Devos et al., "Practical limits of function prediction," Proteins: Structure, Function and Genetics, 2000, vol. 41: 98-107.
Sabarna, "Approaches to isolating a cDNA encoding thebaine synthase of morphine biosynthesis from opium poppy Papaversomniferum L.", Jun. 22, 2007.
Samanani et al., "The role of phloem sieve elements and laticifers in the biosynthesis and accumulation of alkaloids in opium poppy," Plant Journal, 47:547-563 (2006).
International Search Report, issued Dec. 1, 2017, in PCT/US2017/039589.
Written Opinion issued Dec. 1, 2017, in PCT/US2017/039589.
Choe et al., "Genetic and chemical components analysis of Papaver setigerum naturalized in Korea," Forensic Science International, 222:387-393 (2012).
Facchini et al., "Developmental and inducible accumulation of gene transcripts involved in alkaloid biosynthesis in opium poppy," Phytochemi, 64:177-186 (2003).

\* cited by examiner

MS² 330 →

| Empirical m/z | Relative abundance (%) | Theoretical m/z | Error ppm | Composition [M+H]⁺ or [M⁺] |
|---|---|---|---|---|
| 281.11725 | 100 | 281.11722 | -0.1 | $C_{18}H_{17}O_3$ |
| 299.12782 | 61 | 299.12779 | -0.1 | $C_{18}H_{19}O_4$ |
| 249.09117 | 40 | 249.09101 | -0.6 | $C_{17}H_{13}O_2$ |
| 271.13300 | 22 | 271.13287 | -0.8 | $C_{17}H_{19}O_3$ |
| 267.10185 | 9 | 267.10157 | -1.0 | $C_{17}H_{15}O_3$ |
| 221.09624 | 9 | 221.09609 | -0.7 | $C_{16}H_{13}O$ |
| 266.09402 | 4 | 266.09375 | -1.0 | $C_{17}H_{14}O_3$ |
| 330.17005 | 4 | 330.16998 | -0.2 | $C_{19}H_{24}O_4$ |
| 237.09127 | 2 | 237.09101 | -1.1 | $C_{16}H_{13}O_2$ |
| 239.10692 | 2 | 239.10666 | -1.1 | $C_{16}H_{15}O_2$ |
| 256.10963 | 2 | 256.10940 | -0.9 | $C_{16}H_{16}O_3$ |

MS³ 330 → 299 →

| Empirical m/z | Relative abundance (%) | Theoretical m/z | ppm | Composition [M+H]⁺ or [M⁺] |
|---|---|---|---|---|
| 281.11730 | 100 | 281.11722 | -0.3 | $C_{18}H_{17}O_3$ |
| 249.09113 | 32 | 249.09101 | -0.5 | $C_{17}H_{13}O_2$ |
| 299.12790 | 23 | 299.12779 | -0.4 | $C_{18}H_{19}O_4$ |
| 221.09617 | 21 | 221.09609 | -0.4 | $C_{16}H_{13}O$ |
| 252.07822 | 9 | 252.07810 | -0.5 | $C_{16}H_{12}O_3$ |
| 266.09398 | 7 | 266.09375 | -0.8 | $C_{17}H_{14}O_3$ |
| 267.10179 | 8 | 267.10157 | -0.2 | $C_{17}H_{15}O_3$ |

MS³ 330 → 281 →

| Empirical m/z | Relative abundance (%) | Theoretical m/z | ppm | Composition [M+H]⁺ or [M⁺] |
|---|---|---|---|---|
| 281.11722 | 100 | 281.11722 | 0 | $C_{18}H_{17}O_3$ |
| 249.09104 | 94 | 249.09101 | -0.1 | $C_{17}H_{13}O_2$ |
| 266.09383 | 23 | 266.09375 | -0.3 | $C_{17}H_{14}O_3$ |
| 221.09618 | 4 | 221.09609 | -0.4 | $C_{16}H_{13}O$ |
| 218.07271 | 4 | 218.07262 | -0.4 | $C_{15}H_{10}O$ |
| 234.06759 | 4 | 234.06753 | -0.3 | $C_{15}H_{10}O_2$ |

MS³ 330 → 249 →

| Empirical m/z | Relative abundance (%) | Theoretical m/z | ppm | Composition [M+H]⁺ or [M⁺] |
|---|---|---|---|---|
| 249.09105 | 100 | 249.09101 | -0.2 | $C_{17}H_{13}O_2$ |
| 221.09614 | 45 | 221.09609 | -0.2 | $C_{16}H_{13}O$ |
| 234.06760 | 22 | 234.06753 | -0.3 | $C_{15}H_{10}O_2$ |
| 218.07270 | 12 | 218.07262 | -0.4 | $C_{15}H_{10}O$ |
| 217.06484 | 8 | 217.06479 | -0.2 | $C_{15}H_{9}O$ |

FIG. 6B

| Purification step | Total protein (mg) | Specific activity (m/z 312 ion counts µg$^{-1}$ protein) | Fold purification | Yield (%) |
|---|---|---|---|---|
| AS | 48 | 1254087 | 1 | 100 |
| HIC | 16 | 1410214 | 1.1 | 37.4 |
| IEX | 4.2 | 5045200 | 4.0 | 35.2 |
| SEC | 0.1 | 25457966 | 20.2 | 4.2 |

FIG. 6G

| Accession Number | Molecular weight (kDa) | LC-MS spectral count | | | Annotation |
|---|---|---|---|---|---|
| | | Band 1 | Band 2 | Band 3 | |
| c15408_g1_i1 | 18 | 39 | 22 | 17 | Betv1-1 |
| c25055_g1_i1 | 18 | 58 | 34 | 37 | PR10-3 |
| c38417_g1_i1 | 17 | 32 | 75 | 59 | PR10-5 |
| c50593_g1_i1 | 18 | 18 | 29 | 24 | PR10-4 |
| c37788_g2_i4 | 16 | 8 | 15 | 55 | MLP-2 |
| c27108_g1_i1 | 18 | 16 | 42 | 92 | MLP15 |

FIG. 7E

| SEQ ID NO: | | | |
|---|---|---|---|
| SEQ ID NO: 6 | Betv1-1 | MAP-LGVSGLVGKLISTELEVDCDAEKYYNMYKHGEDVKKAVPHLCVDVKI | 49 |
| SEQ ID NO: 5 | PR10-3  | MAH-HGVSGLVGKIVTELELEVNCNADEFYKILKRDEDVPRAVSDLFPPVKI | 49 |
| SEQ ID NO: 8 | PR10-4  | MAHPHPISGLVGKIVTELELEVNCDADYYKIFKHHEDVPKAVPHMYTSVKV | 50 |
| SEQ ID NO: 7 | PR10-5  | MAH-HGVSGLVGKIVTELEVHCNADAYYKIFKHQEDVPKAMPHLYTGGKV | 49 |
| SEQ ID NO: 11| MLP-2   | MAHAHGISGLVGKLITESEVNCNADKEYQMFKHDENITNIIPHIYTSFKV | 50 |
| SEQ ID NO: 9 | MLP-15  | MAHQHTISGLVGKLITESEVNCNADKYYQIFKHHEDLPSAIPHIYTSVKA | 50 |

| | | | |
|---|---|---|---|
| | Betv1-1 | ISGDPTSSGCIKEWNVNIDGKTIRSVEETTHDDETKTLRHRVFEGDVMKD | 99 |
| | PR10-3  | AKGDGLVSGCIKEWDCVLDGKAMSGKEETTHNDETRTLRHRELEGDLMKD | 99 |
| | PR10-4  | VEGHGTISGCVKEWGYLLEGKELIVKETTYDETRTIHHSAVGGHMTKI | 100 |
| | PR10-5  | ISGDATRSGCIKEWNYILEGKALIAVEETTHDDETRTLHRITGGDLTKD | 99 |
| | MPL-2   | VEGDGLISGCTKEWGYLSEGKARIVKEQTTFDDETRTIHHCAKAGDMMN | 100 |
| | MLP-15  | VEGHGTTSGCVKEWCYILEGKPLTVKEKTTYNDETRTINHNGIEGMMTD | 100 |

| | | | |
|---|---|---|---|
| | Betv1-1 | FKKFDTIMVVNPKPDGNGCVVTRSIEYEKTNENSPTPFDYLQFGHQATED | 149 |
| | PR10-3  | YKKFDSIIEVNPKPNGHGSIVTWSIEYEKMNEDSPAPFAYIASFHQNVVE | 149 |
| | PR10-4  | YKKFDATLVVNPKPSGHGSTVSWTIDYEKINEDSPVPFIPYIAFFHKLIED | 150 |
| | PR10-5  | YKKFVKIVEVNPKPNGHGSIVTVSLVYEKMNEGSPTPFNYLQFVHQTIVG | 149 |
| | MPL-2   | YKKFVLTLVVNPKAHGQSTVKWIIDYEKINEDSPVPFAYISLCIKITEG | 150 |
| | MLP-15  | YKKFVATLVVKPKANGQGSIVTWIVDYEKINEDSPVPFDYIAFFQNIED | 150 |

| | | | |
|---|---|---|---|
| | Betv1-1 | MNKYLRDSESN | 160 |
| | PR10-3  | VDSHLCLSE   | 158 |
| | PR10-4  | LNSHLCASD   | 159 |
| | PR10-5  | LNSHICAS    | 157 |
| | MLP-2   | LNSHIYASE   | 159 |
| | MLP-15  | LNSHLCASD   | 159 |

FIG. 7F

Putative secretion signal

| | | |
|---|---|---|
| THS1 | MDSINSSIYFCAYFRELIIKLIMAPIGVSGIVGKLSTELEVDCDAEKYYN | 50 |
| THS2 | MAPIGVSGIVGKLSTELEVDCDAEKYYN | 28 |

SEQ ID NO: 80 THS1  MYKHGEDVQKAVPHLCVDVKVISGDPTRSGCIKEWNVNIDGKTIRSVEET  100
SEQ ID NO: 81 THS1s MYKHGEDVQKAVPHLCVDVKVISGDPTRSGCIKEWNVNIDGKTIRSVEET  50
SEQ ID NO: 6  THS2  MYKHGEDVKKAVPHLCVDVKIISGDPTSSGCIKEWNVNIDGKTIRSVEET  78
SEQ ID NO: 32 THS2s MYKHGEDVKKAVPHLCVDVKIISGDPTSSGCIKEWNVNIDGKTIRSVEET  50

THS1  THNDETKTLRHRVFEGDMMKDFKKFDTIMVVNPKPDGNGCVVTRSIEYEK  150
THS1s THNDETKTLRHRVFEGDMMKDFKKFDTIMVVNPKPDGNGCVVTRSIEYEK  100
THS2  THDDETKTLRHRVFEGDVMKDFKKFDTIMVVNPKPDGNGCVVTRSIEYEK  128
THS2s THDDETKTLRHRVFEGDVMKDFKKFDTIMVVNPKPDGNGCVVTRSIEYEK  100

THS1  TNENSPTPFDYLQFGHQAIEDMNKYLRDSE    180
THS1s TNENSPTPFDYLQFGHQAIEDMNKYLRDSE    130
THS2  TNENSPTPFDYLQFGHQAIEDMNKYLRDSESN  160
THS2s TNENSPTPFDYLQFGHQAIEDMNKYLRDSESN  130

FIG. 11B

| Peptide number | Spectral counts | | | | | |
|---|---|---|---|---|---|---|
| | Stem | | Latex | | Stem + latex | |
| | Number | % of total ($\times 10^{-5}$) | Number | % of total ($\times 10^{-5}$) | Number | % of total ($\times 10^{-5}$) |
| 1 | 3 | 6.98 | 10 | 29.7 | 13 | 27.6 |
| 2 | 1 | 2.33 | 0 | 0 | 3 | 6.38 |
| 3 | 1 (S) | 2.33 | 4 (S) | 11.9 | 7 (S) | 14.9 |
| | 0 (R) | 0 | 0 (R) | 0 | 0 (R) | 0 |
| 4 | 2 | 4.65 | 2 | 5.95 | 6 | 12.8 |
| 5 | 12 (D) | 27.9 | 19 (D) | 56.5 | 21 (D) | 44.7 |
| | 7 (N) | 16.3 | 2 (N) | 5.95 | 12 (N) | 25.5 |
| 6 | 3 (V) | 6.98 | 8 (V) | 23.8 | 5 (V) | 10.6 |
| | 0 (M) | 0 | 0 (M) | 0 | 1 (M) | 2.13 |
| 7 | 1 | 2.33 | 2 | 59.5 | 11 | 23.4 |
| 8 | 2 | 4.65 | 4 | 11.9 | 3 | 6.38 |

FIG. 11C

| | qRT-PCR primers | Sequence | Target region |
|---|---|---|---|
| SEQ ID NO: 65 | qTHS2F | GAATCCCCGGCCAACCTATC | *THS2*-specfic |
| SEQ ID NO: 66 | qTHS2R | ACCTGAAACACCGAGAGGAGC | *THS2*-specfic |
| SEQ ID NO: 67 | qTHS2SF | TAACAGCTAATCCTGAACAGTTTAGTCG | *THS2s*-specific |
| SEQ ID NO: 68 | qTHS2SR | CGCAAAGATGAGGAACTGCCT | *THS2s*-specific |
| SEQ ID NO: 69 | qTHS1F | GCAACATGCCAAAGTTAGAACAGC | *THS1*-specific |
| SEQ ID NO: 70 | qTHS1R | GAAACACCGAGAGGAGCCATC | *THS1*-specific |
| SEQ ID NO: 71 | qTHS1SF | GCAACATGCCAAAGTCTAGTCG | *THS1s*-specific |
| SEQ ID NO: 72 | qTHS1sR | AACCTGAACGGGTTGGGTCT | *THS1s*-specific |

| | cDNA/ genomic PCR primers | Sequence | Target region |
|---|---|---|---|
| SEQ ID NO: 73 | BV1_F1 | TGGGCTCATATGTGACACTGCTTAACCAC | *THS2* 5' UTR |
| SEQ ID NO: 74 | BV1_F2 | TTACATCAATTCTTTATAGCAACATGCCAAAG | *THS1* 5' UTR |
| SEQ ID NO: 75 | BV1_F3 | ACAACGGGACTATACTACTAATACCGAATC | *THS2* 5' UTR nested F1 |
| SEQ ID NO: 76 | BV1_R | TATGTACGTGCATAGGTACACGTACACC | *THS1* and *THS2* conserved 3' UTR |

| | VIGS primers | Sequence | Target region |
|---|---|---|---|
| SEQ ID NO: 77 | TRV2-MSC_F | GGTCAAGGTACGTAGTAGAG | *THS1* and *THS2* |
| SEQ ID NO: 78 | TRV2-MSC_R | CGAGAATGTCAATCTCGTAGG | *THS1* and *THS2* |

| | Synthetic VIGs fragment | |
|---|---|---|
| SEQ ID NO: 79 | AATGTTAACATTGATGGTAAGACGATTCGCTCGGTACAATTCGGCCATCAGGCCATTGAGGACATG AACAAGTACTTACGCGATTCTGAAAGTAACTGATTGATGCCATTTATACATGAACCCATTCGGTGTT GGTGTACGTGTACCTATGCACGTACATATTTTATATTTATCAGTTGCAACTTGTGTGTATTTTATCGT TTCAGTGACTCCAATATTGTGTCAGTGACCCGGTGTATGGGTGTGATT | |

FIG. 12B

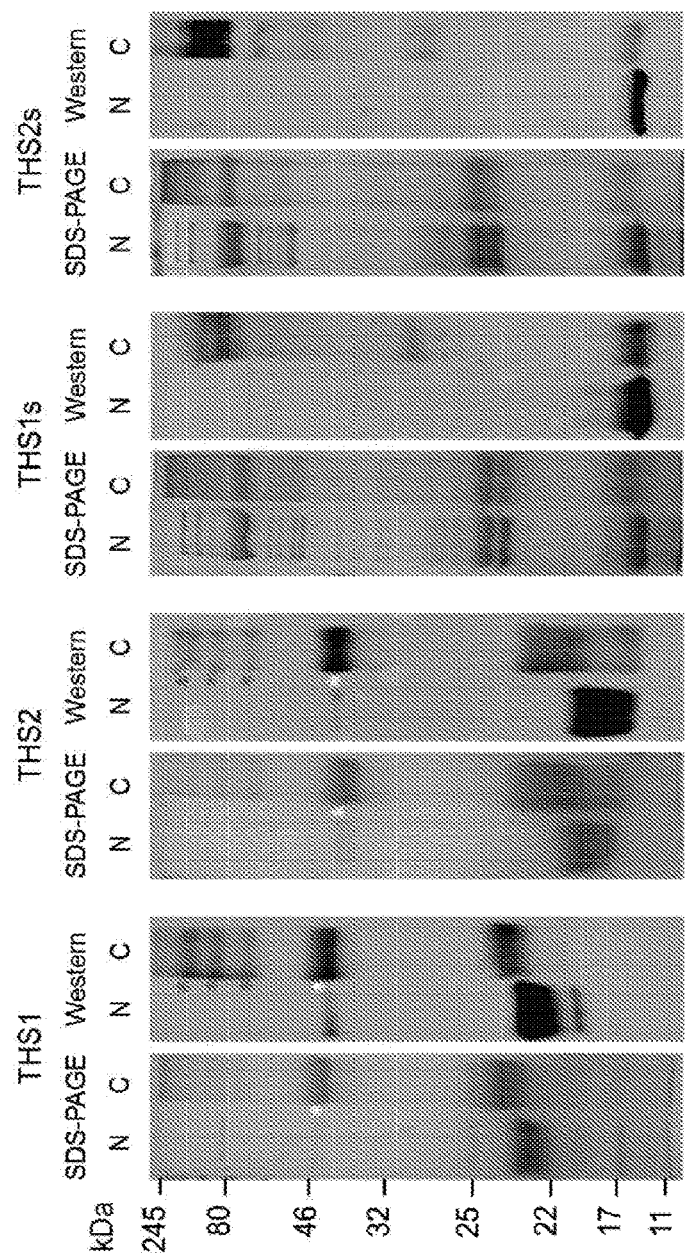
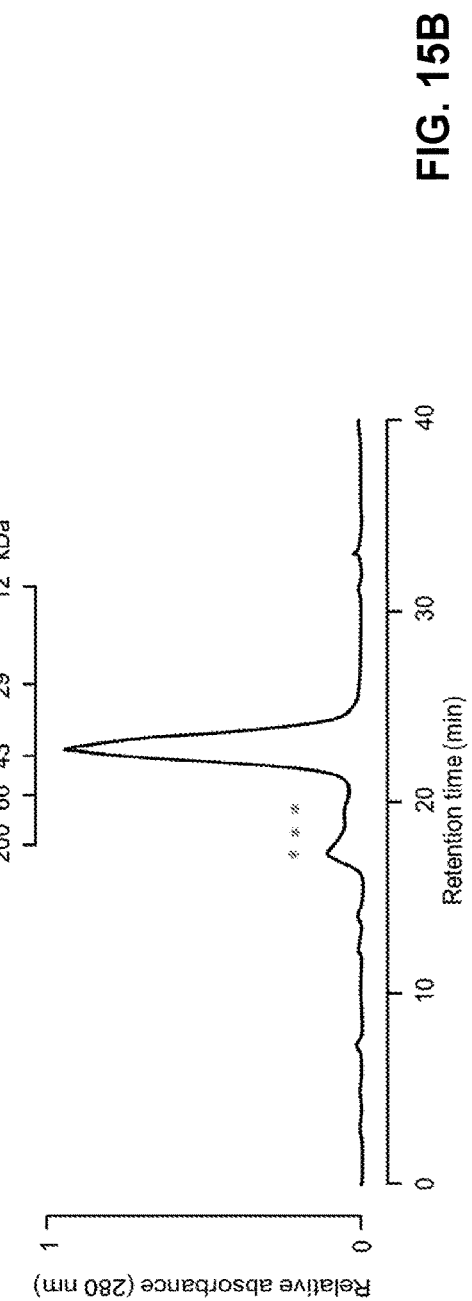
FIG. 15A
FIG. 15B

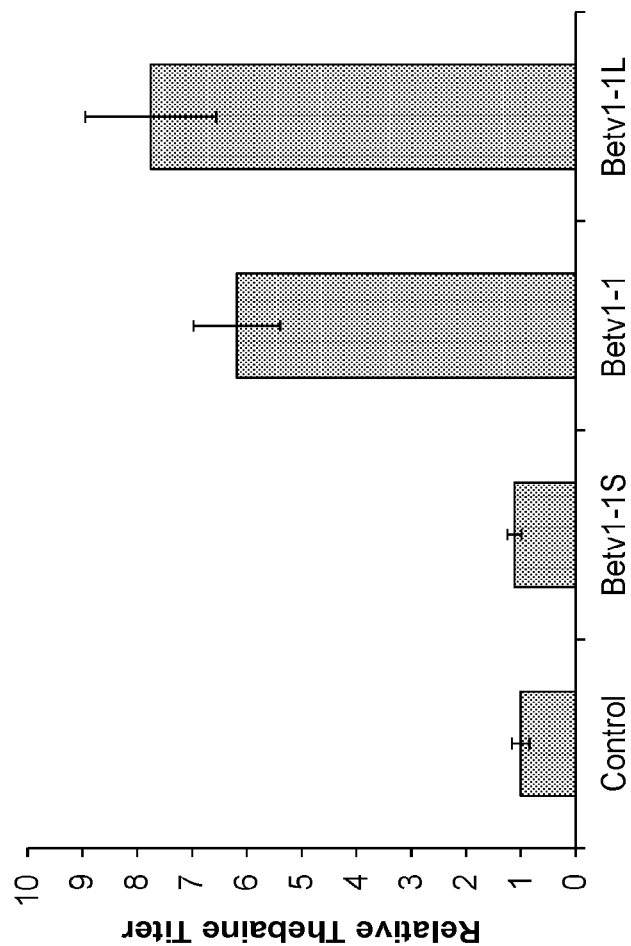
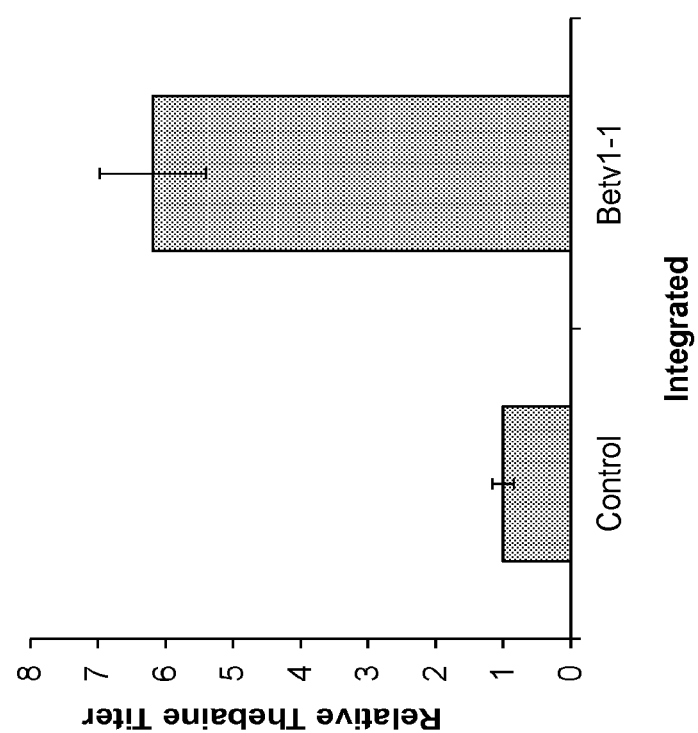
FIG. 20A
FIG. 20B
FIG. 20C

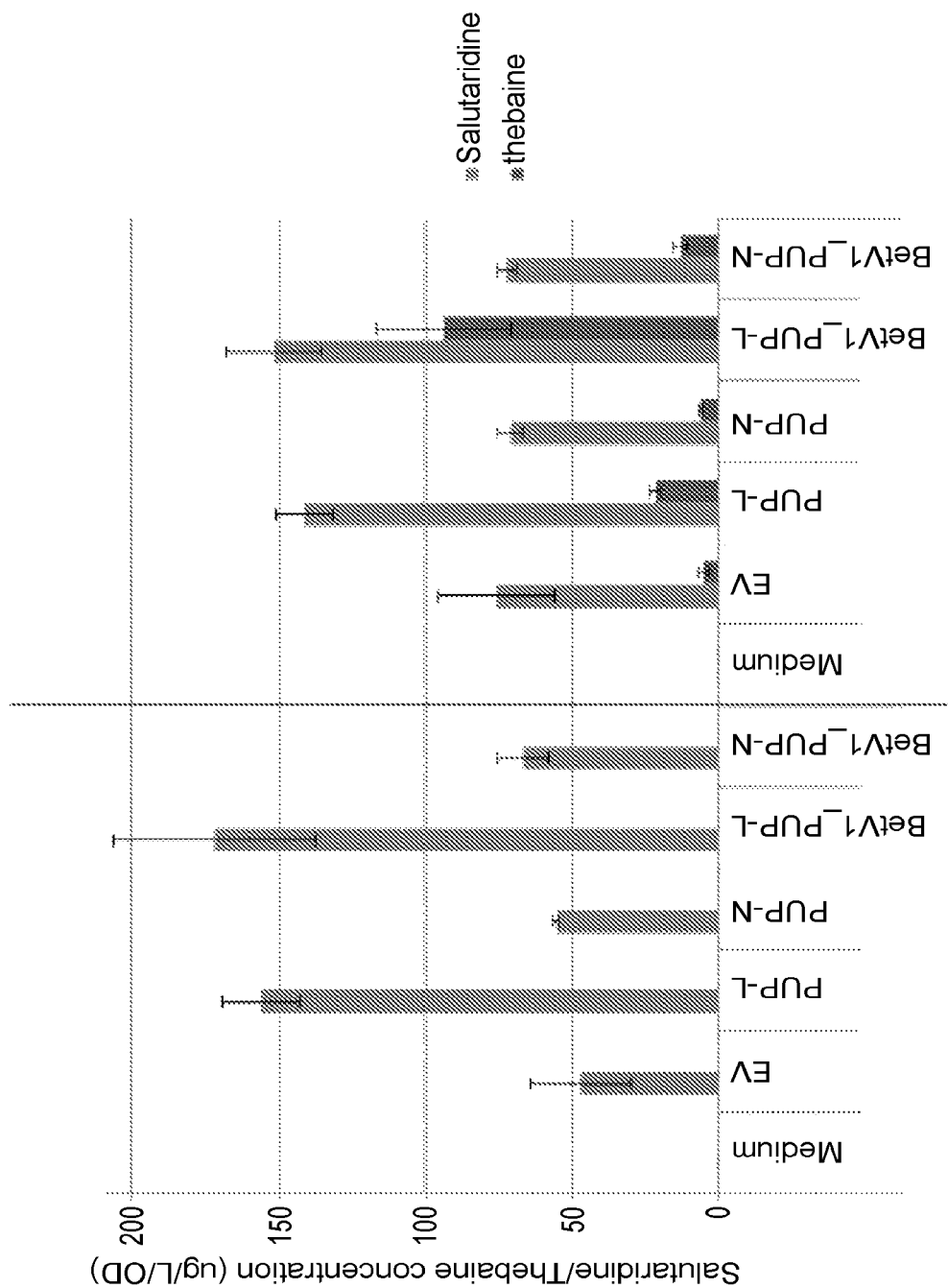

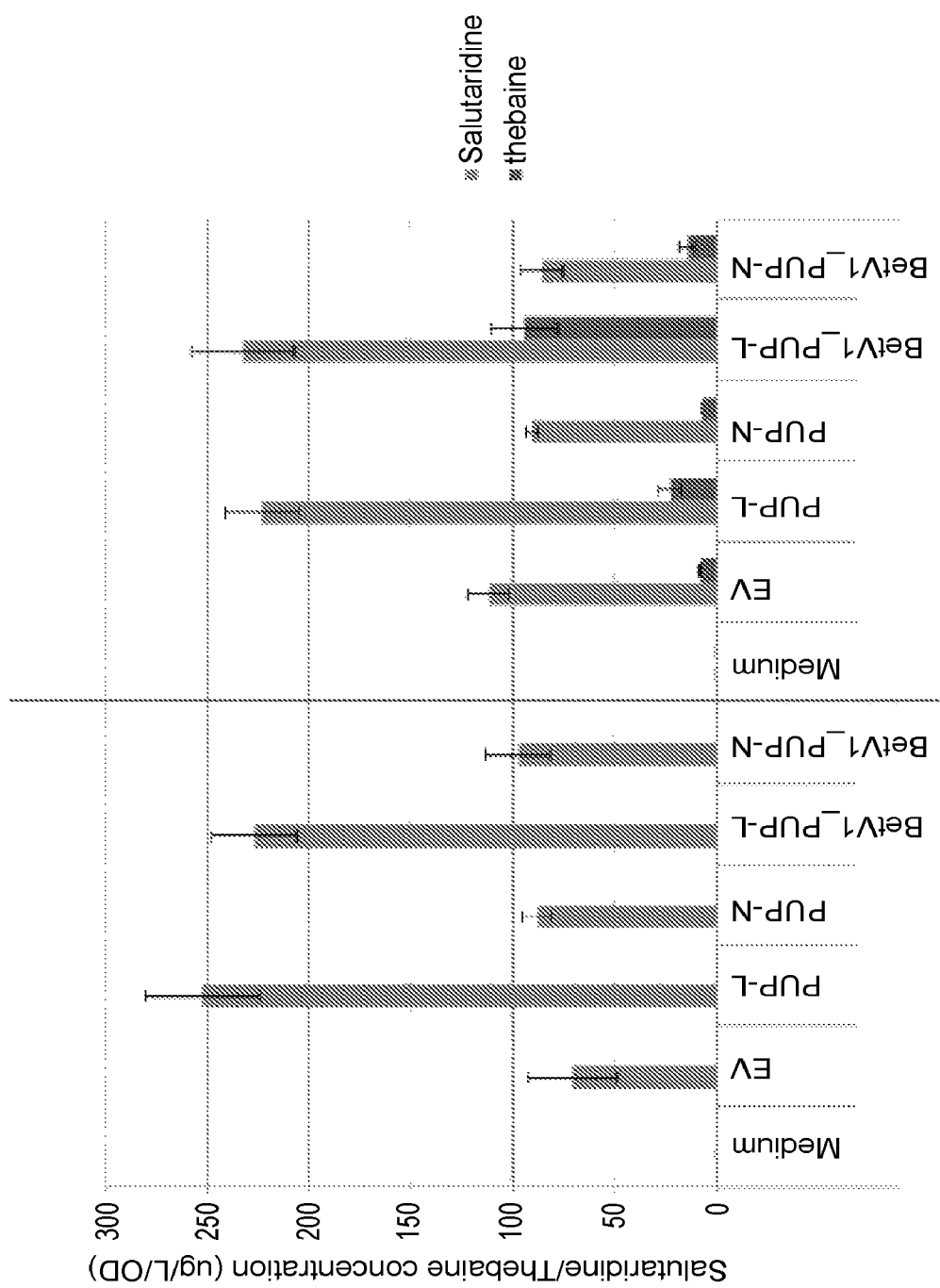

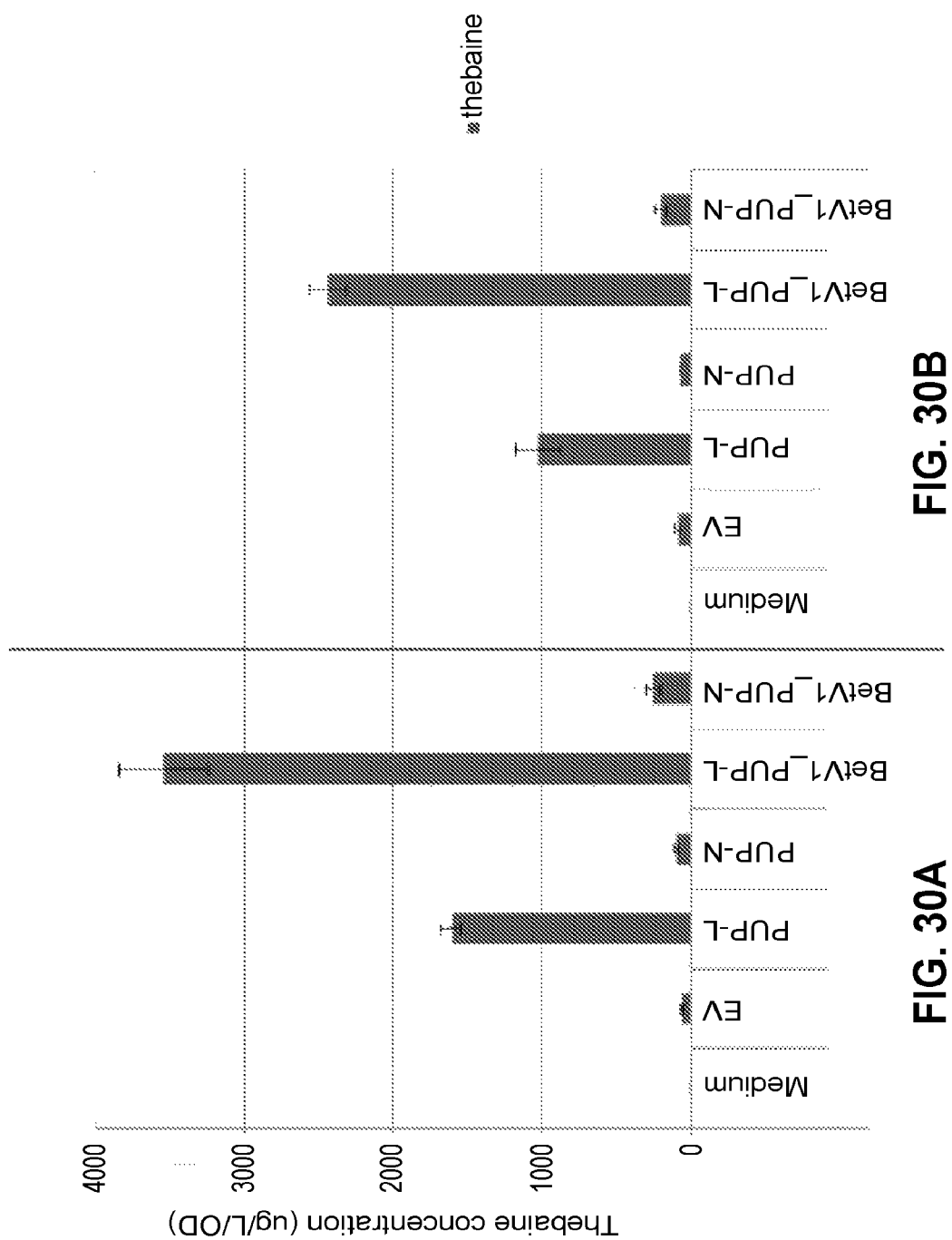

SEQUENCE LISTING

```
<160> NUMBER OF SEQ ID NOS: 81

<210> SEQ ID NO 1
<211> LENGTH: 1425
<212> TYPE: DNA
<213> ORGANISM: Papaver somniferum

<400> SEQUENCE: 1
atggcaacaa tgtatagtgc tgctgttgaa gtgatctcta aggaaaccat taaacccaca      60
actccaaccc catctcaact taaaaacttc aatctgtcac ttctcgatca atgttttcct     120
ttatattatt atgttccaat cattcttttc tacccagcca ccgccgctaa tagtaccggt     180
agcagtaacc atcatgatga tcttgacttg cttaagagtt ctctttccaa aacactagtt     240
cacttttatc caatggctgg taggatgata gacaatattc tggtcgactg tcatgaccaa     300
gggattaact tttacaaagt taaaattaga ggtaaaatgt gtgagttcat gtcgcaaccg     360
gatgtgccac taagccagct tcttccctct gaagttgttt ccgcgagtgt ccctaaggaa     420
gcactggtga tcgttcaagt gaacatgttt gactgtggtg aacagccat ttgttcgagt     480 gtatcacata agattgccga tgcagctaca atgagtacgt tcattcgtag ttgggcaagc     540
accactaaaa catctcgtag tggggttca actgctgccg ttacagatca gaaattgatt     600
ccttctttcg actcggcatc tctattccca cctagtgaac gattgacatc tccatcaggg     660
atgtcagaga taccattttc cagtacccca gaggatacag aagatgataa aactgtcagc     720
aagagatttg tgttcgattt tgcaaagata acatctgtac gtgaaaagtt gcaagtattg     780
atgcatgata actacaaaag ccgcaggcaa acaagggttg aggtggttac ttctctaata     840
tggaagtccg tgatgaaatc cactccagcc ggtttttac cagtggtaca tcatgccgtg     900
aaccttgaaa agaaaatgga cccaccatta caagatgttt cattcggaaa tctatctgta     960
actgtttcgg cgttcttacc agcaacaaca acgacaacaa caaatgcggt caacaagaca    1020
```

-continued

```
atcaatagta cgagtagtga atcacaagtg gtacttcatg agttacatga tttatagct    1080 cagatgagga gtgaaataga taaggtcaag ggtgataaag gtagcttgga gaaagtcatt    1140
caaaattttg cttctggtca tgatgcttca ataagaaaaa tcaatgatgt tgaagtgata    1200
aacttttgga taagtagctg gtgcaggatg ggattatacg agattgattt tggttgggga    1260
aagccaattt gggtaacagt tgatccaaat atcaagccga acaagaattg ttttttcatg    1320
aatgatacga aatgtggtga aggaatagaa gtttgggcga gctttcttga ggatgatatg    1380
gctaagttcg agcttcacct aagtgaaatc cttgaattga tttga                    1425
```

<210> SEQ ID NO 2
<211> LENGTH: 474
<212> TYPE: PRT
<213> ORGANISM: Papaver somniferum

<400> SEQUENCE: 2

```
Met Ala Thr Met Tyr Ser Ala Ala Val Glu Val Ile Ser Lys Glu Thr
1               5                   10                  15

Ile Lys Pro Thr Thr Pro Thr Pro Ser Gln Leu Lys Asn Phe Asn Leu
            20                  25                  30

Ser Leu Leu Asp Gln Cys Phe Pro Leu Tyr Tyr Val Pro Ile Ile
        35                  40                  45

Leu Phe Tyr Pro Ala Thr Ala Ala Asn Ser Thr Gly Ser Ser Asn His
    50                  55                  60

His Asp Asp Leu Asp Leu Leu Lys Ser Ser Leu Ser Lys Thr Leu Val
65                  70                  75                  80

His Phe Tyr Pro Met Ala Gly Arg Met Ile Asp Asn Ile Leu Val Asp
                85                  90                  95

Cys His Asp Gln Gly Ile Asn Phe Tyr Lys Val Lys Ile Arg Gly Lys
            100                 105                 110

Met Cys Glu Phe Met Ser Gln Pro Asp Val Pro Leu Ser Gln Leu Leu
        115                 120                 125

Pro Ser Glu Val Val Ser Ala Ser Val Pro Lys Glu Ala Leu Val Ile
    130                 135                 140

Val Gln Val Asn Met Phe Asp Cys Gly Gly Thr Ala Ile Cys Ser Ser
145                 150                 155                 160

Val Ser His Lys Ile Ala Asp Ala Ala Thr Met Ser Thr Phe Ile Arg
                165                 170                 175

Ser Trp Ala Ser Thr Thr Lys Thr Ser Arg Ser Gly Gly Ser Thr Ala
            180                 185                 190

Ala Val Thr Asp Gln Lys Leu Ile Pro Ser Phe Asp Ser Ala Ser Leu
        195                 200                 205

Phe Pro Pro Ser Glu Arg Leu Thr Ser Pro Ser Gly Met Ser Glu Ile
    210                 215                 220

Pro Phe Ser Ser Thr Pro Glu Asp Thr Glu Asp Asp Lys Thr Val Ser
225                 230                 235                 240

Lys Arg Phe Val Phe Asp Phe Ala Lys Ile Thr Ser Val Arg Glu Lys
                245                 250                 255

Leu Gln Val Leu Met His Asp Asn Tyr Lys Ser Arg Arg Gln Thr Arg
            260                 265                 270

Val Glu Val Val Thr Ser Leu Ile Trp Lys Ser Val Met Lys Ser Thr
        275                 280                 285

Pro Ala Gly Phe Leu Pro Val Val His His Ala Val Asn Leu Arg Lys
    290                 295                 300
```

| | | | | | | | | | | | | | | |
|---|---|---|---|---|---|---|---|---|---|---|---|---|---|---|
Lys | Met | Asp | Pro | Pro | Leu | Gln | Asp | Val | Ser | Phe | Gly | Asn | Leu | Ser | Val
305 | | | | 310 | | | | 315 | | | | 320 | | |

Thr Val Ser Ala Phe Leu Pro Ala Thr Thr Thr Thr Thr Asn Ala
                        325                   330                  335

Val Asn Lys Thr Ile Asn Ser Thr Ser Ser Glu Ser Gln Val Val Leu
          340                   345                   350

His Glu Leu His Asp Phe Ile Ala Gln Met Arg Ser Glu Ile Asp Lys
        355                   360                   365

Val Lys Gly Asp Lys Gly Ser Leu Glu Lys Val Ile Gln Asn Phe Ala
   370                   375                   380

Ser Gly His Asp Ala Ser Ile Lys Lys Ile Asn Asp Val Glu Val Ile
385                   390                   395                  400

Asn Phe Trp Ile Ser Ser Trp Cys Arg Met Gly Leu Tyr Glu Ile Asp
                405                   410                   415

Phe Gly Trp Gly Lys Pro Ile Trp Val Thr Val Asp Pro Asn Ile Lys
            420                   425                   430

Pro Asn Lys Asn Cys Phe Phe Met Asn Asp Thr Lys Cys Gly Glu Gly
        435                   440                   445

Ile Glu Val Trp Ala Ser Phe Leu Glu Asp Asp Met Ala Lys Phe Glu
   450                   455                   460

Leu His Leu Ser Glu Ile Leu Glu Leu Ile
465                  470

<210> SEQ ID NO 3
<211> LENGTH: 936
<212> TYPE: DNA
<213> ORGANISM: Papaver somniferum

<400> SEQUENCE: 3

```
atgcctgaaa catgtccaaa tactgttaca agaggaggt gtgcagttgt tactggcgga    60
aacaagggta tcggatttga gatttgtaag caattatctt ctaatggaat catgttgtt   120
ttaacttgta gagatgtaac taaaggtcat gaagctgttg aaaaactcaa aaattccaat   180
catgagaatg tggtttttca tcaacttgat gttacggatc caattgctac tatgtcttct   240
ttagcggatt tcattaaaac acacttcgga agcttgata tcttggtaaa caatgctggg   300
gttgcaggtt tttcagttga tgctgatcgt tttaaggcaa tgataagtga cattggagag   360
gattcagagg agctcgtgaa gatctacgaa aaaccagaag cccaagaatt aatgtcagag   420
acatatgaat tagcagaaga atgtctcaaa ataaattaca acggtgttaa atcggtaacc   480
gaagttctaa ttcctttact tcaactatct gattcaccaa gaattgttaa tgtttcatca   540
tccacgggaa gcctcaagta tgtatccaat gaaacagctc tagagatact tggagatggt   600
gatgcattaa cagaagagag aattgacatg gtagtgaata tgcttcttaa ggattttaag   660
gaaaatttga tcgaaacaaa tgggtggcct agtttcggag ctgcatacac aacatcaaaa   720
gcatgtttga atgcttacac aagggtgtta gcaaacaaaa ttcccaaatt tcaggtcaat   780
tgtgttttgtc ctggtttggt taaaacagaa atgaactacg gcattggaaa ttatactgcc   840
gaagaaggtg ctgaacatgt agtcagaata gctcttttcc ccgacgatgg accttctggt   900
tttttctatg attgttcaga actatctgca ttttga                            936
```

<210> SEQ ID NO 4
<211> LENGTH: 311
<212> TYPE: PRT
<213> ORGANISM: Papaver somniferum

<400> SEQUENCE: 4

```
Met Pro Glu Thr Cys Pro Asn Thr Val Thr Lys Arg Arg Cys Ala Val
1               5                   10                  15

Val Thr Gly Gly Asn Lys Gly Ile Gly Phe Glu Ile Cys Lys Gln Leu
            20                  25                  30

Ser Ser Asn Gly Ile Met Val Val Leu Thr Cys Arg Asp Val Thr Lys
        35                  40                  45

Gly His Glu Ala Val Glu Lys Leu Lys Asn Ser Asn His Glu Asn Val
    50                  55                  60

Val Phe His Gln Leu Asp Val Thr Asp Pro Ile Ala Thr Met Ser Ser
65                  70                  75                  80

Leu Ala Asp Phe Ile Lys Thr His Phe Gly Lys Leu Asp Ile Leu Val
                85                  90                  95

Asn Asn Ala Gly Val Ala Gly Phe Ser Val Asp Ala Asp Arg Phe Lys
            100                 105                 110

Ala Met Ile Ser Asp Ile Gly Glu Asp Ser Glu Glu Leu Val Lys Ile
        115                 120                 125

Tyr Glu Lys Pro Glu Ala Gln Glu Leu Met Ser Glu Thr Tyr Glu Leu
    130                 135                 140

Ala Glu Glu Cys Leu Lys Ile Asn Tyr Asn Gly Val Lys Ser Val Thr
145                 150                 155                 160

Glu Val Leu Ile Pro Leu Leu Gln Leu Ser Asp Ser Pro Arg Ile Val
                165                 170                 175

Asn Val Ser Ser Ser Thr Gly Ser Leu Lys Tyr Val Ser Asn Glu Thr
            180                 185                 190

Ala Leu Glu Ile Leu Gly Asp Gly Asp Ala Leu Thr Glu Glu Arg Ile
        195                 200                 205

Asp Met Val Val Asn Met Leu Leu Lys Asp Phe Lys Glu Asn Leu Ile
    210                 215                 220

Glu Thr Asn Gly Trp Pro Ser Phe Gly Ala Ala Tyr Thr Thr Ser Lys
225                 230                 235                 240

Ala Cys Leu Asn Ala Tyr Thr Arg Val Leu Ala Asn Lys Ile Pro Lys
                245                 250                 255

Phe Gln Val Asn Cys Val Cys Pro Gly Leu Val Lys Thr Glu Met Asn
            260                 265                 270

Tyr Gly Ile Gly Asn Tyr Thr Ala Glu Gly Ala Glu His Val Val
        275                 280                 285

Arg Ile Ala Leu Phe Pro Asp Asp Gly Pro Ser Gly Phe Phe Tyr Asp
    290                 295                 300

Cys Ser Glu Leu Ser Ala Phe
305                 310
```

<210> SEQ ID NO 5
<211> LENGTH: 158
<212> TYPE: PRT
<213> ORGANISM: Papaver somniferum

<400> SEQUENCE: 5

```
Met Ala His His Gly Val Ser Gly Leu Val Gly Lys Ile Val Thr Glu
1               5                   10                  15

Leu Glu Val Asn Cys Asn Ala Asp Glu Phe Tyr Lys Ile Leu Lys Arg
            20                  25                  30

Asp Glu Asp Val Pro Arg Ala Val Ser Asp Leu Phe Pro Pro Val Lys
        35                  40                  45
```

Ile Ala Lys Gly Asp Gly Leu Val Ser Gly Cys Ile Lys Glu Trp Asp
 50                  55                  60

Cys Val Leu Asp Gly Lys Ala Met Ser Gly Lys Glu Glu Thr Thr His
 65                  70                  75                  80

Asn Asp Glu Thr Arg Thr Leu Arg His Arg Glu Leu Gly Asp Leu
                 85                  90                  95

Met Lys Asp Tyr Lys Lys Phe Asp Ser Ile Ile Glu Val Asn Pro Lys
                100                 105                 110

Pro Asn Gly His Gly Ser Ile Val Thr Trp Ser Ile Glu Tyr Glu Lys
                115                 120                 125

Met Asn Glu Asp Ser Pro Ala Pro Phe Ala Tyr Leu Ala Ser Phe His
130                 135                 140

Gln Asn Val Val Glu Val Asp Ser His Leu Cys Leu Ser Glu
145                 150                 155

<210> SEQ ID NO 6
<211> LENGTH: 160
<212> TYPE: PRT
<213> ORGANISM: Papaver somniferum

<400> SEQUENCE: 6

Met Ala Pro Leu Gly Val Ser Gly Leu Val Gly Lys Leu Ser Thr Glu
 1               5                  10                  15

Leu Glu Val Asp Cys Asp Ala Glu Lys Tyr Tyr Asn Met Tyr Lys His
                 20                  25                  30

Gly Glu Asp Val Lys Lys Ala Val Pro His Leu Cys Val Asp Val Lys
                 35                  40                  45

Ile Ile Ser Gly Asp Pro Thr Ser Ser Gly Cys Ile Lys Glu Trp Asn
 50                  55                  60

Val Asn Ile Asp Gly Lys Thr Ile Arg Ser Val Glu Glu Thr Thr His
 65                  70                  75                  80

Asp Asp Glu Thr Lys Thr Leu Arg His Arg Val Phe Glu Gly Asp Val
                 85                  90                  95

Met Lys Asp Phe Lys Lys Phe Asp Thr Ile Met Val Asn Pro Lys
                100                 105                 110

Pro Asp Gly Asn Gly Cys Val Val Thr Arg Ser Ile Glu Tyr Glu Lys
                115                 120                 125

Thr Asn Glu Asn Ser Pro Thr Pro Phe Asp Tyr Leu Gln Phe Gly His
130                 135                 140

Gln Ala Ile Glu Asp Met Asn Lys Tyr Leu Arg Asp Ser Glu Ser Asn
145                 150                 155                 160

<210> SEQ ID NO 7
<211> LENGTH: 157
<212> TYPE: PRT
<213> ORGANISM: Papaver somniferum

<400> SEQUENCE: 7

Met Ala His His Gly Val Ser Gly Leu Val Gly Lys Leu Val Thr Glu
 1               5                  10                  15

Leu Glu Val His Cys Asn Ala Asp Ala Tyr Tyr Lys Ile Phe Lys His
                 20                  25                  30

Gln Glu Asp Val Pro Lys Ala Met Pro His Leu Tyr Thr Gly Gly Lys
                 35                  40                  45

Val Ile Ser Gly Asp Ala Thr Arg Ser Gly Cys Ile Lys Glu Trp Asn
 50                  55                  60

```
Tyr Ile Leu Glu Gly Lys Ala Leu Ile Ala Val Glu Thr Thr His
 65                  70                  75                  80

Asp Asp Glu Thr Arg Thr Leu Thr His Arg Ile Thr Gly Gly Asp Leu
                 85                  90                  95

Thr Lys Asp Tyr Lys Lys Phe Val Lys Ile Val Glu Val Asn Pro Lys
            100                 105                 110

Pro Asn Gly His Gly Ser Ile Val Thr Val Ser Leu Val Tyr Glu Lys
        115                 120                 125

Met Asn Glu Gly Ser Pro Thr Pro Phe Asn Tyr Leu Gln Phe Val His
130                 135                 140

Gln Thr Ile Val Gly Leu Asn Ser His Ile Cys Ala Ser
145                 150                 155
```

<210> SEQ ID NO 8
<211> LENGTH: 159
<212> TYPE: PRT
<213> ORGANISM: Papaver somniferum

<400> SEQUENCE: 8

```
Met Ala His Pro His Pro Ile Ser Gly Leu Val Gly Lys Leu Val Thr
  1               5                  10                  15

Glu Leu Glu Val Asn Cys Asp Ala Asp Lys Tyr Tyr Lys Ile Phe Lys
                 20                  25                  30

His His Glu Asp Val Pro Lys Ala Val Pro His Met Tyr Thr Ser Val
            35                  40                  45

Lys Val Val Glu Gly His Gly Ile Thr Ser Gly Cys Val Lys Glu Trp
        50                  55                  60

Gly Tyr Leu Leu Glu Gly Lys Glu Leu Ile Val Lys Glu Thr Thr Thr
 65                  70                  75                  80

Tyr Thr Asp Glu Thr Arg Thr Ile His His Ser Ala Val Gly Gly His
                 85                  90                  95

Met Thr Lys Ile Tyr Lys Lys Phe Asp Ala Thr Leu Val Val Asn Pro
            100                 105                 110

Lys Pro Ser Gly His Gly Ser Thr Val Ser Trp Thr Ile Asp Tyr Glu
        115                 120                 125

Lys Ile Asn Glu Asp Ser Pro Val Pro Ile Pro Tyr Leu Ala Phe Phe
130                 135                 140

His Lys Leu Ile Glu Asp Leu Asn Ser His Leu Cys Ala Ser Asp
145                 150                 155
```

<210> SEQ ID NO 9
<211> LENGTH: 159
<212> TYPE: PRT
<213> ORGANISM: Papaver somniferum

<400> SEQUENCE: 9

```
Met Ala His Gln His Thr Ile Ser Gly Leu Val Gly Lys Leu Ile Thr
  1               5                  10                  15

Glu Ser Glu Val Asn Cys Asn Ala Asp Lys Tyr Tyr Gln Ile Phe Lys
                 20                  25                  30

His His Glu Asp Leu Pro Ser Ala Ile Pro His Ile Tyr Thr Ser Val
            35                  40                  45

Lys Ala Val Glu Gly His Gly Thr Thr Ser Gly Cys Val Lys Glu Trp
        50                  55                  60

Cys Tyr Ile Leu Glu Gly Lys Pro Leu Thr Val Lys Glu Lys Thr Thr
 65                  70                  75                  80
```

```
Tyr Asn Asp Glu Thr Arg Thr Ile Asn His Asn Gly Ile Glu Gly Gly
                85                  90                  95

Met Met Thr Asp Tyr Lys Lys Phe Val Ala Thr Leu Val Val Lys Pro
            100                 105                 110

Lys Ala Asn Gly Gln Gly Ser Ile Val Thr Trp Ile Val Asp Tyr Glu
        115                 120                 125

Lys Ile Asn Glu Asp Ser Pro Val Pro Phe Asp Tyr Leu Ala Phe Phe
    130                 135                 140

Gln Gln Asn Ile Glu Asp Leu Asn Ser His Leu Cys Ala Ser Asp
145                 150                 155
```

<210> SEQ ID NO 10
<211> LENGTH: 164
<212> TYPE: PRT
<213> ORGANISM: Papaver somniferum

<400> SEQUENCE: 10

```
Met Arg Tyr Glu Phe Ile Asn Glu Phe Asp Ala His Ala Ser Ala Asp
1               5                   10                  15

Asp Val Trp Gly Gly Ile Tyr Gly Ser Ile Asp Tyr Pro Lys Leu Val
            20                  25                  30

Val Gln Leu Leu Pro Thr Val Leu Glu Lys Lys Glu Ile Leu Glu Gly
        35                  40                  45

Asp Gly His Asn Val Gly Thr Val Leu His Val Tyr Leu Pro Gly
    50                  55                  60

Phe Val Pro Arg Thr Tyr Asn Glu Lys Ile Val Thr Met Asp His Lys
65                  70                  75                  80

Lys Arg Tyr Lys Glu Val Gln Met Val Glu Gly Gly Tyr Leu Asp Met
                85                  90                  95

Gly Phe Thr Tyr Val Met Val Ile His Glu Val Leu Ala Lys Glu Cys
            100                 105                 110

Asn Ser Cys Ile Ile Arg Ser Ile Val Lys Cys Glu Val Lys Asp Glu
        115                 120                 125

Phe Ala Ala Asn Val Ser Asn Ile Arg Asn Thr Phe Asp Gly Tyr Val
    130                 135                 140

Ala Leu Ala Arg Ala Val Pro Glu Tyr Ile Ala Lys Gln His Ala Thr
145                 150                 155                 160

Ser Ala Ala Asn
```

<210> SEQ ID NO 11
<211> LENGTH: 159
<212> TYPE: PRT
<213> ORGANISM: Papaver somniferum

<400> SEQUENCE: 11

```
Met Ala His Ala His Gly Ile Ser Gly Leu Val Gly Lys Leu Ile Thr
1               5                   10                  15

Glu Ser Glu Val Asn Cys Asn Ala Asp Lys Phe Tyr Gln Met Phe Lys
            20                  25                  30

His Asp Glu Asn Ile Thr Asn Ile Ile Pro His Ile Tyr Thr Ser Phe
        35                  40                  45

Lys Val Val Glu Gly Asp Gly Leu Ile Ser Gly Cys Thr Lys Glu Trp
    50                  55                  60

Gly Tyr Leu Ser Glu Gly Lys Ala Arg Ile Val Lys Glu Gln Thr Thr
65                  70                  75                  80
```

```
Phe Asp Asp Glu Thr Arg Thr Ile His His Cys Ala Lys Ala Gly Asp
                85                  90                  95

Met Met Asn Asp Tyr Lys Lys Phe Val Leu Thr Leu Val Val Asn Pro
            100                 105                 110

Lys Ala His Gly Gln Gly Ser Thr Val Lys Trp Ile Ile Asp Tyr Glu
        115                 120                 125

Lys Ile Asn Glu Asp Ser Pro Val Pro Phe Ala Tyr Leu Ser Leu Cys
    130                 135                 140

Ile Lys Ile Thr Glu Gly Leu Asn Ser His Ile Tyr Ala Ser Glu
145                 150                 155
```

<210> SEQ ID NO 12
<211> LENGTH: 157
<212> TYPE: PRT
<213> ORGANISM: Papaver somniferum

<400> SEQUENCE: 12

```
Met Ala Gln His His Thr Ile Ser Gly Leu Ile Gly Lys Leu Val Thr
1               5                   10                  15

Glu Ser Glu Val Asn Cys Asp Ala Glu Lys Tyr Tyr Lys Ile Ile Lys
            20                  25                  30

His His Glu Asp Val Pro Asn Ala Thr Pro Tyr Val Ser Asp Val Lys
        35                  40                  45

Val Thr Glu Gly His Gly Thr Thr Ser Gly Cys Val Lys Gln Trp Asn
    50                  55                  60

Phe Val Val Ala Gly Arg Asn Glu Tyr Val Leu Glu Lys Thr Thr Tyr
65                  70                  75                  80

Asn Asp Glu Thr Arg Thr Ile Cys His Ser Asp Phe Glu Gly Asp Leu
                85                  90                  95

Met Lys Lys Tyr Lys Lys Phe Asp Ala Ile Leu Val Val Lys Pro Lys
            100                 105                 110

Asp Asn Gly His Gly Ser Asn Val Arg Trp Thr Ile Glu Tyr Glu Lys
        115                 120                 125

Asn Asn Glu Asp Ser Pro Val Pro Ile Asp Tyr Leu Gly Phe Phe Gln
    130                 135                 140

Ser Leu Ile Asp Asp Leu Asn Ser His Leu Cys Ser Ser
145                 150                 155
```

<210> SEQ ID NO 13
<211> LENGTH: 180
<212> TYPE: PRT
<213> ORGANISM: Papaver somniferum

<400> SEQUENCE: 13

```
Met Asp Ser Ile Asn Ser Ser Ile Tyr Phe Cys Ala Tyr Phe Arg Glu
1               5                   10                  15

Leu Ile Ile Lys Leu Leu Met Ala Pro Leu Gly Val Ser Gly Leu Val
            20                  25                  30

Gly Lys Leu Ser Thr Glu Leu Glu Val Asp Cys Asp Ala Glu Lys Tyr
        35                  40                  45

Tyr Asn Met Tyr Lys His Gly Glu Asp Val Gln Lys Ala Val Pro His
    50                  55                  60

Leu Cys Val Asp Val Lys Val Ile Ser Gly Asp Pro Thr Ser Ser Gly
65                  70                  75                  80

Cys Ile Lys Glu Trp Asn Val Asn Ile Asp Gly Lys Thr Ile Arg Ser
                85                  90                  95
```

```
Val Glu Glu Thr Thr His Asn Asp Glu Thr Lys Thr Leu Arg His Arg
            100                 105                 110

Val Phe Glu Gly Asp Met Met Lys Asp Phe Lys Lys Phe Asp Thr Ile
        115                 120                 125

Met Val Val Asn Pro Lys Pro Asp Gly Asn Gly Cys Val Val Thr Arg
130                 135                 140

Ser Ile Glu Tyr Glu Lys Thr Asn Glu Asn Ser Pro Thr Pro Phe Asp
145                 150                 155                 160

Tyr Leu Gln Phe Gly His Gln Ala Ile Glu Asp Met Asn Lys Tyr Leu
                165                 170                 175

Arg Asp Ser Glu
            180

<210> SEQ ID NO 14
<211> LENGTH: 160
<212> TYPE: PRT
<213> ORGANISM: Papaver somniferum

<400> SEQUENCE: 14

Met Ala Pro Leu Gly Val Ser Gly Leu Val Gly Lys Leu Ser Thr Glu
1               5                   10                  15

Leu Glu Val Asp Cys Asp Ala Glu Lys Tyr Tyr Asn Met Tyr Lys His
            20                  25                  30

Gly Glu Asp Val Lys Lys Ala Val Pro His Leu Cys Val Asp Val Lys
        35                  40                  45

Ile Ile Ser Gly Asp Pro Thr Ser Ser Gly Cys Ile Lys Glu Trp Asn
50                  55                  60

Val Asn Ile Asp Gly Lys Thr Ile Arg Ser Val Glu Glu Thr Thr His
65                  70                  75                  80

Asp Asp Glu Thr Lys Thr Leu Arg His Arg Val Phe Glu Gly Asp Val
                85                  90                  95

Met Lys Asp Phe Lys Lys Phe Asp Thr Ile Met Val Val Asn Pro Lys
            100                 105                 110

Pro Asp Gly Asn Gly Cys Val Val Thr Arg Ser Ile Glu Tyr Glu Lys
        115                 120                 125

Thr Asn Glu Asn Ser Pro Thr Pro Phe Asp Tyr Leu Gln Phe Gly His
130                 135                 140

Gln Ala Ile Glu Asp Met Asn Lys Tyr Leu Arg Asp Ser Glu Ser Asn
145                 150                 155                 160

<210> SEQ ID NO 15
<211> LENGTH: 132
<212> TYPE: PRT
<213> ORGANISM: Papaver somniferum

<400> SEQUENCE: 15

Met Tyr Lys His Gly Glu Asp Val Lys Lys Ala Val Pro His Leu Cys
1               5                   10                  15

Val Asp Val Lys Ile Ile Ser Gly Asp Pro Thr Ser Ser Gly Cys Ile
            20                  25                  30

Lys Glu Trp Asn Val Asn Ile Asp Gly Lys Thr Ile Arg Ser Val Glu
        35                  40                  45

Glu Thr Thr His Asp Asp Glu Thr Lys Thr Leu Arg His Arg Val Phe
    50                  55                  60

Glu Gly Asp Val Met Lys Asp Phe Lys Lys Phe Asp Thr Ile Met Val
65                  70                  75                  80
```

-continued

Val Asn Pro Lys Pro Asp Gly Asn Gly Cys Val Val Thr Arg Ser Ile
            85                  90                  95

Glu Tyr Glu Lys Thr Asn Glu Asn Ser Pro Thr Pro Phe Asp Tyr Leu
        100                 105                 110

Gln Phe Gly His Gln Ala Ile Glu Asp Met Asn Lys Tyr Leu Arg Asp
        115                 120                 125

Ser Glu Ser Asn
        130

<210> SEQ ID NO 16
<211> LENGTH: 127
<212> TYPE: PRT
<213> ORGANISM: Papaver somniferum

<400> SEQUENCE: 16

Met Asp Ser Ile Asn Ser Ser Ile Tyr Phe Cys Ala Tyr Phe Arg Glu
1               5                   10                  15

Leu Ile Ile Lys Leu Leu Met Ala Pro Pro Gly Val Ser Gly Leu Val
            20                  25                  30

Gly Lys Leu Ser Thr Glu Leu Asp Val Asn Cys Asp Ala Glu Lys Tyr
        35                  40                  45

Tyr Asn Met Tyr Lys His Gly Glu Asp Val Gln Lys Ala Val Pro His
50                  55                  60

Leu Cys Val Asp Val Lys Val Ile Ser Gly Asp Pro Thr Arg Ser Gly
65                  70                  75                  80

Cys Ile Lys Glu Trp Asn Val Asn Ile Gly Asn Val Gln Thr His Tyr
            85                  90                  95

Cys Asn Ser Ser Ile Tyr Phe Thr Cys Phe Trp Ser Val His His
        100                 105                 110

Tyr Ile Tyr Ile Leu Thr Ile Ala Val Ile Tyr Phe Thr Leu Asn
        115                 120                 125

<210> SEQ ID NO 17
<211> LENGTH: 108
<212> TYPE: PRT
<213> ORGANISM: Papaver somniferum

<400> SEQUENCE: 17

Met Ser Ile Ala Met Leu Lys Asn Ile Ile Thr Cys Ile Ser Thr Glu
1               5                   10                  15

Lys Met Cys Lys Arg Gln Phe Leu Ile Phe Ala Leu Thr Ser Lys Leu
            20                  25                  30

Ser Val Glu Thr Gln Pro Val Gln Val Val Ser Arg Asn Gly Met Leu
        35                  40                  45

Thr Ser Val Met Tyr Lys His Thr Ile Ala Ile His Gln Phe Thr Ser
    50                  55                  60

His Ala Phe Gly Ser Pro Cys Ile Ile Ile Tyr Ile Tyr Ser Gln Leu
65                  70                  75                  80

Gln Ser Tyr Ile Ser Arg Leu Ile Arg Phe Asp Leu Gly Phe Thr Thr
            85                  90                  95

Leu Arg Tyr Asn Val Cys Leu His Ala Cys Arg Trp
        100                 105

<210> SEQ ID NO 18
<211> LENGTH: 477
<212> TYPE: DNA
<213> ORGANISM: Papaver somniferum

<400> SEQUENCE: 18

```
atggcgcatc atggtgtttc aggtctagtt gggaaaattg taactgaatt ggaggtgaat    60
tgtaatgccg acgaattta taagattttg aagcgcgatg aagatgttcc acgggcagtt   120
tctgatcttt tccctcccgt caaaattgcc aaaggagatg gacttgtttc tggttgtatc   180
aaggaatggg actgtgttct tgatggtaag gcgatgagcg gcaaggagga acaacacac    240
aacgatgaaa cgaggacttt gcgtcaccgt gaattggaag agacttgat gaaggattac    300
aagaagtttg attccataat tgaagttaat ccaaaaccaa atggacatgg aagcattgtg   360
acgtggtcaa ttgagtatga aaaatgaac gaagattctc cggctccctt gcttatcta    420
gcttccttcc atcagaacgt tgtggaagtt gattctcacc tctgcctttc tgaataa     477
```

<210> SEQ ID NO 19
<211> LENGTH: 483
<212> TYPE: DNA
<213> ORGANISM: Papaver somniferum

<400> SEQUENCE: 19

```
atggctcctc tcggtgtttc aggtttagtc gggaaacttt caactgaatt ggaggtcgat    60
tgcgatgctg aaaaatatta taacatgtat aagcacggag aagatgtaaa aaaggcagtt   120
cctcatcttt gcgttgacgt caaaattatc agtggagatc cgaccagttc aggttgtatc   180
aaggaatgga atgttaacat tgatggtaag acgattcgct cggtagagga aaccacacac   240
gatgatgaaa cgaaaacgtt acgtcaccgt gtatttgaag agacgtgat gaaggatttc    300
aagaagtttg atacgataat ggtagtcaat ccaaagccgg atggaaatgg atgtgttgtg   360
acaaggtcaa ttgagtatga aaaaccaac gagaattctc caactcccctt tgattatcta   420
caattcggcc atcaggccat tgaggacatg aacaagtact acgcgattc tgaaagtaac    480
tga                                                                 483
```

<210> SEQ ID NO 20
<211> LENGTH: 474
<212> TYPE: DNA
<213> ORGANISM: Papaver somniferum

<400> SEQUENCE: 20

```
atggcgcatc atggtgtttc aggtctagtt gggaaacttg taactgaatt ggaggtccat    60
tgcaatgctg acgcatacta taaaatcttt aagcaccaag aagatgtacc aaaggcaatg   120
cctcatcttt acactggcgg gaaagttatc agtggagatg caacccgttc tggttgtatc   180
aaggaatgga actacattct tgagggtaag gcgctgatcg cagtggagga acaacacat    240
gacgatgaaa caaggacctt aacacaccgc ataactggag gagacttgac aaaggattac    300
aaaaagttcg ttaagatcgt tgaagttaat ccaaagccta atggacatgg aagcattgtg   360
actgtatccc ttgtgtatga aaaatgaac gagggttctc caactcccctt taattatcta   420
caatttgtcc atcagaccat tgtaggcttg aattctcaca tctgcgcttc ttag         474
```

<210> SEQ ID NO 21
<211> LENGTH: 480
<212> TYPE: DNA
<213> ORGANISM: Papaver somniferum

<400> SEQUENCE: 21

```
atggctcatc cccatcctat ttcaggtcta gttgggaaac tagtgactga attggaggtt    60
aactgcgacg ctgacaagta ttacaaaatt tttaagcacc atgaagatgt tccaaaagca   120
```

```
gtacctcata tgtacactag cgtcaaagtt gtcgagggac atggaattac ttctggttgt      180
gtcaaggaat ggggttatct tcttgaggga aagaactga ttgtcaagga aacaacaaca      240
tacactgatg aaacaaggac gatacatcat agcgcagtag gaggacacat gacgaagatt      300
tacaagaagt ttgatgcaac gcttgtagtc aatccaaagc ctagtggcca tggaagcacg      360
gtgagttgga ctattgatta tgagaaaatt aacgaggatt ctcccgttcc tattccatat      420
ctagctttct tccataagct catcgaggac ttgaactctc acctctgcgc ttctgattaa      480

<210> SEQ ID NO 22
<211> LENGTH: 480
<212> TYPE: DNA
<213> ORGANISM: Papaver somniferum

<400> SEQUENCE: 22 atgcccatc aacatacaat ttcaggtctt gtgggaaaac ttattactga atcggaggtt       60
aactgcaatg ccgacaagta ttaccaaata tttaagcacc atgaagacct tccaagcgca      120
atccctcata tttacactag cgtcaaagct gtcgagggac atggaactac ttctggatgt      180
gtcaaggagt ggtgctatat tcttgagggg aaaccactta cagttaagga gaaaacaacg      240
tacaatgatg aaacaagaac gataaatcat aatggaatag aaggaggcat gatgactgat      300
tacaagaagt tcgttgcaac acttgtagtt aagccaaaag ctaatgggca ggaagcatc       360 gtgacatgga tagtggatta tgagaagatt aatgaggatt ctccagttcc tttcgactat      420
ctagctttct tccaacaaaa catcgaagac ttgaactctc acctctgtgc ttctgattaa      480

<210> SEQ ID NO 23
<211> LENGTH: 495
<212> TYPE: DNA
<213> ORGANISM: Papaver somniferum

<400> SEQUENCE: 23
atgaggtacg agtttataaa cgagtttgat gcacatgcat cagcagacga tgtttgggga       60
ggaatctatg gctccattga ttaccctaaa ctagtggttc aattacttcc aactgtcctc      120 gaaagaagg aaatcttgga aggcgatggt cataatgttg gtactgttct gcatgttgtg       180
taccttccag gatttgttcc gcggacgtac aacgagaaga ttgtaacgat ggatcacaaa      240
aaacgttaca aggaagtaca aatggttgaa ggaggatact tggatatggg atttacatat      300
gtcatggtaa ttcatgaagt actagcaaaa gaatgtaatt cttgtatcat tagatcaatt      360
gttaagtgtg aagtcaagga tgaatttgct gcaaatgttt ctaatattcg caacaccttt      420
gatggatatg tcgccttagc ccgagccgtt ccggaatata ttgcgaagca gcacgcaaca      480
tcagcagcta attaa                                                       495

<210> SEQ ID NO 24
<211> LENGTH: 480
<212> TYPE: DNA
<213> ORGANISM: Papaver somniferum

<400> SEQUENCE: 24
atggctcatg ctcatggtat ttcaggtcta gttgggaaac ttattactga atcggaggtt       60
aactgcaacg ctgacaagtt ttaccaaatg tttaagcacg atgaaaatat tacaaatata      120
attcctcata tctatactag tttcaaggtt gtcgagggag atggactat ttctggttgt       180 accaaggaat ggggctatct ttctgagggc aaagcaagga ttgttaagga gcaaacgacc      240
```

```
tttgatgacg aaacaaggac gatacatcat tgcgcaaaag caggagacat gatgaatgat      300
tacaagaagt tcgttctaac acttgtagtt aatccaaagg ctcatggaca aggaagcaca      360
gtcaagtgga ttatagatta tgagaagata aatgaggatt ctccagttcc ttttgcttat     420
ctatctctgt gcattaagat cactgaaggt ctgaactctc acatctacgc ttccgaatag     480

<210> SEQ ID NO 25
<211> LENGTH: 474
<212> TYPE: DNA
<213> ORGANISM: Papaver somniferum

<400> SEQUENCE: 25
atggctcaac atcataccat ttcaggtctt attgggaagc ttgtgaccga atcagaagtt      60
aattgcgatg ctgaaaaata ttacaaaata attaagcacc acgaagatgt acctaatgca     120
accccttatg tttccgatgt caaagttact gaaggacatg gtaccacttc gggttgtgtc     180
aagcaatgga actttgttgt tgcgggtcga acgaatatg tccttgaaaa acaacatac      240 aatgatgaaa caaggacaat atgtcacagt gactttgaag agacctgat gaagaaatac    300 aagaagtttg atgcaatcct tgtagttaag ccaaaggata tggacatgg tagtaatgtg    360 agatggacta ttgaatatga agaataac gaggattctc cggttccaat tgattatcta     420
ggtttcttcc aatcgttaat cgatgacttg aactctcatc tttgctcctc ttaa         474

<210> SEQ ID NO 26
<211> LENGTH: 543
<212> TYPE: DNA
<213> ORGANISM: Papaver somniferum

<400> SEQUENCE: 26
atggattcta ttaattcttc catatacttc tgtgcatatt ttagagaact aatcatcaaa      60
ttgttgatgg ctcctcttgg tgtttcaggt ttagtcggga actttcaac tgaattggag     120 gtcgattgcg atgctgaaaa atattataac atgtataagc acggagaaga tgtgcaaaag    180
gcagttcctc atctttgcgt tgacgtcaaa gttatcagtg gagatccgac cagttcaggt    240
tgtatcaagg aatggaatgt taacattgat ggtaagacga ttcgctcagt agaggaaaca    300
acacacaatg atgaaacgaa aacgttgcgt caccgtgtat ttgaaggaga catgatgaag    360
gatttcaaga gttttgatac gataatggta gtcaatccaa agccggatgg aaatggatgt    420
gttgtgacac ggtcaattga gtatgagaaa accaacgaga attctccgac tccctttgat    480
tatctacaat tcggccatca ggccattgaa gacatgaaca atacttacg cgattctgaa    540 taa                                                                  543

<210> SEQ ID NO 27
<211> LENGTH: 483
<212> TYPE: DNA
<213> ORGANISM: Papaver somniferum

<400> SEQUENCE: 27
atggctcctc tcggtgtttc aggtttagtc gggaaacttt caactgaatt ggaggtcgat      60
tgcgatgctg aaaaatatta taacatgtat aagcacggag aagatgtaaa aaggcagtt    120 cctcatcttt gcgttgacgt caaaattatc agtggagatc gaccagttc aggttgtatc     180 aaggaatgga atgttaacat tgatggtaag acgattcgct cggtagagga aaccacacac    240
gatgatgaaa cgaaaacgtt acgtcaccgt gtatttgaag agacgtgat gaggatttc    300 aagaagtttg atacgataat ggtagtcaat ccaaagccgg atggaaatgg atgtgttgtg    360
```

```
acaaggtcaa ttgagtatga gaaaaccaac gagaattctc caactcccctt tgattatcta    420 caattcggcc atcaggccat tgaggacatg aacaagtact tacgcgattc tgaaagtaac    480
tga                                                                  483
```

<210> SEQ ID NO 28
<211> LENGTH: 399
<212> TYPE: DNA
<213> ORGANISM: Papaver somniferum

<400> SEQUENCE: 28

```
atgtataagc acggagaaga tgtaaaaaag gcagttcctc atctttgcgt tgacgtcaaa     60
attatcagtg gagatccgac cagttcaggt tgtatcaagg aatggaatgt taacattgat    120
ggtaagacga ttcgctcggt agaggaaacc acacacgatg atgaaacgaa acgttacgt    180 caccgtgtat ttgaaggaga cgtgatgaag gatttcaaga agtttgatac gataatggta    240
gtcaatccaa agccggatgg aaatggatgt gttgtgacaa ggtcaattga gtatgaaaaa    300
accaacgaga attctccaac tccctttgat tatctacaat tcggccatca ggccattgag    360
gacatgaaca agtacttacg cgattctgaa agtaactga                           399
```

<210> SEQ ID NO 29
<211> LENGTH: 384
<212> TYPE: DNA
<213> ORGANISM: Papaver somniferum

<400> SEQUENCE: 29

```
atggattcta ttaattcttc catatacttc tgtgcatatt ttagagaact aatcattaaa     60
ttgttgatgg ctcctcctgg tgtttcaggt ctagtcggga aactttcaac tgaattggat    120
gtcaattgcg atgctgaaaa atattataac atgtataagc acggagaaga tgtgcaaaag    180
gcagttcctc atctttgcgt tgacgtcaaa gttatcagtg gagacccaac ccgttcaggt    240
tgtatcaagg aatggaatgt taacatcggt aatgtacaaa cacactattg caattcatca    300
atttacttca catgcttttg gttctccgtg catcattata tatatatact cacaattgca    360
gtcatatatt tcacgcttaa ttag                                           384
```

<210> SEQ ID NO 30
<211> LENGTH: 327
<212> TYPE: DNA
<213> ORGANISM: Papaver somniferum

<400> SEQUENCE: 30

```
atgtcaattg cgatgctgaa aaatattata acatgtataa gcacggagaa gatgtgcaaa     60
aggcagttcc tcatctttgc gttgacgtca aagttatcag tggagaccca acccgttcag    120
gttgtatcaa ggaatggaat gttaacatcg gtaatgtaca aacacactat tgcaattcat    180
caatttactt cacatgcttt tggttctccg tgcatcatta tatatatata ctcacaattg    240
cagtcatata tttcacgctt aattagattt gatttgggtt tcacaacttt gcggtataat    300
gtttgtcttc acgcatgcag atggtaa                                        327
```

<210> SEQ ID NO 31
<211> LENGTH: 180
<212> TYPE: PRT
<213> ORGANISM: Papaver somniferum

```
<400> SEQUENCE: 31

Met Asp Ser Ile Asn Ser Ile Tyr Phe Cys Ala Tyr Phe Arg Glu
1               5                   10                  15

Leu Ile Ile Lys Leu Leu Met Ala Pro Leu Gly Val Ser Gly Leu Val
            20                  25                  30

Gly Lys Leu Ser Thr Glu Leu Glu Val Asp Cys Asp Ala Glu Lys Tyr
        35                  40                  45

Tyr Asn Met Tyr Lys His Gly Glu Asp Val Lys Ala Val Pro His
    50                  55                  60

Leu Cys Val Asp Val Lys Ile Ile Ser Gly Asp Pro Thr Ser Ser Gly
65                  70                  75                  80

Cys Ile Lys Glu Trp Asn Val Asn Ile Asp Gly Lys Thr Ile Arg Ser
                85                  90                  95

Val Glu Glu Thr Thr His Asp Asp Glu Thr Lys Thr Leu Arg His Arg
            100                 105                 110

Val Phe Glu Gly Asp Val Met Lys Asp Phe Lys Phe Asp Thr Ile
            115                 120                 125

Met Val Val Asn Pro Lys Pro Asp Gly Asn Gly Cys Val Val Thr Arg
130                 135                 140

Ser Ile Glu Tyr Glu Lys Thr Asn Glu Asn Ser Pro Thr Pro Phe Asp
145                 150                 155                 160

Tyr Leu Gln Phe Gly His Gln Ala Ile Glu Asp Met Asn Lys Tyr Leu
                165                 170                 175

Arg Asp Ser Glu
            180

<210> SEQ ID NO 32
<211> LENGTH: 132
<212> TYPE: PRT
<213> ORGANISM: Papaver somniferum

<400> SEQUENCE: 32

Met Tyr Lys His Gly Glu Asp Val Lys Ala Val Pro His Leu Cys
1               5                   10                  15

Val Asp Val Lys Ile Ile Ser Gly Asp Pro Thr Ser Ser Gly Cys Ile
            20                  25                  30

Lys Glu Trp Asn Val Asn Ile Asp Gly Lys Thr Ile Arg Ser Val Glu
        35                  40                  45

Glu Thr Thr His Asp Asp Glu Thr Lys Thr Leu Arg His Arg Val Phe
    50                  55                  60

Glu Gly Asp Val Met Lys Asp Phe Lys Phe Asp Thr Ile Met Val
65                  70                  75                  80

Val Asn Pro Lys Pro Asp Gly Asn Gly Cys Val Val Thr Arg Ser Ile
                85                  90                  95

Glu Tyr Glu Lys Thr Asn Glu Asn Ser Pro Thr Pro Phe Asp Tyr Leu
            100                 105                 110

Gln Phe Gly His Gln Ala Ile Glu Asp Met Asn Lys Tyr Leu Arg Asp
        115                 120                 125

Ser Glu Ser Asn
    130

<210> SEQ ID NO 33
<211> LENGTH: 166
<212> TYPE: PRT
<213> ORGANISM: Papaver somniferum
```

<400> SEQUENCE: 33

Met Ala His His Gly Val Ser Gly Leu Val Gly Lys Ile Val Thr Glu
1               5                   10                  15

Leu Glu Val Asn Cys Asn Ala Asp Glu Phe Tyr Lys Ile Leu Lys Arg
                20                  25                  30

Asp Glu Asp Val Pro Arg Ala Val Ser Asp Leu Phe Pro Pro Val Lys
            35                  40                  45

Ile Ala Lys Gly Asp Gly Leu Val Ser Gly Cys Ile Lys Glu Trp Asp
    50                  55                  60

Cys Val Leu Asp Gly Lys Ala Met Ser Gly Lys Glu Glu Thr Thr His
65                  70                  75                  80

Asn Asp Glu Thr Arg Thr Leu Arg His Arg Glu Leu Glu Gly Asp Leu
                85                  90                  95

Met Lys Asp Tyr Lys Lys Phe Asp Ser Ile Ile Glu Val Asn Pro Lys
            100                 105                 110

Pro Asn Gly His Gly Ser Ile Val Thr Trp Ser Ile Glu Tyr Glu Lys
        115                 120                 125

Met Asn Glu Asp Ser Pro Ala Pro Phe Ala Tyr Leu Ala Ser Phe His
130                 135                 140

Gln Asn Val Val Glu Val Asp Ser His Leu Cys Leu Ser Glu Asp Tyr
145                 150                 155                 160

Lys Asp Asp Asp Lys
                165

<210> SEQ ID NO 34
<211> LENGTH: 167
<212> TYPE: PRT
<213> ORGANISM: Papaver somniferum

<400> SEQUENCE: 34

Met Asp Tyr Lys Asp Asp Asp Lys Met Ala His His Gly Val Ser
1               5                   10                  15

Gly Leu Val Gly Lys Ile Val Thr Glu Leu Glu Val Asn Cys Asn Ala
                20                  25                  30

Asp Glu Phe Tyr Lys Ile Leu Lys Arg Asp Glu Asp Val Pro Arg Ala
            35                  40                  45

Val Ser Asp Leu Phe Pro Pro Val Lys Ile Ala Lys Gly Asp Gly Leu
    50                  55                  60

Val Ser Gly Cys Ile Lys Glu Trp Asp Cys Val Leu Asp Gly Lys Ala
65                  70                  75                  80

Met Ser Gly Lys Glu Glu Thr Thr His Asn Asp Glu Thr Arg Thr Leu
                85                  90                  95

Arg His Arg Glu Leu Glu Gly Asp Leu Met Lys Asp Tyr Lys Lys Phe
            100                 105                 110

Asp Ser Ile Ile Glu Val Asn Pro Lys Pro Asn Gly His Gly Ser Ile
        115                 120                 125

Val Thr Trp Ser Ile Glu Tyr Glu Lys Met Asn Glu Asp Ser Pro Ala
    130                 135                 140

Pro Phe Ala Tyr Leu Ala Ser Phe His Gln Asn Val Val Glu Val Asp
145                 150                 155                 160

Ser His Leu Cys Leu Ser Glu
                165

<210> SEQ ID NO 35

```
<211> LENGTH: 384
<212> TYPE: PRT
<213> ORGANISM: Papaver somniferum

<400> SEQUENCE: 35

Met Ile Ile Glu Thr Leu Asp Ile Leu Gly Pro Asn Gln Asn Gly Asn
1               5                   10                  15

Ser Gly Thr His Thr Gln Lys Pro Ile Lys Thr Arg Asn Trp Leu Leu
            20                  25                  30

Ile Ile Ile Asn Cys Ala Leu Val Phe Cys Gly Val Ile Gly Gly Pro
        35                  40                  45

Leu Leu Met Arg Leu Tyr Tyr Leu His Gly Ser Arg Lys Trp Leu
    50                  55                  60

Ser Ser Phe Leu Gln Thr Ala Gly Phe Pro Val Leu Ile Phe Pro Leu
65                  70                  75                  80

Ile Phe Leu Tyr Ile Lys Pro Lys Leu Ser Thr Gln Asn Asn Asp Gln
                85                  90                  95

Ser Ser Ser Phe Phe Met Glu Pro Lys Leu Phe Leu Trp Ser Ala Ile
            100                 105                 110

Val Gly Ile Val Phe Gly Val Ser Asn Phe Met Tyr Ala Leu Gly Leu
        115                 120                 125

Ser Tyr Leu Pro Val Ser Thr Ser Thr Ile Leu Phe Ala Thr Gln Leu
    130                 135                 140

Cys Phe Thr Ala Ile Phe Ala Trp Leu Ile Val Lys Gln Lys Phe Thr
145                 150                 155                 160

Ala Phe Ile Ile Asn Ala Val Ile Val Met Thr Leu Gly Ser Ile Leu
                165                 170                 175

Leu Gly Ile Asn Thr Asn Gly Asp Arg Pro Ile Gly Val Ser Lys Thr
            180                 185                 190

Gln Tyr Leu Ile Gly Phe Leu Met Thr Leu Ala Ala Ala Leu Thr
        195                 200                 205

Gly Leu Gly Thr Pro Phe Val Glu Leu Ser Phe Ile Lys Ala Thr Arg
    210                 215                 220

Asn Ile Thr Tyr Pro Thr Leu Leu Gln Phe Gln Val Ile Leu Cys Leu
225                 230                 235                 240

Phe Gly Thr Cys Leu Asn Val Ile Gly Met Leu Ile Asn Lys Asp Phe
                245                 250                 255

Gln Ala Ile Pro Arg Glu Ala Asp Met Phe Glu Leu Gly Lys Ser Lys
            260                 265                 270

Tyr Tyr Met Ile Ile Cys Leu Thr Ala Leu Thr Trp Gln Leu Ser Gly
        275                 280                 285

Ile Gly Leu Val Gly Leu Ile Leu Tyr Thr Asn Ala Leu Phe Asn Gly
    290                 295                 300

Ile Tyr Val Ser Val Leu Val Pro Phe Thr Glu Val Ala Ala Val Ile
305                 310                 315                 320

Phe Phe His Glu Lys Phe Thr Gly Leu Lys Gly Met Ala Leu Ala Leu
                325                 330                 335

Cys Leu Trp Gly Phe Ser Ser Tyr Phe Gly Glu Tyr Lys Met Met
            340                 345                 350

Asn Lys Val Gly Asp Asn Glu Thr His Glu Lys Ile Glu Glu Ala Glu
        355                 360                 365

Ser Glu Pro Lys Arg Leu Glu Asp Gln Gln Ala Pro Tyr Ser Thr Val
    370                 375                 380
```

<210> SEQ ID NO 36
<211> LENGTH: 1155
<212> TYPE: DNA
<213> ORGANISM: Papaver somniferum

<400> SEQUENCE: 36

```
atgatcatcg aaacactaga tatcctggga ccaaatcaga atggcaattc aggaacccat      60
actcaaaaac caatcaaaac cagaaactgg ctgctgatca ttattaactg cgccttagtt     120
ttttgtggtg ttataggtgg tcctctctta atgagactgt actatcttca tggtggtagt     180
cgtaaatggc ttagtagttt tctgcaaact gctggtttcc cagttctcat atttcctctc     240
attttctctc acattaaacc gaaattgtca cacaaaaaca acgatcaaag ttcttccttt     300
tttatggaac caaagttgtt tctttggagt gccatagttg gaatcgtgtt tggtgtttct     360
aatttcatgt acgcattggg tttatcttat cttccagtat caacttcgac aattctcttt     420
gcaactcaac tgtgtttcac agcaattttt gcatggttaa ttgtgaaaca aaaatttaca     480
gcatttatta taaatgcagt gattgtaatg acactaggat cgatcttatt gggtattaat     540
accaatggtg atagaccaat tggggtatca aaaactcagt acttaatagg gtttcttatg     600
acgttagctc ctgctgctct aactggcctc gggacgcctt tgttgagct ttcttcatt     660
aaagccacca gaaatattac ttatccaact ttgttacagt ttcaagtcat tctttgtctg     720
tttggaacct gcctcaacgt cattgggatg ctaataaata aggattttca ggctataccc     780
agagaagcag acatgttcga gcttgggaaa agcaagtatt atatgataat atgcttgact     840
gcattgacat ggcaattatc aggaattgga ctcgtaggcc taattttgta cacaaatgct     900
cttttcaacg gtatatacgt atccgttctt gttccgttca cagaagttgc agcggtcata     960
tttttccatg agaagtttac gggattaaag ggaatggcat tggcattatg tctttgggt    1020
ttctcttcct atttctatgg agaatacaag atgatgaata agtgggtga taatgaaaca    1080
catgagaaaa tcgaggaagc cgaaagcgag cccaaaagat tagaggatca acaagcacca    1140
tacagtactg tatga                                                    1155
```

<210> SEQ ID NO 37
<211> LENGTH: 284
<212> TYPE: PRT
<213> ORGANISM: Papaver somniferum

<400> SEQUENCE: 37

```
Met Ile Ile Glu Thr Leu Asp Ile Leu Gly Pro Asn Gln Asn Gly Asn
1               5                   10                  15

Ser Gly Thr His Thr Gln Lys Pro Ile Lys Thr Arg Asn Trp Leu Leu
            20                  25                  30

Ile Ile Ile Asn Cys Ala Leu Val Phe Cys Gly Val Ile Gly Gly Pro
        35                  40                  45

Leu Leu Met Arg Leu Tyr Tyr Leu His Gly Gly Ser Arg Lys Trp Leu
    50                  55                  60

Ser Ser Phe Leu Gln Thr Ala Gly Phe Pro Val Leu Ile Phe Pro Leu
65                  70                  75                  80

Ile Phe Leu Tyr Ile Lys Pro Lys Leu Ser Thr Gln Asn Asn Asp Gln
                85                  90                  95

Ser Ser Ser Phe Phe Met Glu Pro Lys Leu Phe Leu Trp Ser Ala Ile
            100                 105                 110

Val Gly Ile Val Phe Gly Val Ser Asn Phe Met Tyr Ala Leu Gly Leu
        115                 120                 125
```

```
Ser Tyr Leu Pro Val Ser Thr Ser Thr Ile Leu Phe Ala Thr Gln Leu
    130                 135                 140

Cys Phe Thr Ala Ile Phe Ala Trp Leu Ile Val Lys Gln Lys Phe Thr
145                 150                 155                 160

Ala Phe Ile Ile Asn Ala Val Ile Val Met Thr Leu Gly Ser Ile Leu
                165                 170                 175

Leu Gly Ile Asn Thr Asn Gly Asp Arg Pro Ile Gly Val Ser Lys Thr
            180                 185                 190

Gln Tyr Leu Ile Gly Phe Leu Met Thr Leu Ala Ala Ala Ala Leu Thr
        195                 200                 205

Gly Leu Gly Thr Pro Phe Val Glu Leu Ser Phe Ile Lys Ala Thr Arg
    210                 215                 220

Asn Ile Thr Tyr Pro Thr Leu Leu Gln Phe Gln Val Ile Leu Cys Leu
225                 230                 235                 240

Phe Gly Thr Cys Leu Asn Val Ile Gly Met Leu Ile Asn Lys Asp Phe
                245                 250                 255

Gln Val Arg Asn Cys Tyr Arg Arg Leu Thr Thr Phe Leu Ile Phe Leu
            260                 265                 270

Ile Leu Glu Gln Lys Leu Ile Ser Glu Glu Asp Leu
        275                 280
```

<210> SEQ ID NO 38
<211> LENGTH: 825
<212> TYPE: DNA
<213> ORGANISM: Papaver somniferum

<400> SEQUENCE: 38

```
atgatcatcg aaacactaga tatcctggga ccaaatcaga atggcaattc aggaacccat      60
actcaaaaac caatcaaaac cagaaactgg ctgctgatca ttattaactg cgccttagtt     120
ttttgtggtg ttataggtgg tcctctctta atgagactgt actatcttca tggtggtagt     180
cgtaaatggc ttagtagttt tctgcaaact gctggtttcc cagttctcat atttcctctc     240
attttctctc acattaaacc gaaattgtca acacaaaaca acgatcaaag ttcttccttt     300
tttatggaac caaagttgtt tctttggagt gccatagttg aatcgtgtt  tggtgtttct     360
aatttcatgt acgcattggg tttatcttat cttccagtat caacttcgac aattctcttt     420
gcaactcaac tgtgtttcac agcaattttt gcatggttaa ttgtgaaaca aaaatttaca     480
gcatttatta taaatgcagt gattgtaatg acactaggat cgatcttatt gggtattaat     540
accaatggtg atagaccaat tggggtatca aaaactcagt acttaatagg gtttcttatg     600
acgttagctg ctgctgctct aactggcctc gggacgcctt ttgttgagct ttctttcatt     660
aaagccacca gaaatattac ttatccaact tgttacagt  ttcaagtcat tctttgtctg     720
tttggaacct gcctcaacgt cattgggatg ctaataaata aggattttca ggtacgtaac     780
tgttatagga ggcttacaac cttttttgatt ttccttattc tctga                    825
```

<210> SEQ ID NO 39
<211> LENGTH: 855
<212> TYPE: DNA
<213> ORGANISM: Papaver somniferum

<400> SEQUENCE: 39

```
atgatcatcg aaactttgga tatcttgggt ccaaaccaaa acgtaactc  aggtactcat       60
acacaaaaac caattaaaac aagaaactgg ttgttgatca ttattaactg tgctttagtt     120
ttctgtggtg ttattggtgg tccattgttg atgagattgt actacttgca tggtggttct     180
```

```
agaaagtggt tatcttcatt tttgcaaact gcaggttttc cagttttgat cttcccattg    240
attttcttgt acattaaacc aaaattgtca acacaaaaca acgatcaatc ttcttctttc    300
tttatggaac caaagttgtt tttatggtct gctattgttg gtatcgtttt cggtgtttca    360
aacttcatgt acgcattggg tttgtcttac ttgccagttt caacttctac aatcttgttc    420
gctactcaat tgtgtttcac agctatcttc gcatggttga tcgttaagca aaagtttact    480
gcttttatta ttaatgcagt tattgttatg actttgggtt caatcttgtt gggtattaat    540
acaaacggtg acagaccaat cggtgtttct aagactcaat atttgatcgg tttcttgatg    600
acattggctg cagctgcatt aactggtttg ggtacaccat tgttgaatt gtcttttatt    660 aaggctacta gaaacatcac ttacccaaca tgttgcaat tccaagttat tttgtgtttg    720
ttcggtacat gtttgaacgt tatcggcatg ttgattaata aggatttcca agttagaaac    780
tgttacagaa gattgacaac attcttgatc ttcttgatct tggaacaaaa attaatttct    840
gaagaagatt tgtaa                                                     855

<210> SEQ ID NO 40
<211> LENGTH: 10
<212> TYPE: PRT
<213> ORGANISM: Artificial Sequence
<220> FEATURE:
<223> OTHER INFORMATION: Myc-Tag

<400> SEQUENCE: 40

Glu Gln Lys Leu Ile Ser Glu Glu Asp Leu
1               5                   10

<210> SEQ ID NO 41
<211> LENGTH: 356
<212> TYPE: PRT
<213> ORGANISM: Arabidopsis thaliana

<400> SEQUENCE: 41

Met Lys Asn Gly Leu Ile Ile Asn Cys Ile Ile Leu Thr Ile Gly
1               5                   10                  15

Thr Cys Gly Gly Pro Leu Leu Thr Arg Leu Tyr Phe Thr Asn Gly Gly
                20                  25                  30

Lys Arg Ile Trp Phe Met Ser Phe Leu Ser Thr Ala Gly Phe Pro Ile
            35                  40                  45

Ile Leu Ile Pro Leu Leu Val Ser Phe Leu Ser Arg Arg Arg Ser Asn
        50                  55                  60

Arg Asn Pro Asn Asn Ala Glu Asn Lys Arg Lys Thr Lys Leu Phe Leu
65                  70                  75                  80

Met Glu Thr Pro Leu Phe Ile Ala Ser Ile Val Ile Gly Leu Leu Thr
                85                  90                  95

Gly Leu Asp Asn Tyr Leu Tyr Ser Tyr Gly Leu Ala Tyr Leu Pro Val
            100                 105                 110

Ser Thr Ser Ser Leu Ile Ile Gly Thr Gln Leu Ala Phe Asn Ala Leu
        115                 120                 125

Phe Ala Phe Leu Leu Val Lys Gln Lys Phe Thr Pro Phe Ser Ile Asn
    130                 135                 140

Ala Val Val Leu Leu Thr Val Gly Ile Gly Ile Leu Ala Leu His Ser
145                 150                 155                 160

Asp Gly Asp Lys Pro Ala Lys Glu Ser Lys Lys Glu Tyr Val Val Gly
                165                 170                 175
```

```
Phe Leu Met Thr Val Ala Ala Leu Leu Tyr Ala Phe Ile Leu Pro
            180                 185                 190

Leu Val Glu Leu Thr Tyr Lys Lys Ala Arg Gln Glu Ile Thr Phe Pro
        195                 200                 205

Leu Val Leu Glu Ile Gln Met Val Met Cys Leu Ala Ala Thr Phe Phe
    210                 215                 220

Cys Val Ile Gly Met Phe Ile Val Gly Asp Phe Lys Val Ile Ala Arg
225                 230                 235                 240

Glu Ala Arg Glu Phe Lys Ile Gly Gly Ser Val Phe Tyr Tyr Ala Leu
                245                 250                 255

Ile Val Ile Thr Gly Ile Ile Trp Gln Gly Phe Phe Leu Gly Ala Ile
            260                 265                 270

Gly Ile Val Phe Cys Ala Ser Ser Leu Ala Ser Gly Val Leu Ile Ser
        275                 280                 285

Val Leu Leu Pro Val Thr Glu Val Phe Ala Val Val Cys Phe Arg Glu
    290                 295                 300

Lys Phe Gln Ala Glu Lys Gly Val Ser Leu Leu Leu Ser Leu Trp Gly
305                 310                 315                 320

Phe Val Ser Tyr Phe Tyr Gly Glu Phe Lys Ser Gly Lys Lys Val Val
                325                 330                 335

Asp Lys Pro Gln Pro Pro Glu Thr Glu Leu Pro Ile Leu Pro Val Ser
            340                 345                 350

Asp Tyr Val Ala
        355

<210> SEQ ID NO 42
<211> LENGTH: 1071
<212> TYPE: DNA
<213> ORGANISM: Arabidopsis thaliana

<400> SEQUENCE: 42
atgaagaacg tttgattat tattaactgc attattttga ctatcggtac atgtggtggt      60
cctttattga caagattata ctttaccaat ggtggtaaaa gaatttggtt catgtcattt     120
ttgtcaactg ctggtttccc aatcatcttg atcccattgt ggtttcatt tttgtcaaga     180
agaagatcta acagaaaccc aaacaatgca gaaaacaaga gaaagactaa attattttg     240
atggaaacac cattattcat cgcttcaatc gttatcggtt tgttgacagg tttagataac     300
tacttgtact cttatggttt agcatacttg ccagtttcaa cttcttcatt gatcatcggt     360
acacaattag cttcaacgc attgttcgca ttttgttgg ttaagcaaaa gttcactcca     420
ttctctatca cgctgttgt tttgttgaca gttggtatcg gtattttagc attgcattct     480
gatggtgata agccagctaa ggaatctaaa aaagaatatg ttgttggttt cttgatgact     540
gttgttgctg cattgttgta cgcattcatc ttgccattgg ttgaattgac ttacaagaag     600
gctagacaag aaatcacatt cccattagtt ttggaaatcc aaatggttat gtgtttagct     660
gcaactttct tttgtgttat cggcatgttc atcgttggtg atttcaaggt tatcgcaaga     720
gaagctagag aatttaagat cggtggttct gttttctatt acgcattgat cgttattact     780
ggtattattt ggcaaggttt cttttgggt gctattgta ttgttttctg tgcatcttca     840
ttagcttctg gtgttttgat ttcagttttg ttaccagtta cagaagtttt cgcagttgtt     900
tgtttcagag aaaagttcca agctgaaaag ggtgtttctt tgttgttgtc attgtggggt     960
tttgtttctt acttttatgg tgaatttaaa tcaggtaaaa aagttgttga caaacctcaa    1020
ccaccagaaa ccgaattacc tatcttacca gtctccgatt atgtagcata a             1071
```

```
<210> SEQ ID NO 43
<211> LENGTH: 345
<212> TYPE: PRT
<213> ORGANISM: Jatropha curcas

<400> SEQUENCE: 43

Met Arg Arg Ala Leu Leu Val Leu Asn Cys Val Ile Leu Ser Ile Gly
1               5                   10                  15

Asn Cys Gly Gly Pro Leu Ile Met Arg Leu Tyr Phe Ile His Gly Gly
                20                  25                  30

Lys Arg Val Trp Leu Ser Ser Trp Leu Glu Thr Ala Gly Trp Pro Ile
            35                  40                  45

Ile Phe Ile Pro Leu Leu Ile Ser Tyr Phe His Arg Arg Ser Thr Thr
        50                  55                  60

Asp Pro Thr Thr Ala Lys Leu Phe Tyr Met Lys Pro Ser Leu Phe Leu
65                  70                  75                  80

Ala Ala Thr Gly Ile Gly Ile Leu Thr Gly Phe Asp Asp Tyr Leu Tyr
                85                  90                  95

Ala Tyr Gly Val Ala Arg Leu Pro Val Ser Thr Ser Ser Leu Ile Ile
            100                 105                 110

Ala Thr Gln Leu Ala Phe Thr Ala Gly Phe Ala Phe Leu Leu Val Lys
        115                 120                 125

Gln Lys Phe Thr Ser Tyr Ser Ile Asn Ala Val Val Leu Leu Thr Val
130                 135                 140

Gly Ala Gly Val Leu Ala Leu His Thr Ser Ser Asp Arg Pro Glu His
145                 150                 155                 160

Glu Ser Lys Lys Glu Tyr Asn Leu Gly Phe Val Met Thr Leu Gly Ala
                165                 170                 175

Ala Val Leu Tyr Gly Leu Ile Leu Pro Leu Val Glu Leu Thr Tyr Arg
            180                 185                 190

Lys Ala Lys Gln Glu Ile Ser Tyr Thr Leu Val Met Glu Ile Gln Met
        195                 200                 205

Ile Met Cys Leu Phe Ala Thr Val Val Cys Thr Val Gly Met Leu Val
    210                 215                 220

Asn Asn Asp Phe Lys Val Ile Pro Arg Glu Ala Lys Glu Phe Glu Leu
225                 230                 235                 240

Gly Glu Thr Lys Tyr Tyr Val Ile Met Val Trp Ser Ala Ile Trp
                245                 250                 255

Gln Cys Phe Phe Leu Gly Ala Ile Gly Ile Val Phe Cys Ala Ser Ser
            260                 265                 270

Leu Ala Ser Gly Val Val Ile Ala Val Leu Leu Pro Val Thr Glu Ile
        275                 280                 285

Leu Ala Val Ile Phe Tyr Gln Glu Lys Phe Gln Ala Glu Lys Gly Val
    290                 295                 300

Ala Leu Ala Leu Ser Leu Trp Gly Phe Leu Ser Tyr Phe Tyr Gly Glu
305                 310                 315                 320

Ile Lys Gln Ser Lys Lys Thr Asn Leu Thr Ser Glu Ile Glu Thr Ser
                325                 330                 335

Glu Ser Ser Ile Pro Thr Gln Asn Val
            340                 345

<210> SEQ ID NO 44
<211> LENGTH: 1038
<212> TYPE: DNA
```

<213> ORGANISM: Jatropha curcas

<400> SEQUENCE: 44

```
atgagaagag ctttgttagt tttgaactgt gttatcttgt ctatcggtaa ttgtggtggt      60
ccattgatca tgagattgta cttcattcat ggtggtaaaa gagtttggtt gtcttcatgg     120
ttagaaactg ctggttggcc aatcatcttc atcccattgt taatttctta ctttcataga    180
agatcaacta cagatccaac tacagcaaaa ttgttttata tgaagccatc tttgttttta    240
gctgcaactg gtattggtat tttgacaggt ttcgatgatt acttgtacgc ttatggtgtt    300
gctagattgc cagtttcaac ttcttcattg atcatcgcta ctcaattagc ttttacagca    360
ggttttgcat ttttgttggt taagcaaaag ttcacatctt actcaatcaa tgcagttgtt    420
ttgttaactg ttggtgcagg tgttttggct tacatacat cttcagatag accagaacat    480
gaatctaaaa aagaatacaa cttgggtttt gttatgacat gggtgctgc tgttttgtac    540
ggtttgatct tgccattggt tgaattaact tacagaaagg ctaagcaaga aatttcatac    600
acattggtta tggaaattca atgatcatg tgtttgttcg caactgttgt ttgtacagtt    660
ggcatgttgg ttaacaacga tttcaaggtt atcccaagag aagctaagga atttgaatta    720
ggtgaaacta gtattacgt tattatggtt tggtctgcaa ttatttggca atgtttctt     780
ttgggtgcta ttggtattgt tttctgtgca tcttcattag cttcaggtgt tgttattgca    840
gttttgttac cagttacaga aattttggct gttattttct atcaagaaaa gttccaagca    900
gaaaagggtg ttgctttagc attgtcttta tggggtttct tgtcatactt ttatggtgaa    960
atcaagcaat ctaagaaaac taacttgaca tctgaaatcg aaacttcaga atcttcaatc   1020
ccaacacaaa atgttttaa                                                 1038
```

<210> SEQ ID NO 45
<211> LENGTH: 350
<212> TYPE: PRT
<213> ORGANISM: Papaver somniferum

<400> SEQUENCE: 45

```
Met Gly Lys Tyr Leu Ile Phe Cys Cys Met Leu Leu Leu Val Gly Gln
1               5                   10                  15

Val Gly Gly Pro Leu Leu Leu Arg Leu Tyr Tyr Leu His Gly Gly Gln
                20                  25                  30

Arg Lys Trp Leu Thr Ser Trp Leu Gln Thr Ala Ala Phe Pro Ile Leu
            35                  40                  45

Leu Ile Pro Ile Leu Val Ser Trp Ser Lys Ser Lys Ser Lys Ser Gln
        50                  55                  60

Ser Ile Ser Thr Asn Ala Val Asn Pro Thr Asp His Arg Asn Leu Phe
65                  70                  75                  80

Cys Val Thr Arg Lys Leu Phe Ile Ser Val Ile Leu Gly Ile Met
                85                  90                  95

Phe Gly Leu Asp Ala Phe Leu Phe Ser Ile Gly Leu Ser Asn Leu Pro
                100                 105                 110

Val Ser Thr Ser Thr Leu Leu Met Ala Thr Gln Leu Ala Phe Thr Val
            115                 120                 125

Phe Phe Ala Ser Ile Leu Val Lys Gln Lys Phe Thr Pro Tyr Ser Ile
        130                 135                 140

Asn Ser Val Val Leu Leu Thr Leu Gly Ala Val Val Leu Ala Phe His
145                 150                 155                 160
```

```
Thr Asn Gly Asp Lys Pro Ile Gly Val Ser Lys Asp Gln Tyr Phe Leu
            165                 170                 175

Gly Phe Phe Val Thr Leu Gly Ala Ala Leu Phe Gly Phe Met Leu
        180                 185                 190

Pro Phe Ile Glu Leu Val Tyr Arg Lys Ala Cys Glu Ala Val Thr Tyr
            195                 200                 205

Asp Leu Val Met Arg Met Gln Phe Ile Thr Ser Met Val Ala Thr Val
    210                 215                 220

Phe Cys Thr Ile Ala Met Leu Ile Asn Lys Asp Phe Gln Ala Ile Ser
225                 230                 235                 240

Arg Glu Ala Lys Gly Phe Glu Leu Gly Glu Thr Lys Tyr Tyr Ile Val
                245                 250                 255

Leu Ile Phe Thr Ala Val Ser Met Gln Cys Ala Val Val Gly Thr Leu
            260                 265                 270

Gly Val Ile His Cys Ala Ser Ser Leu Phe Ser Gly Val Leu Met Thr
        275                 280                 285

Leu Leu Leu Pro Ile Gln Gln Ile Cys Ala Ile Phe Phe Asn Glu
290                 295                 300

Lys Phe Ser Ala Glu Lys Gly Met Ser Leu Gly Leu Ser Ile Trp Gly
305                 310                 315                 320

Phe Ala Ser Tyr Phe Tyr Gly Glu Tyr Lys Gln Thr Lys Lys Thr
                325                 330                 335

His Gln His Lys Ala Val Ser Thr Lys Ser Gln Glu Ile Pro
            340                 345                 350

<210> SEQ ID NO 46
<211> LENGTH: 1053
<212> TYPE: DNA
<213> ORGANISM: Papaver somniferum

<400> SEQUENCE: 46
atgggcaagt acttgatttt ctgttgtatg ttgttattgg ttggtcaagt tggtggtcca      60
ttgttgttga gattgtacta cttgcatggt ggtcaaagaa atggttaac ttcttggttg     120
caaacagctg cattcccaat cttgttgatc ccaattttag tttcttggtc aaaatctaaa    180
tcaaagtctc aatcaatttc tactaacgct gttaacccaa cagatcatag aaacttattt    240
tgtgttacta gaaaattgtt tatttcttca gttattttag gtatcatgtt cggtttagat    300
gcatttttgt tttcaatcgg tttatctaac ttgccagttt caacttctac attgttaatg    360
gcaactcaat tggcttttac agttttcttt gcttcaattt tagttaagca aaagttcact    420
ccatattcaa ttaattctgt tgttttgtta actttaggtg cagttgtttt ggcttttcat    480
acaaatggtg ataagccaat cggtgtttct aaggatcaat actttttggg ttctttgtt    540
acattaggtg ctgctgcttt gtttggtttc atgttgccat tcatcgaatt ggtttataga    600
aaagcatgtg aagctgttac ttacgatttg gttatgagaa tgcaattcat cacatcaatg    660
gttgcaactg ttttctgtac aatcgctatg ttgatcaaca aggattttca agctatttca    720
agagaagcta agggtttcga attgggtgaa actaagtact acatcgtttt gatcttcaca    780
gcagtttcaa tgcaatgtgc tgttgttggt actttaggtg ttatccattg tgcttcttca    840
ttattttctg tgtttttgat gacattgttg ttgccaatcc aacaaatttg tgcaattttc    900
tttttcaatg aaaagttctc agctgaaaag ggcatgtcat tgggtttgtc tatttggggt    960
```

```
ttcgcatctt acttctacgg tgaatacaag caaactaaaa agaaaactca tcaacataag    1020
gctgtttcaa caaagtctca agaaattcca taa                                 1053
```

<210> SEQ ID NO 47
<211> LENGTH: 348
<212> TYPE: PRT
<213> ORGANISM: Papaver somniferum

<400> SEQUENCE: 47

```
Met Gly Lys Tyr Leu Leu Phe Asn Cys Ile Leu Ala Val Ser
1               5                   10                  15

Ser Ala Gly Gly Pro Leu Leu Arg Leu Tyr Phe Ile His Gly Gly
                20                  25                  30

Lys Arg Leu Trp Leu Ser Ser Trp Leu Glu Thr Ala Gly Trp Pro Ile
            35                  40                  45

Leu Phe Leu Pro Leu Ser Leu Ser Tyr Phe Leu Lys Arg Arg Arg Phe
    50                  55                  60

Lys Asn Gly Gln Asp Glu Lys Pro Ser Lys Phe Met Ile Thr Pro
65                  70                  75                  80

Phe Leu Phe Met Ala Ser Ala Phe Ile Gly Leu Leu Val Gly Leu Asp
                85                  90                  95

Asp Tyr Leu Tyr Thr Tyr Gly Val Ser Leu Leu Pro Val Ser Thr Ser
                100                 105                 110

Ala Leu Ile Met Ser Thr His Leu Ala Phe Thr Ala Gly Phe Ala Leu
            115                 120                 125

Phe Met Val Lys Gln Lys Phe Thr Ser Tyr Ser Val Asn Ala Val Ile
    130                 135                 140

Leu Leu Thr Val Gly Ala Ile Leu Leu Gly Leu His Ser Asn Gly Asp
145                 150                 155                 160

Thr Pro Val His Glu Ser Asn Arg Asp Tyr Tyr Leu Gly Phe Val Met
                165                 170                 175

Thr Ile Gly Ala Ser Ile Ile Gly Gly Leu Leu Leu Pro Leu Val Glu
                180                 185                 190

Leu Met Tyr Lys Lys Ser Lys Gln Thr Ile Thr Tyr Ser Leu Val Ile
            195                 200                 205

Glu Leu Gln Ile Val Ile Ser Val Phe Ala Thr Leu Leu Cys Thr Val
    210                 215                 220

Gly Met Leu Val Asn Asn Asp Phe Lys Val Ile Gln Arg Glu Gly Lys
225                 230                 235                 240

Glu Tyr Glu Leu Gly Glu Thr Asn Tyr Tyr Val Val Leu Val Ala Ser
                245                 250                 255

Ser Ile Thr Trp Gln Leu Cys Tyr Leu Gly Thr Ile Gly Val Ile Phe
            260                 265                 270

Cys Ser Thr Ser Leu Leu Ala Gly Val Ile Gly Ala Val Val Leu Pro
    275                 280                 285

Val Ile Glu Ile Leu Ala Val Ile Phe Tyr His Glu Ser Phe Lys Ala
    290                 295                 300

Glu Lys Gly Ile Ala Leu Phe Leu Ser Leu Trp Gly Phe Ile Ser Tyr
305                 310                 315                 320

Phe Tyr Leu Glu Ile Lys Glu Ser Thr Lys Pro Lys Lys Arg Ser
                325                 330                 335

Leu Glu Leu Glu Gln Gly Asp Leu Thr Val Ser Ser
            340                 345
```

<210> SEQ ID NO 48
<211> LENGTH: 1047
<212> TYPE: DNA
<213> ORGANISM: Papaver somniferum

<400> SEQUENCE: 48

```
atgggcaagt acttgttgtt gttcaactgt atcttattgg cagtttcttc agctggtggt      60
ccattgttgt tgagattgta cttcattcat ggtggtaaaa gattatggtt gtcttcatgg     120
ttagaaacag caggttggcc aatcttattt ttgccattat ctttgtcata cttttttgaag    180
agaagaagat tcaagaatgg tcaagatgaa aaaccatcta agtttttcat gatcactcca     240
tttttattca tggcttcagc attcattggt ttgttagttg gtttggatga ttacttgtac     300
acttatggtg tttctttgtt accagtttct acttcagcat tgatcatgtc aactcatttg     360
gctttcacag caggttttgc tttgttcatg gttaagcaaa agttcacatc ttactcagtt     420
aatgcagtta tcttgttgac tgttggtgct atcttgttag gtttgcattc taatggtgat     480
acaccagttc atgaatcaaa cagagattac tacttgggtt tcgttatgac tatcggtgct     540
tctatcattg gtggtttgtt gttgccattg gttgaattaa tgtacaaaaa atctaagcaa     600
actattacat attcattggt tattgaatta caaattgtta tttctgtttt tgcaactttg     660
ttgtgtacag ttggcatgtt ggttaacaac gatttcaagg ttatccaaag agaaggcaag     720
gaatacgaat tgggtgaaac aaactactac gttgttttag ttgcttcttc aatcacttgg     780
caattgtgtt acttgggtac aatcggtgtt attttctgtt ctacttcatt attggcaggt     840
gttattggtg ctgttgtttt gccagttatc gaaattttag ctgttatttt ctatcatgaa     900
tcttttaagg cagaaaaggg tatcgcttta tttttgtctt tatggggttt catctcatac     960
ttctatttgg aaatcaaaga atctacaaag ccaaaaaaga aagatcatt ggaattggaa    1020
cagggtgatt taactgtttc ttcataa                                        1047
```

<210> SEQ ID NO 49
<211> LENGTH: 329
<212> TYPE: PRT
<213> ORGANISM: Papaver somniferum

<400> SEQUENCE: 49

Met Gly Lys Tyr Leu Leu Leu Arg Leu Tyr Tyr Leu His Gly Gly Gln
1               5                   10                  15

Arg Lys Trp Leu Ser Ser Trp Leu Gln Thr Val Ala Phe Pro Phe Leu
            20                  25                  30

Leu Ile Pro Ile Ser Val Ser Trp Phe Lys Ser Lys Ser Lys Ser His
        35                  40                  45

Asp Ser Arg Ser Ile Ser Ala Ile Asp Val Asn Pro Thr Thr Asp Arg
50                  55                  60

Lys Leu Arg Phe Gly Gly Phe Ser Pro Lys Leu Phe Ile Ser Cys Ile
65                  70                  75                  80

Phe Leu Gly Ile Ile Val Gly Leu Asp Ser Phe Leu Tyr Ala Tyr Gly
                85                  90                  95

Val Ser Tyr Leu Pro Val Ser Thr Ser Ser Leu Leu Met Ser Thr Gln
            100                 105                 110

Leu Ala Phe Thr Ala Ala Phe Ala Leu Leu Leu Val Arg Gln Lys Phe
        115                 120                 125

Thr Pro Tyr Ser Ile Asn Ser Val Val Leu Leu Thr Leu Gly Ala Val
    130                 135                 140

Val Leu Ala Phe His Thr Asn Gly Asp Lys Pro Ile Gly Val Ser Lys
145                 150                 155                 160

Asp Gln Tyr Phe Leu Gly Phe Phe Val Thr Leu Gly Ala Ala Ala Leu
            165                 170                 175

Phe Gly Phe Met Leu Pro Phe Ile Glu Leu Val Tyr Arg Lys Ala Cys
            180                 185                 190

Glu Ala Val Thr Tyr Asp Leu Val Met Arg Met Gln Phe Ile Ile Ser
            195                 200                 205

Met Val Ala Thr Val Phe Cys Thr Ile Ala Met Leu Ile Asn Lys Asp
            210                 215                 220

Phe Gln Ala Ile Ser Arg Glu Ala Lys Gly Phe Glu Leu Gly Glu Thr
225                 230                 235                 240

Lys Tyr Tyr Ile Val Leu Ile Phe Thr Ala Val Ser Met Gln Cys Ala
            245                 250                 255

Val Val Gly Thr Leu Gly Val Ile His Cys Ala Ser Ser Leu Phe Ser
            260                 265                 270

Gly Val Leu Met Thr Leu Leu Leu Pro Ile Gln Gln Ile Cys Ala Ile
            275                 280                 285

Phe Phe Phe Asn Glu Lys Phe Ser Ala Glu Lys Gly Met Ser Leu Gly
290                 295                 300

Leu Ser Ile Trp Gly Phe Ala Ser Tyr Phe Tyr Gly Glu Tyr Lys Gln
305                 310                 315                 320

Thr Glu Lys Lys Thr Asn Gln His Lys
            325

<210> SEQ ID NO 50
<211> LENGTH: 990
<212> TYPE: DNA
<213> ORGANISM: Papaver somniferum

<400> SEQUENCE: 50
atgggcaagt acttgttgtt gagattgtac tacttgcatg gtggtcaaag aaaatggtta      60
tcttcatggt tgcaaactgt tgcattccca ttttattga tcccaatttc tgtttcatgg     120
ttcaagtcta agtcaaagtc tcatgattca agatcaattt ctgctatcga tgttaaccca     180
actacagata gaaaattgag attcggtggt ttctctccaa aattgttcat ctcatgtatt     240
ttcttgggta tcatcgttgg tttagattca ttttgtacg cttacggtgt ttcttacttg     300
ccagtttcaa cttcttcatt attgatgtca actcaattgg catttacagc tgcattcgct     360
ttgttgttag ttagacaaaa gttcacacca tactctatca actcagttgt tttgttgact     420
ttgggtgcag ttgttttggc ttttcataca aatggtgata agccaatcgg tgtttctaag     480
gatcaatact ttttgggttt ctttgttact ttaggtgctg ctgctttgtt tggtttcatg     540
ttgccattca tcgaattggt ttatagaaaa gcatgtgaag ctgttacata cgatttggtt     600
atgagaatgc aattcatcat ctctatggtt gcaactgttt tctgtacaat cgctatgttg     660
atcaacaagg attttcaagc tatttcaaga gaagctaagg gtttcgaatt aggtgaaact     720
aagtactaca tcgttttgat cttcacagca gtttctatgc aatgtgctgt tgttggtact     780
ttgggtgtta tccattgtgc atcttcatta ttttcaggtg ttttgatgac attgttgttg     840
ccaatccaac aaatttgtgc aattttcttt ttcaatgaaa agttctctgc tgaaaagggc     900
atgtctttgg gtttgtcaat ttggggtttc gcttcatact tctacggtga atacaaacaa     960
actgaaaaga aaactaatca acataaataa                                     990

```
<210> SEQ ID NO 51
<211> LENGTH: 384
<212> TYPE: PRT
<213> ORGANISM: Papaver somniferum

<400> SEQUENCE: 51
```

Met Ile Ile Glu Thr Leu Asp Ile Leu Gly Pro Asn Gln Asn Gly Asn
1               5                   10                  15

Ser Gly Thr His Thr Gln Lys Pro Ile Lys Thr Arg Asn Trp Leu Leu
            20                  25                  30

Ile Ile Ile Asn Cys Ala Leu Val Phe Cys Gly Val Ile Gly Gly Pro
        35                  40                  45

Leu Leu Met Arg Leu Tyr Tyr Leu His Gly Gly Ser Arg Lys Trp Leu
    50                  55                  60

Ser Ser Phe Leu Gln Thr Ala Gly Phe Pro Val Leu Ile Phe Pro Leu
65                  70                  75                  80

Ile Phe Leu Tyr Ile Lys Pro Lys Leu Ser Thr Gln Asn Asn Asp Gln
                85                  90                  95

Ser Ser Ser Phe Phe Met Glu Pro Lys Leu Phe Leu Trp Ser Ala Ile
            100                 105                 110

Val Gly Ile Val Phe Gly Val Ser Asn Phe Met Tyr Ala Leu Gly Leu
        115                 120                 125

Ser Tyr Leu Pro Val Ser Thr Ser Thr Ile Leu Phe Ala Thr Gln Leu
    130                 135                 140

Cys Phe Thr Ala Ile Phe Ala Trp Leu Ile Val Lys Gln Lys Phe Thr
145                 150                 155                 160

Ala Phe Ile Ile Asn Ala Val Ile Val Met Thr Leu Gly Ser Ile Leu
                165                 170                 175

Leu Gly Ile Asn Thr Asn Gly Asp Arg Pro Ile Gly Val Ser Lys Thr
            180                 185                 190

Gln Tyr Leu Ile Gly Phe Leu Met Thr Leu Ala Ala Ala Leu Thr
        195                 200                 205

Gly Leu Gly Thr Pro Phe Val Glu Leu Ser Phe Ile Lys Ala Thr Arg
    210                 215                 220

Asn Ile Thr Tyr Pro Thr Leu Leu Gln Phe Gln Val Ile Leu Cys Leu
225                 230                 235                 240

Phe Gly Thr Cys Leu Asn Val Ile Gly Met Leu Ile Asn Lys Asp Phe
                245                 250                 255

Gln Ala Ile Pro Arg Glu Ala Asp Met Phe Glu Leu Gly Lys Ser Lys
            260                 265                 270

Tyr Tyr Met Ile Ile Cys Leu Thr Ala Leu Thr Trp Gln Leu Ser Gly
        275                 280                 285

Ile Gly Leu Val Gly Leu Ile Leu Tyr Thr Asn Ala Leu Phe Asn Gly
    290                 295                 300

Ile Tyr Val Ser Val Leu Val Pro Phe Thr Glu Val Ala Ala Val Ile
305                 310                 315                 320

Phe Phe His Glu Lys Phe Thr Gly Leu Lys Gly Met Ala Leu Ala Leu
                325                 330                 335

Cys Leu Trp Gly Phe Ser Ser Tyr Phe Tyr Gly Glu Tyr Lys Met Met
            340                 345                 350

Asn Lys Val Gly Asp Asn Glu Thr His Glu Lys Ile Glu Glu Ala Glu
        355                 360                 365

Ser Glu Pro Lys Arg Leu Glu Asp Gln Gln Ala Pro Tyr Ser Thr Val
    370                 375                 380

<210> SEQ ID NO 52
<211> LENGTH: 1155
<212> TYPE: DNA
<213> ORGANISM: Papaver somniferum

<400> SEQUENCE: 52

```
atgatcatcg aaactttgga tatcttgggt ccaaaccaaa acggtaactc aggtactcat      60
acacaaaaac caattaaaac aagaaactgg ttgttgatca ttattaactg tgctttggtt     120
ttctgtggtg ttattggtgg tccattgttg atgagattgt actacttgca tggtggttct     180
agaaagtggt tgtcttcatt tttgcaaact gcaggttttc cagttttgat cttcccattg     240
atttctttgt acattaaacc aaaattgtca acacaaaaca acgatcaatc ttcatctttc     300
tttatggaac caaagttgtt tttatggtct gctattgttg gtatcgtttt cggtgtttca     360
aacttcatgt acgcattggg tttatcttac ttgccagttt caacttctac aatcttgttc     420
gctactcaat tgtgtttcac agctatcttc gcatggttga tcgttaagca aaagtttact     480
gcttttatta ttaatgcagt tattgttatg actttgggtt caatcttgtt gggtattaat     540
acaaacggtg acagaccaat cggtgtttct aagactcaat atttgatcgg tttcttgatg     600
acattggctg cagctgcatt aactggtttg gtacaccatt tgttgaatt gtcttttatt     660
aaggctacta gaaacatcac ttacccaaca ttgttgcaat ccaagttat tttgtgtttg     720
ttcggtacat gtttgaacgt tatcggcatg ttgattaata aggatttcca agctatccca     780
agagaagcag atatgtttga attgggtaaa tcaaagtact acatgatcat ctgtttaact     840
gctttgacat ggcaattatc tggtattggt ttggttggtt tgatcttgta cacaaacgca     900
ttgtttaatg gtatctatgt ttctgttttg gttccttta ctgaagttgc tgctgttatt     960
ttctttcatg aaaagtttac tggtttaaag ggtatggctt tggcattgtg tttgtggggt    1020
ttttcatctt acttctacgg tgaatacaag atgatgaata aggttggtga caatgaaact    1080
catgaaaaga ttgaagaagc tgaatcagaa ccaaaaagat tggaagatca acaagcacca    1140
tactctacag tttaa                                                     1155
```

<210> SEQ ID NO 53
<211> LENGTH: 348
<212> TYPE: PRT
<213> ORGANISM: Papaver alpinum

<400> SEQUENCE: 53

```
Met Asn Thr Tyr Leu Leu Leu Phe Asn Gly Ile Leu Leu Ala Val Ser
1               5                   10                  15

Ser Ile Ala Gly Pro Leu Leu Arg Leu Tyr Phe Ile His Gly Gly
            20                  25                  30

Lys Arg Ile Trp Leu Ser Ser Cys Leu Glu Thr Ala Gly Phe Pro Val
        35                  40                  45

Leu Ile Phe Pro Leu Trp Leu Ser Tyr Phe Leu Arg Arg Arg Gly Phe
    50                  55                  60

Ile Lys Gly Asp Asp Asp Glu Lys Pro Lys Lys Leu Phe Thr Ile Thr
65                  70                  75                  80

Leu Pro Leu Phe Ile Ala Ser Ala Val Ile Gly Leu Val Thr Gly Leu
                85                  90                  95

Asp Asp Tyr Leu Tyr Thr Tyr Gly Val Ser Leu Leu Pro Ile Ser Thr
            100                 105                 110

Ala Thr Ile Ile Met Ser Thr His Leu Ala Phe Thr Ala Gly Phe Ala
        115                 120                 125
```

Leu Val Met Val Lys Gln Lys Phe Thr Ser Phe Ser Val Asn Ala Val
130                 135                 140

Val Leu Leu Thr Ile Gly Ala Ile Leu Leu Gly Leu His Gly Asn Gly
145                 150                 155                 160

Asp Lys Pro Val Asn Glu Ser Lys Lys Asp Tyr Tyr Leu Gly Phe Leu
            165                 170                 175

Ile Thr Ile Ala Ala Ser Val Phe Asn Gly Leu Met Leu Pro Met Val
            180                 185                 190

Glu Leu Met Tyr Met Lys Ser Lys Gln Thr Ile Thr Tyr Ser Leu Val
            195                 200                 205

Ile Glu Leu Gln Met Val Ile Ser Gly Phe Ala Thr Leu Phe Cys Thr
210                 215                 220

Ile Gly Met Ile Ala Asn Asn Asp Phe Lys Val Ile Pro Arg Glu Gly
225                 230                 235                 240

Arg Glu Tyr Gly Leu Gly Glu Ile Asn Tyr Tyr Ile Val Leu Val Ala
            245                 250                 255

Ser Ala Ile Thr Trp Gln Met Tyr Phe Val Gly Thr Val Gly Val Ile
            260                 265                 270

Phe Cys Ser Thr Ser Leu His Ala Gly Val Ile Ser Val Val Leu
            275                 280                 285

Pro Leu Thr Glu Ile Leu Ser Val Val Phe Tyr His Glu Ser Phe Lys
290                 295                 300

Ala Glu Lys Gly Ile Ala Leu Phe Leu Ser Leu Trp Gly Phe Ile Ser
305                 310                 315                 320

Tyr Phe Tyr Leu Glu Ile Lys Ala Ser Arg Lys Pro Lys Lys Gln Cys
            325                 330                 335

Ser Glu Leu Glu Gln Gly Gly Leu Thr Val Ser Ser
            340                 345

<210> SEQ ID NO 54
<211> LENGTH: 1047
<212> TYPE: DNA
<213> ORGANISM: Papaver alpinum

<400> SEQUENCE: 54

```
atgaatacat acttgttgtt gttcaacggt attttattgg cagtttcttc aattgctggt    60
ccattgttgt tgagattgta cttcattcat ggtggtaaaa gaatttggtt atcttcatgt   120
ttggaaactg ctggttttcc agttttgatc ttcccattgt ggttgtctta cttttaaga   180
agaagaggtt tcatcaaggg tgatgatgat gaaaagccta aaaaattgtt cactatcaca   240
ttgccattgt tcatcgcttc agcagttatc ggtttagtta ctggtttgga tgattacttg   300
tacacttatg tgtttctttt gttgccaatt tcaactgcta caatcatcat gtctactcat   360
ttggctttta cagcaggttt tgctttagtt atggttaagc aaaagttcac atctttttca   420
gttaacgcag ttgttttgtt gactatcggt gctatcttgt taggtttgca tggtaatggt   480
gataaaccag ttaacgaatc taaaaaagat tactacttag gtttcttgat cacaatcgct   540
gcatcagttt tcaacggttt gatgttgcca atggttgaat tgatgtacat gaagtctaag   600
caaactatca catactcatt ggttatcgaa ttacaaatgg ttatttctgg tttcgcaact   660
ttattttgta caattggtat gatcgctaac aacgatttca aggttattcc aagagaaggt   720
agagaatacg gtttgggtga aatcaactac tacatcgttt tagttgcttc tgcaattact   780
tggcaaatgt attttgttgg tacagttggt gttattttct gttctacttc attgcatgca   840
```

```
ggtgttattt cagttgttgt tttgccattg acagaaattt tatctgttgt tttctatcat    900
gaatcattta aggcagaaaa gggtatcgct ttgtttttat ctttgtgggg tttcatctca    960
tacttctatt tagaaatcaa agctagtaga aagcctaaaa aacaatgttc agaattggaa   1020
caaggtggtt taactgtttc ttcataa                                       1047
```

<210> SEQ ID NO 55
<211> LENGTH: 347
<212> TYPE: PRT
<213> ORGANISM: Papaver atlanticum

<400> SEQUENCE: 55

```
Met Glu Lys Tyr Leu Leu Leu Phe Asn Cys Ile Leu Leu Ala Val Cys
1               5                   10                  15

Ser Ala Gly Gly Pro Leu Leu Arg Leu Tyr Phe Ile His Gly Gly
            20                  25                  30

Lys Arg Leu Trp Leu Ser Ser Trp Leu Glu Thr Ala Gly Trp Pro Ile
        35                  40                  45

Leu Phe Leu Pro Leu Ser Leu Ser Tyr Phe Leu Lys Arg Arg Arg Phe
    50                  55                  60

Lys Asn Gly Gln Asp Glu Lys Pro Ser Lys Phe Phe Met Ile Thr Pro
65                  70                  75                  80

Phe Leu Phe Met Ala Ser Ala Phe Ile Gly Leu Leu Val Gly Leu Asp
                85                  90                  95

Asp Tyr Leu Tyr Thr Tyr Gly Val Ser Leu Leu Pro Val Ser Thr Ala
            100                 105                 110

Ser Leu Ile Met Ser Thr His Val Ala Phe Thr Ala Gly Phe Ala Leu
        115                 120                 125

Phe Met Val Lys Gln Lys Phe Thr Ser Tyr Ser Val Asn Ala Val Ile
    130                 135                 140

Leu Leu Thr Val Gly Ala Val Leu Leu Gly Leu His Ser Asn Gly Asp
145                 150                 155                 160

Arg Ser Val His Glu Ser Asn Arg Asp Tyr Tyr Leu Gly Phe Val Met
                165                 170                 175

Thr Ile Gly Ala Ser Val Ile Gly Gly Leu Leu Leu Pro Leu Val Glu
            180                 185                 190

Leu Met Tyr Lys Lys Ser Lys Gln Thr Ile Thr Tyr Thr Leu Val Thr
        195                 200                 205

Glu Leu Gln Ile Val Ile Ser Val Phe Ala Thr Leu Phe Cys Thr Val
    210                 215                 220

Gly Met Leu Val Asn Asn Asp Phe Lys Val Ile Gln Arg Glu Gly Lys
225                 230                 235                 240

Glu Tyr Asp Leu Gly Glu Thr Lys Tyr Tyr Val Val Leu Val Ala Ser
                245                 250                 255

Ser Ile Thr Trp Gln Leu Cys Phe Leu Gly Thr Ile Gly Val Ile Phe
            260                 265                 270

Cys Ser Thr Ser Leu Leu Ala Gly Val Ile Gly Ala Val Leu Pro
        275                 280                 285

Val Ile Glu Ile Leu Gly Val Ile Phe Tyr His Glu Ser Phe Lys Ala
    290                 295                 300

Glu Lys Gly Ile Ala Leu Phe Leu Ser Leu Trp Gly Phe Ile Ser Tyr
305                 310                 315                 320

Phe Tyr Leu Glu Ile Lys Ala Ser Arg Lys Pro Lys Arg Gln Cys Ser
                325                 330                 335
```

```
Glu Leu Glu Gln Gly Gly Leu Thr Val Ser Ser
        340                 345

<210> SEQ ID NO 56
<211> LENGTH: 1044
<212> TYPE: DNA
<213> ORGANISM: Papaver atlanticum

<400> SEQUENCE: 56
atggaaaagt acttgttgtt gttcaactgt atcttattgg cagtttgttc agctggtggt      60
ccattgttgt tgagattgta cttcattcat ggtggtaaaa gattatggtt gtcttcatgg     120
ttggaaactg ctggttggcc aatcttattt ttgccattat ctttgtcata cttttttgaag   180
agaagaagat tcaagaatgg tcaagatgaa aaaccatcta agttttttcat gatcacacca    240
ttttattca tggcttcagc attcattggt ttgttagttg gtttggatga ttacttgtac      300
acttatggtg tttctttgtt accagtttct acagcttcat tgattatgtc aacacatgtt     360
gcttttactg ctggtttcgc tttgttcatg gttaagcaaa agtttacttc ttattcagtt     420
aatgcagtta ttttgttaac agttggtgct gttttgttag gtttgcattc taatggtgat    480
agatcagttc atgaatcaaa cagagattac tacttgggtt tcgttatgac tattggtgca    540
tctgttattg gtggtttgtt gttgccattg gttgaattaa tgtacaaaaa atcaaagcaa    600
actattacat atactttggt tacagaatta caaattgtta tttctgtttt tgctacattg     660
ttttgtactg ttggcatgtt ggttaacaac gatttcaagg ttatccaaag agaaggcaag    720
gaatacgatt tgggtgaaac taaatactac gttgttttag ttgcatcttc aattacatgg    780
caattgtgtt tcttgggtac tatcggtgtt attttctgtt ctacatcatt attggctggt   840
gttattggtg ctgctgtttt gccagttatc gaaatttttag gtgttatttt ctatcatgaa   900
tcttttaagg cagaaaaggg tatcgctttta ttttttgtctt tatggggttt catctcatac   960
ttctatttgg aaatcaaagc tagtagaaag ccaaagagac aatgttcaga attggaacaa   1020
ggtggtttaa cagtttcttc ataa                                          1044

<210> SEQ ID NO 57
<211> LENGTH: 351
<212> TYPE: PRT
<213> ORGANISM: Papaver miyabeanum

<400> SEQUENCE: 57

Met Glu Lys Tyr Leu Leu Phe Asn Cys Ile Leu Leu Ala Val Gly
1                 5                  10                  15

Ser Thr Ala Gly Pro Leu Leu Arg Leu Tyr Phe Ile His Gly Gly
            20                  25                  30

Lys Arg Leu Trp Leu Ser Ser Trp Leu Glu Thr Ala Gly Trp Pro Ile
        35                  40                  45

Leu Phe Leu Pro Leu Ser Leu Ser Tyr Phe Leu Lys Arg Arg Arg Phe
    50                  55                  60

Lys Thr Gly Gln Asp Glu Lys Pro Ser Lys Phe Met Ile Thr Pro
65                  70                  75                  80

Phe Leu Phe Met Ala Ser Ala Phe Ile Gly Ile Leu Val Gly Leu Asp
                85                  90                  95

Asp Tyr Leu Tyr Thr Tyr Gly Val Ser Leu Leu Pro Val Ser Thr Ser
                100                 105                 110

Ala Leu Ile Met Ser Thr His Leu Ala Phe Thr Ala Gly Phe Ala Leu
            115                 120                 125
```

```
Phe Met Val Lys Gln Lys Phe Thr Ser Tyr Ser Val Asn Ala Val Val
    130                 135                 140

Leu Leu Thr Val Gly Ala Ile Leu Leu Gly Leu His Ser Asn Gly Asp
145                 150                 155                 160

Arg Pro Leu Tyr Glu Ser Asn Arg Asp Tyr Tyr Leu Gly Phe Val Met
                165                 170                 175

Thr Ile Gly Ala Ser Val Ile Gly Gly Leu Leu Thr Pro Leu Val Glu
            180                 185                 190

Leu Met Tyr Lys Lys Ser Lys Gln Thr Ile Thr Tyr Thr Leu Val Ile
        195                 200                 205

Glu Leu Gln Ile Val Met Ser Val Phe Ala Thr Leu Phe Cys Thr Val
    210                 215                 220

Gly Met Leu Val Asn Asn Asp Phe Lys Val Ile Gln Arg Glu Gly Lys
225                 230                 235                 240

Glu Tyr Asp Leu Gly Glu Thr Lys Tyr Tyr Val Val Leu Val Ala Ser
                245                 250                 255

Ser Ile Thr Trp Gln Leu Cys Phe Leu Gly Ile Gly Val Val Phe
            260                 265                 270

Cys Ser Thr Ser Leu Leu Ala Gly Val Ile Gly Ala Val Val Pro
        275                 280                 285

Val Ile Glu Ile Leu Gly Val Ile Phe Tyr His Glu Ser Phe Lys Ala
    290                 295                 300

Glu Lys Gly Ile Ala Leu Phe Leu Ser Leu Trp Gly Phe Ile Ser Tyr
305                 310                 315                 320

Phe Tyr Leu Glu Leu Lys Glu Ile Lys Lys Pro Lys Asn His His Ser
                325                 330                 335

Glu Leu Glu Glu Asp Leu Thr Val Ser Ser Gln Ser Asn Leu Ala
            340                 345                 350

<210> SEQ ID NO 58
<211> LENGTH: 1056
<212> TYPE: DNA
<213> ORGANISM: Papaver miyabeanum

<400> SEQUENCE: 58
atggaaaagt acttgttgtt gttcaactgt atcttattgg cagttggttc tacagctggt      60
ccattgttgt tgagattgta cttcattcat ggtggtaaaa gattgtggtt atcttcatgg     120
ttggaaactg ctggttggcc aatcttgttt ttaccattgt ctttatcata cttttttgaag    180 agaagaagat tcaagacagg tcaagatgaa aagccatcta agttttttcat gatcactcca    240 tttttattca tggcttcagc attcatcggt attttagttg gtttggatga ttacttgtac    300
acttatggtg tttctttgtt accagtttct acttcagcat tgatcatgtc aacacatttg    360
gctttcactg ctggtttcgc tttgttcatg gttaagcaaa agtttacatc ttactcagtt    420
aatgcagttg ttttgttaac tgttggtgct atcttgttgg gtttacattc aacggtgat    480 agaccattgt acgaatcaaa cagagattac tacttgggtt tcgttatgac aattggtgct    540
tctgttattg gtggtttgtt gactccatta gttgaattga tgtacaaaaa atcaaagcaa    600
actatcacat acactttagt tattgaattg caaatcgtta tgtctgtttt cgcaacatta    660
ttttgtactg ttggcatgtt ggttaacaac gatttcaagg ttatccaaag agaaggcaag    720
gaatacgatt tgggtgaaac aaagtactac gttgttttgg ttgcttcttc aatcacttgg    780
caattgtgtt tcttgggtat tggtgttgtt gttttctgtt ctacatcatt gttagcaggt    840
gttattggtg ctgttgttgt tccagttatc gaaattttag gtgttatttt ctatcatgaa    900
```

```
tcttttaagg cagaaaaggg tatcgctttg tttttatctt tgtggggttt catctcatac    960
ttctatttag aattgaaaga aattaagaaa ccaaaaaatc atcattctga attagaagaa   1020
gatttgactg tttcttcaca atcaaacttg gcttaa                            1056
```

<210> SEQ ID NO 59
<211> LENGTH: 355
<212> TYPE: PRT
<213> ORGANISM: Papaver nudicale

<400> SEQUENCE: 59

```
Met Asn Thr Cys Leu Leu Trp Phe Asn Gly Leu Leu Ala Ile Ser
1               5                   10                  15

Ser Ile Gly Gly Pro Leu Leu Arg Leu Tyr Phe Ile His Gly Gly
            20                  25                  30

Lys Arg Ile Trp Leu Ser Ser Cys Leu Glu Thr Ala Gly Phe Pro Val
        35                  40                  45

Leu Phe Leu Pro Leu Trp Leu Ser Tyr Phe Leu Lys Arg Arg Gly Val
    50                  55                  60

Ile Lys Gly Asp Glu Gly Glu Lys Pro Ser Lys Leu Phe Thr Ile Thr
65                  70                  75                  80

Arg Pro Leu Phe Ile Ala Ser Ala Gly Ile Gly Leu Ile Thr Gly Leu
                85                  90                  95

Asp Asp Tyr Leu Tyr Thr Tyr Gly Val Ser Leu Leu Pro Ile Ser Thr
            100                 105                 110

Ala Thr Ile Ile Met Ser Thr His Leu Ala Phe Thr Ala Gly Phe Ala
        115                 120                 125

Leu Val Met Val Lys Gln Lys Phe Thr Ser Phe Ser Val Asn Ala Val
    130                 135                 140

Val Leu Leu Thr Val Gly Ala Ile Leu Leu Gly Leu His Ser Asn Gly
145                 150                 155                 160

Asp Arg Pro Ala Asn Glu Ser Thr Lys Glu Tyr Tyr Leu Gly Phe Leu
                165                 170                 175

Ile Thr Ile Ala Ala Ser Val Ile Asn Gly Leu Met Leu Pro Leu Val
            180                 185                 190

Glu Leu Met Tyr Met Lys Ser Lys Gln Val Ile Thr Tyr Ser Leu Val
        195                 200                 205

Ile Glu Leu Gln Ile Val Ile Ser Ala Phe Ala Thr Leu Phe Cys Thr
    210                 215                 220

Ile Gly Met Ile Val Asp Asn Asp Phe Lys Val Ile Pro Arg Glu Gly
225                 230                 235                 240

Arg Glu Tyr Gly Leu Gly Glu Val Asn Tyr Tyr Val Leu Val Ser
                245                 250                 255

Ser Ala Ile Met Trp Gln Met Tyr Phe Val Gly Thr Val Gly Val Ile
            260                 265                 270

Phe Cys Ser Thr Ser Leu Leu Ala Gly Val Ile Ala Val Val Leu
    275                 280                 285

Pro Leu Thr Glu Ile Leu Ser Val Phe Tyr His Glu Ser Phe Lys
    290                 295                 300

Ala Glu Lys Gly Ile Ala Leu Phe Leu Ser Leu Trp Gly Phe Ile Ser
305                 310                 315                 320

Tyr Phe Trp Gly Glu Leu Lys Gly Ser Arg Lys Ala Lys Lys Gln Ile
                325                 330                 335
```

Ser Glu Leu Glu Gln Asp Ser Ser Asn Ser Pro Thr Ser Leu His Ile
                340                 345                 350

Leu Asp Tyr
        355

<210> SEQ ID NO 60
<211> LENGTH: 1068
<212> TYPE: DNA
<213> ORGANISM: Papaver nudicale

<400> SEQUENCE: 60
atgaatactt gtttgttgtg gttcaacggt ttgttattgg caatttcttc aatcggtggt      60
ccattgttgt tgagattgta cttcattcat ggtggtaaaa gaatttggtt gtcttcatgt     120
ttagaaacag ctggttttcc agttttgttt ttaccattgt ggttgtctta cttttttgaag    180 agaagaggtg ttatcaaggg tgatgaaggt gaaaagccat ctaaattgtt cactatcaca    240
agaccattgt tcatcgcttc agcaggtatc ggtttgatca ctggtttaga tgattacttg    300
tacacttatg gtgtttcttt gttgccaatt tcaactgcaa caatcatcat gtctactcat    360 ttggcttttta cagcaggttt tgctttggtt atggttaagc aaaagttcac ttcttttttca    420 gttaacgcag ttgttttgtt aacagttggt gctatcttgt gggtttaca ttctaacggt     480 gatagaccag ctaacgaatc aactaaggaa tactacttgg gtttcttgat cacaatcgct    540
gcatctgtta tcaacggttt tgatgttgcca ttggttgaat taatgtacat gaagtctaag    600
caagttatca cttactcatt agttattgaa ttgcaaatcg ttatttcagc tttcgcaact    660
ttgttttgta caatcggtat gatcgttgat aacgatttca aggttattcc aagagaaggt    720
agagaatacg gttaggtga agttaactac tacgttgttt tggtttcttc agcaattatg    780
tggcaaatgt atttttgttgg tactgtcggt gttatttttct gttctacatc attgttagca    840
ggtgttattg ctgttgttgt tttgccattg actgaaattt tgtctgttgt tttctatcat    900
gaatcattta aggcagaaaa gggtatcgct ttattttttgt ctttatgggg tttcatctca    960
tacttctggg gtgaattaaa aggttcaaga aaggctaaaa acaaatttc agaattggaa   1020 caagattctt caaattctcc aacatcattg catattttag attactaa                 1068

<210> SEQ ID NO 61
<211> LENGTH: 341
<212> TYPE: PRT
<213> ORGANISM: Papaver radicatum

<400> SEQUENCE: 61

Met Lys Lys Ser Leu Met Leu Phe Asn Thr Ile Leu Leu Gly Ile Gly
1               5                   10                  15

Ala Thr Gly Gly Pro Leu Leu Leu Arg Leu Tyr Phe Val Arg Gly Gly
                20                  25                  30

Lys Arg Ile Trp Leu Ser Ser Ala Leu Gly Ser Ala Gly Trp Pro Val
            35                  40                  45

Leu Ile Leu Pro Leu Ser Leu Ser Tyr Phe Phe Asn Arg Gly Gly Arg
        50                  55                  60

Gly Gly Asp Lys Arg Trp Tyr Lys Phe Tyr Thr Ile Thr Pro Pro Leu
65                  70                  75                  80

Ile Val Phe Ser Ala Phe Ile Gly Ile Ile Leu Gly Ser Asn Asp Tyr
                85                  90                  95

Leu Tyr Thr His Gly Ile Ser Leu Leu Pro Val Ser Thr Ser Thr Leu
                100                 105                 110

Ile Met Ser Thr His Leu Ala Phe Thr Ala Gly Phe Ala Phe Val Ile
        115                 120                 125

Val Lys His Lys Phe Thr Pro Tyr Ser Ile Asn Ala Val Val Leu Leu
130                 135                 140

Thr Val Gly Ala Val Leu Leu Gly Leu Asn Ser Ser Gly Asp Lys Pro
145                 150                 155                 160

Val Asn Gln Ser Lys Lys Asp Tyr Tyr Leu Gly Phe Phe Leu Thr Val
        165                 170                 175

Gly Ala Ser Val Ile Ser Gly Phe Leu Phe Pro Leu Ser Glu Leu Met
            180                 185                 190

Tyr Met Lys Ala Lys Glu Arg Leu Thr Tyr Ser Leu Val Ile Glu Met
        195                 200                 205

Gln Ile Val Thr Ala Val Val Ala Ser Leu Phe Cys Ile Val Gly Met
        210                 215                 220

Ile Val Asn Asn Asp Phe Gln Ala Ile Pro Arg Glu Gly Arg Asp Tyr
225                 230                 235                 240

Glu Leu Gly Glu Val Lys Tyr Tyr Val Val Leu Val Ala Ile Ala Ile
            245                 250                 255

Met Trp Gln Ile Tyr Phe Val Thr Ala Gly Val Ile Phe Cys Ser
        260                 265                 270

Thr Ser Leu Tyr Ala Gly Ile Ile Thr Ala Val Ile Leu Pro Val Thr
    275                 280                 285

Glu Ile Leu Ser Val Val Phe Tyr His Glu Ser Phe Lys Ser Glu Lys
        290                 295                 300

Gly Leu Ala Leu Phe Leu Ser Cys Trp Gly Phe Ile Ser Tyr Leu Tyr
305                 310                 315                 320

Gly Asp Tyr Lys Glu Asn Leu Lys Leu Lys Lys Ala Gln Lys Gln Ser
            325                 330                 335

Ser Glu Met Glu Leu
            340

<210> SEQ ID NO 62
<211> LENGTH: 1026
<212> TYPE: DNA
<213> ORGANISM: Papaver radicatum

<400> SEQUENCE: 62
atgaaaaaat cattaatgtt gttcaacact atcttgttgg gtatcggtgc aacaggtggt        60
ccattgttgt tgagattgta cttcgttaga ggtggtaaaa gaatttggtt atcttcagca       120
ttgggttctg ctggttggcc agtttttgatc ttgccattat ctttgtcata tttctttaat      180
agaggtggta gaggtggtga taagagatgg tacaagttct acactatcac accaccattg       240
atcgttttct ctgctttcat cggtatcatc ttgggttcaa acgattactt gtacactcat       300
ggtatttctt tattgccagt ttctacttca acattgatca tgtcaactca tttggctttt      360
acagcaggtt tcgctttcgt tatcgttaag cataagttta ctccatattc aattaatgca       420
gttgttttat tgacagttgg tgctgttttg ttgggtttaa attcttcagg tgataagcca       480
gttaaccaat ctaaaaaaga ttactactta ggtttctttt tgacagttgg tgcatctgtt       540
atttcaggtt tcttgttccc attgtctgaa ttgatgtaca tgaaggctaa ggaaagattg       600
acttactcat tggttatcga aatgcaaatc gttacagcag ttgttgcttc tttattttgt      660
atcgttggta tgatcgttaa taatgatttt caagcaattc aagagaagg tagagattac      720 gaattaggtg aggttaagta ctacgttgtt ttggttgcta tcgcaatcat gtggcaaatt       780

```
tatttcgttg gtactgctgg tgttattttc tgttctacat cattgtacgc aggtatcatc      840
actgctgtta tcttgccagt tacagaaatt ttgtctgttg ttttctatca tgaatctttt      900
aagtcagaaa aaggtttagc attgttttta tcttgttggg gtttcatctc atacttatac      960
ggtgattaca aggaaaactt gaaattgaaa aaagctcaaa acaatcttc agaaatggaa      1020 ttgtaa                                                                 1026
```

<210> SEQ ID NO 63
<211> LENGTH: 348
<212> TYPE: PRT
<213> ORGANISM: Papaver trinifolium

<400> SEQUENCE: 63

```
Met Gly Lys Tyr Leu Leu Phe Asn Cys Ile Leu Leu Ala Val Ser
1               5                   10                  15

Ser Ala Ala Gly Pro Leu Leu Arg Leu Tyr Phe Ile His Gly Gly
                20                  25                  30

Lys Arg Leu Trp Leu Leu Ser Trp Leu Glu Thr Ala Gly Trp Pro Ile
            35                  40                  45

Leu Phe Leu Pro Leu Ser Leu Ser Tyr Phe Leu Lys Arg Arg Arg Phe
        50                  55                  60

Lys Asn Gly Gln Asp Glu Lys Pro Ser Lys Phe Phe Met Ile Thr Pro
65                  70                  75                  80

Phe Leu Phe Met Ala Ser Ala Phe Ile Gly Leu Leu Ile Gly Leu Asp
                85                  90                  95

Asp Tyr Leu Tyr Thr Tyr Gly Val Ser Leu Leu Pro Val Ser Thr Ser
                100                 105                 110

Ala Leu Ile Met Ser Thr His Leu Ala Phe Thr Ala Gly Phe Ala Leu
            115                 120                 125

Phe Met Val Lys Gln Lys Phe Thr Ser Tyr Ser Val Asn Ala Val Ile
        130                 135                 140

Leu Leu Thr Val Gly Ala Val Leu Leu Gly Leu His Ser Asn Gly Asp
145                 150                 155                 160

Lys Pro Val His Glu Ser Asn Arg Asp Tyr Tyr Leu Gly Phe Val Ile
                165                 170                 175

Thr Ile Gly Ala Ser Val Ile Gly Gly Leu Leu Leu Pro Leu Val Glu
            180                 185                 190

Leu Met Tyr Lys Lys Ser Lys Gln Thr Ile Thr Tyr Ser Leu Val Ile
        195                 200                 205

Glu Leu Gln Ile Val Ile Ser Val Phe Ala Thr Leu Phe Cys Thr Val
    210                 215                 220

Gly Met Leu Val Asn Asn Asp Phe Lys Val Ile Gln Arg Glu Gly Lys
225                 230                 235                 240

Glu Tyr Asn Leu Gly Glu Thr Lys Tyr Tyr Val Val Leu Val Ala Ser
                245                 250                 255

Ser Ile Ser Trp Gln Leu Cys Phe Leu Gly Thr Ile Gly Val Ile Phe
            260                 265                 270

Cys Ser Thr Ser Leu Leu Ala Gly Val Ile Gly Ala Val Val Leu Pro
        275                 280                 285

Val Ile Glu Ile Leu Ala Val Ile Phe Tyr His Glu Ser Phe Lys Ala
    290                 295                 300

Glu Lys Gly Ile Ala Leu Phe Leu Ser Leu Trp Gly Phe Ile Ser Tyr
305                 310                 315                 320
```

```
            Phe Tyr Leu Glu Leu Lys Ala Ser Arg Lys Pro Lys Lys Gln Ser
                            325                 330                 335

Leu Glu Leu Glu Gln Gly Asp Leu Thr Val Ser Ser
                    340                 345
```

<210> SEQ ID NO 64
<211> LENGTH: 1047
<212> TYPE: DNA
<213> ORGANISM: Papaver trinifolium

<400> SEQUENCE: 64

```
atgggcaagt acttgttgtt gttcaactgt atcttgttgg ctgtttcttc tgctgctggt      60
ccattgttgt tgagattgta cttcattcat ggtggtaaaa gattgtggtt gttatcttgg    120
ttagaaactg ctggttggcc aatcttattt ttgccattat ctttgtcata cttttttgaag   180
agaagaagat tcaagaatgg tcaagatgaa aaaccatcta agttttttcat gatcacacca   240
tttttattca tggcttcagc attcatcggt tgttgatcg gtttggatga ttacttgtac     300
acttatggtg tttctttgtt accagtttct acatcagcat tgatcatgtc aactcatttg   360
gctttcacag caggtttcgc tttgttcatg gttaagcaaa agtttacttc ttattcagtt    420
aatgcagtta ttttgttaac agttggtgct gttttgttag gtttgcattc taatggtgat   480
aagccagttc atgaatcaaa cagagattac tacttggggtt tcgttatcac tatcggtgct   540
tctgttattg tggtttgtt gttgccattg gttgaattaa tgtacaaaaa atctaagcaa     600
actattacat attcattggt tattgaatta caaattgtta tttcagtttt tgcaactttg    660
ttttgtacag ttggcatgtt ggttaacaac gatttcaagg ttattcaaag agaaggcaag   720
gaatacaact tgggtgaaac aaagtactac gttgttttag ttgcttcttc aatttcttgg   780
caattgtgtt tcttgggtac tatcggtgtt attttctgtt ctacatcatt attggcaggt   840
gttattggtg ctgttgtttt gccagttatc gaaattttag cagttatttt ctatcatgaa   900
tcttttaagg cagaaaaggg tatcgcttta ttttttgtctt tatggggttt catctcatac  960
ttctatttgg aattaaaagc tagtagaaag ccaaagaaaa aacaatcatt ggaattagaa  1020
cagggtgatt tgactgtttc ttcataa                                        1047
```

<210> SEQ ID NO 65
<211> LENGTH: 20
<212> TYPE: DNA
<213> ORGANISM: Artificial Sequence
<220> FEATURE:
<223> OTHER INFORMATION: qRT-PCR forward primer for THS2F

<400> SEQUENCE: 65

```
gaatccccgg ccaacctatc                                                  20
```

<210> SEQ ID NO 66
<211> LENGTH: 21
<212> TYPE: DNA
<213> ORGANISM: Artificial Sequence
<220> FEATURE:
<223> OTHER INFORMATION: qRT-PCR reverse primer for THS2

<400> SEQUENCE: 66

```
acctgaaaca ccgagaggag c                                                21
```

<210> SEQ ID NO 67
<211> LENGTH: 28
<212> TYPE: DNA
<213> ORGANISM: Artificial Sequence

```
<220> FEATURE:
<223> OTHER INFORMATION: qRT-PCR forward primer for THS2S

<400> SEQUENCE: 67
taacagctaa tcctgaacag tttagtcg                                    28

<210> SEQ ID NO 68
<211> LENGTH: 21
<212> TYPE: DNA
<213> ORGANISM: Artificial Sequence
<220> FEATURE:
<223> OTHER INFORMATION: qRT-PCR reverse primer for THS2S2

<400> SEQUENCE: 68
cgcaaagatg aggaactgcc t                                           21

<210> SEQ ID NO 69
<211> LENGTH: 24
<212> TYPE: DNA
<213> ORGANISM: Artificial Sequence
<220> FEATURE:
<223> OTHER INFORMATION: qRT-PCR forward primer for THS1

<400> SEQUENCE: 69
gcaacatgcc aaagttagaa cagc                                        24

<210> SEQ ID NO 70
<211> LENGTH: 21
<212> TYPE: DNA
<213> ORGANISM: Artificial Sequence
<220> FEATURE:
<223> OTHER INFORMATION: qRT-PCR reverse primer for THS1

<400> SEQUENCE: 70
gaaacaccga gaggagccat c                                           21

<210> SEQ ID NO 71
<211> LENGTH: 22
<212> TYPE: DNA
<213> ORGANISM: Artificial Sequence
<220> FEATURE:
<223> OTHER INFORMATION: qRT-PCR forward primer for THS1S

<400> SEQUENCE: 71
gcaacatgcc aaagtctagt cg                                          22

<210> SEQ ID NO 72
<211> LENGTH: 20
<212> TYPE: DNA
<213> ORGANISM: Artificial Sequence
<220> FEATURE:
<223> OTHER INFORMATION: qRT-PCR reverse primer for THS1S

<400> SEQUENCE: 72
aacctgaacg ggttgggtct                                             20

<210> SEQ ID NO 73
<211> LENGTH: 29
<212> TYPE: DNA
<213> ORGANISM: Artificial Sequence
<220> FEATURE:
<223> OTHER INFORMATION: genomic PCR forward primer for BV1 (5' UTR)

<400> SEQUENCE: 73
tgggctcata tgtgacactg cttaaccac                                   29
```

<210> SEQ ID NO 74
<211> LENGTH: 32
<212> TYPE: DNA
<213> ORGANISM: Artificial Sequence
<220> FEATURE:
<223> OTHER INFORMATION: genomic PCR forward primer for BV1 (5' UTR)
      (THS1)

<400> SEQUENCE: 74
ttacatcaat tctttatagc aacatgccaa ag                                32

<210> SEQ ID NO 75
<211> LENGTH: 30
<212> TYPE: DNA
<213> ORGANISM: Artificial Sequence
<220> FEATURE:
<223> OTHER INFORMATION: genomic PCR forward primer for BV1 (5' UTR)
      (nested)

<400> SEQUENCE: 75
acaacgggac tatactacta ataccgaatc                                   30

<210> SEQ ID NO 76
<211> LENGTH: 28
<212> TYPE: DNA
<213> ORGANISM: Artificial Sequence
<220> FEATURE:
<223> OTHER INFORMATION: genomic PCR reverse primer for BV1 (5' UTR)

<400> SEQUENCE: 76
tatgtacgtg cataggtaca cgtacacc                                     28

<210> SEQ ID NO 77
<211> LENGTH: 20
<212> TYPE: DNA
<213> ORGANISM: Artificial Sequence
<220> FEATURE:
<223> OTHER INFORMATION: VIGS forward primer - TRV2

<400> SEQUENCE: 77
ggtcaaggta cgtagtagag                                              20

<210> SEQ ID NO 78
<211> LENGTH: 21
<212> TYPE: DNA
<213> ORGANISM: Artificial Sequence
<220> FEATURE:
<223> OTHER INFORMATION: VIGS reverse primer - TRV2

<400> SEQUENCE: 78
cgagaatgtc aatctcgtag g                                            21

<210> SEQ ID NO 79
<211> LENGTH: 249
<212> TYPE: DNA
<213> ORGANISM: Artificial Sequence
<220> FEATURE:
<223> OTHER INFORMATION: Synthetic VIGs fragment - TRV2

<400> SEQUENCE: 79
aatgttaaca ttgatggtaa gacgattcgc tcggtacaat tcggccatca ggccattgag    60
gacatgaaca agtacttacg cgattctgaa agtaactgat tgatgccatt tatacatgaa   120
cccattcggt gttggtgtac gtgtacctat gcacgtacat attttatatt tatcagttgc   180

```
aacttgtgtg tattttatcg tttcagtgac tccaatattg tgtcagtgac ccggtgtatg    240
ggtgtgatt                                                            249
```

<210> SEQ ID NO 80
<211> LENGTH: 180
<212> TYPE: PRT
<213> ORGANISM: Papaver somniferum

<400> SEQUENCE: 80

```
Met Asp Ser Ile Asn Ser Ser Ile Tyr Phe Cys Ala Tyr Phe Arg Glu
1               5                   10                  15

Leu Ile Ile Lys Leu Leu Met Ala Pro Leu Gly Val Ser Gly Leu Val
            20                  25                  30

Gly Lys Leu Ser Thr Glu Leu Glu Val Asp Cys Asp Ala Glu Lys Tyr
        35                  40                  45

Tyr Asn Met Tyr Lys His Gly Glu Asp Val Gln Lys Ala Val Pro His
50                  55                  60

Leu Cys Val Asp Val Lys Val Ile Ser Gly Asp Pro Thr Arg Ser Gly
65                  70                  75                  80

Cys Ile Lys Glu Trp Asn Val Asn Ile Asp Gly Lys Thr Ile Arg Ser
                85                  90                  95

Val Glu Glu Thr Thr His Asn Asp Glu Thr Lys Thr Leu Arg His Arg
            100                 105                 110

Val Phe Glu Gly Asp Met Met Lys Asp Phe Lys Lys Phe Asp Thr Ile
        115                 120                 125

Met Val Val Asn Pro Lys Pro Asp Gly Asn Gly Cys Val Val Thr Arg
130                 135                 140

Ser Ile Glu Tyr Glu Lys Thr Asn Glu Asn Ser Pro Thr Pro Phe Asp
145                 150                 155                 160

Tyr Leu Gln Phe Gly His Gln Ala Ile Glu Asp Met Asn Lys Tyr Leu
                165                 170                 175

Arg Asp Ser Glu
            180
```

<210> SEQ ID NO 81
<211> LENGTH: 130
<212> TYPE: PRT
<213> ORGANISM: Papaver somniferum

<400> SEQUENCE: 81

```
Met Tyr Lys His Gly Glu Asp Val Gln Lys Ala Val Pro His Leu Cys
1               5                   10                  15

Val Asp Val Lys Val Ile Ser Gly Asp Pro Thr Arg Ser Gly Cys Ile
            20                  25                  30

Lys Glu Trp Asn Val Asn Ile Asp Gly Lys Thr Ile Arg Ser Val Glu
        35                  40                  45

Glu Thr Thr His Asn Asp Glu Thr Lys Thr Leu Arg His Arg Val Phe
50                  55                  60

Glu Gly Asp Met Met Lys Asp Phe Lys Lys Phe Asp Thr Ile Met Val
65                  70                  75                  80

Val Asn Pro Lys Pro Asp Gly Asn Gly Cys Val Val Thr Arg Ser Ile
                85                  90                  95

Glu Tyr Glu Lys Thr Asn Glu Asn Ser Pro Thr Pro Phe Asp Tyr Leu
            100                 105                 110
```

```
Gln Phe Gly His Gln Ala Ile Glu Asp Met Asn Lys Tyr Leu Arg Asp
        115                 120                 125

Ser Glu
    130
```

COMPOSITIONS AND METHODS FOR MAKING BENZYLISOQUINOLINE ALKALOIDS, MORPHINAN ALKALOIDS, THEBAINE, AND DERIVATIVES THEREOF

CROSS-REFERENCE

This application is a Continuation of U.S. application Ser. No. 16/312,776, filed on Dec. 21, 2018, U.S. patent Ser. No. 11/142,780, which is a 371 of International Application No. PCT/US2017/039589, filed on Jun. 27, 2017 which claims the priority benefit of U.S. Provisional Patent Application Ser. Nos. 62/355,022, filed Jun. 27, 2016; 62/433,431, filed Dec. 13, 2016; 62/438,540, filed Dec. 23, 2016; 62/438,601, filed Dec. 23, 2016; 62/438,702, filed Dec. 23, 2016; 62/438,588, filed Dec. 23, 2016; 62/438,695, filed Dec. 23, 2016; 62/469,006, filed Mar. 9, 2017; and 62/514,104, filed on Jun. 2, 2017, all of which are hereby incorporated herein by reference in their entirety.

SEQUENCE LISTING

The instant application contains a Sequence Listing which has been submitted electronically in ASCII format and is hereby incorporated by reference in its entirety. The ASCII copy was created on Mar. 16, 2022, Sep. 24, 2019, is named 125US12 SequenceListing.txt, and is 114,679 bytes in size.

BACKGROUND OF THE DISCLOSURE

The following paragraphs are provided by way of background and not an admission that anything discussed therein is prior art or part of the knowledge of persons skilled in the art.

Thebaine, a chemical compound also known as paramorphine and codeine methyl enol ether, belongs to the class of compounds known as benzylisoquinoline alkaloids ("BIAs"), and within that class, to a BIA subclass of compounds known as morphinan alkaloids, and has long been recognized as a useful feedstock compound in the manufacture of therapeutic agents, including, for example, morphine and codeine. Other agents that can be manufactured can include but are not limited to oripavine, oxycodone, hydrocodone, oxymorphone, hydromorphone, naltrexone, naloxone, hydroxycodeinone and neopinone. It is known that thebaine in planta is produced from a precursor compound named salutaridine via intermediate morphinan alkaloids named salutaridinol and salutaridinol 7-O-acetate. Currently thebaine may be harvested from natural sources, such as opium poppy capsules (see e.g., U.S. Pat. Appl. Pub. No 2002/0106761; see also e.g., Poppy, the genus *Papaver*, 1998, pp 113, Harwood Academic Publishers, Editor: Bernáth, J.). Alternatively, thebaine may be prepared synthetically. The latter may be achieved by a reaction sequence starting with ketalization of iodoisovanillin (see e.g., Rinner, U. and Hudlicky, T., 2012, Top. Cur. Chem. 309; 33-66; Stork, G., 2009, J. Am. Chem. Soc. 131 (32) pp 11402-11406).

The existing manufacturing methods for BIAs, including thebaine and other morphinan alkaloids and their derivatives, suffer from low yields and/or are expensive. Some of the known methodologies for the manufacture of thebaine exist in the production of undesirable quantities of morphinan alkaloid by-products (see e.g., Rinner, U., and Hudlicky, J., 2012, Top. Cur. Chem. 209: 33-66). No methods exist to commercially biosynthetically manufacture BIAs, including thebaine and other morphinan alkaloids and their derivatives. Therefore, there is a need for improved methods for the synthesis of BIAs including thebaine and other morphinan alkaloids and their derivatives.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

SUMMARY

This application discloses certain alkaloids belonging to the class of benzylisoquinoline alkaloids ("BIAs"), morphinan alkaloids, and their derivatives, as well as to methods of making such BIAs, including morphinan alkaloids (and their derivatives). For example, one BIA that can be made is thebaine.

BIAs, such as morphinan alkaloids, more specifically thebaine, can be produced from sugar (or other substrates). Disclosed herein is a cell (e.g., a microorganism) that comprises one or more nucleic acids encoding for heterologous enzymes that can perform any one of the following reactions: i) sugar to 1-tyrosine; ii) 1-tyrosine to 1-DOPA; iii) 1-DOPA to dopamine; iv) dopamine to (S)-norcoclaurine; v) (S)-norcoclaurine to (S)/(R)-reticuline; vi) (R)-reticuline to salutardine; vii) salutardine to salutaridinol; viii) salutaridinol to salutaridinol-7-O-acetate; ix) salutaridinol-7-O-acetate to thebaine; x) thebaine to oripavine; morphinone; morphine; codeine; codeinone; and/or neopinone. In some instances, the enzyme that converts salutaridinol-7-O-acetate to thebaine is a thebaine synthesis polypeptide (a.k.a. thebaine synthase or BetV1). In some instances, a purine permease is also present within the cell.

The method of converting a sugar (or other substrate) into a BIA, such as thebaine, can also be performed in vitro. The one or more enzymes that can perform any one of the following reactions: i) sugar to 1-tyrosine; ii) 1-tyrosine to 1-DOPA; iii) 1-DOPA to dopamine; iv) dopamine to (S)-norcoclaurine; v) (S)-norcoclaurine to (S)/(R)-reticuline; vi) (R)-reticuline to salutardine; vii) salutardine to salutaridinol; viii) salutaridinol to salutaridinol-7-O-acetate; ix) salutaridinol-7-O-acetate to thebaine; x) thebaine to oripavine, codeine, morphine, oxycodone, hydrocodone, oxymorphone, hydromorphone, naltrexone, naloxone, hydroxycodeinone, neopinone, and/or buprenorphine; can be isolated (or contained in a cellular extract) and used in an in vitro reaction. In some cases, some of the reactions can be performed in vivo (e.g., within a cell), while others can be performed in vitro. For example, sugar can be converted to salutardine in vivo, while the reaction of salutardine to thebaine can occur in vitro. Should thebaine be the end product, a thebaine synthesis polypeptide can be used to covert salutaridinol-7-O-acetate to thebaine in vitro.

In cases where a thebaine synthesis polypeptide is used, a *Papaver* thebaine synthesis polypeptide can be chosen. For example, the thebaine synthesis polypeptide can be a *Papaver somniferum* thebaine synthesis polypeptide. The thebaine synthesis polypeptide can comprise an amino acid sequence substantially identical to SEQ ID NO. 6. In some cases, the thebaine synthesis polypeptide can comprise an amino acid sequence substantially identical SEQ ID NO. 31.

In cases where a purine permease is used, a purine permease from the genus *Papaver* can be chosen. For example, the purine permease can be from a *Papaver somniferum*. The purine permease can comprise a nucleotide sequence substantially identical to SEQ ID NO. 36. The purine permease can comprise a nucleotide sequence substantially identical to SEQ ID NO. 38. The purine permease can comprise a nucleotide sequence substantially identical to any one of SEQ ID NOs. 42, 44, 46, 48, 50, 52, 54, 56, 58, 60, 62, or 64. In some cases, the purine permease can comprise an amino acid sequence substantially identical SEQ ID NO. 35. In some cases, the purine permease can comprise an amino acid sequence substantially identical SEQ ID NO. 37. In some cases, the purine permease can comprise an amino acid sequence substantially identical to any one of SEQ ID NOs. 41, 43, 45, 47, 49, 51, 53, 55, 57, 59, 61, or 63.

In some cases, the cell disclosed herein can be a prokaryote. The cell can also be a eukaryote in some cases. Other microorganisms that can be used are *Saccharomyces cerevisiae, Yarrowia lipolytica*, or *Escherichia coli*.

Also disclosed herein are vectors or chimeric polynucleotides comprising one or more polynucleotides capable of controlling expression in a host cell which is operably linked to a polynucleotide encoding a thebaine synthesis polypeptide. In some cases, a polynucleotide encoding for a purine permease can be within the vector or chimeric polynucleotides.

Another method disclosed herein is a screening method for modulating expression of polynucleotide sequences in a cell expressing thebaine synthesis polypeptide (and/or a purine permease). The screening method can comprise (a) mutagenizing a cell expressing thebaine synthesis polypeptide (and/or purine permease); (b) growing the cell to obtain a plurality of cells; and determining if a cell from has modulated levels of thebaine synthesis polypeptide (and/or purine permease) or if the thebaine synthesis polypeptide (and/or purine permease) has increased/decreased levels of activity compared to a non-mutagenized cell.

Other substrates besides sugar can be used to make BIAs. For example, the method or the microorganism can use sugar, glycerol, L-tyrosine, tyramine, L-3,4-dihydroxyphenyl alanine (L-DOPA), an alcohol, dopamine, or combination thereof, as a substrate to make BIAs.

The BIAs such as thebaine and other morphinan alkaloids and their derivatives obtained from the cells and/or methods disclosed can be used as a feedstock compound in the manufacture of a medicinal compound.

BRIEF DESCRIPTION OF THE DRAWINGS

The disclosure is in the hereinafter provided paragraphs described in relation to its Figures. The Figures provided herein are provided for illustration purposes and are not intended in any way to be limiting.

FIG. 1A depicts the pathway from glucose to L-tyrosine in yeast. TKT, transketolase; E4P, erythrose 4-phosphate; (PEP) phosphoenolpyruvic acid; PEPS (PEP synthetase; DAHPS, DAHP synthase; DAHP, 3-deoxy-D-arabinoheptulosonate 7-phosphate; CM/PDH, chorismate mutase/prephenate dehydrogenase; HPP, hydroxyphenylpyruvate. FIG. 1B depicts the pathway from glucose to L-tyrosine in *E. coli*. XSP, xylulose 5-phosphate; PYR, pyruvate; EPSP, 5-enolpyruvoylshikimate 3-phosphate; CHA, chorismate; PPA, prephenate; HPP, 4-hydroxyphenlypyruvate; L-Glu, glutamic acid; and α-KG, α-ketoglutarate. The enzymes (in boldface) are as follows: PpsA, phosphoenolpyruvate synthase; TktA, transketolase A; AroG, DAHP synthase; AroB, DHQ synthase; AroD, DHQ dehydratase; YdiB, quinate/shikimate dehydrogenase; AroE, shikimate dehydrogenase; AroK/L, shikimate kinase I/II; AroA, EPSP synthase; AroC, chorismate synthase; TyrA, chorismate mutase/prephenate dehydrogenase; and TyrB, tyrosine aminotransferase. QUIN and gallic acid (GA) are side products. QUIN is formed by YdiB from DHQ, while GA is formed by AroE from DHS. The dashed lines indicate where feedback inhibitions occur. FIG. 1C. depicts the pathway from L-tyrosine to thebaine and other morphinan alkaloids such as codeine. FIG. 1D shows another depiction of the biosynthetic pathway from tyrosine to morphine in opium poppy. The enzymes listed are as follows: TYDC, tyrosine/DOPA decarboxylase; TyrAT, tyrosine aminotransferase; NCS, norcoclaurine synthase; 6OMT, norcoclaurine 6-O-methyltransferase; CNMT, coclaurine N-methyltransferase; NMCH, N-methylcoclaurine 3'-hydroxylase; 3'-hydroxyl-N-methylcoclaurine 4'-O-methyltransferase; REPI, reticuline epimerase; SalSyn, salutaridine synthase; SalR, salutaridine reductase; SalAT, salutaridinol 7-O-acetyltransferase; THS, thebaine synthesis polypeptide (a.k.a., thebaine synthase or Betv1); T6ODM, thebaine 6-O-methyltransferase; COR, codeinone reductase; CODM, codeine O-demethylase.

FIGS. 6A-6G. FIG. 6A shows that thebaine formation is enhanced using latex protein extracts in SalAT-coupled assays. Using SalAT alone, a major product with m/z 330 and little thebaine were formed. With the addition of latex protein extracts, thebaine (m/z 312) formation increased substantially and the relative abundance of the m/z 330 compound decreased. The additional mannitol during latex protein extraction further enhanced thebaine formation. Denatured latex protein was as a negative control. FIG. 6B shows the LC-MS$_n$ characterization of the m/z 330 by-product(s) of SalAT-coupled assays performed in the absence of latex protein extracts. FIG. 6C depicts the proposed identity and reaction mechanism leading to the formation of the m/z 330 by-product(s) of SalAT-coupled assays performed in the absence of latex protein extracts. Either or all of the putative m/z 330 by-products could be formed. FIGS. 6D-6F show the elution profiles for hydrophobic interaction chromatography (HIC) on a butyl-S sepharose column (FIG. 6D), ion-exchange (IEX) on a HiTrap Q column (FIG. 6E), and size-exclusion chromatography (SEC) on a Superdex 75 HR 10/30 column (FIG. 6F). Elution fractions containing thebaine-forming protein active in SalAT-coupled assays are shown as grey bars. Fractions 10-13 from the SEC step were pooled and subjected to proteomics analysis. FIG. 6G shows a partial purification table for the thebaine-forming protein active in SalAT-coupled assays.

FIG. 7A-7G. FIG. 7A depicts certain experimental results, notably relative amounts of thebaine produced by SalAT in the presence of several protein fractions (AS, HIC, IEC and HA fractions) from the purification process, as further described in Example 1. Also shown is a polyacrylamide gel following gel electrophoresis of the same protein extracts. FIGS. 7B-7D depict an SDS-PAGE for of each step in the purification of the thebaine-forming protein active in SalAT-coupled assays. FIG. 7B show crude latex protein, ammonium sulphate (AS) precipitate, and HIC and IEX chromatographic fractions resolved on 10% SDS-PAGE gels. FIG. 7C show fractions 10-13 from the SEC step resolved on a 10% SDS-PAGE gel. FIG. 7D show the combined SEC fractions 10-13 resolved on a 14% SDS-PAGE gel. FIG. 7E shows the top six candidates for the thebaine-forming protein active in SalAT-coupled assays from proteomics analysis of the three bands resolved on a 14% SDS-PAGE gel of the combined SEC fractions 10-13 (FIG. 7D). FIG. 7F depicts a protein sequence alignment of the top six candidates for the thebaine-forming protein active in SalAT-coupled assays. Betv1-1 (SEQ ID NO. 6) is also referred to as thebaine synthesis polypeptide or thebaine synthase throughout the disclosure. FIG. 7G depicts certain experimental results, notably two polyacrylamide gels following gel electrophoresis of protein extracts (SEC and HA fractions) and purification of the 16-18 kDa bands after inclusion of the SEC step before the hydroxyapatite (HA) step, with retention of the thebaine synthesis protein (TS) activity, as further described in Example 1.

FIG. 8A shows $His_6$-tag affinity-purified candidate proteins resolved by SDS-PAGE. FIG. 8B shows LC-MS chromatographs in SalAT-coupled assays showing enhanced thebaine (m/z 312) and reduced m/z 330 by-product formation by one candidate, Betv1-1.

FIGS. 9A-9C depict the testing of the top six candidates for the thebaine-forming protein active in *Saccharomyces cerevisiae* cultures fed salutaridine for 24 hours. FIG. 9A depicts the pathway showing the conversion of salutaridine to thebaine by the successive actions of SalR, SalAT and thebaine synthesis polypeptide (THS). Betv1-1 is also referred to as thebaine synthesis polypeptide or thebaine synthase throughout the disclosure. FIG. 9B depicts an immunoblot showing the occurrence of all six candidate proteins in independent yeast strains.

FIG. 9C shows thebaine formation in engineered yeast strains expressing the six candidate genes. Empty vector refers to a yeast strain expressing only SalR and SalAT. FIG. 9D shows thebaine production titers from extracts of *E. coli* expressing SaltAT, Bet v1-1A, Bet v1-1B, PR10-3A, PR10-3B, and all constructs together. Bet v1-1A refers to a C-terminal HA tagged Betv1, whereas Bet v1-1B corresponds to an N-terminal HA tagged Betv1. Bet v1-1B produced the most thebaine from single construct extracts whereas Bet v1-1A produced slightly less. Extracts from *E. coli* expressing all constructs together produced the highest titers of thebaine.

FIGS. 11A-D. FIG. 11A shows the genomic organization of genes encoding two isoforms of reticuline epimerase (REPI), salutaridine synthase (SalSyn), salutaridine reductase (SalR), salutaridine 7-O-acetyltransferase (SalAT), and thebaine synthesis polypeptide (THS) as present in the *Papaver somniferum*. Several other uncharacterized genes are also physically linked to the cluster of genes involved in the conversion of (S)-reticuline to thebaine. THS1 is a thebaine synthesis polypeptide isoform represented by SEQ ID NO. 80; and THS2 is a thebaine synthesis polypeptide isoform represented by SEQ ID NO. 6. FIG. 11B shows the alignment of THS1 and THS2 isoforms. THS1 is a thebaine synthesis polypeptide isoform represented by SEQ ID NO. 80; THS1s is a thebaine synthesis polypeptide isoform represented by SEQ ID NO. 81; THS2 is a thebaine synthesis polypeptide isoform represented by SEQ ID NO. 6; and THS2s is a thebaine synthesis polypeptide isoform represented by SEQ ID NO. 32. FIG. 11C shows a proteomics analysis of protein extracts derived from whole stem, latex-free stem, and latex isolated from the opium poppy T chemotype. FIG. 11D depicts a phylogenetic tree of selected PR10-family proteins from plants. Characterized PR10 proteins with resolved 3D structures were selected from *Arabidopsis thaliana, Betula pendula, Lupinus luteus, Thalictrum flavum*, and *Vigna* radiate. Uncharacterized THS orthologs were selected from related *Papaver* species including *Papaver bacterium, Papaver rhoeas*, and *Papaver setigerum*. An alignment was constructed using CLUSTALW with a cost matrix of BLOSUM. The phylogenetic tree was then built on the basis of the alignment using PHYML with a substitution model of LG and 100 bootstraps.

FIGS. 12A-12C. FIG. 12A is a schematic representation showing the location of primers used for the detection of specific THS genes and splice-variants. The location of fragments used for virus-induced gene silencing (VIGS) is also shown. THS1 is a thebaine synthesis polypeptide isoform represented by SEQ ID NO. 80; THS is a thebaine synthesis polypeptide isoform represented by SEQ ID NO. 81; THS2 is a thebaine synthesis polypeptide isoform represented by SEQ ID NO. 6, and THS2s is a thebaine synthesis polypeptide isoform represented by SEQ ID NO. 32. FIG. 12B show the primers used for the detection of specific THS genes and splice-variants and the analysis of VIGS experiments. (SEQ ID NOs. 65 to 78) The synthesized VIGS fragment consisting of two fused THS-specific transcript sequences is also provided. (SEQ ID NO. 79) FIG. 12C shows tissue-specific expression patterns of THS genes and splice-variants within *Papaver somniferum*. SYBR Green-based qRT-PCR was performed using gene-specific primers. Values represent the mean±standard deviation of three biological replicates.

FIG. 13A demonstrates the detection of the pTRV2 (EV) and pTRV2-THS (THS) vectors in *Agrobacterium tumefaciens*-infiltrated plants. FIG. 13B shows virus-induced gene-silencing (VIGS) of THS transcripts and corresponding effects on selected alkaloid levels compared with empty-vector controls. Values represent the mean±standard deviation of three biological replicates.

FIG. 14A shows affinity His$_6$-tag purification of THS isoforms produced in *Escherichia coli*. Purified proteins were resolved on by SDS-PAGE. FIG. 14B shows in vitro enzyme assays of THS isoforms in a SalAT-coupled assay. THS1 and THS2 were active and increased thebaine (m/z 312) formation substantially at the expense of the m/z 330 compound(s). The THS1s and THS2s spice variants were not active.

FIGS. 15A-15B shows homodimerization of THS proteins. THS1 is a thebaine synthesis polypeptide isoform represented by SEQ ID NO. 80; THS1s is a thebaine synthesis polypeptide isoform represented by SEQ ID NO. 81; THS2 is a thebaine synthesis polypeptide isoform represented by SEQ ID NO. 6, and THS2s is a thebaine synthesis polypeptide isoform represented by SEQ ID NO. 32. FIG. 15A is an SDS-PAGE and immunoblot analysis showing the cross-linking of purified recombinant THS1 and TH2 isoforms (asterisks in the middle near 46 kDa) and the formation of higher molecular weight oligomers (upper asterisks), and the limited cross-linking of the THS1s and TH2s splice-variants. FIG. 15B shows an SEC chromatography of purified recombinant THS2 showing a predominant homodimer with a molecular weight of ~40 kDa, and several higher molecular weight oligomers (upper asterisks).

FIG. 16A shows compounds tested as alternative substrates or competitive inhibitors of salutaridinol 7-O-acetate. FIG. 16B shows the relative conversion of salutaridinol 7-O-acetate to thebaine in standard THS2 assays using different concentrations of alternative substrates or competitive inhibitors.

FIG. 18A displays the engineered yeast strains for production salutaridine and thebaine from norlaudanosoline. FIG. 18B shows thebaine titers in supernatants of three engineered yeast strains (SC-2, SC-3 and SC-4). FIG. 18C shows relative peak area of unknown side product (m/z 330) in the supernatant in SC-3 and SC-4 strains. Yeast were grown in medium supplemented with 2.5 mM NLDS and 10 mM L-methionine for 96 hours. Error bars indicate standard deviations from four biological replicates.

FIG. 19A shows relative thebaine titers produced from yeast expressing various constructs. The various constructs include PR10-3; Bet v1-1; PR10-4; PR10-5; PR10-7; MLP15; MLP-2; and MLP-3, with either C- or N-terminus HA-tags. The N-terminally tagged Bet v1-1 (HA-Betv1-1) demonstrates the highest level of relative thebaine production. 50 µM salutaridine was fed for 48 hours. Each construct was expressed on a high copy plasmid. n=3. FIG. 19B shows the relative peak area of unknown side product (m/z 330). The N-terminally tagged Bet v1-1 (HA-Betv1-1) demonstrates the lowest level of relative m/z 330 production. Peak area is shown relative to the empty vector control. Error bars indicate standard deviations from three biological replicates.

FIGS. 20A-20C. FIG. 20A shows relative thebaine titers produced from yeast expressing integrated Bet v1-1. 1 mM Salutaridine was fed for 48 hours. Bet v1-1 splice variants were tested from a single integrated copy on the genome (under a pGAL promoter). N=4. The control strain contained pGAL1 SalR and pTEA1 SalAT. Betv1-1 is a thebaine synthesis polypeptide represented by SEQ ID NO. 6 (i.e., Betv1-1 is the same as THS2). FIG. 20B shows relative thebaine titers produced from yeast expressing integrated Bet v1-1, Bet v1-1S, and Bet v1-1L. Bet v1-1S is a thebaine synthesis polypeptide represented by SEQ ID NO 32 (i.e., Betv1-1S is the same as THS2s). Bet v1-1L is a thebaine synthesis polypeptide represented by SEQ ID NO 31. Same conditions were used. FIG. 20C shows the amino acid sequences of the splice variants used in the experiments of FIG. 20B.

FIG. 21A shows thebaine titers produced from three yeast strains (Sc-2, Sc-3, Sc-4, the components of which are shown in FIG. 18A). FIG. 21B shows reticuline titers produced from the three yeast strains. FIG. 21C shows salutaridine titers produced from the three yeast strains.

FIG. 22A shows the effect of fusing green fluorescent protein (GFP) on the catalytic function of THS1 and THS2 in engineered yeast with chromosomally integrated SalR and SalAT. THS2 is a thebaine synthesis polypeptide isoform represented by SEQ ID NO. 6. Yeast were fed salutaridine and thebaine accumulation in the culture medium was monitored at 24 hours. FIG. 22B depicts the location of GFP florescence in various yeast strains containing a THS1-GFP and THS2-GFP fusions, compared with an native GFP, and fusion of GFP to a previously characterized protein possessing an N-terminal secretion signal (ssp-GFP). GFP-mediated florescence was only detected in cells, but not in the culture medium. FIG. 22C shows the cellular localization of GFP-mediated florescence in yeast producing native GFP, THS2-GFP and THS1-GFP. Only THS1, which possesses a putative secretion signal peptide, resulted in an altered localization of florescence associated the yeast cell periphery.

FIGS. 23A-23C show titers of S-reticuline, R-reticuline, and salutaridine in identical yeast strains except for expressing 1 of 11 different purine permeases. The yeast strains were given a NLDS feed. FIG. 23 shows S-reticuline titers grown for 24 (left) and 48 (right) hours in the presence of an NLDS feed. FIG. 23B shows R-reticuline titers grown for 24 (left) and 48 (right) hours in the presence of an NLDS feed. FIG. 23C shows salutaridine titers grown for 24 (left) and 48 (right) hours in the presence of an NLDS feed. FIG. 23D shows NLDS and reticuline titers grown for 24 (left) and 48 (right) hours in the presence of an L-DOPA feed. PsomPUP1-4 was expressed on a high copy plasmid under the control of pGAL.

Figure 25:
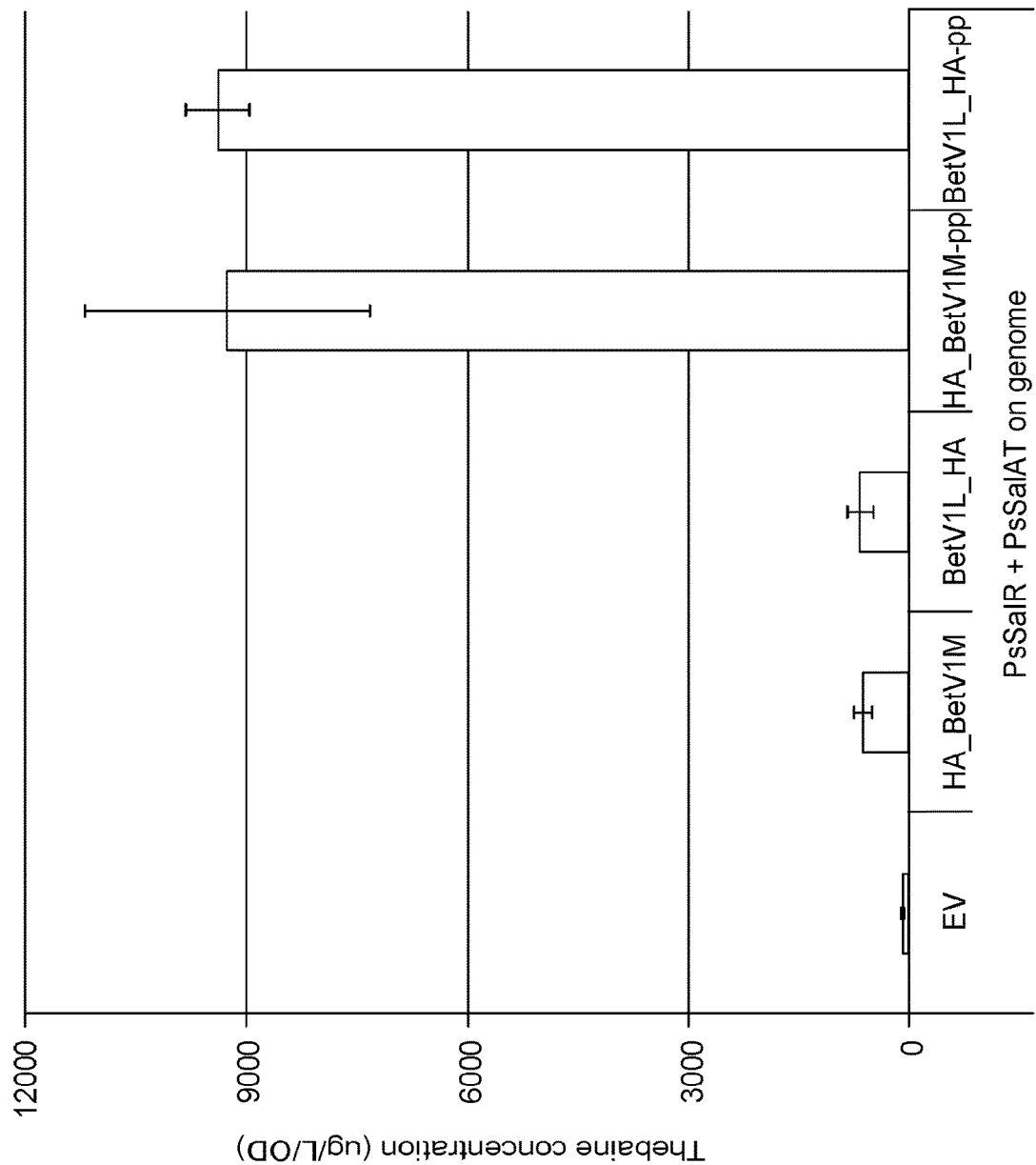

FIG. 25 shows a graph showing concentrations of thebaine (μg/I/OD) present in growth medium comprising salutaridine following growth of different yeast strains expressing Betv-1 alone (HA_BetV1M and BetV1L_HA), or Betv-1 together with purine permease (HA_BetV1M-pp and BetV1L_HA-pp), as well as a control (EV). HA_BetV1M is an HA tagged thebaine synthesis polypeptide, where the thebaine synthesis polypeptide is represented by SEQ ID NO. 6. BetV1L_HA is an HA tagged thebaine synthesis polypeptide, where the thebaine synthesis polypeptide is represented by SEQ ID NO. 31. The purine permease used in this experiment is represented by SEQ ID NO. 35.

Figure 26:
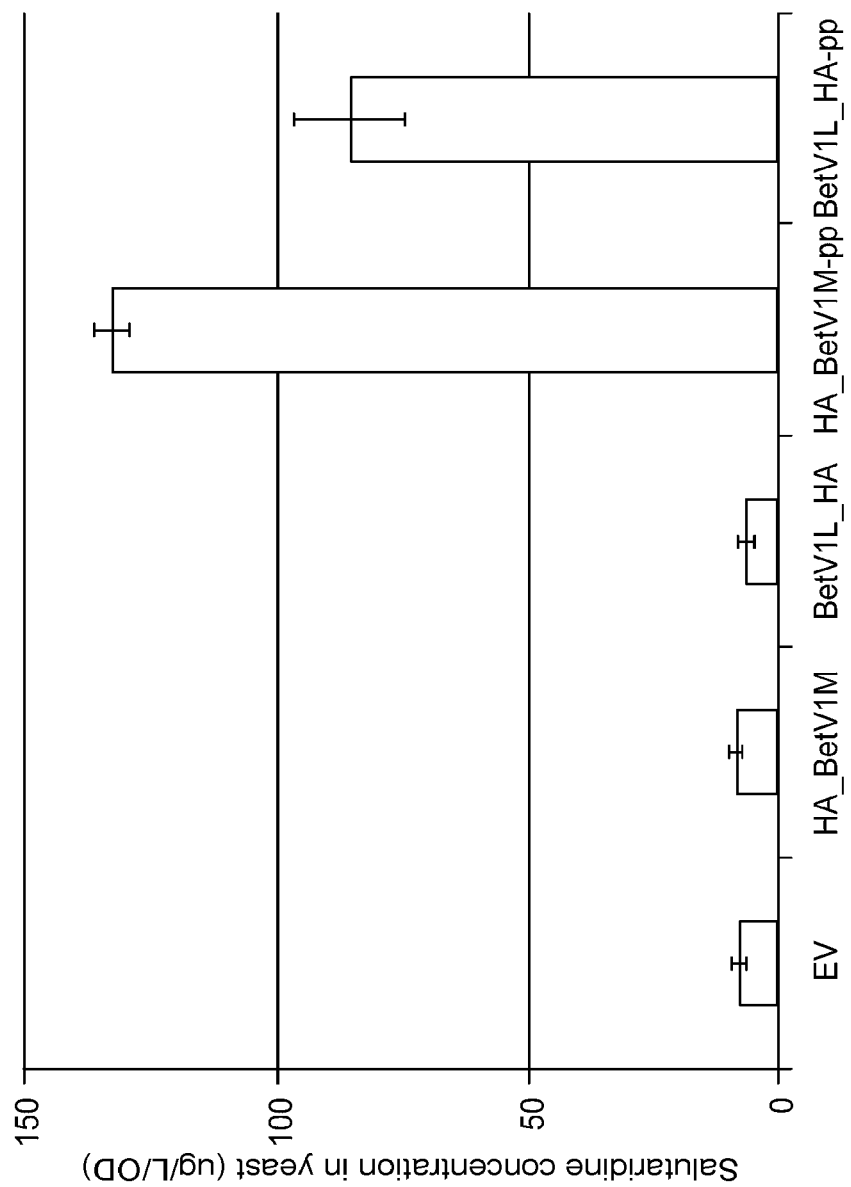

FIG. 26 depicts a graph showing salutaridine (μg/I/OD) present in growth medium comprising salutaridine following growth of different yeast strains expressing Betv-1 alone (HA_BetV1M and BetV1L_HA), or Betv-1 together with purine permease (HA_BetV1M-pp and BetV1L_HA-pp), as well as a control (EV). HA_BetV1M is an HA tagged thebaine synthesis polypeptide, where the thebaine synthesis polypeptide is represented by SEQ ID NO. 6. BetV1L_HA is an HA tagged thebaine synthesis polypeptide, where the thebaine synthesis polypeptide is represented by SEQ ID NO. 31. The purine permease used in this experiment is represented by SEQ ID NO. 35.

Figure 27A:
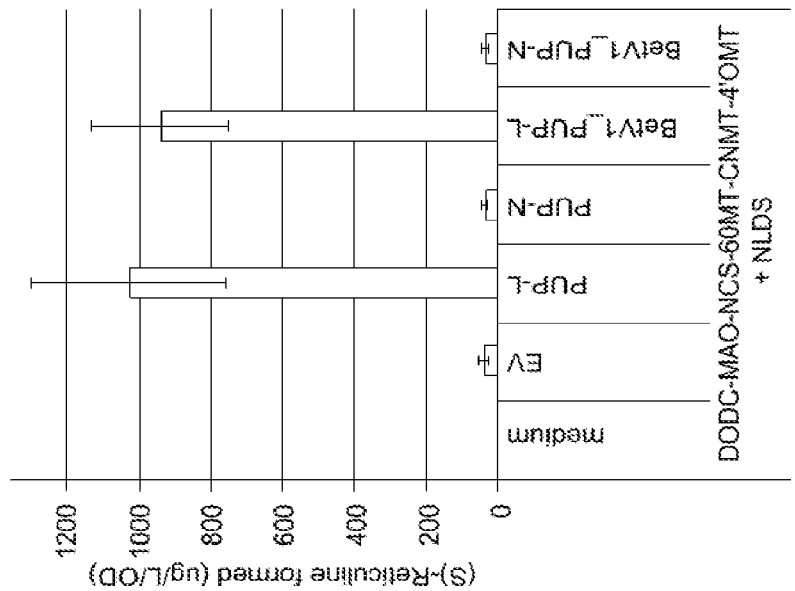
Figure 27B:
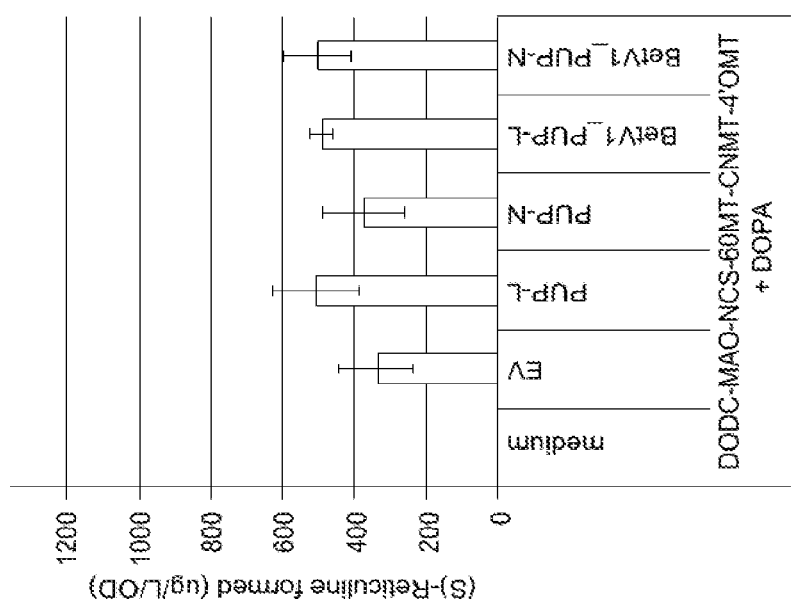

FIGS. 27A and 27B depicts a graph showing reticuline (μg/I/OD) present in a growth medium comprising either DOPA (FIG. 27A) or norlaudanosoline (NLDS) (FIG. 27B), following growth of yeast strains expressing DODC, MAO, NCS, 6OMT, CNMT and 4'OMT genes, and transformed with a gene expressing a first purine permease (PUP-L) or a second purine permease (PUP-N), each either alone or together with Betv-1. Betv-1 is a the thebaine synthesis polypeptide represented by SEQ ID NO. 6. The PUP-L is a purine permease represented by SEQ ID NO. 35. The PUP-N is a purine permease represented by SEQ ID NO. 37.

FIGS. 28A and 28B depicts a graph showing reticuline and thebaine (μg/I/OD) present in a growth medium comprising (S)-reticuline in a yeast expressing REPI, CPR and SalSyn (FIG. 28A) or REPI, CPR, SalSyn, SalAT and SalR (FIG. 28B), each yeast strain transformed with a first purine permease (PUP-L) or a second purine permease (PUP-N), each either alone or together with Betv-1. Betv-1 is a the thebaine synthesis polypeptide represented by SEQ ID NO. 6. The PUP-L is a purine permease represented by SEQ ID NO. 35. The PUP-N is a purine permease represented by SEQ ID NO. 37.

FIGS. 29A and 29B depicts a graph showing reticuline and thebaine (μg/I/OD) present in a growth medium comprising (R)-reticuline in a yeast expressing REPI, CPR and SalSyn (FIG. 29A) or REPI, CPR, SalSyn, SalAT and SalR (FIG. 29B), each yeast strain transformed with a first purine permease (PUP-L) or a second purine permease (PUP-N), each either alone or together with Betv-1. Betv-1 is a the thebaine synthesis polypeptide represented by SEQ ID NO. 6. The PUP-L is a purine permease represented by SEQ ID NO. 35. The PUP-N is a purine permease represented by SEQ ID NO. 37.

FIGS. 30A and 30B depicts a graph showing thebaine (μg/I/OD) present in a growth medium comprising salutaridine in a yeast expressing SalR and SalAT (FIG. 30A) or REPI, CPR, SalSyn, SalAT and SalR (FIG. 30B), each yeast strain transformed with a first purine permease (PUP-L) or a second purine permease (PUP-N), each either alone or together with Betv-1. Betv-1 is a the thebaine synthesis polypeptide represented by SEQ ID NO. 6. The PUP-L is a purine permease represented by SEQ ID NO. 35. The PUP-N is a purine permease represented by SEQ ID NO. 37.

The figures together with the following detailed description make apparent to those skilled in the art how the disclosure may be implemented in practice.

DETAILED DESCRIPTION OF THE DISCLOSURE

BIAs can be produced in cells (e.g., microorganisms) by genetic engineering. For example, when producing morphinan alkaloids from microbial fermentation, a sugar substrate can be used to produce morphinan alkaloids. From sugar to the first morphinan alkaloid thebaine, there are at least 9 conversions required.

Figure 1A:
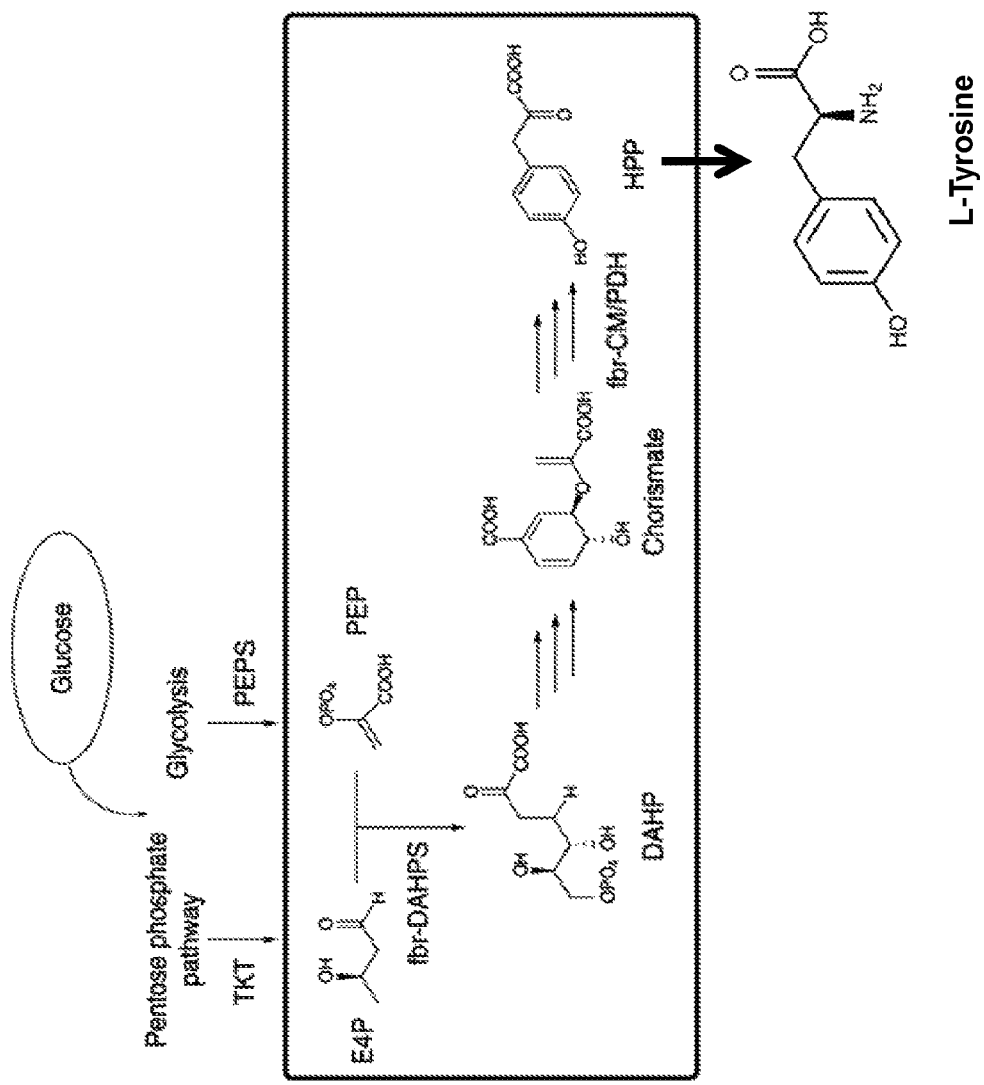
FIGS. 1A-1D.
Figure 1B:
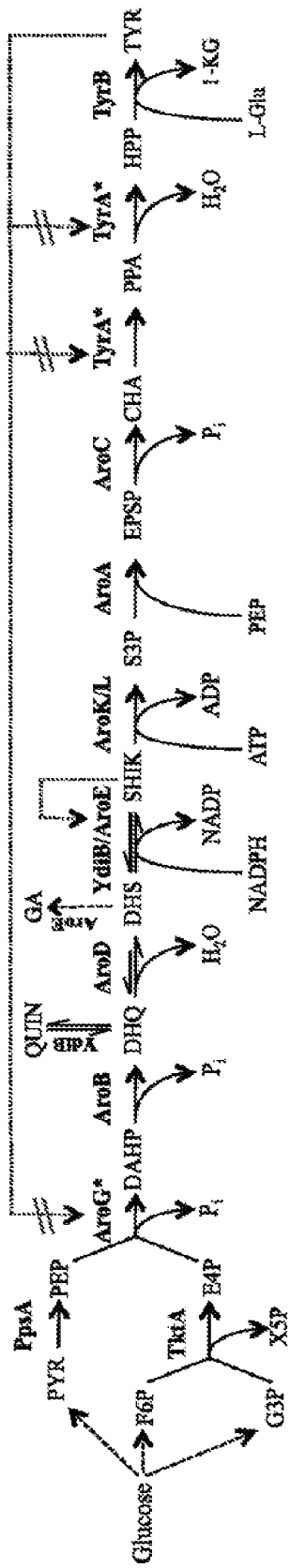
Figure 1C:
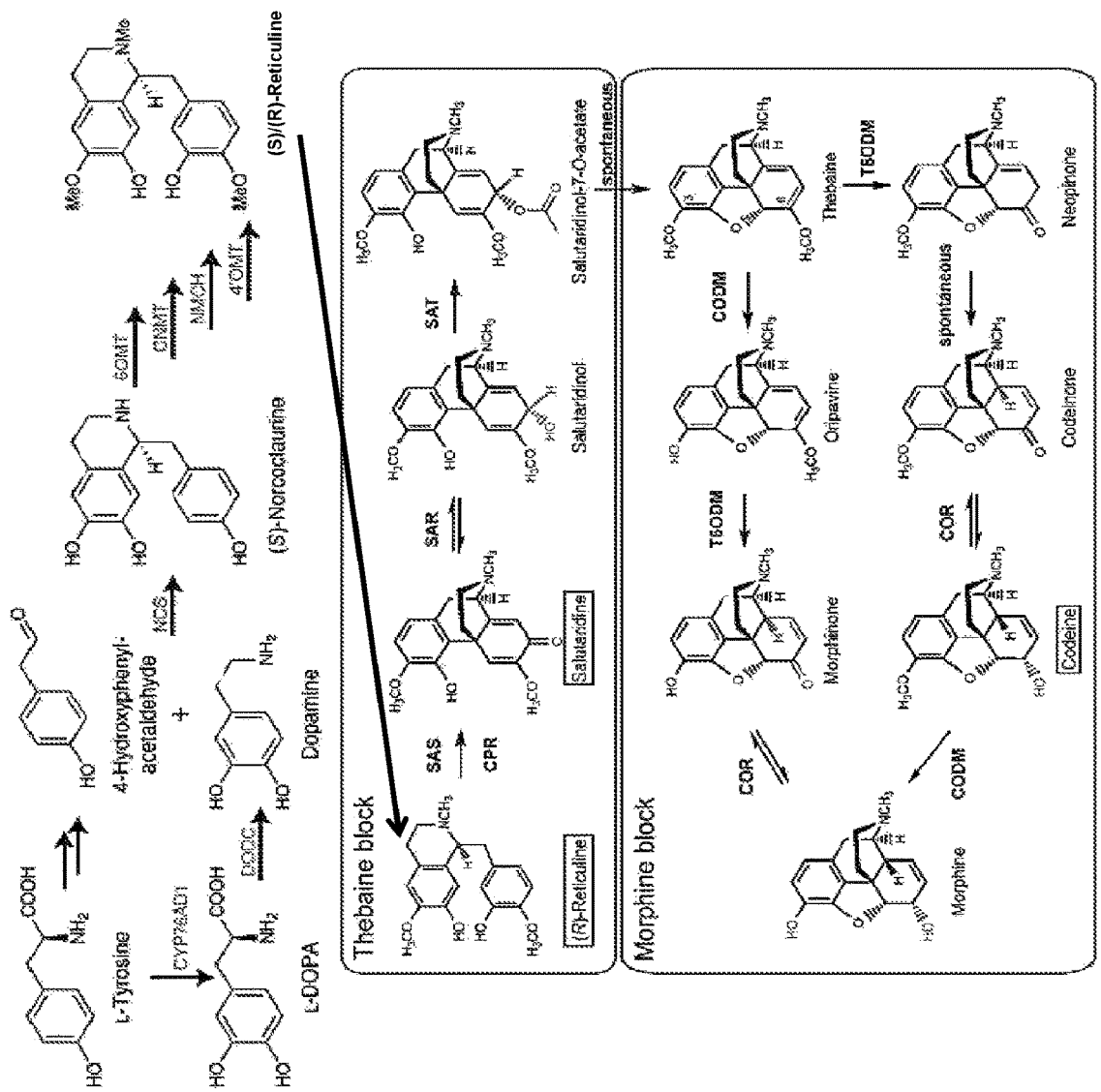
Figure 1D:
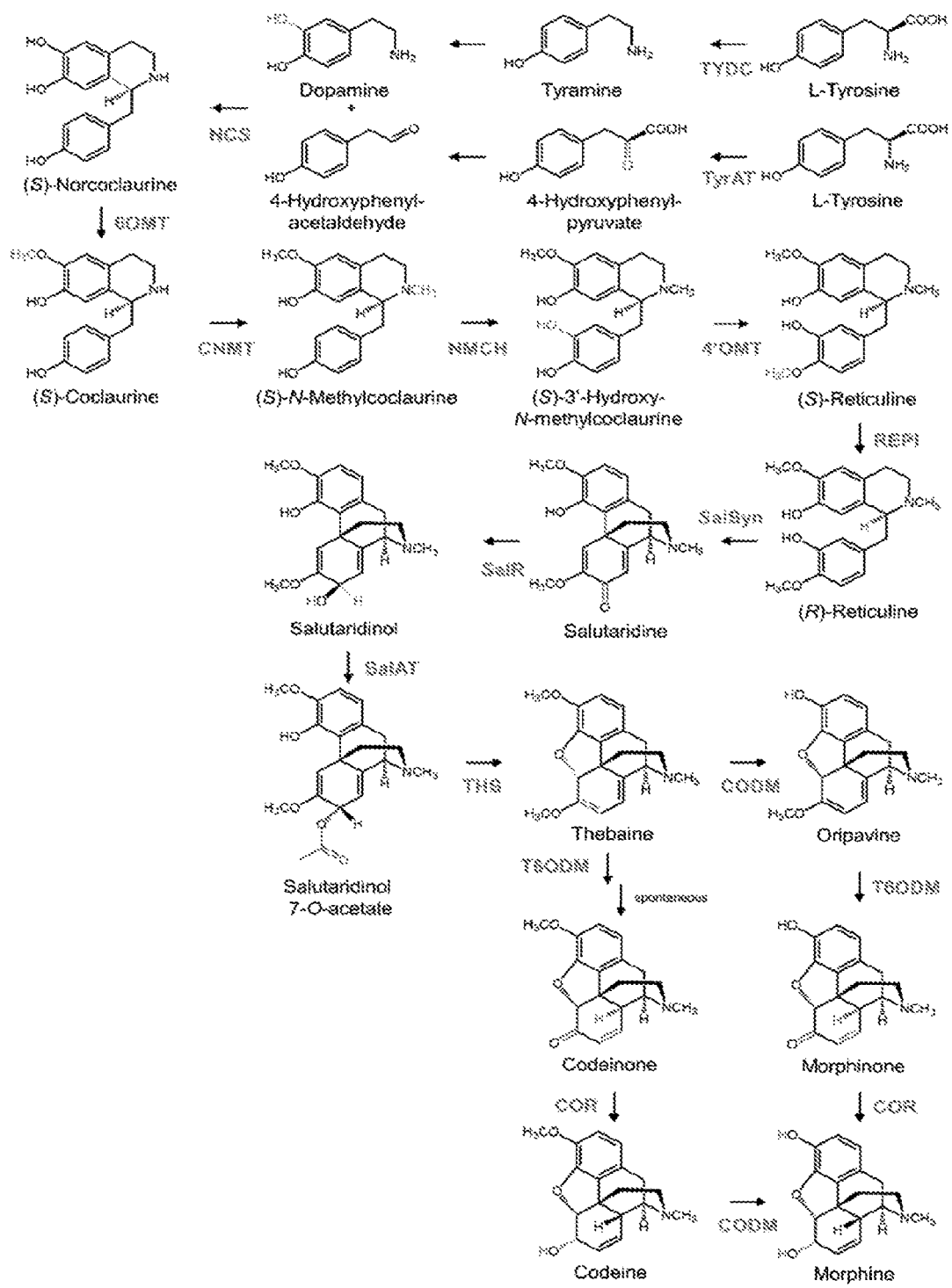

In the first conversion, sugar, such as glucose, can be converted into L-tyrosine. FIG. 1A shows the molecular pathway from glucose to L-tyrosine in yeast. In bacteria, glucose can be converted into L-tyrosine by using a variety of enzymes. FIG. 1B shows the molecular pathway from glucose to L-tyrosine in bacteria such as *E. coli*.

The second conversion, 1-tyrosine to 1-DOPA can be performed by using a tyrosine hydroxylase (e.g., a cytochrome p450 such as CYP76AD1) to catalyze this reaction. The third conversion 1-DOPA to dopamine can be catalyzed by a DOPA decarboxylase (DODC). The fourth conversion makes use of one norcoclaurine synthase (NCS). The fifth conversion from (S)-norcoclaurine to (S)/(R)-reticuline takes advantage of one or more of several enzymes including but not limited to: 6OMT (6-O-Methyltransferase), CNMT (coclaurine N-methyltransferase), NMCH (cytochrome P450 N-methylcoclaurine hydroxylase a.k.a. CYP80B1), and 4OMT (4-O-Methyltransferase). The sixth conversion of (R)-reticuline to salutardine requires CPR (cytochrome P450 reductase) and SAS (salutaridine synthase). The seventh conversion of salutardine to salutaridinol uses salutaridine reductase. The eighth conversion of salutaridinol to salutaridinol-7-O-acetate takes advantage of salutaridinol-7-O-acetyltransferase. The ninth conversion of salutaridinol-7-O-acetate to thebaine was previously thought to be a spontaneous process (e.g., at an elevated pH). However, the inventors herein have found that a thebaine synthesis polypeptide can catalyze this reaction, orders of magnitude over a spontaneous reaction. Further, the addition of a purine permease can further greatly increase thebaine (and other intermediate) titers.

Thebaine can be further converted into derivative morphinan alkaloids such as oripavine, codeine, morphine, oxycodone, hydrocodone, oxymorphone, hydromorphone, naltrexone, naloxone, hydroxycodeinone, neopinone, and/or buprenorphine. For example, the conversion of thebaine to oripavine uses codeine O-demethylase (CODM). Oripavine can be further converted to morphinone using a thebaine 6-O-demethylase (T6ODM). Morphinone can be converted to morphine using codeinone reductase (COR). COR can also convert morphine into morphinone. Thebaine can be converted into neopinone by a thebaine 6-O-demethylase. The reaction of neopinone into codeinone is believed to be spontaneous. Codeinone can be converted into codeine through the use of COR. The reverse reaction from codeine to codienone can also be catalyzed by COR. Codeine can be converted into morphine by using a CODM.

Definitions

Figure 2:
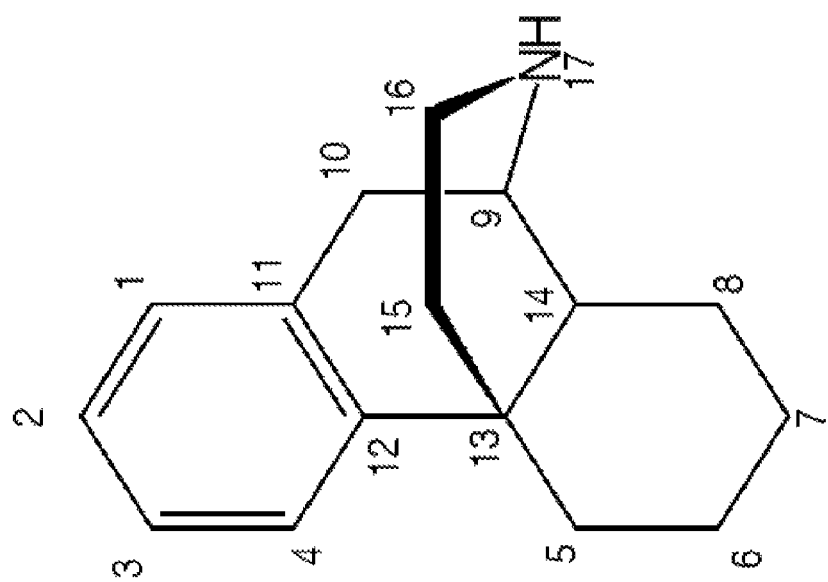
FIG. 2 depicts a prototype chemical structure of a morphinan alkaloid. Various atoms within the structures have been numbered for ease of reference.

The terms "morphinan alkaloid", or "morphinan alkaloid compound", as may be used interchangeably herein, can refer to a class of chemical compounds comprising the prototype chemical structure shown in FIG. 2. Certain specific carbon and nitrogen atoms are numbered and may be referred to herein by reference to their position within the morphinan alkaloid structure e.g. $C_1$, $C_2$, $N_{17}$, etc. The pertinent atom numbering is shown in FIG. 2.

The term "oxo group", as used herein, can refer to a group represented by "=O".

The term "O-acetyl group", as used herein, can refer to a group represented by

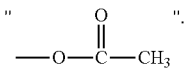

Figures 3A, 3B, 3C:
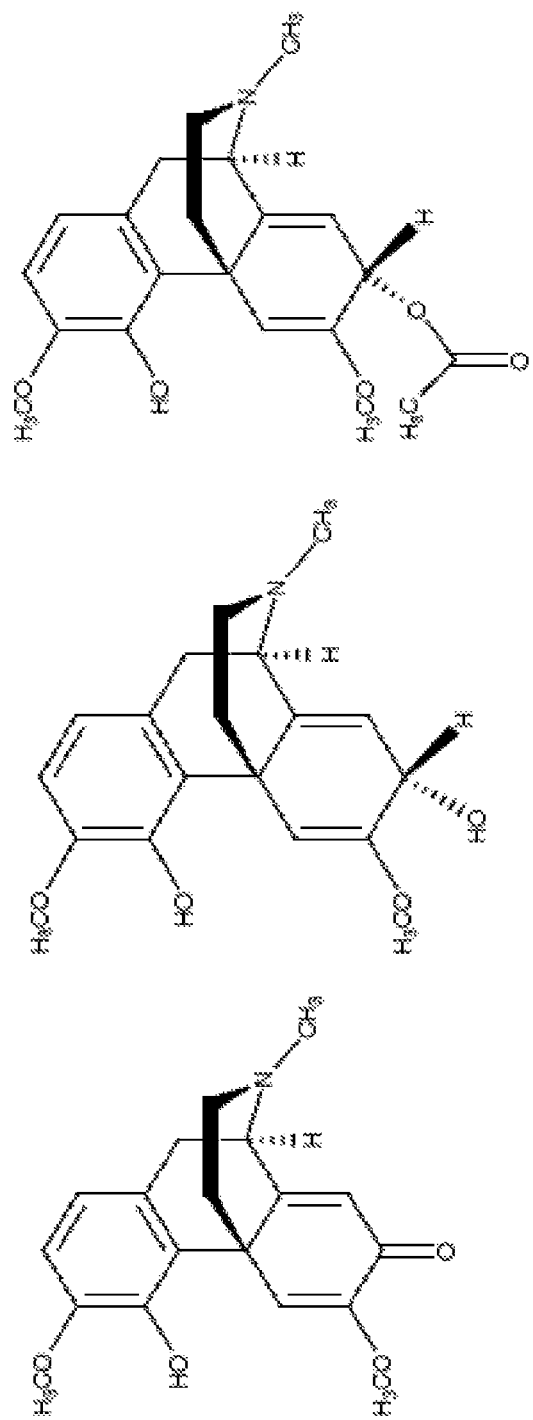
FIGS. 3A-C depicts the chemical structures of example substrate morphinan alkaloids, notably salutaridine (FIG. 3A), salutaridinol (FIG. 3B), and salutaridinol 7-O-acetate (FIG. 3C).
Figure 4:
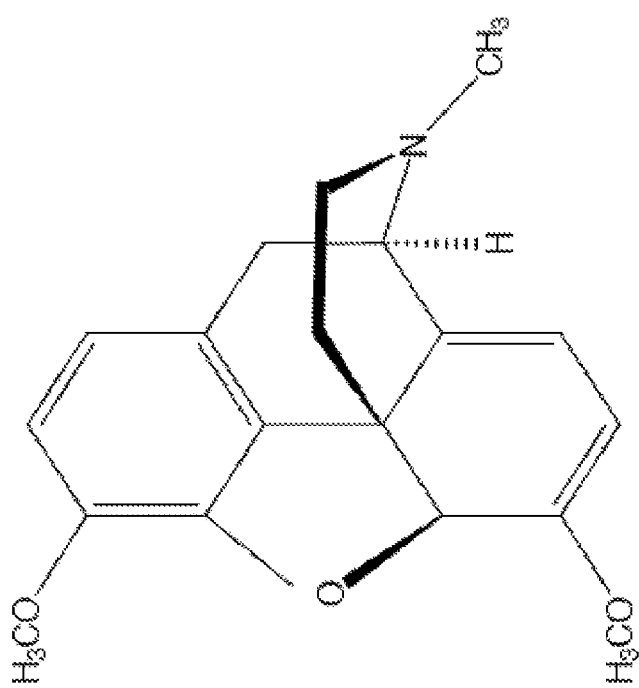
FIG. 4 depicts the chemical structure of the morphinan alkaloid compound thebaine.

The term "substrate morphinan alkaloid", as used herein, can refer to a morphinan alkaloid compound that can be converted into a morphinan alkaloid such as thebaine or other morphinan alkaloid or derivatives thereof. For example, exogenously or endogenously provided substrate morphinan alkaloids can be more efficiently converted in a first in vivo or in vitro reaction mixture into thebaine in the presence of thebaine synthesis polypeptide, than in a second reaction mixture identical to the first reaction mixture but for the absence of thebaine synthesis polypeptide. A conversion is deemed "more efficient" if larger quantities of thebaine are obtained in the reaction mixture and/or if thebaine accumulates in the reaction mixture at a faster rate. Substrate morphinan alkaloids include, but are not limited to the morphinan alkaloid compounds set forth in FIGS. 3 A-C.

The term "intermediate morphinan alkaloid compound", as used herein, can refer to a morphinan alkaloid compound formed upon chemical conversion of a substrate morphinan alkaloid compound, and which subsequently can be converted into a BIA such as thebaine or other morphinan alkaloid compound derivatives.

The term "substrate", as used herein, can refer to any compound that can be converted into a different compound. For example, 1-DOPA can be a substrate for DODC and can be converted into dopamine. For clarity, the term "substrate" includes all substrates including but not limited to base substrates, substrate morphinan alkaloids, and/or intermediate morphinan alkaloid compound.

The term "base substrate", as used herein, can refer to any exogenously provided organic carbon compounds which can be metabolized by a microorganism to permit the microorganism to produce an alkaloid, e.g., a morphinan alkaloid. Examples of base substrates include, without limitation, sugar compounds, such as, for example, glucose, fructose, galactose and mannose, as well as glycerol, L-tyrosine, tyramine, L-3,4-dihydroxyphenylalanine (L-DOPA), alcohols (e.g., ethanol), dopamine, or any combination thereof.

The term "morphinan alkaloid derivative of thebaine", as used herein can refer to a morphinan alkaloid compound that can be obtained by chemical conversion of thebaine and includes, without limitation, oripavine, codeine, morphine, oxycodone, hydrocodone, oxymorphone, hydromorphone, naltrexone, naloxone, hydroxycodeinone, neopinone, buprenorphine, or any combination thereof.

The term "thebaine synthesis polypeptide", can refer to any polypeptide that can facilitate the conversion of a substrate into thebaine. For example, a thebaine synthesis polypeptide can be polypeptide that can convert salutaridinol-7-O-acetate into thebaine. In one example, thebaine synthesis polypeptide can be called "Bet v1" (or derivatives, fragments, variants thereof). Thebaine synthesis polypeptide can also be called "thebaine synthase" (THS). Further, variants/isoforms of the thebaine synthesis polypeptide are described throughout. For example, Betv1/Betv1M/BetV1-1/THS2 can refer to a sequence that is represented by SEQ ID NO. 6. BetV1L and BetV1-1L can refer to a sequence that is represented by SEQ ID NO. 31. THS2s and BetV1-1S can refer to a sequence that is represented by SEQ ID NO. 32. THS1 can refer to a sequence that is represented by SEQ ID NO. 80. THS1s can refer to a sequence that is represented by SEQ ID NO. 81. Bet v1-1A can refer to a C-terminal HA tagged Betv1, whereas Bet v1-1B can correspond to N-terminal HA tagged Betv1.

The terms "salutaridinol 7-O-acetyltransferase", "SalAT", and "SalAT polypeptide", can be used interchangeably herein, and can refer to any polypeptide that can facilitate the conversion of a substrate into salutaridinol 7-O-acetate. For example, SalAT can refer to any and all polypeptides that can convert salutaridinol to salutaridinol-7-O-acetate.

The terms "salutaridine reductase", "SalR", and "SalR polypeptide", can be used interchangeably herein, and can refer to any polypeptide that can facilitate the conversion of a substrate into salutaridinol. For example, SalR can refer to any and all polypeptides that can convert salutaridine to salutaridinol.

The term "polynucleotide encoding a thebaine synthesis polypeptide" can refer to any and all polynucleotide sequences encoding a thebaine synthesis polypeptide.

The terms "polynucleotide encoding a SalAT" and "polynucleotide encoding a SalAT polypeptide", can be used interchangeably herein, and can refer to any and all polynucleotide sequences encoding a salutaridinol 7-O-acetyltransferase ("SalAT") polypeptide.

The terms "polynucleotide encoding a SalR" and "polynucleotide encoding a SalR polypeptide", can be used interchangeably herein, and can refer to any and all polynucleotide sequences encoding a salutaridine reductase ("SalR") polypeptide.

The phrase "at least moderately stringent hybridization conditions" can mean that conditions are selected which promote selective hybridization between two complementary polynucleotide molecules in solution. Hybridization may occur to all or a portion of a polynucleotide molecule. The hybridizing portion is typically at least 15 (e.g. 20, 25, 30, 40 or 50) nucleotides in length. Those skilled in the art will recognize that the stability of a polynucleotide duplex, or hybrids, is determined by the Tm, which in sodium containing buffers is a function of the sodium ion concentration and temperature (Tm=81.5° C.?16.6 (Log 10 [Na+])+ 0.41(% (G+C)?600/1), or similar equation). Accordingly, the parameters in the wash conditions that determine hybrid stability are sodium ion concentration and temperature. In order to identify molecules that are similar, but not identical, to a known polynucleotide molecule a 1% mismatch may be assumed to result in about a 1° C. decrease in Tm, for example if polynucleotide molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm (based on the above equation) −5° C., followed by a wash of 0.2×SSC/ 0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "substantially identical" and its grammatical equivalents in reference to another sequence as used herein can mean at least 50% identical. In some instances, the term substantially identical refers to a sequence that is 55% identical. In some instances, the term substantially identical refers to a sequence that is 60% identical. In some instances, the term substantially identical refers to a sequence that is 65% identical. In some instances, the term substantially identical refers to a sequence that is 70% identical. In some instances, the term substantially identical refers to a sequence that is 75% identical. In some instances, the term substantially identical refers to a sequence that is 80% identical. In other instances, the term substantially identical refers to a sequence that is 81% identical. In other instances, the term substantially identical refers to a sequence that is 82% identical. In other instances, the term substantially identical refers to a sequence that is 83% identical. In other instances, the term substantially identical refers to a sequence that is 84% identical. In other instances, the term substantially identical refers to a sequence that is 85% identical. In other instances, the term substantially identical refers to a sequence that is 86% identical. In other instances, the term substantially identical refers to a sequence that is 87% identical. In other instances, the term substantially identical refers to a sequence that is 88% identical. In other instances, the term substantially identical refers to a sequence that is 89% identical. In some instances, the term substantially identical refers to a sequence that is 90% identical. In some instances, the term substantially identical refers to a sequence that is 91% identical. In some instances, the term substantially identical refers to a sequence that is 92% identical. In some instances, the term substantially identical refers to a sequence that is 93% identical. In some instances, the term substantially identical refers to a sequence that is 94% identical. In some instances, the term substantially identical refers to a sequence that is 95% identical. In some instances, the term substantially identical refers to a sequence that is 96% identical. In some instances, the term substantially identical refers to a sequence that is 97% identical. In some instances, the term substantially identical refers to a sequence that is 98% identical. In some instances, the term substantially identical refers to a sequence that is 99% identical. In some instances, the term substantially identical refers to a sequence that is 100% identical. In order to determine the percentage of identity between two sequences, the two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids/nucleotides is determined between the two sequences. For example, methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990:215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

The term "chimeric", as used herein in the context of polynucleotides, can refer to at least two polynucleotides that are not naturally linked. Chimeric polynucleotides include linked polynucleotides of different natural origins. For example, a polynucleotide constituting a yeast promoter linked to a polynucleotide sequence encoding a plant thebaine synthesis polypeptide is considered chimeric. Chimeric polynucleotides also may comprise polynucleotides of the same natural origin, provided they are not naturally linked. For example a polynucleotide sequence constituting a promoter obtained from a particular cell-type may be linked to a polynucleotide sequence encoding a polypeptide obtained from that same cell-type, but not normally linked to the polynucleotide sequence constituting the promoter. Chimeric polynucleotide sequences also include polynucleotide sequences comprising naturally occurring polynucleotide sequences linked to non-naturally occurring polynucleotide sequences.

The term "isolated", as used herein, describes a compound, e.g., a morphinan alkaloid or a polypeptide, which has been separated from components that naturally accompany it. Typically, a compound is isolated when at least 60%, 75%, 80%, 85%, 90%, 95%, 96%, 97%, 98%, or 99% of the total material (by volume, by wet or dry weight, or by mole percent or mole fraction) in a sample is the compound of interest. The percentage of a material of interest can be measured by any appropriate method, e.g., in the case of polypeptides, by chromatography, gel electrophoresis or HPLC analysis.

The term "heterologous" and its grammatical equivalents as used herein can mean "derived from a different species or cell type." For example, a "heterologous gene" can mean a gene that is from a different species or cell type. For example, a heterologous thebaine synthesis polypeptide can refer to a thebaine synthesis polypeptide which is present in a cell or cell type in which it is not naturally present.

The term "functional variant", as used herein, in reference to polynucleotide sequences or polypeptide sequences, can refer to polynucleotide sequences or polypeptide sequences capable of performing the same function as a noted polynucleotide sequence or polypeptide sequence. It is contemplated that for any of the polypeptides disclosed throughout, a functional variant can also be used in addition to the polypeptide or the polypeptide can be substituted.

The term "in vivo", as used herein, can refer to within a living cell, including, for example, a microorganism or a plant cell.

The term "in vitro", as used herein, can refer to outside a living cell, including, without limitation, for example, in a microwell plate, a tube, a flask, a beaker, a tank, a reactor and the like.

It should be noted that terms of degree such as "substantially", "about" and "approximately", as used herein, can refer to a reasonable amount of deviation of the modified term such that the end result is not significantly changed. These terms of degree should be construed as including a deviation of the modified term if this deviation would not negate the meaning of the term it modifies. For example, in relation to a reference numerical value the terms of degree can include a range of values plus or minus 10% from that value. For example, with regards to "about", the amount "about 10" can include any amounts from 9 to 11. The terms of degree in relation to a reference numerical value can also include a range of values plus or minus 9%, 8%, 7%, 6%, 5%, 4%, 3%, 2%, or 1% from that value.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

As used herein, the word "assist" and as used herein can mean to help, support, facilitate, or the like. For example, when used in context with an enzyme that converts X to Y, a polypeptide that "assists" the enzyme can increase the efficiency of which X is converted to Y. In some cases, the polypeptide that "assists" cannot directly convert X into Y.

General Implementation

Certain alkaloids belong to a class of chemical compounds known as benzylisoquinoline alkaloids ("BIAs"). Certain polypeptides capable of mediating chemical reactions involving the conversion of a substrate (e.g., a substrate benzylisoquinoline) into a product (e.g., a product) benzylisoquinoline are disclosed. The benzylisoquinoline (either the substrate or product) can belong to the benzylisoquinoline subclass of morphinan alkaloids, depending on what product is desired. Accordingly, disclosed are certain polypeptides capable of mediating chemical reactions involving conversion of a substrate into thebaine or other target morphinan alkaloids or morphinan alkaloid derivatives. Further, disclosed are methods that represent a novel and efficient means of making thebaine, or other target morphinan alkaloids or morphinan alkaloid derivatives.

The general pathways from a sugar substrate to a BIA, such as thebaine, includes enzymes that can perform any one of the following reactions: i) sugar to 1-tyrosine; ii) 1-tyrosine to 1-DOPA; iii) 1-DOPA to dopamine; iv) dopamine to (S)-norcoclaurine; v) (S)-norcoclaurine to (S)/(R)-reticuline; vi) (R)-reticuline to salutardine; vii) salutardine to salutaridinol; viii) salutaridinol to salutaridinol-7-O-acetate; ix) salutaridinol-7-O-acetate to the BIA thebaine; x) thebaine to other BIAs (such as oripavine, codeine, morphine, oxycodone, hydrocodone, oxymorphone, hydromorphone, naltrexone, naloxone, hydroxycodeinone, neopinone, and/or buprenorphine). Depending on the substrate used, any of the products of the pathway can be made by increasing or decreasing the expression of the enzymes that promote the formation of the desired product.

Some of the chemical conversions can be performed by one or more enzymes, including but not limited to tyrosine hydroxylase (TYR); DOPA decarboxylase (DODC); norcoclaurine synthase (NCS); 6-O-Methyltransferase (6OMT); coclaurine N-methyltransferase (CNMT), cytochrome P450 N-methylcoclaurine hydroxylase (NMCH), and 4-O-methyltransferase (4OMT); cytochrome P450 reductase (CPR); salutaridine synthase (SAS); salutaridine reductase (SalR); salutaridinol-7-O-acetyltransferase (SalAT); purine permease (PUP); or any combination thereof. Further to form a BIA, such as thebaine or morphinan alkaloids, the product should be contacted with a thebaine synthesis polypeptide; a codeine O-demethylase (CODM); a thebaine 6-O-demethylase (T6ODM); a codeinone reductase (COR); or any combination thereof.

Some of the methods herein involve the use of novel polypeptides known as thebaine synthesis polypeptides, as well as novel polynucleotides encoding the thebaine synthesis polypeptides. The thebaine synthesis polypeptides disclosed and used throughout, can be a polypeptide that is capable of converting salutaridinol-7-O-acetate to thebaine. Currently, it is thought that the reaction of converting salutaridinol-7-O-acetate to thebaine occurs by a spontaneous reaction at certain elevated pH levels. However, this reaction is extremely slow and thermodynamically unfavorable at normal conditions. Some of methods described throughout take advantage of using a thebaine synthesis polypeptide that can convert the salutaridinol-7-O-acetate to thebaine at an accelerated rate.

Some of the methods herein involve the use of a purine permease. In some cases, the purine permease can be used in combination with other polypeptides, such as a thebaine synthesis polypeptide (THS). The purine permease disclosed and used throughout, can be a polypeptide that is capable of increase the production titers of thebaine or other BIA intermediate by any cell or methods disclosed throughout.

Different substrates can be used with the enzymes described throughout. For example, one such substrate can be a substrate morphinan alkaloid having the chemical formula (I):

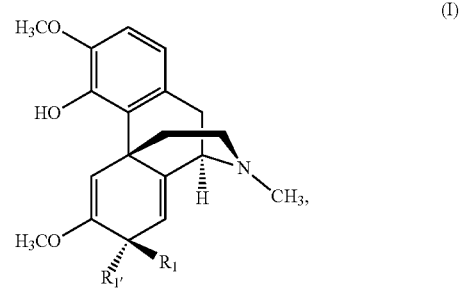

wherein, wherein $R_1$ represents a hydrogen atom and $R_{1'}$ represents an O-acetyl group, or wherein $R_1$ represents a hydrogen atom and $R_{1'}$ represents a hydroxyl group, or wherein, taken together, $R_1$ and $R_{1'}$ form an oxo group.

The substrate can also have the chemical formula (II):

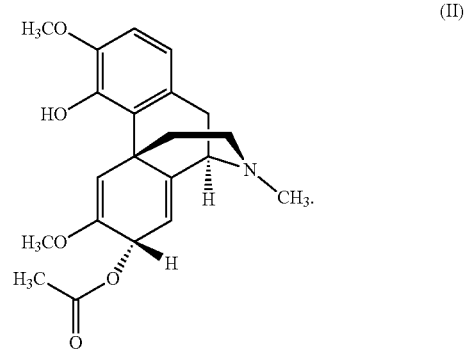

wherein, wherein $R_1$ represents a hydrogen atom and $R_{1'}$ represents an O-acetyl group, or wherein $R_1$ represents a hydrogen atom and $R_1'$ represents a hydroxyl group, or wherein, taken together, $R_1$ and $R_{1'}$ form an oxo group.

The substrate can also have the chemical formula (III):

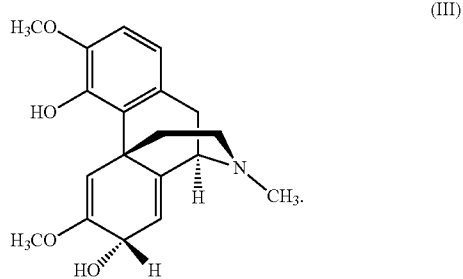

(III)

wherein, wherein $R_1$ represents a hydrogen atom and $R_{1'}$ represents an O-acetyl group, or wherein $R_1$ represents a hydrogen atom and $R_1'$ represents a hydroxyl group, or wherein, taken together, $R_1$ and $R_{1'}$ form an oxo group.

The substrate can also have the chemical formula (IV):

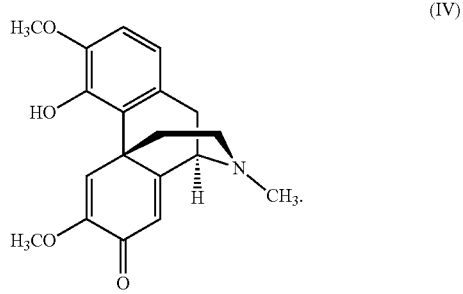

(IV)

wherein, wherein $R_1$ represents a hydrogen atom and $R_{1'}$ represents an O-acetyl group, or wherein $R_1$ represents a hydrogen atom and $R_1'$ represents a hydroxyl group, or wherein, taken together, $R_1$ and $R_{1'}$ form an oxo group.

In embodiments where substrates are used, for example substrates that have the chemical formula represented by (I), (II), (III), or (IV), one or more additional polypeptides can assist in the reaction. For example, SalAT polypeptide and a SalR polypeptide can be used to make a BIA, such as thebaine. Other polypeptides can assist in making thebaine as well. However, focusing here on SalAT and SalR, the SalAT polypeptide and/or a SalR polypeptide can be provided through adding the polypeptides directly to the culture media, transfections (transient or stable) of polynucleotide into the cells prior to culturing, or other means.

Synthesis of Benzylisoquinoline Alkaloids (Bias)

In Vivo Synthesis of BIAs

BIAs (e.g., thebaine, oripavine, codeine, morphine, oxycodone, hydrocodone, oxymorphone, hydromorphone, naltrexone, naloxone, hydroxycodeinone, neopinone, and/or buprenorphine) can be produced in at least in two ways. The first way is that the BIA is synthesized within a cell. This is referred to as the in vivo synthesis of the BIAs. This generally requires the use of a cell that can naturally produce BIAs from a substrate, or the use of a genetically modified cell that is either 1) enhanced to produce more BIAs compared to a non-modified cell or 2) produces BIAs even though it does not do so naturally.

Genetically Modified Cells to Produce BIAs

Thebaine Synthesis Polypeptide

Described herein is a genetically modified cell (e.g., a microorganism) that comprises a polynucleotide encoding a heterologous enzyme capable of converting salutaridinol-7-O-acetate to thebaine. The enzyme that is capable of converted salutaridinol-7-O-acetate to thebaine can be a thebaine synthesis polypeptide. Currently, there is no known enzyme that converts salutaridinol-7-O-acetate to thebaine, as it is thought that this conversion occurs spontaneously.

The thebaine synthesis polypeptide can be artificially synthesized or altered from how it exists in nature.

The thebaine synthesis polypeptide can also be expressed in cells that it is not normally expressed in. For example, a thebaine synthesis polypeptide from a plant can be expressed in yeast. This generally requires that the thebaine synthesis polypeptide be under the control of a yeast promoter.

The thebaine synthesis polypeptide can be from a plant. For example, the thebaine synthesis polypeptide can be from a plant that is from the genus *Papaver*. More specifically, *Papaver* plants that can be used include, but are not limited to *Papaver bracteatum, Papaver somniferum, Papaver cylindricum, Papaver decaisnei, Papaver fugax, Papaver nudicale, Papaver oreophyllum, Papaver orientate, Papaver paeonifolium, Papaver persicum, Papaver pseudo-orientale, Papaver rhoeas, Papaver rhopalothece, Papaver armeniacum, Papaver setigerum, Papaver tauricolum,* and *Papaver triniaefolium*. A particularly useful *Papaver* thebaine synthesis polypeptide is a *Papaver somniferum* thebaine synthesis polypeptide.

The thebaine synthesis polypeptide can be a polypeptide that is encoded by a polynucleotide that is substantially identical to SEQ ID NO. 19. For example, the thebaine synthesis polypeptide can be encoded by a polynucleotide that is at least 50%, 60%, 70%, 80%, 85%, 90%, 95%, 96%, 97%, 98% or 99% identical to any one of SEQ. ID NO. 19. Further, codon optimized polynucleotides (for a particular host cell/organism) for the above referenced sequences can be used herein.

In some cases, the thebaine synthesis polypeptide can be encoded by a polynucleotide capable of hybridizing under at least moderately stringent conditions to a polynucleotide that is substantially identical to SEQ ID NO. 19 or codon optimized sequenced.

The thebaine synthesis polypeptide can also be a polypeptide having an amino acid sequence that is substantially identical to SEQ ID NO. 6. For example, the thebaine synthesis polypeptide can be an amino acid sequence that is at least 50%, 60%, 70%, 80%, 85%, 90%, 95%, 96%, 97%, 98% or 99% identical to any one of SEQ ID NO. 6. Polypeptides that are substantially identical to SEQ ID NO. 6 can be used as a thebaine synthesis polypeptide.

In some cases, the thebaine synthesis polypeptide can be a fragment thereof. The fragment can still retain thebaine synthesis activity. In some cases, the thebaine synthesis activity can be decreased or increased compared to the activity produced by SEQ ID NO. 6. In one case, the thebaine synthesis polypeptide can a polypeptide having an amino acid sequence that is substantially identical to SEQ ID NO. 31 or 32.

In some cases, the thebaine synthesis polypeptide can be a variant or isoform. In some cases, variant or isoform can still retain thebaine synthesis activity. In some cases, the thebaine synthesis activity can be decreased or increased compared to the activity produced by SEQ ID NO. 6. In one case, the thebaine synthesis polypeptide can a polypeptide having an amino acid sequence that is substantially identical to SEQ ID NO. 80 or 81.

In some cases, the thebaine synthesis polypeptide can comprise a sequence encoding for a secretion signal, HA-tag, myc-tag, or other signal/tag. In some cases, these tags or signals do not affect the activity of the thebaine synthesis polypeptide.

Polypeptides that can Assist the Thebaine Synthesis Polypeptide

The thebaine synthesis polypeptide can also be assisted by one or more polypeptides. For example, thebaine synthesis polypeptide can be assisted (e.g., help synthesize more thebaine) by one or more polypeptides that are encoded by a polynucleotide that is substantially identical to SEQ ID NO. 18; SEQ ID NO. 20; SEQ ID NO. 21; SEQ ID NO. 22; SEQ ID NO. 23; SEQ ID NO. 24; SEQ ID NO. 25; SEQ ID NO. 26; SEQ ID NO. 27; SEQ ID NO. 28; SEQ ID NO. 29 or SEQ ID NO. 30. Codon optimized polynucleotides (for a particular host cell/organism) for the above referenced sequences can be used herein.

In some cases, the thebaine synthesis polypeptide can also be assisted by one or more polypeptides that are capable of hybridizing under at least moderately stringent conditions to a polynucleotide that is substantially identical to SEQ ID NO. 18; SEQ ID NO. 20; SEQ ID NO. 21; SEQ ID NO. 22; SEQ ID NO. 23; SEQ ID NO. 24; SEQ ID NO. 25; SEQ ID NO. 26; SEQ ID NO. 27; SEQ ID NO. 28; SEQ ID NO. 29 or SEQ ID NO. 30, or codon optimized sequences.

In some instances the thebaine synthesis polypeptide can also be assisted by one or more polypeptides that is substantially identical to SEQ ID NO. 5; SEQ ID NO. 7; SEQ ID NO. 8; SEQ ID NO. 9; SEQ ID NO. 10; SEQ ID NO. 11; SEQ ID NO. 12; SEQ ID NO. 13; SEQ ID NO. 14: SEQ ID NO. 15: SEQ ID NO. 16 or SEQ ID NO. 17.

For example, the thebaine synthesis polypeptide can also be assisted by one or more polypeptides that is at least 50%, 60%, 70%, 80%, 85%, 90%, 95%, 96%, 97%, 98% or 99% identical to any one of SEQ. ID NOs 5, and 7 to 17. The thebaine synthesis polypeptide can also be assisted by one or more polypeptides that is substantially identical to SEQ ID NO. 5. The thebaine synthesis polypeptide can be assisted by one or more polypeptides that is substantially identical to SEQ ID NO. 7 can also be used. The thebaine synthesis polypeptide can be assisted by one or more polypeptides that is substantially identical to SEQ ID NO. 8. Polypeptides that are substantially identical to SEQ ID NO. 9 can be used to assist the thebaine synthesis polypeptide. A polypeptide that is substantially identical to SEQ ID NO. 10 can also be used to assist thebaine synthesis polypeptide. The thebaine synthesis polypeptide can be assisted by one or more polypeptides that is substantially identical to SEQ ID NO. 11. Polypeptides that are substantially identical to SEQ ID NO. 12 can be used to assist thebaine synthesis polypeptide. A polypeptide that is substantially identical to SEQ ID NO. 13 can also be used to assist a thebaine synthesis polypeptide. The thebaine synthesis polypeptide can be assisted by one or more polypeptides that is substantially identical to SEQ ID NO. 14. Polypeptides that are substantially identical to SEQ ID NO. 15 can be used to assist thebaine synthesis polypeptide. A polypeptide that is substantially identical to SEQ ID NO. 16 can also be used to assist a thebaine synthesis polypeptide. The thebaine synthesis polypeptide can be assisted by one or more polypeptides that is substantially identical to SEQ ID NO. 17.

Purine Permease

Described herein is a genetically modified cell (e.g., a microorganism) that comprises a polynucleotide encoding an enzyme (e.g., heterologous enzyme) capable of increasing thebaine titers compared to a non-genetically modified cell. The enzyme that is capable of increasing thebaine titers can be a purine permease. The purine permease can sometimes work by itself or in conjunction with a thebaine synthesis polypeptide or other enzyme. For example, in some cases, the combination of purine permease and thebaine synthesis polypeptide can significantly increase thebaine titers compared to a non-genetically modified cell or a cells that is transformed with only a purine permease or only a thebaine synthesis polypeptide.

The purine permease can be artificially synthesized or altered from how it exists in nature.

The purine permease can also be expressed in cells that it is not normally expressed in. For example, a purine permease from a plant can be expressed in yeast. This generally requires that the purine permease be under the control of a yeast promoter.

The purine permease can be from a plant. For example, the purine permease can be from a plant that is from the genus *Papaver*. More specifically, *Papaver* plants that can be used include, but are not limited to *Papaver bracteatum*, *Papaver somniferum*, *Papaver cylindricum*, *Papaver decaisnei*, *Papaver fugax*, *Papaver nudicale*, *Papaver oreophyllum*, *Papaver orientate*, *Papaver paeonifolium*, *Papaver persicum*, *Papaver pseudo-orientale*, *Papaver rhoeas*, *Papaver rhopalothece*, *Papaver armeniacum*, *Papaver setigerum*, *Papaver tauricolum*, and *Papaver triniaefolium*. A particularly useful purine permease is a *Papaver somniferum* purine permease.

The purine permease can be encoded by a polynucleotide that is substantially identical to SEQ ID NO. 36. For example, the purine permease can be encoded by a polynucleotide that is at least 50%, 60%, 70%, 80%, 85%, 90%, 95%, 96%, 97%, 98% or 99% identical to any one of SEQ. ID NO. 36. Further, codon optimized polynucleotides (for a particular host cell/organism) for the above referenced sequences can be used herein.

In some cases, the purine permease can be encoded by a polynucleotide capable of hybridizing under at least moderately stringent conditions to a polynucleotide that is substantially identical to SEQ ID NO. 36 or codon optimized sequenced. Additionally, the purine permease can be substantially identical to SEQ ID NO. 38 or 39.

The purine permease can also be a polypeptide having an amino acid sequence that is substantially identical to SEQ ID NO. 35. For example, the purine permease can be an amino acid sequence that is at least 50%, 60%, 70%, 80%, 85%, 90%, 95%, 96%, 97%, 98% or 99% identical to any one of SEQ ID NO. 35. Polypeptides that are substantially identical to SEQ ID NO. 35 can be used as a purine permease. The purine permease can also be a polypeptide having an amino acid sequence that is substantially identical to SEQ ID NO. 37. For example, the purine permease can be an amino acid sequence that is at least 50%, 60%, 70%, 80%, 85%, 90%, 95%, 96%, 97%, 98% or 99% identical to any one of SEQ ID NO. 37. Polypeptides that are substantially identical to SEQ ID NO. 37 can be used as a purine permease.

In some cases, the purine permease can be encoded by a polynucleotide that is substantially identical to any one of SEQ ID NOs. 42, 44, 46, 48, 50, 52, 54, 56, 58, 60, 62, or 64. For example, the purine permease can be encoded by a polynucleotide that is at least 50%, 60%, 70%, 80%, 85%, 90%, 95%, 96%, 97%, 98% or 99% identical to any one of SEQ ID NOs. 42, 44, 46, 48, 50, 52, 54, 56, 58, 60, 62, or 64. Further, codon optimized polynucleotides (for a particular host cell/organism) for the above referenced sequences can be used herein.

In some cases, the purine permease can be encoded by a polynucleotide capable of hybridizing under at least moderately stringent conditions to a polynucleotide that is substantially identical to any one of SEQ ID NOs. 42, 44, 46, 48, 50, 52, 54, 56, 58, 60, 62, or 64 or codon optimized sequences.

The purine permease can also be a polypeptide having an amino acid sequence that is substantially identical to any one of SEQ ID NOs. 41, 43, 45, 47, 49, 51, 53, 55, 57, 59, 61, or 63. For example, the purine permease can be an amino acid sequence that is at least 50%, 60%, 70%, 80%, 85%, 90%, 95%, 96%, 97%, 98% or 99% identical to any one of SEQ ID NOs. 41, 43, 45, 47, 49, 51, 53, 55, 57, 59, 61, or 63. Polypeptides that are substantially identical to SEQ ID NOs. 41, 43, 45, 47, 49, 51, 53, 55, 57, 59, 61, or 63 can be used as a purine permease.

In some cases, the purine permease can be a fragment thereof. The fragment can still retain purine permease activity. In some cases, the fragment can result in purine permease activity that is decreased or increased compared to the activity produced by any one of SEQ ID NO. 35, 37, 41, 43, 45, 47, 49, 51, 53, 55, 57, 59, 61, or 63.

Additional Enzymes Useful in Making BIAS

The genetically modified cell can also comprise a polynucleotide encoding a SalAT polypeptide and/or a SalR polypeptide. The SalAT and/or SalR can be from a plant, for example, a plant from the genus *Papaver*, or from *Papaver* species such as *Papaver bracteatum, Papaver somniferum, Papaver cylindricum, Papaver decaisnei, Papaver fugax, Papaver nudicale, Papaver oreophyllum, Papaver orientale, Papaver* paeonifolium, *Papaver persicum, Papaver pseudoorientale, Papaver rhoeas, Papaver rhopalothece, Papaver armeniacum, Papaver setigerum, Papaver tauricolum*, and *Papaver triniaefolium*. A particularly useful *Papaver* SalAT and/or SalR is a *Papaver somniferum* SalAT and/or SalR.

In certain instances, the SalAT polypeptide can be encoded by a polynucleotide sequence that is substantially identical to SEQ ID NO. 1 or a fragment or functional variant thereof. Additionally, the SalAT can in some instances be encoded by a polynucleotide capable of hybridizing under at least moderately stringent conditions to a polynucleotide (e.g., SEQ ID NO. 1) encoding a SalAT polypeptide. In some cases, the SalAT can comprise an amino acid sequence which is substantially identical to SEQ ID NO. 2.

The SalR polypeptide can be encoded by a polynucleotide sequence that is substantially identical to SEQ ID NO. 3 or a fragment or functional variant thereof. Additionally, the SalR can in some cases be encoded by a polynucleotide capable of hybridizing under at least moderately stringent conditions to any polynucleotide (e.g., SEQ ID NO. 3) encoding a SalR polypeptide. In some cases, the SalR polypeptide can comprise an amino acid sequence which is substantially identical to SEQ ID NO. 4.

The genetically modified cell can also further comprises one or more nucleic acids encoding for an enzyme capable of catalyzing one or more of the reactions:
  a) a sugar to L-tyrosine;
  b) L-tyrosine to L-DOPA;
  c) L-DOPA to Dopamine;
  d) Dopamine to (S)-Norcoclaurine;
  e) (S)-Norcoclaurine to (S)/(R)-Reticuline;
  f) (R)-Reticuline to Salutardine;
  g) Salutardine to Salutaridinol;
  h) Salutaridinol to Salutaridinol-7-O-acetate; or
  i) thebaine to oripavine, codeine, morphine, oxycodone, hydrocodone, oxymorphone, hydromorphone, naltrexone, naloxone, hydroxycodeinone, neopinone, buprenorphine, or any combination thereof.
  Depending on the substrate used, any of the products of the pathway can be made by increasing or decreasing the expression of the enzymes that promote the formation of the desired product.

The genetically modified cell can also further one or more enzymes (in some cases heterologous enzymes), including but not limited to tyrosine hydroxylase (TYR); DOPA decarboxylase (DODC); norcoclaurine synthase (NCS); 6-O-Methyltransferase (6OMT); coclaurine N-methyltransferase (CNMT), cytochrome P450 N-methylcoclaurine hydroxylase (NMCH), and 4-O-methyltransferase (4OMT); cytochrome P450 reductase (CPR), salutaridine synthase (SAS); salutaridine reductase (SalR); salutaridinol-7-O-acetyltransferase (SalAT); purine permease (PUP); or any combination thereof. Further to form a BIA, such as thebaine or morphinan alkaloids, contacting the product of should be contacted with a thebaine synthesis polypeptide; a codeine O-demethylase (CODM); a thebaine 6-O-demethylase (T6ODM); a codeinone reductase (COR); or any combination thereof.

The expression (or overexpression) of the thebaine synthesis polypeptide in certain cells can lead to increased production of BIAs, such as thebaine. Additionally, the expression of other enzymes within the sugar→BIA pathway, can result in greater production of BIAs, such as thebaine. For example, expression (or overexpression) of purine permease in certain cells can lead to increased production of BIAs, such as thebaine.

Fragments, including functional fragments, of any and all polypeptides described here, are contemplated herein, even without directly mentioning fragments of the polypeptides. For example, fragments of thebaine synthesis polypeptides and/or purine permease are contemplated.

Polynucleotides Useful in Making BIAs

The polynucleotide encoding the thebaine synthetic polypeptide or any enzyme disclosed herein can be linked to a polynucleotide capable of controlling expression of the thebaine synthesis polypeptide and/or purine permease (or other enzyme) in a cell. A chimeric polynucleotide comprising as operably linked components: (a) one or more polynucleotides capable of controlling expression in a host cell; and (b) a polynucleotide encoding a thebaine synthetic polypeptide and/or purine permease (or other enzymes) can be used to express the desired polypeptide/enzyme.

Polynucleotides capable of controlling expression in host cells that may be used herein include any transcriptional promoter capable of controlling expression of polypeptides in host cells. Generally, promoters obtained from bacterial cells are used when a bacterial host is selected in accordance herewith, while a fungal promoter will be used when a fungal host is selected, a plant promoter will be used when a plant cell is selected, and so on. Further polynucleotide elements capable of controlling expression in a host cell include transcriptional terminators, enhancers and the like, all of which may be included in the polynucleotides molecules (including chimeric polynucleotides) disclosed herein. A skilled artisan would understand that operable linkage of polynucleotide sequences can include linkage of promoters and sequences capable of controlling expression to coding sequences in the 5' to 3' direction of transcription.

The polynucleotide molecules disclosed herein can be integrated into a recombinant expression vector which ensures good expression in the host cell. For example, the polynucleotides herein can comprise one or more polynucleotides capable of controlling expression in a host cell and can subsequently be linked to a polynucleotide sequence encoding a thebaine synthetic polypeptide and/or purine permease (or other sequence encoding for a desired enzyme). These vectors can be stably integrated into the genome of a desired cell or simply transfected without any integration.

Disclosed is also a recombinant polynucleotide expression vector comprising as operably linked components: (a) one or more polynucleotides capable of controlling expression in a host cell; and (b) a polynucleotide encoding a thebaine synthetic polypeptide and/or purine permease, wherein the expression vector is suitable for expression in a host cell. The term "suitable for expression in a host cell" can mean that the recombinant polynucleotide expression vector comprises the chimeric polynucleotide molecule linked to genetic elements required to achieve expression in a host cell.

Genetic elements that can be included in the expression vector include a transcriptional termination region, one or more polynucleotides encoding marker genes, one or more origins of replication and the like. The expression vector can also further comprise genetic elements required for the integration of the vector or a portion thereof in the host cell's genome. For example, if a plant host cell is used the T-DNA left and right border sequences which facilitate the integration into the plant's nuclear genome can be used.

The recombinant expression vector can further contain a marker gene. Marker genes that can be used and included in all genes that allow the distinction of transformed cells from non-transformed cells, including selectable and screenable marker genes. A marker gene may be a resistance marker such as an antibiotic resistance marker against, for example, kanamycin or ampicillin. Screenable markers that may be employed to identify transformants through visual inspection include β-glucuronidase (GUS) (see e.g., U.S. Pat. Nos. 5,268,463 and 5,599,670) and green fluorescent protein (GFP) (see e.g., Niedz et al., 1995, Plant Cell Rep., 14: 403).

The preparation of the vectors may be accomplished using commonly known techniques such as restriction digestion, ligation, gel electrophoresis, DNA sequencing, Polymerase Chain Reaction (PCR) and other methodologies. A wide variety of cloning vectors are available to perform the necessary steps required to prepare a recombinant expression vector. Among the vectors with a replication system functional in bacteria such as *E. coli* are vectors such as pBR322, the pUC series of vectors, the M13 mp series of vectors, pBluescript etc. Typically these cloning vectors contain a marker allowing selection of transformed cells. Polynucleotides may be introduced in these vectors, and the vectors may be introduced in the host cell by preparing competent cells, electroporation or using other methodologies. The host cell may be grown in an appropriate medium including but not limited to, Luria-Broth medium, dulbecco eagle modified medium (DMEM) or Opti-mem, and subsequently harvested. Recombinant expression vectors can be recovered from cells upon harvesting and lysing of the cells. Further, general guidance with respect to the preparation of recombinant vectors and growth of recombinant organisms may be found in, for example: Sambrook et al., Molecular Cloning, a Laboratory Manual, Cold Spring Harbor Laboratory Press, 2001, Third Ed.

Modifying Endogenous Gene Expression

The genetically modified cells disclosed herein can have their endogenous genes regulated. This can be useful, for example, when there is negative feedback to the expression of a desired polypeptide, such as a thebaine synthesis polypeptide and/or purine permease. Modifying this negative regulator can lead to increased expression of a desired polypeptide.

Therefore, disclosed herein is a method for modifying expression of polynucleotide sequences in a cell naturally expressing a desired polypeptide, the method comprising: (a) providing a cell naturally expressing a desired polypeptide; (b) mutagenizing the cell; (c) growing the cell to obtain a plurality of cells; and (d) determining if the plurality of cells comprises a cell with modulated levels of the desired polypeptide. In some cases, the desired polypeptide is a thebaine synthesis polypeptide. In some cases, the desired polypeptide is a purine permease. In other cases, the desired polypeptide is an enzyme that can perform any one of the following reactions: i) sugar to 1-tyrosine; ii) 1-tyrosine to 1-DOPA; iii) 1-DOPA to dopamine; iv) dopamine to (S)-norcoclaurine; v) (S)-norcoclaurine to (S)/(R)-reticuline; vi) (R)-reticuline to salutardine; vii) salutardine to salutaridinol; viii) salutaridinol to salutaridinol-7-O-acetate; ix) salutaridinol-7-O-acetate to thebaine; x) thebaine to oripavine, codeine, morphine, oxycodone, hydrocodone, oxymorphone, hydromorphone, naltrexone, naloxone, hydroxycodeinone, neopinone, and/or buprenorphine.

The method can further comprise selecting a cell comprising modulated levels of the desired polypeptide and growing such cell to obtain a plurality of cells.

In some cases, the decrease expression of the thebaine synthesis polypeptide is desired. For example, an endogenous thebaine synthesis polypeptide may be silenced or knocked out. The polynucleotides encoding thebaine synthesis polypeptide may be used to produce a cell that has modified levels of expression of a desired polypeptide by gene silencing. For example, disclosed herein is a method of reducing the expression of thebaine synthesis polypeptide in a cell, comprising: (a) providing a cell expressing a desired polypeptide; and (b) silencing expression of the desired polypeptide in the cell. In some cases, the desired polypeptide can be a thebaine synthesis polypeptide.

In some cases, a decreased expression of a purine permease is desired. For example, an endogenous purine permease may be silenced or knocked out. The polynucleotides encoding purine permease may be used to produce a cell that has modified levels of expression of a desired polypeptide by gene silencing. For example, disclosed herein is a method of reducing the expression of purine permease in a cell, comprising: (a) providing a cell expressing a desired polypeptide; and (b) silencing expression of the desired polypeptide in the cell. In some cases, the desired polypeptide can be a purine permease.

Modifying the expression of endogenous genes may be achieved in a variety of ways. For example, antisense or RNA interference approaches may be used to down-regulate expression of the polynucleotides of the present disclosure, e.g., as a further mechanism for modulating cellular phenotype. That is, antisense sequences of the polynucleotides of the present disclosure, or subsequences thereof, may be used to block expression of naturally occurring homologous polynucleotide sequences. In particular, constructs comprising a desired polypeptide coding sequence, including fragments thereof, in antisense orientation, or combinations of sense and antisense orientation, may be used to decrease or effectively eliminate the expression of the desired polypeptide in a cell or plant and obtain an improvement in shelf life as is described herein. Accordingly, this may be used to "knock-out" the desired polypeptide or homologous sequences thereof. A variety of sense and antisense technologies, e.g., as set forth in Lichtenstein and Nellen (Antisense Technology: A Practical Approach IRL Press at Oxford University, Oxford, England, 1997), can be used. Sense or antisense polynucleotide can be introduced into a cell, where they are transcribed. Such polynucleotides can include both simple oligonucleotide sequences and catalytic sequences such as ribozymes.

Other methods for a reducing or eliminating expression (i.e., a "knock-out" or "knockdown") of a desired polypeptide (e.g., thebaine synthesis polypeptide and/or purine permease) in a transgenic cell or plant can be done by introduction of a construct which expresses an antisense of the desired polypeptide coding strand or fragment thereof. For antisense suppression, the desired polypeptide cDNA or fragment thereof is arranged in reverse orientation (with respect to the coding sequence) relative to the promoter sequence in the expression vector. Further, the introduced sequence need not always correspond to the full length cDNA or gene, and need not be identical to the cDNA or gene found in the cell or plant to be transformed.

Additionally, the antisense sequence need only be capable of hybridizing to the target gene or RNA of interest. Thus, where the introduced polynucleotide sequence is of shorter length, a higher degree of homology to the endogenous transcription factor sequence will be needed for effective antisense suppression. While antisense sequences of various lengths can be utilized, in some embodiments, the introduced antisense polynucleotide sequence in the vector is at least 10, 20, 30, 40, 50, 100 or more nucleotides in length in certain embodiments. Transcription of an antisense construct as described results in the production of RNA molecules that comprise a sequence that is the reverse complement of the mRNA molecules transcribed from the endogenous gene to be repressed.

Other methods for a reducing or eliminating expression can be done by introduction of a construct that expresses siRNA that targets a desired polypeptide (e.g., thebaine synthesis polypeptide and/or purine permease). In certain embodiments, siRNAs are short (20 to 24-bp) double-stranded RNA (dsRNA) with phosphorylated 5' ends and hydroxylated 3' ends with two overhanging nucleotides.

Other methods for a reducing or eliminating expression can be done by insertion mutagenesis using the T-DNA of *Agrobacterium tumefaciens* or a selection marker cassette or any other non-sense DNA fragments. After generating the insertion mutants, the mutants can be screened to identify those containing the insertion in the thebaine synthesis polypeptide and/or purine permease (or other desired polypeptide) gene. Plants containing one or more transgene insertion events at the desired gene can be crossed to generate homozygous plant for the mutation, as described in Koncz et al., (Methods in Arabidopsis Research; World Scientific, 1992).

Suppression of gene expression may also be achieved using a ribozyme. Ribozymes are RNA molecules that possess highly specific endoribonuclease activity. The production and use of ribozymes are disclosed in U.S. Pat. Nos. 4,987,071 and 5,543,508. Synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

A cell or plant gene may also be modified by using the Cre-lox system (for example, as described in U.S. Pat. No. 5,658,772). A cellular or plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

In addition, silencing approach using short hairpin RNA (shRNA) system, and complementary mature CRISPR RNA (crRNA) by CRISPR/Cas system, and virus inducing gene silencing (VIGS) system may also be used to make down regulated or knockout of synthase mutants. Dominant negative approaches may also be used to make down regulated or knockout of desired polypeptides.

The RNA-guided endonuclease can be derived from a clustered regularly interspersed short palindromic repeats (CRISPR)/CRISPR-associated (Cas) system. The CRISPR/Cas system can be a type I, a type II, or a type III system. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas1O, Cas1Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx1O, Csx16, CsaX, Csx3, Csz1, Csx15, Csf1, Csf2, Csf3, Csf4, and Cu1966.

In general, CRISPR/Cas proteins comprise at least one RNA recognition and/or RNA binding domain. RNA recognition and/or RNA binding domains interact with guide RNAs. CRISPR/Cas proteins can also comprise nuclease domains (i.e., DNase or RNase domains), DNA binding domains, helicase domains, RNAse domains, protein-protein interaction domains, dimerization domains, as well as other domains.

The CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzyme activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the function of the fusion protein. The CRISPR/Cas-like protein can also be truncated or modified to optimize the activity of the effector domain of the fusion protein.

One method to silence a desired gene (or a thebaine synthesis polypeptide and/or purine permease gene) is virus induced gene silencing (known to the art as VIGS). In general, in plants infected with unmodified viruses, the viral genome is targeted. However, when viral vectors have been modified to carry inserts derived from host genes (e.g. portions of sequences encoding a desired polypeptide such as thebaine synthesis polypeptide and/or purine permease), the process is additionally targeted against the corresponding mRNAs. Thus disclosed is a method of producing a plant expressing reduced levels of a desired gene (such as thebaine synthesis polypeptide and/or purine permease) or other desired gene(s), the method comprising (a) providing a plant expressing a desired gene (e.g., a thebaine synthesis polypeptide and/or purine permease); and (b) reducing expression of the desired gene in the plant using virus induced gene silencing.

Cell-Types

The cells that can be used include but are not limited to plant or animal cells, fungus, yeast, algae, or bacterium. The cells can be prokaryotes or in some cases can be eukaryotes. For example, the cell can be a *Papaver somniferum* cell, *Saccharomyces cerevisiae, Yarrowia lipolytica*, or *Escherichia coli*, or any other cell disclosed throughout.

In certain cases, the living cells are cells not naturally capable of producing thebaine (or other target morphinan alkaloids or morphinan alkaloid derivatives). In some cases, the cells are able to produce BIAs, such as thebaine, but at a low level. By implementation of the methods described herein, the cells can be modified such that the level of thebaine in the cells is higher relative to the level of thebaine produced in the unmodified cells. This can also allow the cells to produce higher levels of other target morphinan alkaloids or morphinan alkaloid derivatives.

The levels of thebaine in the modified cells can be higher than the levels of thebaine in the unmodified cells.

In some cases, the modified cell is capable of producing a substrate morphinan alkaloid, but not capable of naturally producing thebaine. The genetically modified cells in some cases are unable to produce a substrate morphinan alkaloid, and the substrate morphinan alkaloid is provided to the cells as part of the cell's growth medium. In this case, the genetically modified cell can process the substrate morphinan alkaloid into a desired product such as thebaine or other BIA.

The genetically modified cell in some cases produces a substrate morphinan alkaloid when exogenously supplied with a base substrate, for example, supplied in a host cell growth medium. In some cases, the cell is capable of producing substrate morphinan alkaloid (or able to produce thebaine or other BIAs) only if a base substrate is included in host cell's growth medium.

The genetically modified cell can comprise one or more enzyme capable of catalyzing one or more of the reactions: a sugar to L-tyrosine; L-tyrosine to L-DOPA; L-DOPA to Dopamine; Dopamine to (S)-Norcoclaurine; (S)-Norcoclaurine to (S)/(R)-Reticuline; (R)-Reticuline to Salutardine; Salutardine to Salutaridinol; or Salutaridinol to Salutaridinol-7-O-acetate.

BIA Production Levels

The genetic modifications to the cells described throughout can be made to produce BIAs (e.g., thebaine) over what would have been made without any genetic modifications. For example, compared to a non-genetically altered cell, the genetically modified cells described throughout can produce BIAs greater than 1.1 times (compared to the production levels of a non-genetically modified cell). In some cases, the genetically modified cells described throughout can produce BIAs greater than 1.2; 1.3; 1.4; 1.5; 1.6; 1.7; 1.8; 1.9; 2.0; 2.5; 3.0; 3.5; 4.0; 4.5; 5.0; 6.0; 7.0; 8.0; 9.0; 10.0; 12.5; 15.0; 17.5; 20.0; 25.0; 30.0; 50.0; 75.0; or 100.0 times compared to the production level of a non-genetically modified cell.

In some cases, the BIA can be thebaine. In other cases, the BIA can be other BIAs described herein such as oripavine, codeine, morphine, oxycodone, hydrocodone, oxymorphone, hydromorphone, naltrexone, naloxone, hydroxycodeinone, neopinone, buprenorphine, or any combination thereof.

Methods of Making BIAs (or Morphinan Alkaloid, e.g., Thebaine)

The genetically modified cells described throughout can be used to make BIAs, including morphinan alkaloids, e.g., thebaine. A substrate morphinan alkaloid can be brought in contact with a thebaine synthesis polypeptide in a reaction mixture under reaction conditions permitting a thebaine synthesis polypeptide mediated reaction resulting in the conversion of the substrate morphinan alkaloid into thebaine, or other target morphinan alkaloids or morphinan alkaloid derivatives, under in vivo reaction conditions. Under such in vivo reaction conditions living cells are modified in such a manner that they produce morphinan alkaloids, e.g., thebaine, or other target morphinan alkaloids or morphinan alkaloid derivatives. Additionally, a purine permease can be present within the cells to increase the overall thebaine production titers.

The BIAs (morphinan alkaloids, e.g., thebaine) produced may be recovered and isolated from the modified cells. The BIAs (morphinan alkaloids, e.g., thebaine) in some cases may be secreted into the media of a cell culture, in which BIA is extracted directly from the media. In some cases, the BIA may be within the cell itself, and the cells will need to be lysed in order to recover the BIA. In some instances, both cases may be true, where some BIAs are secreted and some remains within the cells. In this case, either method or both methods can be used.

Accordingly, disclosed is a method for preparing a thebaine (or other BIAs), the method comprising: (a) providing a chimeric polynucleotide comprising as operably linked components: (i) a polynucleotide encoding a thebaine synthesis polypeptide; (ii) one or more polynucleotides capable of controlling expression in a host cell; (b) introducing the chimeric polynucleotide into a host cell that endogenously produces or is exogenously supplied with a substrate morphinan alkaloid; and (c) growing the host cell to produce the thebaine synthesis polypeptide and thebaine. The cell can also further comprise a purine permease. The method can further comprise recovering thebaine from the host cell.

The substrate that can be used in these methods can be a substrate morphinan alkaloid. The substrate morphinan alkaloid can be salutaridine, salutaridinol, salutaridinol 7-O-acetate, or any combination thereof.

The host cells can in some cases be capable of producing a substrate morphinan alkaloid, including salutaridine, salutaridinol, salutaridinol 7-O-acetate or any combination thereof. If the host cell cannot produce a substrate morphinan alkaloid, the substrate morphinan alkaloids, including salutaridine, salutaridinol and/or salutaridinol 7-O-acetate, are exogenously supplied to the host cells in order to produce a BIA.

Disclosed herein is also a method of producing a BIA (or thebaine) comprising: (a) providing a host cell growth medium comprising a base substrate; (b) providing a host cell capable of (i) producing a thebaine synthesis polypeptide; and (ii) metabolizing the base substrate to form a substrate morphinan alkaloid; and (c) growing the host cell in the growth medium under conditions permitting a thebaine synthesis polypeptide mediated chemical reaction resulting in the conversion of the substrate morphinan alkaloid to form thebaine. Additionally, after (ii), the method can include producing a morphinan alkaloid derivative of thebaine by converting thebaine. In some instances, the method can further include isolating the morphinan alkaloid derivative of thebaine from the host cell culture. In some cases, the cells used in the method can comprise a purine permease.

The thebaine synthesis polypeptides may further be used to produce thebaine or another target morphinan alkaloid or a morphinan alkaloid derivative of thebaine using processes involving growth of a host cell comprising the thebaine synthesis polypeptides in a growth medium comprising a base substrate. Therefore, disclosed herein is a method of using a thebaine synthesis polypeptide to produce thebaine, morphinan alkaloid, or morphinan alkaloid derivative of thebaine, in a cell grown in a growth medium comprising a base substrate, wherein the cell comprises the thebaine synthesis polypeptide. In some case, the cell can comprise a purine permease.

The base substrate used in the methods to make a BIA can be a sugar. For example, the sugar can include but is not limited to glucose, fructose, galactose, mannose, or any combination thereof. The base substrate can also be a precursor compound of a substrate alkaloid morphinan including, without limitation, glycerol, L-tyrosine, tyramine, L-3,4-dihydroxyphenyl alanine (L-DOPA), dopamine, or any combination thereof.

The methods disclosed herein can make a morphinan alkaloid derivative of thebaine. For clarity these morphinan alkaloid derivative of thebaine are also BIAs and can include without limitation, oripavine, codeine, morphine, oxycodone, hydrocodone, oxymorphone, hydromorphone, naltrexone, naloxone, hydroxycodeinone, neopinone, buprenorphine, or any combination thereof.

The inclusion of thebaine synthesis polypeptides (and/or purine permease) in reaction mixtures comprising a morphinan alkaloid substrate can lead to substantially avoiding the synthesis of morphinan alkaloid by-products, which in the absence of a thebaine synthesis polypeptide (and/or purine permease) can accumulate at the expense of thebaine, or other target morphinan alkaloids or morphinan alkaloid derivatives. To the best of the inventors' knowledge, the current disclosure provides, for the first time, a methodology to use recombinant techniques to manufacture BIAs, thebaine or other target morphinan alkaloids or morphinan alkaloid derivatives via a process involving the use of thebaine synthesis polypeptides (and/or purine permease). The methodologies and compositions herein allow the synthesis of BIAs, thebaine, or other target morphinan alkaloids or morphinan alkaloid derivatives, at commercial levels, using cells that are not normally capable of synthesizing BIAs, thebaine, or other target morphinan alkaloids or morphinan alkaloid derivatives. Such cells may be used as a source of BIAs, thebaine, or other target morphinan alkaloids or morphinan alkaloid derivatives and may eventually be economically extracted from the cells itself or from culture media. The BIAs, thebaine, or other target morphinan alkaloids or morphinan alkaloid derivatives, produced can be useful inter alia in the manufacture of pharmaceutical compositions.

Disclosed herein is also a method of making a morphinan alkaloid derivative of thebaine. This method can be performed by providing a substrate morphinan alkaloid and then contacting the substrate morphinan alkaloid with a thebaine synthesis polypeptide in a reaction mixture under reaction conditions that first permit a thebaine synthesis polypeptide mediated chemical reaction. This reaction results in the conversion of the substrate morphinan alkaloid to thebaine. If desired, then at least one additional chemical reaction can results in the conversion of thebaine to a morphinan alkaloid derivative of thebaine. The additional reaction can be mediated by a polypeptide.

In order to convert the substrate alkaloid morphinan to thebaine, the substrate alkaloid morphinan is contacted with a thebaine synthesis polypeptide under reaction conditions permitting the conversion of the substrate alkaloid morphinan into thebaine. The thebaine synthesis polypeptide may be any thebaine synthesis polypeptide capable of mediating the conversion of the substrate alkaloid morphinan into thebaine. In some cases, more than one thebaine synthesis polypeptide may be used, e.g., one, two, three, four, five, six, seven, eight or more of the thebaine synthesis polypeptides or any functional variants or fragments thereof can be used. In some cases, a purine permease can be used in conjunction with the thebaine synthesis polypeptide to increase thebaine titers. In some cases, more than purine permease may be used, e.g., one, two, three, four, five, six, seven, eight or more of the purine permeases or any functional variants or fragments thereof can be used.

The reaction conditions may be a reaction condition that permits the conversion of a substrate to a desired product. The reaction conditions can include in vivo or in vitro conditions, as hereinafter further detailed. The thebaine synthesis polypeptide, and other optional enzymes such as purine permease, SalAT, and SalR polypeptides, are provided in catalytic quantities. The reaction conditions can further include the presence of water and buffering agents. The reaction is can be conducted at neutral pH or mild basic or acidic pH (from approximately pH 5.5 to approximately pH 9.5). Further, other additives can be included in a reaction mixture, such as cofactors like NADPH and acetyl-CoA. In particular, reaction mixtures comprising SalAT further comprise Acetyl-CoA, and reaction mixtures comprising SalR further comprise NADPH.

The substrate alkaloid morphinan can be converted to thebaine via one or more intermediate morphinan alkaloid compounds. In some cases, the substrate morphinan alkaloid can be salutaridinol and the intermediate morphinan alkaloid compound can be salutaridinol 7-O-acetate. In other cases, the substrate morphinan alkaloid can be salutaridine and the intermediate morphinan alkaloid compounds can be salutaridinol and salutaridinol 7-O-acetate.

The time period during which a substrate morphinan alkaloid and intermediate alkaloid morphinan compound exist, once the reaction is started, can vary and can depend on the reaction conditions selected. Furthermore, an equilibrium between the substrate morphinan alkaloid, and thebaine, or morphinan alkaloid or morphinan alkaloid derivative, as well as the optional intermediate morphinan alkaloid compounds, can form, wherein the reaction can comprise various amounts of the substrate alkaloid compound and thebaine, or morphinan alkaloid or morphinan alkaloid derivative, and, optionally, one or more intermediate morphinan alkaloid compounds. The relative amounts of each of these compounds may vary depending on the reaction conditions selected. In general, in accordance herewith, the amount of thebaine, or morphinan alkaloid or morphinan alkaloid derivative, upon substantial completion of the reaction, present in the reaction mixture is at least 50% (w/w), at least 60% (w/w), at least 70% (w/w), at least 80% (w/w), at least 90% (w/w), at least, 95% (w/w), or at least 99% (w/w) of the total morphinan alkaloid compounds in the reaction mixture.

In general, the presence of thebaine synthesis polypeptide in the reaction mixture results in a more efficient conversion of the substrate morphinan alkaloid, i.e. when comparing conversion of a substrate morphinan alkaloid in a first reaction mixture comprising a thebaine synthesis polypeptide, with conversion in a second reaction mixture identical to the first reaction mixture, but for the presence of a thebaine synthesis polypeptide therein, conversion of the substrate morphinan alkaloid compound into thebaine occurs in a more efficient fashion in the first reaction mixture. Additionally, the presence of a purine permease in the reaction mixture results in a more efficient conversion of the substrate morphinan alkaloid into a BIA, such as thebaine. In this regard, a conversion is deemed "more efficient" if larger quantities of thebaine are obtained in the reaction mixture upon substantial completion of the reaction, and/or if thebaine accumulates in the reaction mixture at a faster rate. Thus, for example, in certain cases, in the presence of a thebaine synthesis polypeptide (and/or purine permease), few or no newly formed morphinan alkaloid reaction products, other than the target production such as thebaine, morphinan alkaloids, or morphinan alkaloid derivatives, accumulate in the reaction mixture. In other cases, few or no newly formed morphinan alkaloid compounds, other than the target products such as thebaine, morphinan alkaloids, or morphinan alkaloid derivatives and the intermediate morphinan alkaloid compounds salutaridinol and/or salutaridinol 7-O-acetate, accumulate in the reaction mixture.

Figure 5:
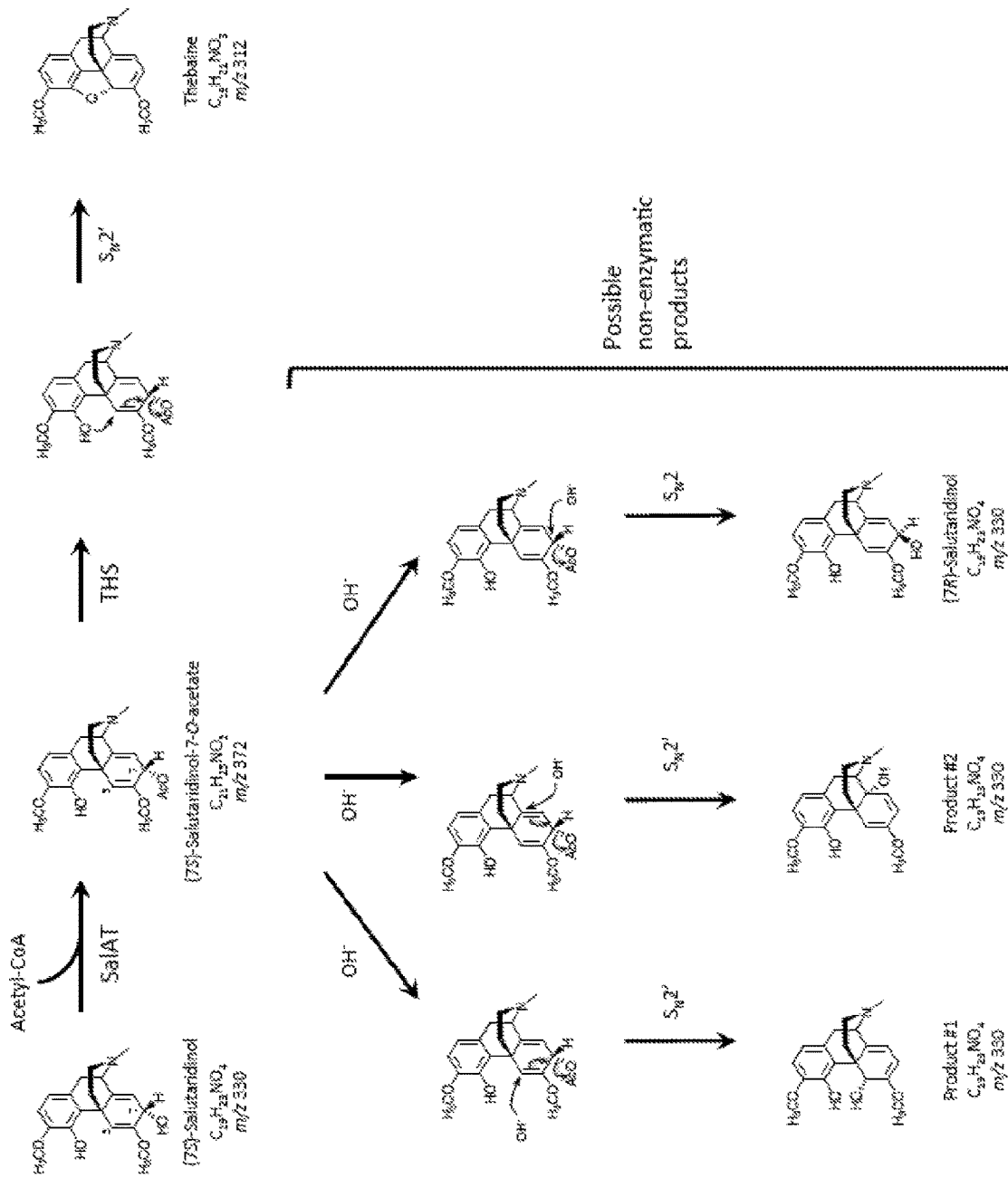
FIG. 5 depicts a chemical reaction illustrating the formation of thebaine in the presence of thebaine synthesis polypeptide (THS), and three morphinan alkaloid non-enzymatic by-products, referred to, as denoted, as Product #1, Product #2 and (7R)-salutaridinol, in the absence of THS. Compounds with m/z 330 are alternative reaction products of (7S)-salutaridinol-7-O-acetate, and are not thebaine.

Referring now to FIG. 5, shown therein is, by way of example, that in some embodiments, in the absence (−) in a reaction mixture of thebaine synthesis polypeptide (TS), the morphinan alkaloid by-products m/z 330 (a) and m/z 330 (b) denoted in FIG. 5 can accumulate in such reaction mixture. Conversely, in the presence (+) of thebaine synthesis polypeptide (THS), few morphinan alkaloids other than the measured morphinan alkaloid thebaine, and in some embodiments salutaridinol and/or salutaridinol 7-O-acetate accumulate in the reaction mixture, notably no substantive quantities of the morphinan alkaloid b-products m/z 330 (a) and m/z 330 (b) denoted in FIG. 5 accumulate in the reaction mixture.

In some instances, upon substantial completion of the reaction, the reaction mixture comprises thebaine, or morphinan alkaloid or morphinan alkaloid derivative, in a weight percentage of least 50% (w/w), at least 60% (w/w), at least 70% (w/w), at least 80% (w/w), at least 90% (w/w), at least 95% (w/w), or at least 99% (w/w) of total morphinan alkaloid compounds in the reaction mixture. In some other cases, upon substantial completion of the reaction, the reaction mixture comprises thebaine, or other target morphinan alkaloid or morphinan alkaloid derivative, salutaridinol and/or salutaridinol 7-O-acetate, together in a weight percentage of at least 60% (w/w), at least 70% (w/w), at least 80% (w/w), at least 90% (w/w), at least 95% (w/w), or at least 99% (w/w) of total morphinan alkaloid compounds in the reaction mixture. In some cases, upon substantial completion of the reaction, the reaction mixture comprises morphinan alkaloid compounds other than thebaine (or other target morphinan alkaloid or morphinan alkaloid derivative), in a weight percentage of less than 25% (w/w), less than 20% (w/w), less than 15% (w/w), less than 10% (w/w), less than 5% (w/w), or less than 1% (w/w) of total morphinan alkaloids in the reaction mixture. In other cases, upon substantial completion of the reaction, the reaction mixture comprises morphinan alkaloid compounds other than thebaine, or other target morphinan alkaloid or morphinan alkaloid derivative, salutaridinol and/or salutaridinol acetate in a weight percentage of less than 15% (w/w), less than 10% (w/w), less than 5% (w/w), or less than 1% (w/w) of total morphinan alkaloids in the reaction mixture. In some cases, upon substantial completion of the reaction, the reaction mixture comprises morphinan alkaloid compounds m/z 330 (a) and/or m/z 330 (b) together in a weight percentage of less than 25% (w/w), less than 20% (w/w), less than 15% (w/w), less than 10% (w/w), less than 5% (w/w), or less than 1% (w/w) of total morphinan alkaloids in the reaction mixture.

The thebaine synthesis polypeptide (and/or purine permease) can mediate the conversion by preventing the formation of reaction products, other than thebaine, or in some embodiments, reaction products other than salutaridinol or salutaridinol 7-O-acetate, in the reaction mixture, and in particular by preventing the formation of morphinan alkaloid compounds m/z 330 (a) and/or m/z 330 (b). Furthermore, the thebaine synthesis polypeptide (and/or purine permease) may act by preventing certain oxidation reactions, for example, oxidation by molecular oxygen ($O_2$) and/or oxidation by water ($H_2O$). In particular, the thebaine synthesis polypeptide (and/or purine permease) may act by preventing the oxidation of carbon atom $C_5$ to form alkaloid morphinan compound m/z 330 (b), and/or by preventing the oxidation of carbon atom $C_{14}$ to form alkaloid morphinan compound m/z 330 (a), at the expense of the formation of thebaine.

The thebaine, other target morphinan alkaloid or morphinan alkaloid derivative formed form the methods described herein can be isolated from the reaction mixture. Methods for the isolation of morphinan compounds can be selected as desired. For example, the thebaine (or other target morphinan alkaloid or morphinan alkaloid derivative) may be isolated from aqueous mixtures using a liquid/liquid extraction with toluene (see: United States Patent Application No 2002/0106761) or ethyl acetate or ethyl acetate (see: Lenz, R., and Zenk M. H., 1995, Eur. J. Biochem, 233, 132-139). Further techniques and guidance for the isolation of thebaine from reaction mixture may be found in, for example, Hansen, S. H. J. Sep. Sci. (2009), 32 (5-6), 825-834; U.S. Pat. No. 7,094,351; and in (Rinner, U., and Hudlicky, J., 2012 Top. Cur. Chem. 209: 33-66.

BIA Production Levels

The methods described throughout can be used to produce BIAs over what would have been made without any genetic modifications. For example, the methods described throughout can produce BIAs greater than 1.1 times (compared to levels of standard methods, e.g., methods that do not use genetically modified cells). In some cases, the genetically modified cells described throughout can produce BIAs greater than 1.2; 1.3; 1.4; 1.5; 1.6; 1.7; 1.8; 1.9; 2.0; 2.5; 3.0; 3.5; 4.0; 4.5; 5.0; 6.0; 7.0; 8.0; 9.0; 10.0; 12.5; 15.0; 17.5; 20.0; 25.0; 30.0; 50.0; 75.0; or 100.0 times compared to standard methods (including methods that do not use genetically modified cells).

In some cases, the BIA can be thebaine. In other cases, the BIA can be other BIAs described herein such as oripavine, codeine, morphine, oxycodone, hydrocodone, oxymorphone, hydromorphone, naltrexone, naloxone, hydroxycodeinone, neopinone, buprenorphine, or any combination thereof.

Other Methods and Uses

Mutagenesis

Mutagenesis can be used to create cells and plants that comprise improved polypeptides. The improved polypeptides can be used to increase the production of BIAs (or certain components within the BIA pathway) from genetically modified cells and plants.

For example, cells, such as plant seed cells can be used to perform the mutagenesis. Mutagenic agents that can be used are chemical agents, including without limitation, base analogues, deaminating agents, alkylating agents, intercalating agents, transposons, bromine, sodium azide, ethyl methanesulfonate (EMS) as well as physical agents, including, without limitation, radiation, such as ionizing radiation and UV radiation. After mutagenesis of a cell, the activity of the desired polypeptide (e.g., a thebaine synthesis polypeptide and/or purine permease) can be measured and compared to a cell that was not mutagenized.

For example, the following is a method to alter the activity of a thebaine synthesis polypeptide by mutagenesis of a seed setting plant. Disclosed herein is a method for producing a seed setting plant comprising modulated levels of expression of thebaine synthesis polypeptide and/or purine permease in a plant cell naturally expressing thebaine synthesis polypeptide and/or purine permease, the method comprising: (a) providing a seed setting plant naturally expressing thebaine synthesis polypeptide and/or purine permease; (b) mutagenizing seed of the plant to obtain mutagenized seed; (c) growing the mutagenized seed into the next generation mutagenized plants capable of setting the next generation seed; and (d) obtaining the next generation seed, or another portion of the mutagenized plants, and analyzing if the next generation plants or next generation seed exhibits modulated thebaine synthesis polypeptide and/or purine permease expression.

The analysis of the mutagenized cells or plants can be done in several ways. After a plurality of generations of plants and/or seeds is obtained, the portions of plants and/or seeds obtained in any or all of such generations can be analyzed. The analysis can be performed by comparison of expression levels of, for example, RNA levels or protein, in non-mutagenized (wild type) plants or seed, with expression levels in mutagenized plants or seed. The analysis can be performed by analysis of heteroduplex formation between wildtype DNA and mutated DNA. In some instances, the analysis can comprise: (i) extracting DNA from mutated plants; (ii) amplifying a portion of the DNA comprising a polynucleotide encoding thebaine synthesis polypeptide and/or purine permease to obtain amplified mutated DNA; (iii) extracting DNA from wild type plants; (iv) mixing the DNA from wild type plants with the amplified mutated DNA and form a heteroduplexed polynucleotide; (v) incubating the heteroduplexed polynucleotide with a single stranded restriction nuclease capable of restricting at a region of the heteroduplexed polynucleotide that is mismatched; and (vi) determining the site of mismatch in the heteroduplexed polynucleotide.

The methods that modify the expression levels of thebaine synthesis polypeptide and/or purine permease (or other desired gene) may result in modulations in the levels of plant morphinan alkaloids, in plants including but not limited to, thebaine, oripavine, codeine, morphine, oxycodone, hydrocodone, oxymorphone, hydromorphone, naltrexone, naloxone, hydroxycodeinone, neopinone, buprenorphine, or any combination thereof.

Genotyping

The polynucleotides encoding thebaine synthesis polypeptide and/or purine permease can be used to genotype plants. In general, genotyping provides a means of distinguishing homologs of a chromosome pair and can be used to identify segregants in subsequent generations of a plant population. Molecular marker methodologies can be used for phylogenetic studies, characterizing genetic relationships among plant varieties, identifying crosses or somatic hybrids, localizing chromosomal segments affecting monogenic traits, map based cloning, and the study of quantitative inheritance. See, e.g., Plant Molecular Biology: A Laboratory Manual, Chapter 7, Clark, Ed., Springer-Verlag, Berlin (1997). For molecular marker methodologies, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7-21. The particular method of genotyping in accordance with the disclosure may involve the employment of any molecular marker analytic technique including, but not limited to, restriction fragment length polymorphisms (RFLPs). RFLPs reflect allelic differences between DNA restriction fragments caused by nucleotide sequence variability. As is known to those of skill in the art, RFLPs are typically detected by extraction of plant genomic DNA and digestion of the genomic DNA with one or more restriction enzymes. Typically, the resulting fragments are separated according to size and hybridized with a nucleic acid probe. Restriction fragments from homologous chromosomes are revealed. Differences in fragment size among alleles represent an RFLP. Thus, disclosed is a means to follow segregation of a portion or genomic DNA encoding thebaine synthesis polypeptide, and/or purine permease as well as chromosomal polynucleotides genetically linked to these thebaine synthesis polypeptides and/or purine permease encoding polynucleotides using such techniques as RFLP analysis. Linked chromosomal nucleic sequences are within 50 centiMorgans (cM), often within 40 or 30 cM, preferably within 20 or 10 cM, more preferably within 5, 3, 2, or 1 cM of a genomic polynucleotide encoding thebaine synthesis polypeptide and/or purine permease. Thus, the thebaine synthesis polypeptide and/or purine permease encoded by polynucleotide sequences may be used as markers to evaluate in a plant population the segregation of polynucleotides genetically linked thereto.

Some plants that can be useful to genotype with the method disclosed herein are such a plant preferably belongs to the plant genus *Papaver* or the plant species *Papaver bracteatum, Papaver somniferum, Papaver cylindricum, Papaver decaisnei, Papaver fugax, Papaver nudicale, Papaver oreophyllum, Papaver orientate, Papaver paeonifolium, Papaver persicum, Papaver pseudo-orientale, Papaver rhoeas, Papaver rhopalothece, Papaver armeniacum, Papaver setigerum, Papaver tauricolum*, and *Papaver triniaefolium.*

Polynucleotide probes employed for molecular marker mapping of plant nuclear genomes can selectively hybridize, under selective hybridization conditions, to a genomic sequence encoding a thebaine synthesis polypeptide and/or purine permease (or other gene of interest). The probes can be selected from the polynucleotides encoding thebaine synthesis polypeptides and/or purine permease disclosed herein. In other words, the probes can be designed to be complementary to at least a portion of the polynucleotide sequences disclosed herein, e.g., the polynucleotide sequences for the thebaine synthesis polypeptide (e.g., SEQ ID NO. 19) and/or purine permease (e.g., any one of SEQ ID NOs. 36, 38, 39, 42, 44, 46, 48, 50, 52, 54, 56, 58, 60, 62, or 64). In some cases, SEQ ID NOs. 6, 31, 32, 35, 41, 43, 45, 47, 49, 51, 53, 55, 57, 59, 61, and/or 63 can be particularly useful for designing a probe.

The probes can be cDNA probes. The probes can also be at least 5, 6, 7, 8 or 9 bases in length, more preferably at least 10, 15, 20, 25, 30, 35, 40, 50 or 100 bases in length. Generally, however, the probes are less than about 1 kilobase in length. For example, the probes can be anywhere from 10 bp to 30 bps in length. The probes can be single copy probes that hybridize to a unique locus in a haploid plant chromosome complement. In some cases, the polynucleotide is a primer. Some exemplary restriction enzymes employed in RFLP mapping are EcoRI, EcoRv, and SstI. As used herein the term "restriction enzyme" includes reference to a composition that recognizes and, alone or in conjunction with another composition, cleaves a polynucleotide at a specific polynucleotide sequence.

Other methods of differentiating polymorphic (allelic) variants of the polynucleotides can be used by utilizing molecular marker techniques, including, without limitation: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein; and 6) allele-specific PCR. Other approaches based on the detection of mismatches between the two complementary DNA strands include, without limitation, clamped denaturing gel electrophoresis (CDGE); heteroduplex analysis (HA), and chemical mismatch cleavage (CMC). Thus, disclosed is a method of genotyping comprising contacting, under stringent hybridization conditions, a sample suspected of comprising a nucleic acid encoding a thebaine synthesis polypeptide and/or purine permease (or other interested genes), with a nucleic acid probe capable of hybridizing thereto. For example, a sample can comprise plant material, including, a sample suspected of comprising a *Papaver somniferum* polynucleotide encoding a thebaine synthesis polypeptide and/or purine permease (e.g., gene, mRNA). The polynucleotides probe selectively hybridizes, under stringent conditions, to a subsequence of the polynucleotide encoding thebaine synthesis polypeptide and/or purine permease comprising a polymorphic marker. Selective hybridization of the polynucleotide probe to the polymorphic marker polynucleotide yields a hybridization complex. Detection of the hybridization complex indicates the presence of that polymorphic marker in the sample. In preferred embodiments, the polynucleotide probe comprises a portion of a polynucleotide encoding thebaine synthesis polypeptide and/or purine permease.

In Vitro Synthesis of BIAs

The BIAs disclosed herein can be synthesized outside of a cell. For example, one or more of the enzymes (e.g., including the thebaine synthesis polypeptide and/or purine permease) disclosed throughout can be isolated and put into the media outside of a cell. These enzymes can then catalyze the reaction from a substrate into a product outside of a cell. In the case of the thebaine synthesis polypeptide, the substrate can sometimes be salutaridinol 7-O-acetate and the product can be thebaine.

Enzymes and Other Components

For in vitro synthesis of a BIA (such as thebaine), a method can include contacting in vitro a substrate with one or more enzymes that are able to convert the substrate. The one or more enzymes can be any of the following: a tyrosine hydroxylase (TYR); DOPA decarboxylase (DODC); norcoclaurine synthase (NCS); 6-O-Methyltransferase (6OMT); coclaurine N-methyltransferase (CNMT), cytochrome P450 N-methylcoclaurine hydroxylase (NMCH), and 4-O-methyltransferase (4OMT); cytochrome P450 reductase (CPR), salutaridine synthase (SAS); salutaridine reductase (SalR); salutaridinol-7-O-acetyltransferase (SalAT); purine permease (PUP); thebaine synthesis polypeptide (THS); a codeine O-demethylase (CODM); a thebaine 6-O-demethylase (T6ODM); a codeinone reductase (COR); or any combination thereof.

Pure forms of the enzymes necessary for this method may be obtained by isolation of the polypeptide from certain sources including, without limitation, the plants. For example, the plants that can be used include plants from the genus *Papaver*, or from the plant species such as *Papaver somniferum*. Other plants can include without limitation, plant species belonging to the plant families of Eupteleaceae, Lardizabalaceae, Circaeasteraceae, Menispermaceae, Berberidaceae, Ranunculaceae, and Papaveraceae (including those belonging to the subfamilies of Pteridophylloideae, Papaveroideae and Fumarioideae) and further includes plants belonging to the genus *Argemone*, including *Argemone mexicana* (Mexican Prickly Poppy), plants belonging to the genus *Berberis*, including *Berberis thunbergii* (Japanese Barberry), plants belonging to the genus *Chelidonium*, including *Chelidonium majus* (Greater Celandine), plants belonging to the genus *Cissampelos*, including *Cissampelos mucronata* (Abuta), plants belonging to the genus *Cocculus*, including *Cocculus trilobus* (Korean Moonseed), plants belonging to the genus *Corydalis*, including *Corydalis chelanthifolia* (Ferny Fumewort), *Corydalis cava; Corydalis ochotenis; Corydalis ophiocarpa; Corydalis platycarpa; Corydalis tuberosa*; and *Cordyalis bulbosa*, plants belonging to the genus *Eschscholzia*, including *Eschscholzia californica* (California Poppy), plants belonging to the genus *Glaucium*, including *Glaucium flavum* (Yellowhorn Poppy), plants belonging to the genus *Hydrastis*, including *Hydrastis canadensis* (Goldenseal), plants belonging to the genus *Jeffersonia*, including *Jeffersonia diphylla* (Rheumatism Root), plants belonging to the genus *Mahonia*, including *Mahonia aquifolium* (Oregon Grape), plants belonging to the genus *Menispermum*, including *Menispermum canadense* (Canadian Moonseed), plants belonging to the genus *Nandina*, including *Nandina domestica* (Sacred Bamboo), plants belonging to the genus *Nigella*, including *Nigella sativa* (Black Cumin), plants belonging to the genus *Papaver*, including *Papaver bracteatum* (Persian Poppy), *Papaver somniferum, Papaver cylindricum, Papaver decaisnei, Papaver fugax, Papaver nudicale, Papaver oreophyllum, Papaver orientate, Papaver paeonifolium, Papaver persicum, Papaver pseudo-orientale, Papaver rhoeas, Papaver rhopalothece, Papaver armeniacum, Papaver setigerum, Papaver tauricolum*, and *Papaver triniaefolium*, plants belonging to the genus *Sanguinaria*, including *Sanguinaria canadensis* (Bloodroot), plants belonging to the genus *Stylophorum*, including *Stylophorum diphyllum* (Celandine Poppy), plants belonging to the genus *Thalictrum*, including *Thalictrum flavum* (Meadow Rue), plants belonging to the genus *Tinospora*, including *Tinospora cordifolia* (Heartleaf Moonseed), plants belonging to the genus *Xanthoriza*, including *Xanthoriza simplicissima* (Yellowroot) and plants belonging to the genus *Romeria* including *Romeria carica*. The enzymes of the methods can also be prepared with recombinant techniques using a polynucleotide encoding the enzymes. For example, a thebaine synthesis polypeptide can be made recombinantly by expressing a sequence that is substantially identical to SEQ ID NO. 19, derivatives, fragments, or variants thereof. In a preferred embodiment, SEQ ID NO. 19, derivatives, fragments, or variants can be expressed to make a thebaine synthesis polypeptide. The expressed thebaine synthesis polypeptides can be recovered and used to make BIAs in vitro. Disclosed herein is a method for preparing a thebaine synthesis polypeptide, the method comprising: (a) introducing into a host cell a heterologous polynucleotide comprising operably linked (i) polynucleotides encoding a thebaine synthesis polypeptide; and (ii) one or more a polynucleotides capable of controlling expression in the host cell; (b) growing the host cell to produce the thebaine synthesis polypeptide; and (c) recovering the thebaine synthesis polypeptide from the host cell. A polynucleotide encoding for a thebaine synthesis polypeptide may be obtained in accordance herewith include, without limitation, from plant species listed above.

Additionally, a purine permease can be made recombinantly by expressing a sequence that is substantially identical to any one of SEQ ID NOs. 35 to 64, derivatives, fragments, or variants thereof. In a preferred embodiment, a sequence that is substantially identical to any one of SEQ ID NOs. 35 to 64, derivatives, fragments, or variants can be expressed to make a purine permease. The expressed purine permease can be recovered and used to make BIAs in vitro. Disclosed herein is a method for preparing a purine permease, the method comprising: (a) introducing into a host cell a heterologous polynucleotide comprising operably linked (i) polynucleotides encoding a purine permease; and (ii) one or more a polynucleotides capable of controlling expression in the host cell; (b) growing the host cell to produce the purine permease; and (c) recovering the purine permease from the host cell. A polynucleotide encoding for a purine permease may be obtained in accordance herewith include, without limitation, from plant species listed above.

The polynucleotide sequences described herein (e.g., SEQ ID NO. 19 or any other THS sequence disclosed throughout) encoding thebaine synthesis polypeptides (or any other desired genes) can be used to screen the genomes of plant species and other organisms, for the presence of polynucleotides encoding thebaine synthesis polypeptides (or other desired genes). For example, SEQ ID NO. 19 can be used to screen for other thebaine synthesis polypeptides. Upon identifying polynucleotides encoding thebaine synthesis polypeptides (or other desired genes), the genes can be isolated and used to prepare additional thebaine synthesis polypeptides (or other desired polypeptides). Sequences that are substantially identical can also be used.

The polynucleotide sequences described herein (e.g., any one of SEQ ID NOs. 36, 38, 39, 42, 44, 46, 48, 50, 52, 54, 56, 58, 60, 62, and/or 64) encoding a purine permease (or any other desired genes) can be used to screen the genomes of plant species and other organisms, for the presence of polynucleotides encoding a purine permease (or other desired genes). For example, SEQ ID NO. 36 can be used to screen for other purine permeases. Additionally, any one of SEQ ID NOs. 38, 39, 42, 44, 46, 48, 50, 52, 54, 56, 58, 60, 62, and/or 64 can be used to screen for other purine permeases. Upon identifying polynucleotides encoding purine permeases (or other desired genes), the genes can be isolated and used to prepare additional purine permeases (or other desired polypeptides). Sequences that are substantially identical can also be used.

The preparation (used in the in vitro method) can also comprise a mixture of different thebaine synthesis polypeptides and/or purine permeases (e.g., from different sources or from a single source that expresses multiple thebaine synthesis polypeptides and/or purine permeases). The thebaine synthesis polypeptide and/or purine permease is polypeptide obtainable or obtained from the plant genus *Papaver*, or plant species *Papaver somniferum*. The thebaine synthesis polypeptide can be a polypeptide set forth in any one of SEQ ID NO. 6 or 31. In some cases, SEQ ID NO. 6 or 31 is a thebaine synthesis polypeptide. In some cases, SEQ ID NO. 32, 80, or 81 is a thebaine synthesis polypeptide. The purine permease can be a polypeptide set forth in SEQ ID NO. 35. In some cases, SEQ ID NO. 35 is a purine permease. In other cases, the purine permease can be any purine permease described throughout, such as those encoded by any one of SEQ ID NOs. 37, 41, 43, 45, 47, 49, 51, 53, 55, 57, 59, 61, and/or 63. Substantially identical polypeptides, derivatives, functional fragments, and variants can be used. The preparation can also be substantially pure of other proteins that are not thebaine synthesis polypeptides and/or purine permeases.

Polypeptides that can assist the thebaine synthesis polypeptides can also be used. Any of the polypeptides that assist the thebaine synthesis polypeptide described throughout can be used. For example, the in vitro method can comprise one or more polypeptides that are encoded by a polynucleotide that is substantially identical to SEQ ID NO. 18; SEQ ID NO. 20; SEQ ID NO. 21; SEQ ID NO. 22; SEQ ID NO. 23; SEQ ID NO. 24; SEQ ID NO. 25; SEQ ID NO. 26; SEQ ID NO. 27; SEQ ID NO. 28; SEQ ID NO. 29; SEQ ID NO. 30; SEQ ID NO. 36; SEQ ID NO. 38; SEQ ID NO. 42; SEQ ID NO. 44; SEQ ID NO. 46; SEQ ID NO. 48; SEQ ID NO. 50; SEQ ID NO. 52; SEQ ID NO. 54; SEQ ID NO. 56; SEQ ID NO. 58; SEQ ID NO. 60; SEQ ID NO. 62; or SEQ ID NO. 64. In some instances, the in vitro method can comprise one or more polypeptides that are substantially identical to SEQ ID NO. 5; SEQ ID NO. 7; SEQ ID NO. 8; SEQ ID NO. 9; SEQ ID NO. 10; SEQ ID NO. 11; SEQ ID NO. 12; SEQ ID NO. 13; SEQ ID NO. 14: SEQ ID NO. 15: SEQ ID NO. 16; SEQ ID NO. 17; SEQ ID NO. 35; SEQ ID NO. 37; SEQ ID NO. 41; SEQ ID NO. 43; SEQ ID NO. 45; SEQ ID NO. 47; SEQ ID NO. 49; SEQ ID NO. 51; SEQ ID NO. 53; SEQ ID NO. 55; SEQ ID NO. 57; SEQ ID NO. 59; SEQ ID NO. 61; or SEQ ID NO. 63.

Also disclosed herein is an isolated polynucleotide comprising a polynucleotide sequence encoding a thebaine synthesis polypeptide and/or purine permease. In some cases, the polynucleotides encoding a thebaine synthesis polypeptide and/or purine permease can be obtainable or obtained from the plant genus *Papaver* or from the plant species *Papaver somniferum*.

The polynucleotide encoding a thebaine synthesis polypeptide and/or purine permease (or other desired enzyme) can be isolated or prepared using any desirable methodology. For example, a polynucleotide encoding a thebaine synthesis polypeptide and/or purine permease can be obtained or prepared following identification and isolation of a thebaine synthesis polypeptide, as further described in detail in Example 1.

The thebaine synthesis polypeptide and/or purine permease (or other desired enzyme) may be recovered, isolated and separated from other host cell components by a variety of different protein purification techniques including, e.g. ion-exchange chromatography, size exclusion chromatography, affinity chromatography, hydrophobic interaction chromatography, reverse phase chromatography, gel filtration, etc. Further general guidance with respect to protein purification may for example be found in: Cutler, P. Protein Purification Protocols, Humana Press, 2004, Second Ed.

The thebaine synthesis polypeptide may be any thebaine synthesis polypeptide capable of mediating the conversion of the substrate alkaloid morphinan into thebaine. In some cases, more than one thebaine synthesis polypeptide may be used, e.g., one, two, three, four, five, six, seven, eight or more of the thebaine synthesis polypeptides or any functional variants or fragments thereof can be used.

The purine permease may be any purine permease capable of mediating increasing thebaine titers in a cell. In some cases, more than one purine permeases may be used, e.g., one, two, three, four, five, six, seven, eight or more of the purine permeases or any functional variants or fragments thereof can be used.

Disclosed herein is a preparation comprising one or more isolated thebaine synthesis polypeptides and/or purine permeases. Such preparations generally are aqueous preparations containing additionally, for example, buffering agents, salts, reducing agents, and stabilizing elements to maintain solubility and stability of the thebaine synthesis polypeptides and/or purine permeases. The preparation can be substantially free of proteins other than thebaine synthesis polypeptides and/or purine permeases. Thus, for example, in some preparations the thebaine synthesis polypeptide comprises at least 90% (w/w), at least 95% (w/w), at least 96% (w/w), at least 97% (w/w), at least 98% (w/w), or at least 99% (w/w) of the protein constituents in a preparation. The preparation can also comprise a single thebaine synthesis polypeptide and is substantially free of other thebaine synthesis polypeptides. Thus, for example, in some preparations a single thebaine synthesis polypeptide comprises at least 90% (w/w), at least 95% (w/w), at least 96% (w/w), at least 97% (w/w), at least 98% (w/w), or at least 99% (w/w) of the thebaine synthesis polypeptide constituents in the preparation.

In some preparations the purine permease comprises at least 90% (w/w), at least 95% (w/w), at least 96% (w/w), at least 97% (w/w), at least 98% (w/w), or at least 99% (w/w) of the protein constituents in a preparation. The preparation can also comprise a single purine permease and is substantially free of other purine permeases. Thus, for example, in some preparations a single purine permease comprises at least 90% (w/w), at least 95% (w/w), at least 96% (w/w), at least 97% (w/w), at least 98% (w/w), or at least 99% (w/w) of the purine permeases constituents in the preparation.

Methods of Making BIA Outside of a Cell

For in vitro synthesis of a BIA (such as thebaine), a method can include (a) contacting a substrate that is capable of being converted by one or more enzymes, where the one or more enzymes comprise a tyrosine hydroxylase (TYR); DOPA decarboxylase (DODC); norcoclaurine synthase (NCS); 6-O-Methyltransferase (6OMT); coclaurine N-methyltransferase (CNMT), cytochrome P450 N-methylcoclaurine hydroxylase (NMCH), and 4-O-methyltransferase (4OMT); cytochrome P450 reductase (CPR), salutaridine synthase (SAS); salutaridine reductase (SalR); salutaridinol-7-O-acetyltransferase (SalAT); purine permease (PUP); or any combination thereof and (b) contacting the product of (a) with one or more of a thebaine synthesis polypeptide; a codeine O-demethylase (CODM); a thebaine 6-O-demethylase (T6ODM); a codeinone reductase (COR); or any combination thereof.

One or more the above mentioned enzymes may also be within a living cell. For example, TYR may be outside the cell while the rest of the enzymes may be contained with the cell. In another example, TYR, DODC, NCS, 6OMT, CNMT, NMCH, 4OMT; CPR, SAS, SalR, PUP, and SalAT are contained within a living cell, while a thebaine synthesis polypeptide (THS) is outside the cell in the medium. Further, CODM, T6ODM, and COR can also be outside the cell in the medium.

The substrate can be any of the substrates disclosed throughout, including but not limited to a sugar (e.g., glucose), glycerol, L-tyrosine, tyramine, L-3,4-dihydroxyphenyl alanine (L-DOPA), alcohol, dopamine, or any combination thereof.

The substrate can be contacted with one enzyme before it is contacted with another, in a sequential manner. For example, the substrate can be contacted with salutaridine synthase (SAS) before it is contacted with a thebaine synthesis polypeptide.

After the BIA is formed, the method can comprise recovering the BIA.

In the case of making thebaine, some of the methods can include bringing a substrate morphinan alkaloid in contact with a thebaine synthesis polypeptide in a reaction mixture under reaction conditions permitting a thebaine synthesis polypeptide mediated reaction resulting in the conversion of the substrate morphinan alkaloid into thebaine under in vitro reaction conditions. Under such in vitro reaction conditions the initial reaction constituents are provided in a more or less isolated form, and the constituents are mixed under conditions that permit the reaction to substantially proceed.

One or more plant cells or microorganisms can also be co-cultured with one or more different substrates to provide necessary reaction constituents. If one or more plant cells or microorganisms are used in these in vivo reactions, the necessary reaction constituents can be secreted.

Should substrate morphinan alkaloids be used, substrate morphinan alkaloids may be purchased as a substantially pure chemical compound, chemically synthesized from precursor compounds, or isolated from certain sources including from the plants, such as from the plant genus *Papaver*, or from the plant species such as *Papaver somniferum*. Such compounds may be compounds provided with a high degree of purity, for example, a purity of at least 75%, 80%, 85%, 90%, 95%, or 99% or more. Other plant species that may be used to obtain the substrate morphinan alkaloid include, without limitation, plant species belonging to the plant families described above.

With regards to making thebaine, the thebaine synthesis polypeptide may be used to produce thebaine (or other target morphinan alkaloids or morphinan alkaloid derivatives). Accordingly, described is a use of a thebaine synthesis polypeptide to make thebaine (or other target morphinan alkaloids or morphinan alkaloid derivatives). Additionally, a purine permease can also be used alone or in combination with a thebaine synthesis polypeptide to make substantial amounts of thebaine.

The thebaine synthesis polypeptide and/or purine permease can be included in a reaction mixture in which a substrate alkaloid morphinan is converted to thebaine, or other target morphinan alkaloids or morphinan alkaloid derivatives. In accordance herewith in order to perform a reaction under in vitro conditions, a substrate morphinan alkaloid is brought in contact with catalytic quantities of thebaine synthesis polypeptide, under reaction conditions permitting a chemical conversion of the substrate morphinan alkaloid into thebaine, or other target morphinan alkaloids or morphinan alkaloid derivatives. In some cases, the agents are brought in contact with each other and mixed to form a mixture. The mixture can be an aqueous mixture comprising water and further optionally additional agents to mediate the reaction, including buffering agents, salts, pH-modifying agents and co-factors such as acetyl-CoA and NADPH. The reaction may be performed at a range of different temperatures, including between about 18° C. and about 50° C., e.g., between about 18° C. and about 45° C., about 25° C. to about 40° C., about 32° C. to about 38° C., or at about 37° C. The mixture can also comprise one or more purine permeases.

The reaction mixture can further comprise SalAT and/or SalR. Polynucleotide sequences of SalAT and SalR that can be used are those identified as SEQ ID NO. 1 and SEQ ID NO. 3, respectively, or sequences that are substantially identical. These sequences may be used to in recombinant techniques to prepare SalAT and/or SalR polypeptides and polynucleotides encoding SalAt and/or SalR. Alternatively SalAT and/or SalR may be obtained from certain sources, including from a plant, including the plants disclosed herein.

Upon substantial completion of the in vitro reaction a reaction mixture comprising thebaine is obtained. In some cases, other BIAs can be obtained. Thebaine or other BIA can then be isolated from the reaction mixture. In some cases, thebaine is left in the reaction mixture to form other target morphinan alkaloids or morphinan alkaloid derivatives (or other BIAs). In some cases, in order to form other target morphinan alkaloids or morphinan alkaloid derivatives, additional enzymes must be added to the reaction mixture.

BIA Production Levels

The in vitro methods described throughout can be made to produce BIAs over what would have been made with standard methods (including methods that do not use a thebaine synthesis polypeptide and/or purine permease and/or other polypeptides described throughout). For example, the in vitro methods described throughout can produce BIAs greater than 1.1 times (compared to standard methods, including methods that do not use a thebaine synthesis polypeptide and/or purine permease and/or other polypeptides described throughout). In some cases, the in vitro methods described throughout can produce BIAs greater than 1.2; 1.3; 1.4; 1.5; 1.6; 1.7; 1.8; 1.9; 2.0; 2.5; 3.0; 3.5; 4.0; 4.5; 5.0; 6.0; 7.0; 8.0; 9.0; 10.0; 12.5; 15.0; 17.5; 20.0; 25.0; 30.0; 50.0; 75.0; or 100.0 times compared to the production level of standard methods (including methods that do not use a thebaine synthesis polypeptide and/or purine permease and/or other polypeptides described throughout).

In some cases, the BIA can be thebaine. In other cases, the BIA can be other BIAs described herein such as oripavine, codeine, morphine, oxycodone, hydrocodone, oxymorphone, hydromorphone, naltrexone, naloxone, hydroxycodeinone, neopinone, buprenorphine, or any combination thereof.

Exemplary Uses of the BIAS

Preparations of BIAs (e.g., thebaine) obtained may be used for a variety of compositions and methods. The BIAs can be isolated and sold as purified products. Or these purified products can be a feedstock to make additional BIAs or morphinan alkaloids.

Derivative morphinan alkaloid compounds may be used to manufacture medicinal compounds. Thus, for example when considering thebaine, it be converted to a derivative morphinan alkaloid compound selected from oripavine, codeine, morphine, oxycodone, hydrocodone, oxymorphone, hydromorphone, naltrexone, naloxone, hydroxycodeinone, neopinone, buprenorphine, or any combination thereof.

Accordingly, in one aspect, disclosed is a use of thebaine (or other BIA) as a feedstock compound in the manufacture of a medicinal compound.

The medicinal compound can be a natural derivative morphinan alkaloid compound or, in some cases, a semi-synthetic derivative morphinan alkaloid compound. For example, thebaine may be converted to oripavine, codeine, morphine, oxycodone, hydrocodone, oxymorphone, hydromorphone naltrexone, naloxone, hydroxycodeinone, neopinone, buprenorphine, or any combination thereof which each may subsequently be used to prepare a pharmaceutical formulation.

The disclosure is now described with reference to the following Examples. These Examples are provided for the purpose of illustration only and the disclosure should in no way be construed as being limited to these Examples, but rather should be construed to encompass any and all variations which become evident as a result of the teaching provided herein.

EXAMPLES

Example 1—Preparation of Extracts from Plant Latex Containing Thebaine Synthesis Polypeptides Opium poppy plants were cultivated in growth chambers under a combination of fluorescent and incandescent lighting with a photoperiod of 16 h, and at 20° C./18° C. (light/dark).

In order to prepare extracts containing thebaine synthesis polypeptides, a latex preparation was obtained from mature *Papaver somniferum* seedpods using the following procedure to obtain a purified plant extract containing thebaine synthesis polypeptide extract.

A latex sample from mature *Papaver somniferum* seed capsules was extracted using phosphate buffer (Na—$PO_4$), pH 7.0, containing 500 mM mannitol. The extract was centrifuged and the supernatant was recovered. The total soluble protein in the supernatant was desalted using a PD-10 desalting column consisting of Sephadex G-25 resin. Ammonium sulfate was added to the desalted protein sample to 40% (w/v) saturation. After centrifugation, additional ammonium sulfate was added to the supernatant to 80% (w/v) saturation. Subsequent centrifugation yielded a protein pellet, which was then resuspended in Na—$PO_4$ buffer, pH 7.0, yielding the crude thebaine synthesis polypeptide extract. The protein extract was further purified using a series of chromatography methods. The sequential purification steps are described below.

Following ammonium sulfate precipitation, the protein sample was loaded onto a butyl-S sepharose 6 Fast Flow column (12 mm×100 mm; GE Healthcare) equilibrated with 50 mM Na—$PO_4$ buffer, pH 7.0, containing 1.7 M ammonium sulfate. Protein was eluted stepwise at 2 mL/min using 50 mM Na—$PO_4$ buffer, pH 7.0, containing 1.0 M arginine-HCl, initially at 40% (v/v), then increasing to 79% (v/v) and finally reaching 100%. Elution fractions were collected and assayed for thebaine synthesis protein activity.

Active fractions from butyl-S sepharose 6 chromatography were pooled, buffer exchanged to 20 mM Tris-HCl, pH 8.0, and loaded onto a 1.0 mL HiTrap Q HP column (GE Healthcare). Protein elution was performed with 20 mM Tris-HCl, pH 8.0, and 1.0 M NaCl applied with linear gradient of 0-60% (v/v) at a flow rate of 1 mL/min for 20 min. Elution fractions were collected and assayed for thebaine synthesis protein activity.

Active fractions from HiTrap Q HP chromatography were concentrated and loaded onto two Superdex 75 HR 10/30 columns (GE Healthcare) connected in tandem. Isocratic elution was performed with 20 mM Tris-HCl, pH 8.0, 0.15 M NaCl and 10% (v/v) glycerol at a flow rate of 1 mL/min. Elution fractions were collected and assayed for thebaine synthesis protein activity.

Active fractions from Superdex 75 HR 10/30 chromatography were pooled and applied to a Macro-Prep Ceramic Hydroxyapatite TYPE I column (BioRad) pre-equilibrated with 100 mM Na—$PO_4$, pH 6.7, 90 mM NaCl and 20 mg/L $CaCl_2$. Stepwise elution was performed using 500 mM Na—$PO_4$, pH 6.7, containing 100 mM NaCl applied initially at 7% (v/v) for 7 mL, then increased to 10% (v/v) for 7 mL and finally reaching 100% for 15 mL at a flow rate of 1 mL/min.

It was observed that when a *Papaver somniferum* latex preparation was extracted using a phosphate buffer without mannitol, thebaine synthesis polypeptide activity could not be detected. Extracts using a phosphate buffer with and without 500 mM mannitol were prepared and proteomically analyzed for the quantitative differential presence of individual polypeptides. The presence of relatively higher quantities in the proteome of a protein extract obtained following extraction using a phosphate buffer with mannitol was deemed indicative of a thebaine synthesis polypeptide. Several thebaine synthesis polypeptide candidates were identified. Accordingly, protein extracts comprising polypeptides having the sequences set forth in SEQ ID NO. 5; SEQ ID NO. 6; SEQ ID NO. 7; SEQ ID NO. 8; SEQ ID NO. 9; SEQ ID NO. 10; SEQ ID NO. 11; and SEQ ID NO. 12 resulted in a thebaine synthesis polypeptide mediated chemical reaction resulting in the conversion of substrate salutaridinol into thebaine. In particular, SEQ ID NO. 6 (known herein as Bet v1 (a.k.a., Betv1M/BetV1-1/THS2) showed a very high increase a thebaine synthesis polypeptide mediated chemical reaction.

Thebaine synthesis polypeptide activity was measured by incubating protein extracts with salutaridinol and assaying for the presence of compounds having an m/z=312, corresponding with thebaine and compounds have an m/z=330, corresponding with morphinan alkaloid by-products, and further assaying for the possible presence of non-converted quantities of salutaridinol.

Figure 7A:
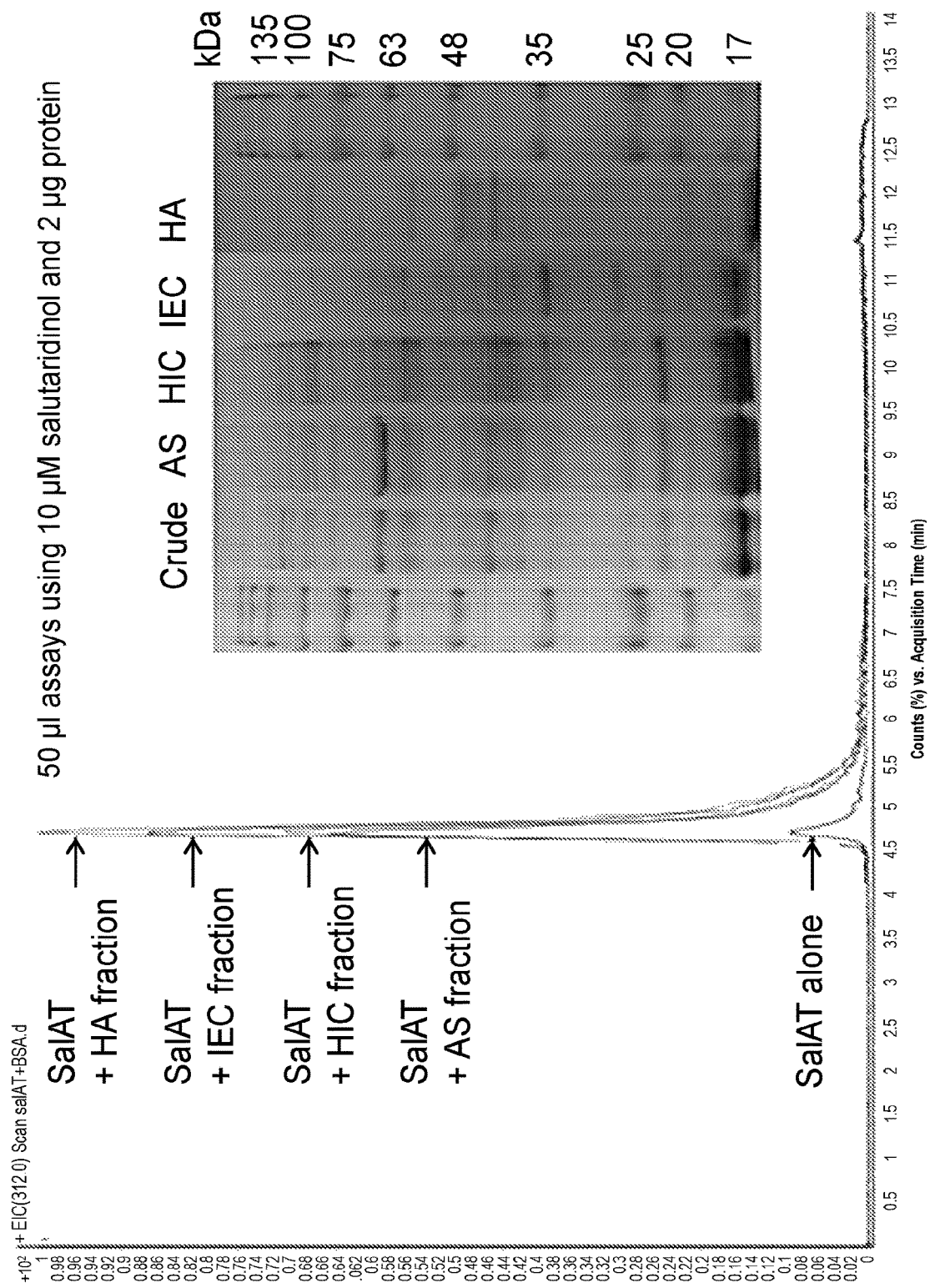
Figures 7B, 7C, 7D:
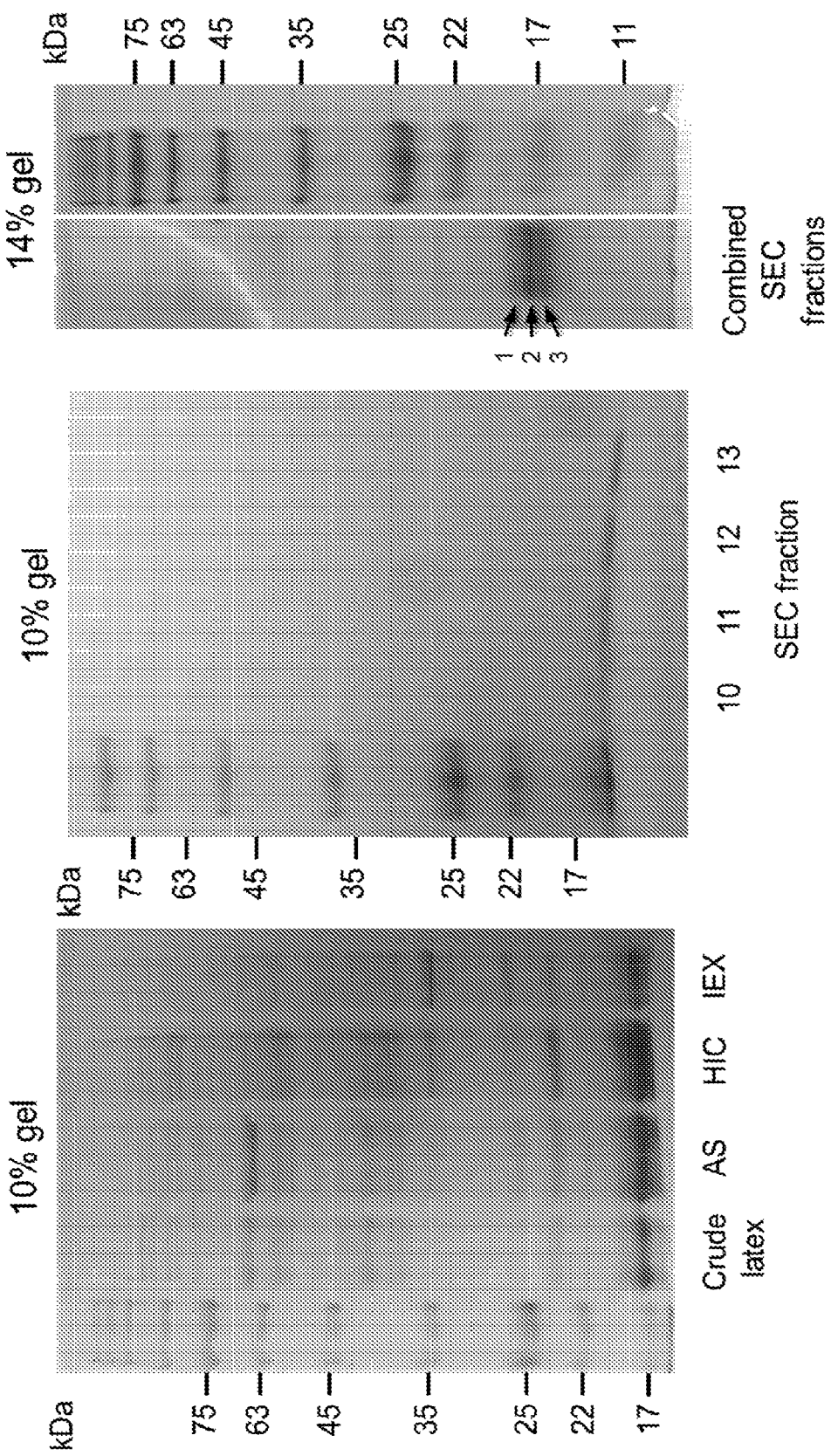
Figure 7G:
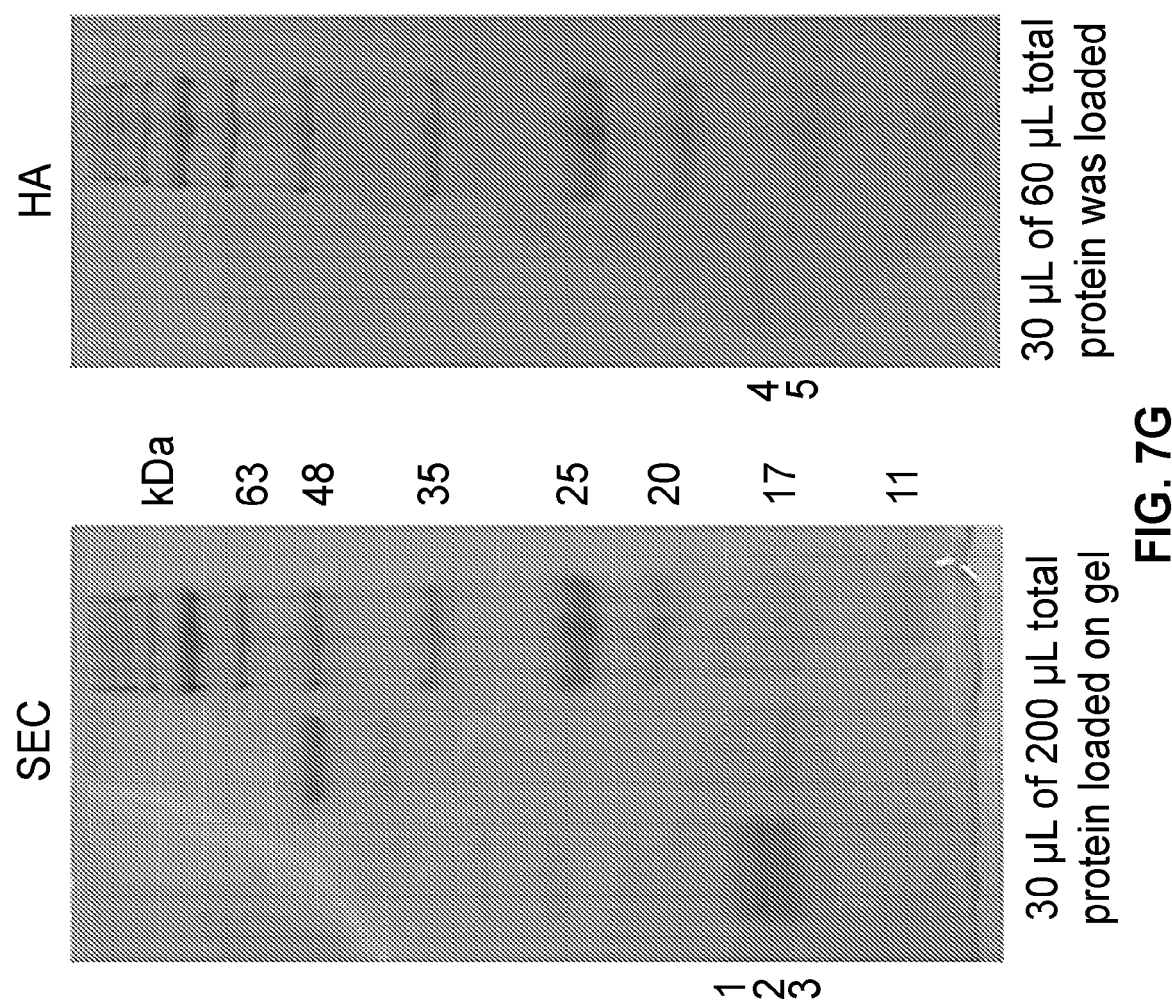

Results are shown in FIGS. 7-8. In particular, FIG. 7 depicts certain relative amounts of thebaine produced by SalAT in the presence of several protein fractions (AS, HIC, IEC, HA, fractions) from the purification process this Example 1. Also shown is a polyacrylamide gel following gel electrophoresis of the same protein extracts and thus show thebaine synthesis protein activity present in these fractions. FIG. 7G depicts two polyacrylamide gels following gel electrophoresis of protein extracts (SEC and HA fraction) and purification of the 16-18 kDa bands after inclusion of the SEC step before the hydroxyapatite (HA) step, with retention of the thebaine synthesis protein (TS) activity.

Figure 6A:
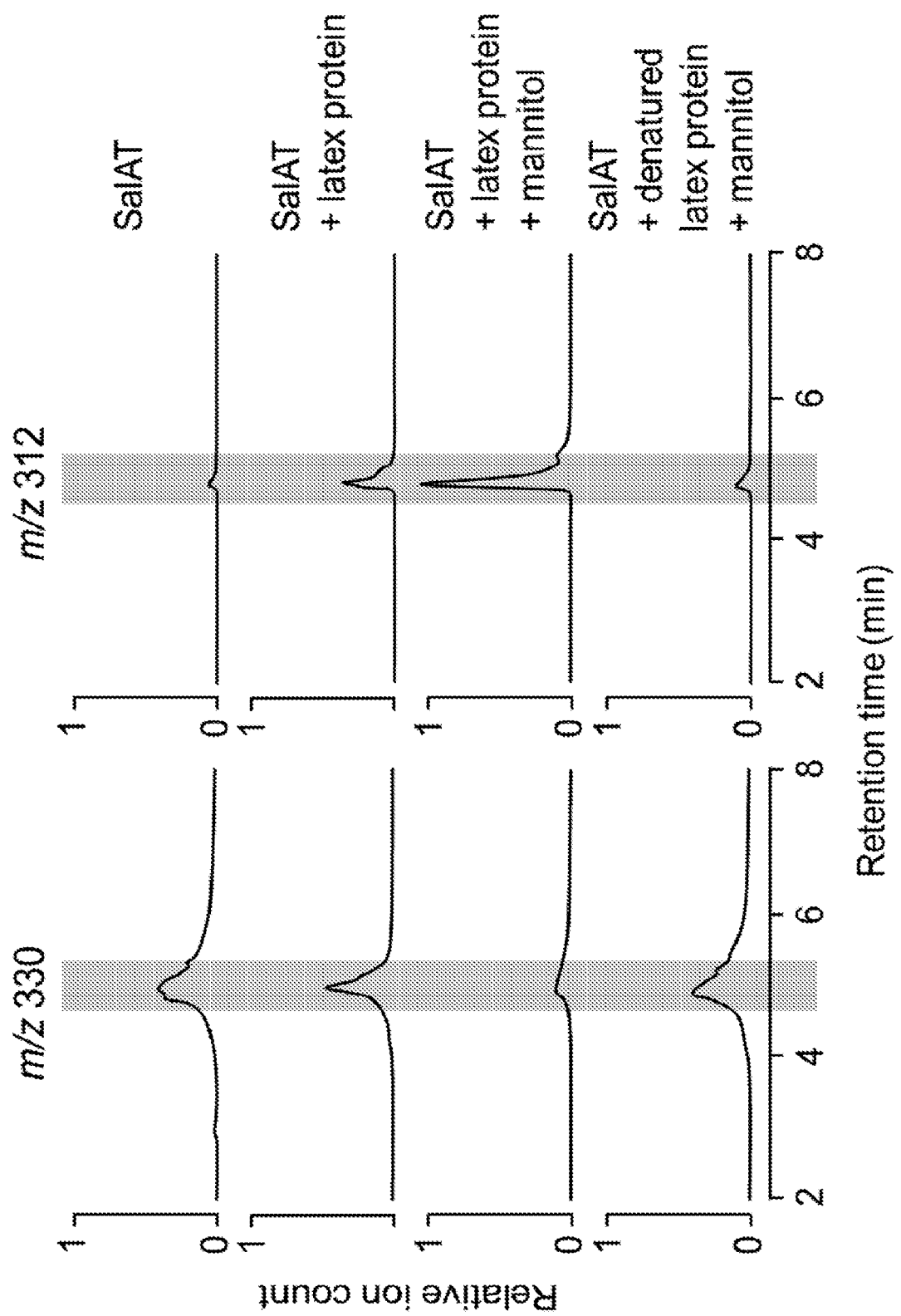
Figure 6C:
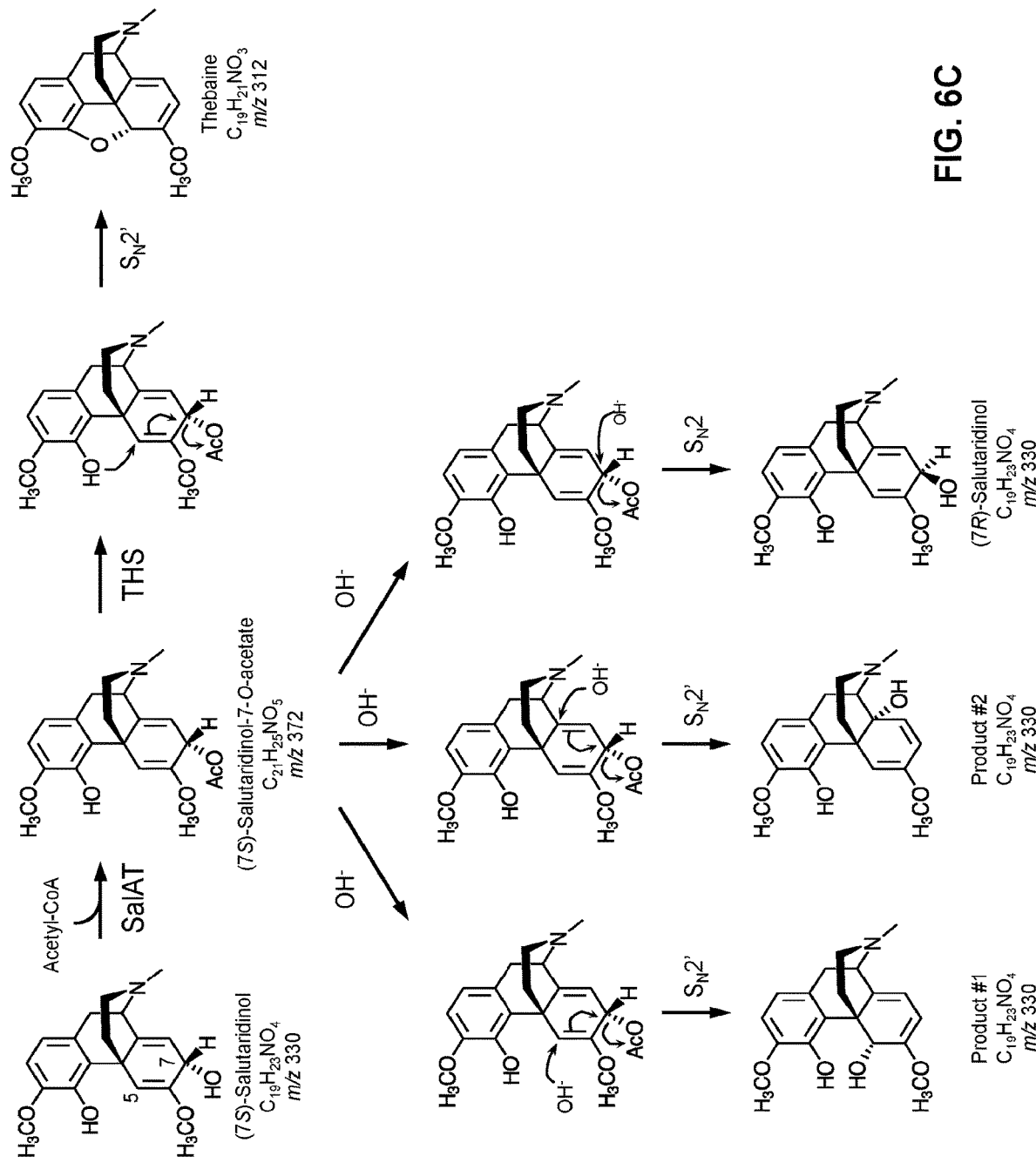

SalAT-coupled enzyme assays showed that less than 10% of the initial salutaridinol substrate was converted to thebaine (FIG. 6A). The major product was a compound, or a set of compounds, with m/z 330 that had not previously been reported in opium poppy (FIGS. 6B and 6C). The addition of a soluble protein extract from opium poppy latex to the SalAT-couples assays increased thebaine formation at the expense of the m/z 330 compound (FIG. 6A). Interestingly, latex protein extracted with sodium phosphate buffer containing 500 mM mannitol resulted in substantially higher thebaine formation compared with latex protein extracted in the absence of mannitol.

Figure 6D:
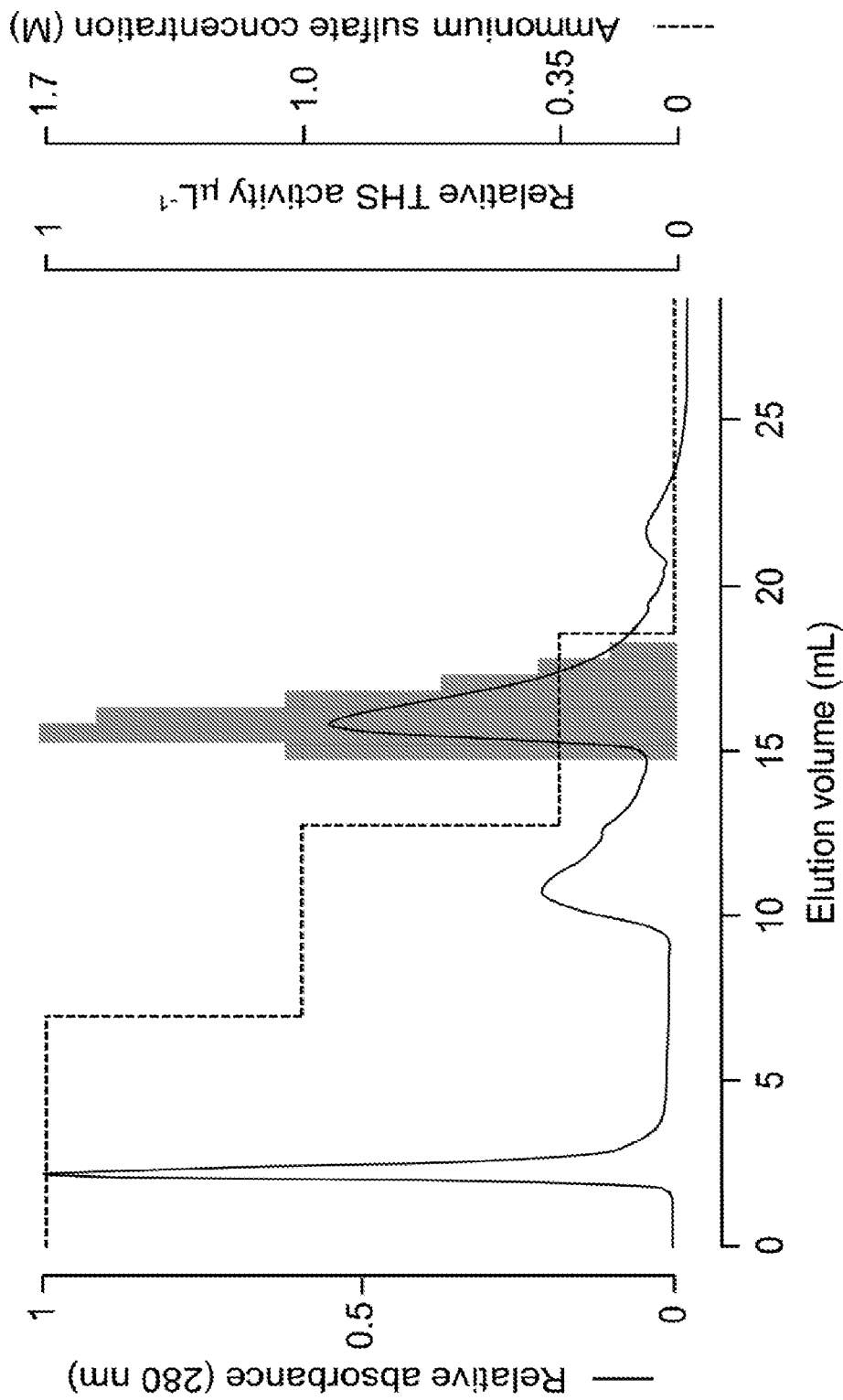
Figure 6E:
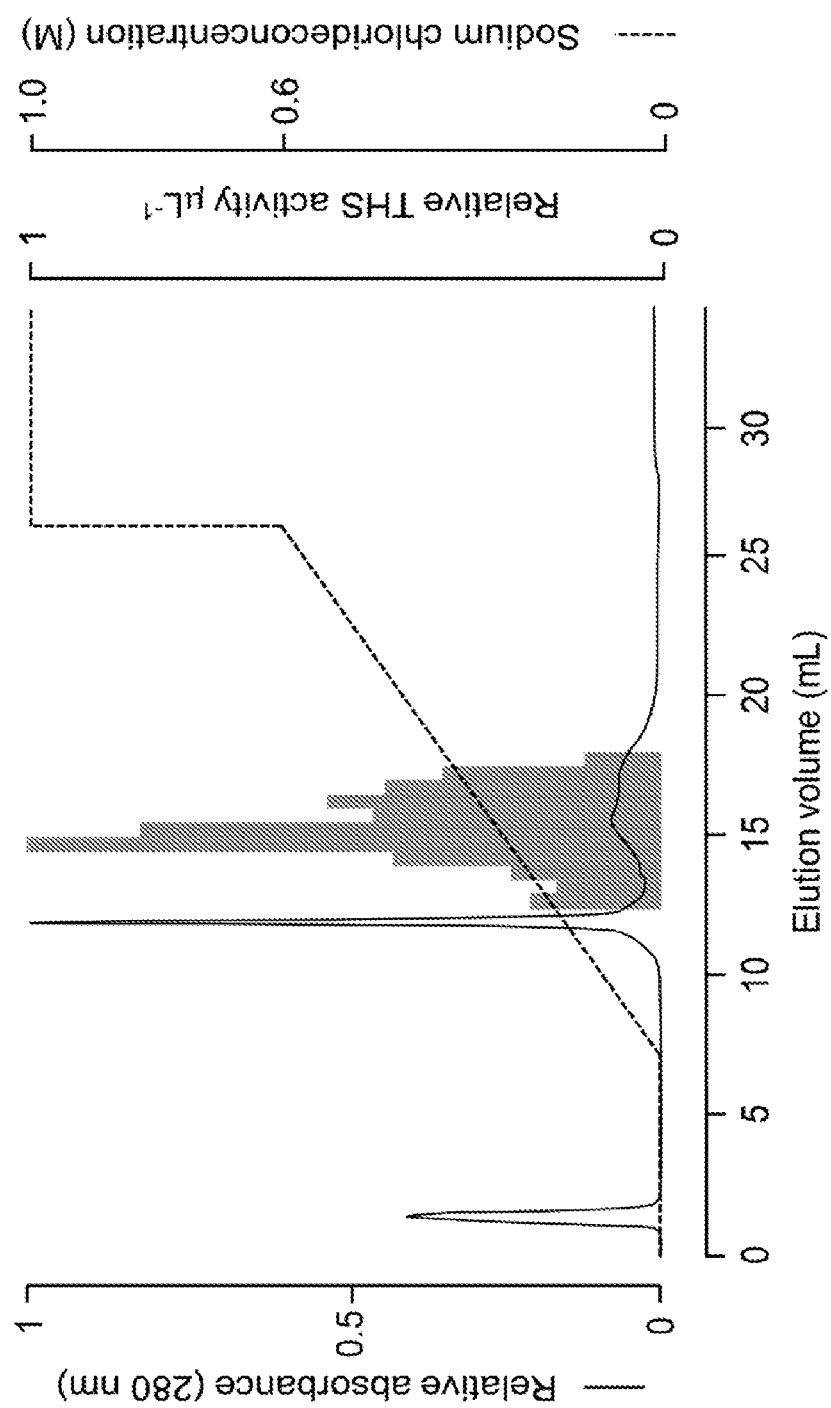
Figure 6F:
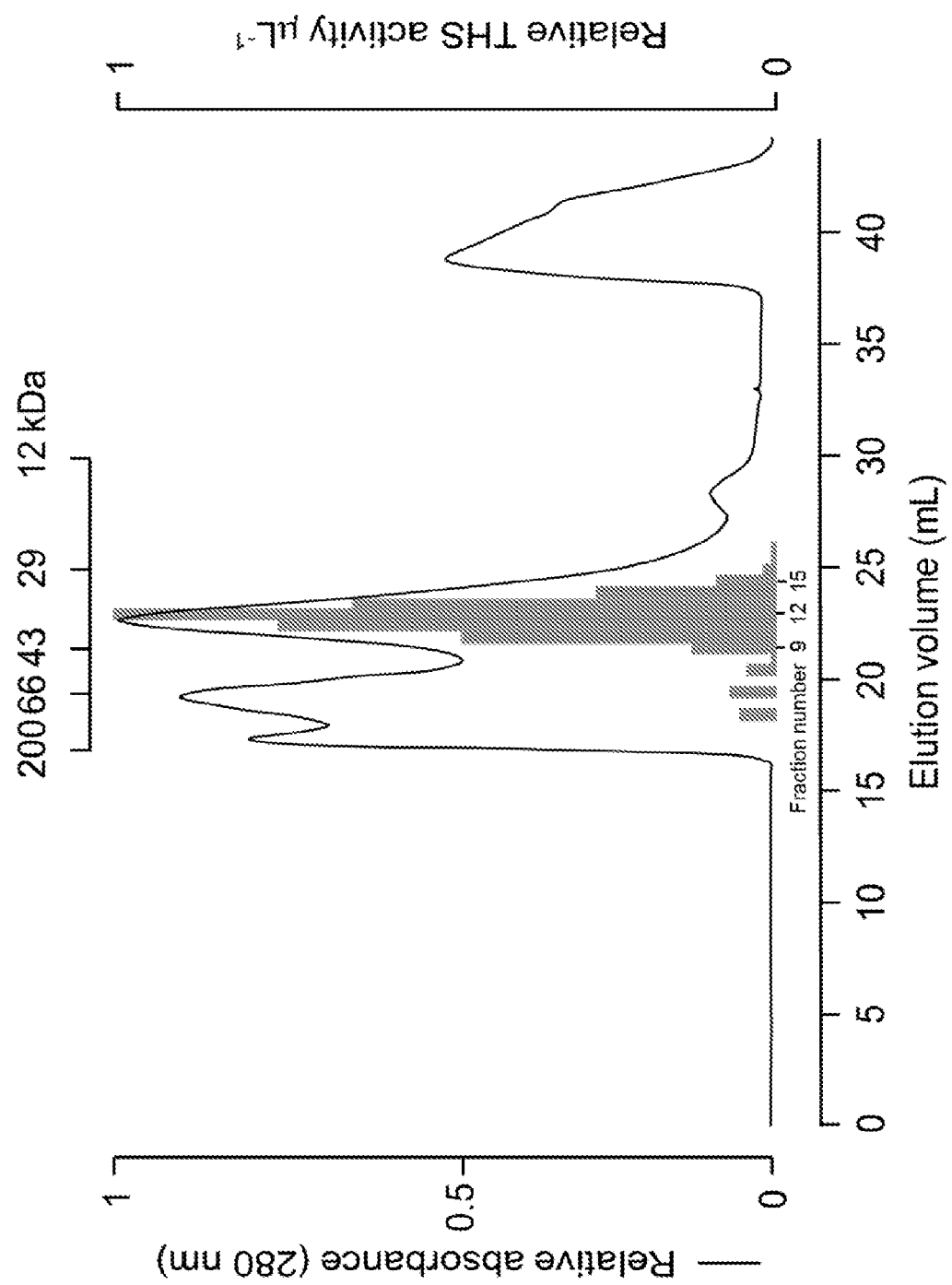

Opium poppy latex protein extracted from the high-thebaine and high-oripavine chemotype T was subjected to ammonium sulfate precipitation and, subsequently, a series of three different methods of chromatographic separation (i.e. hydrophobic-interaction [HIC] (FIG. 6D), ion-exchange [IEX] (FIG. 6E) and size exclusion [SEC] (FIG. 6F)). The partial purification resulted in a 20-fold increase in specific activity with respect to thebaine formation, and suggested a native protein molecular weight of approximately 40 kDa (FIG. 6G). Four successive SEC elution fractions were initially resolved on a 10% (w/v) SDS-PAGE gel as a single protein band of approximately 17 kDa (FIGS. 7B-7D). The protein samples were then pooled and the combined proteins resolved on a 14% (w/v) SDS-PAGE gel, which revealed three dominant bands of approximately 17 kDa (FIGS. 7B-7D). The three dominant protein bands were excised from the 14% (w/v) gel and analyzed individually by LC-MS/MS Protein identification was performed using Scaffold (Proteome Software) proteomics software and a translated opium poppy latex transcriptome database. Over 100 proteins were detected in the three protein bands, yet the majority were represented by only a few spectral counts. The top six proteins showing the highest spectral counts (FIG. 7E) were produced individually in E. coli and Saccharomyces cerevisiae from codon-optimized genes. A protein sequence alignment showed that six candidates shared considerable amino acid sequence identity and all belong to the MLP- and Betv1-type PR10 protein family (FIG. 7F).

Figure 8A:
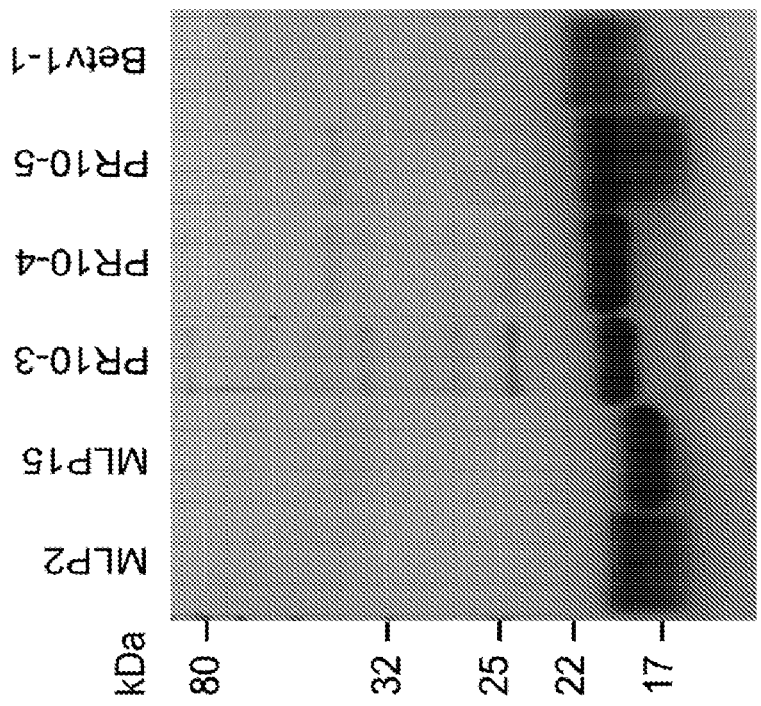
FIGS. 8A and 8B shows SalAT-coupled enzyme assays of recombinant proteins produced in *Escherichia coli* representing the top six candidates responsible for the enhanced conversion of salutaridinol to thebaine. Betv1-1 is also referred to as thebaine synthesis polypeptide or thebaine synthase throughout the disclosure.
Figure 8B:
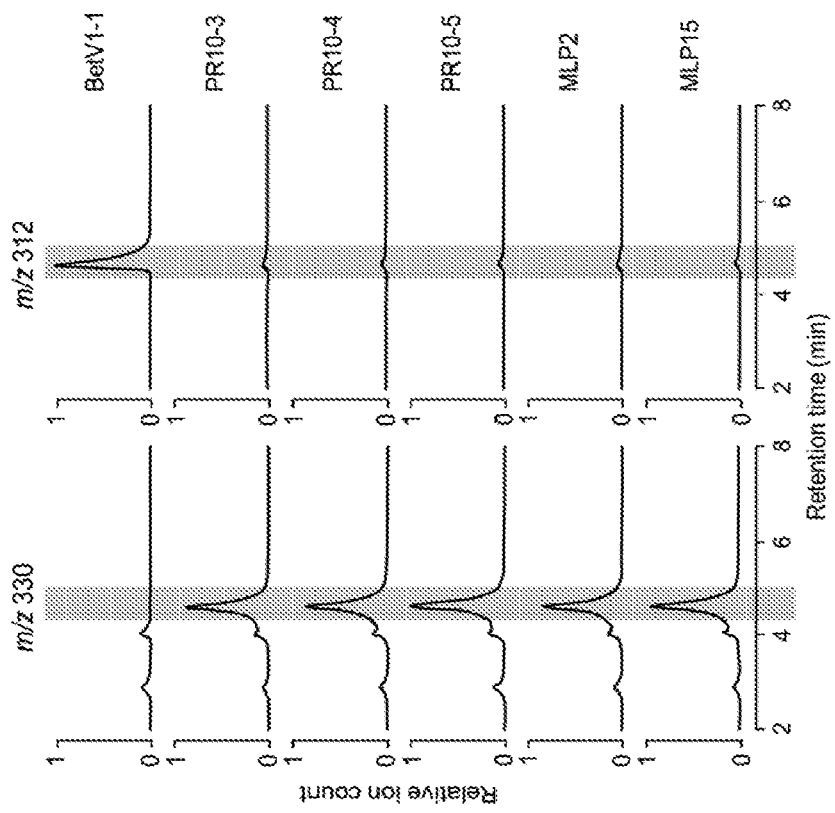
Figure 9B:
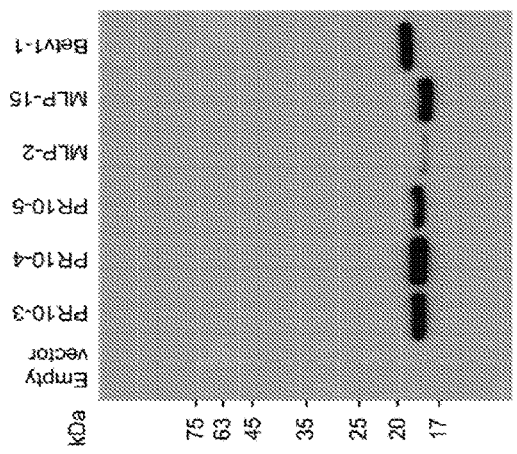
FIGS. 9A-D.
Figure 9C:
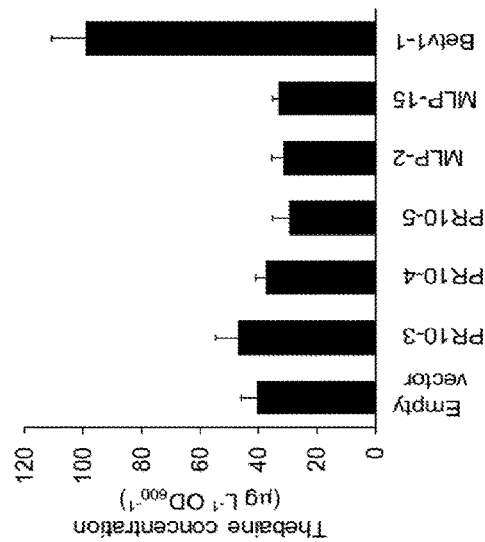
Figure 9A:
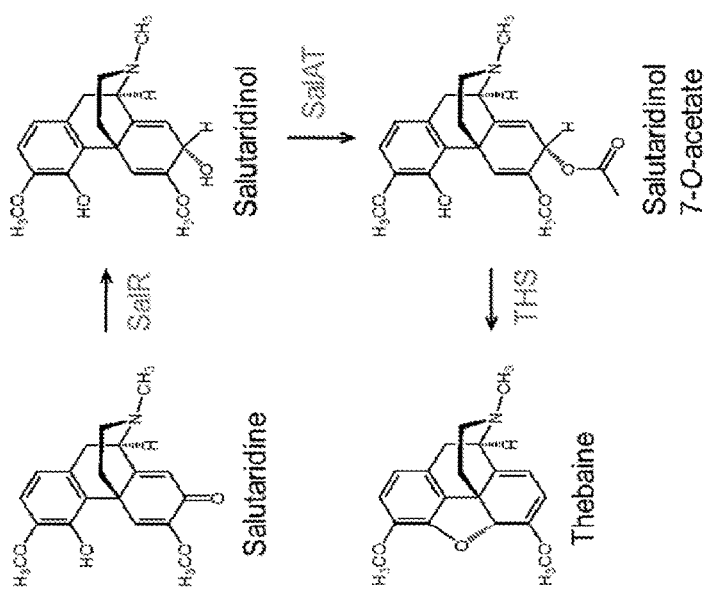

SalAT-coupled enzyme assays were then performed with purified recombinant proteins. One of the six candidates (i.e., Betv1-1) substantially increased thebaine formation. The addition of 2 µg of the Betv1-1 (SEQ ID NO. 6) protein in a 50-4 SalAT-coupled reaction containing 20 µM salutaridinol as the substrate effectively eliminated production of the m/z-330 by-product (FIGS. 8A and 8B). Betv1 (SEQ ID NO. 6) alone (i.e. without SalAT in the assay) did not transform salutaridinol into a product. In yeast containing an salutaridine reductase (SalR) and SalAT gene and, individually, each of the six candidates transiently expressed from a plasmid, only Betv1-1 (SEQ ID NO. 6) facilitated the enhanced conversion of exogenous salutaridine to the thebaine (FIGS. 9A-9C). Betv1-1 (SEQ ID NO. 6) was designated as the primary thebaine synthase (THS).

Example 2—Enzymatic Production of Thebaine In Vitro

Bet v1-1A (corresponding to C-terminal HA tagged), Bet v1-1B (corresponding to N-terminal HA tagged), PR10-3A (SEQ ID NO. 33), and PR10-3B (SEQ ID NO. 34) were expressed in E. coli (Rosetta). Bet v1 corresponds to SEQ ID NO. 6. The transformants were used to produce crude extracts and tested for thebaine synthesis activity. Extracts for each expression construct were prepared and used to prepare various thebaine assay mixtures, as shown in Table 1.

TABLE 1

|  | SalAT | Bet v1-1A | Bet v1-1B | PR10-3A | PR10-3B | "All-in-One" |
|---|---|---|---|---|---|---|
| Purified SalAT | √ | √ | √ | √ | √ | √ |
| Salutaridinol | √ | √ | √ | √ | √ | √ |
| Acetyl-CoA | √ | √ | √ | √ | √ | √ |
| Phosphate buffer pH7 | √ | √ | √ | √ | √ | √ |
| Crude E. coli extract |  | √ | √ | √ | √ |  |

The assay mixtures were used to determine the presence thebaine and m/z 330 (an unknown product).

Figure 9D:
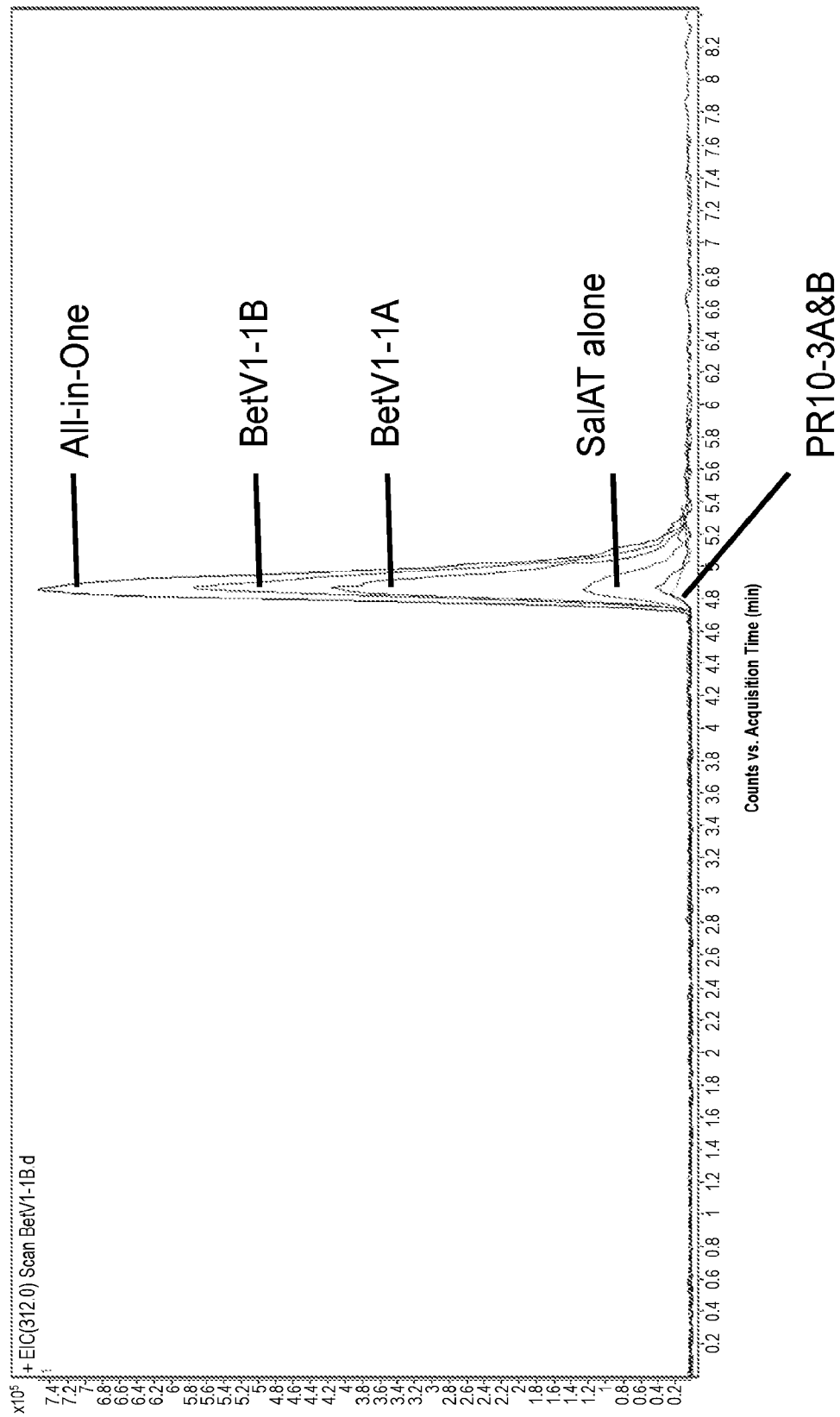

Extracts from E. coli expressing Bet v1-1B produced the most thebaine whereas Bet v1-1A produced slightly less. Extracts from E. coli expressing SaltAT, Bet v1-1A, Bet v1-1B, PR10-3A and PR10-3B, produced the highest titers of thebaine. FIG. 9D.

In the assays using thebaine synthesis polypeptide candidates in E. coli extracts, the majority of salutaridinol was not consumed, whereas with SalAT alone, all salutaridinol was used and formed m/z 330 byproduct. FIG. 9D.

Figure 10:
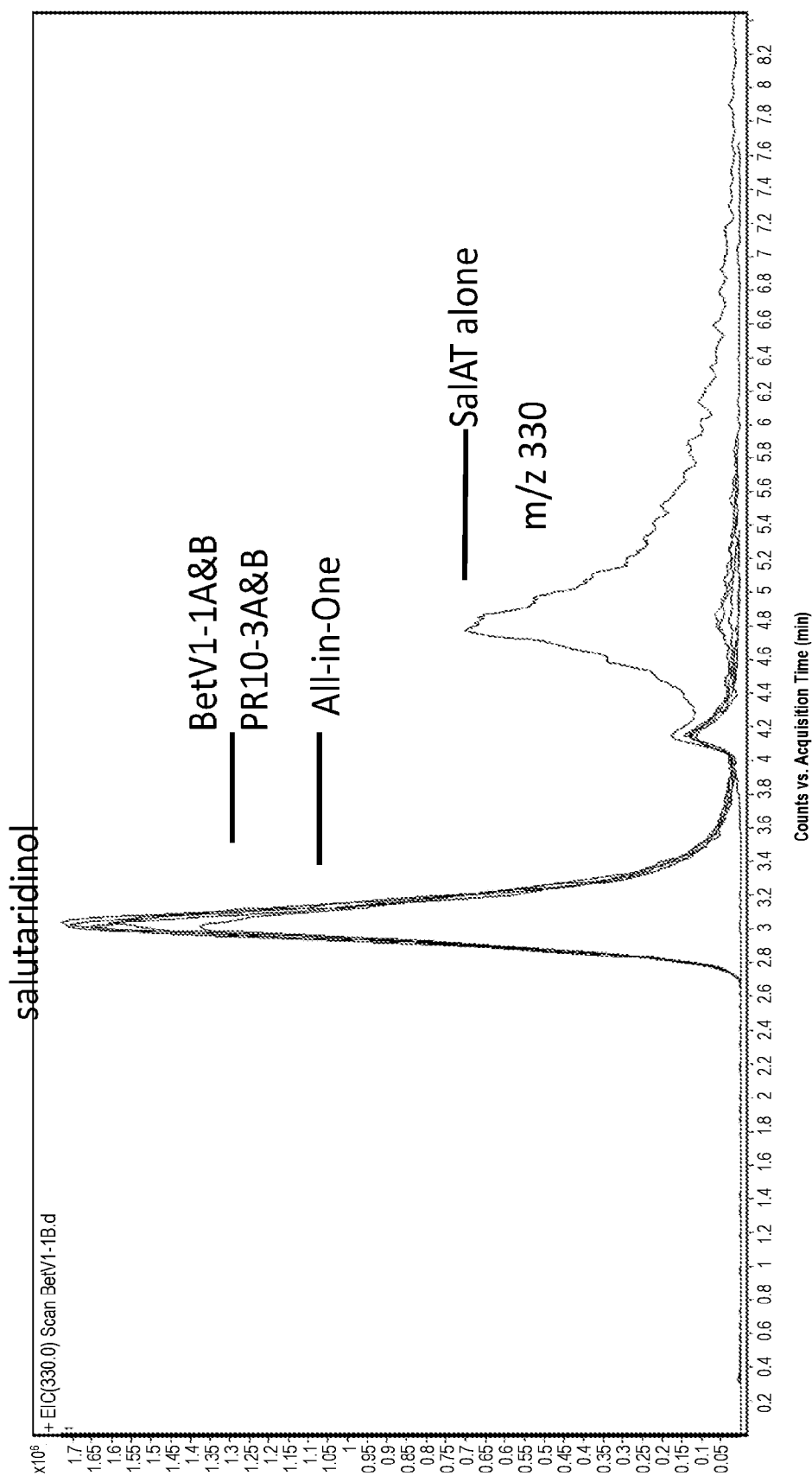
FIG. 10 shows that the majority of salutaridinol was not consumed in extracts of *E. coli* expressing Bet v1-1A, Bet v1-1B, PR10-3A, PR10-3B, and all constructs together. However, with SalAT alone, all salutaridinol was used and formed m/z 330 byproduct. Bet v1-1A refers to a C-terminal HA tagged Betv1, whereas Bet v1-1B corresponds to an N-terminal HA tagged Betv1.

Bet v1-1A and Bet v1-1B produce thebaine and no m/z 330 byproduct. PR10-3A and PR10-3B produce little to no thebaine, but also had no m/z 330 byproduct formation. In cases of mixtures containing Bet v1-1A and Bet v1-1B or PR10-3A and PR10-3B, consumption of salutaridinol was inhibited (FIG. 10). With SalAT alone, all salutaridinol was converted mostly to m/z 330 (FIG. 10) and very little to no thebaine (FIG. 9D).

Example 3—the Thebaine Synthase Cluster

Figure 11A:
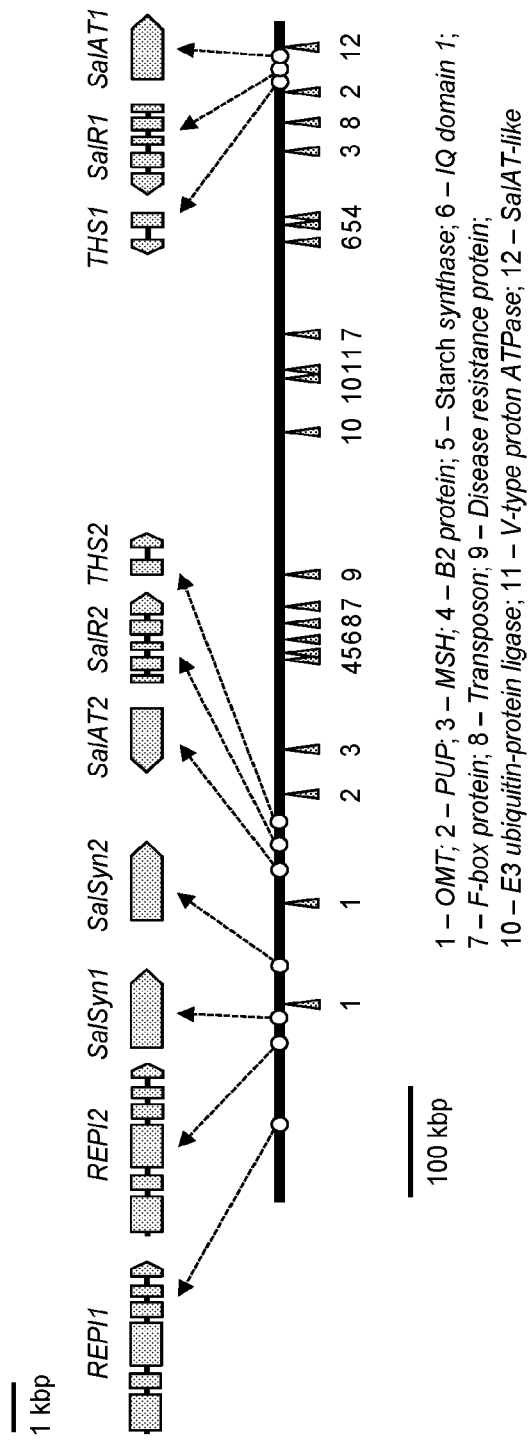

A draft genomic DNA sequencing of opium poppy chemotype Roxanne provided information about the genomic structural relationship between THS and other thebaine biosynthetic genes (FIG. 11A). On a genomic scaffold of approximately 1 megabase pairs duplicate copies for each of 5 thebaine biosynthetic genes were physically linked. The five gene products, reticuline epimerase (REPI), salutaridine synthase (SalSyn), SalR, SalAT, and THS, sequentially convert (S)-reticuline to thebaine. The duplication of each of the five genes in a single cluster suggests the occurrence of complex genomic rearrangement to coordinate and enhance the expression of thebaine biosynthetic genes. The two THS genes encode two highly similar yet distinct THS isoforms, one (THS1; SEQ ID NO. 80) composed of 181 amino acids and the other (THS2; SEQ ID NO. 6) containing 163 amino acids (FIG. 11B). A conserved cryptic downstream start codon in both THS1 and THS2 yield N-terminally truncated versions of each protein, designated THS1s (131 amino acids; SEQ ID NO. 81) and THS2s (133 amino acids; SEQ ID NO. 32). An additional 12 amino acids at the N-terminus of THS1, compared with THS2, is predicted to encode a secretion signal peptide. Moreover, compared with THS2, THS2s results from alternate splicing that the first ~130 base pairs at the 5' end (including both UTR and ORF regions) of THS2, which are missing in the corresponding transcript. Compared with THS2, four additional nucleotides near the start of the THS1 transcript result in an upstream translation start site. Alternate splicing in THS1 also yields the shorter THS product.

Figure 11D:
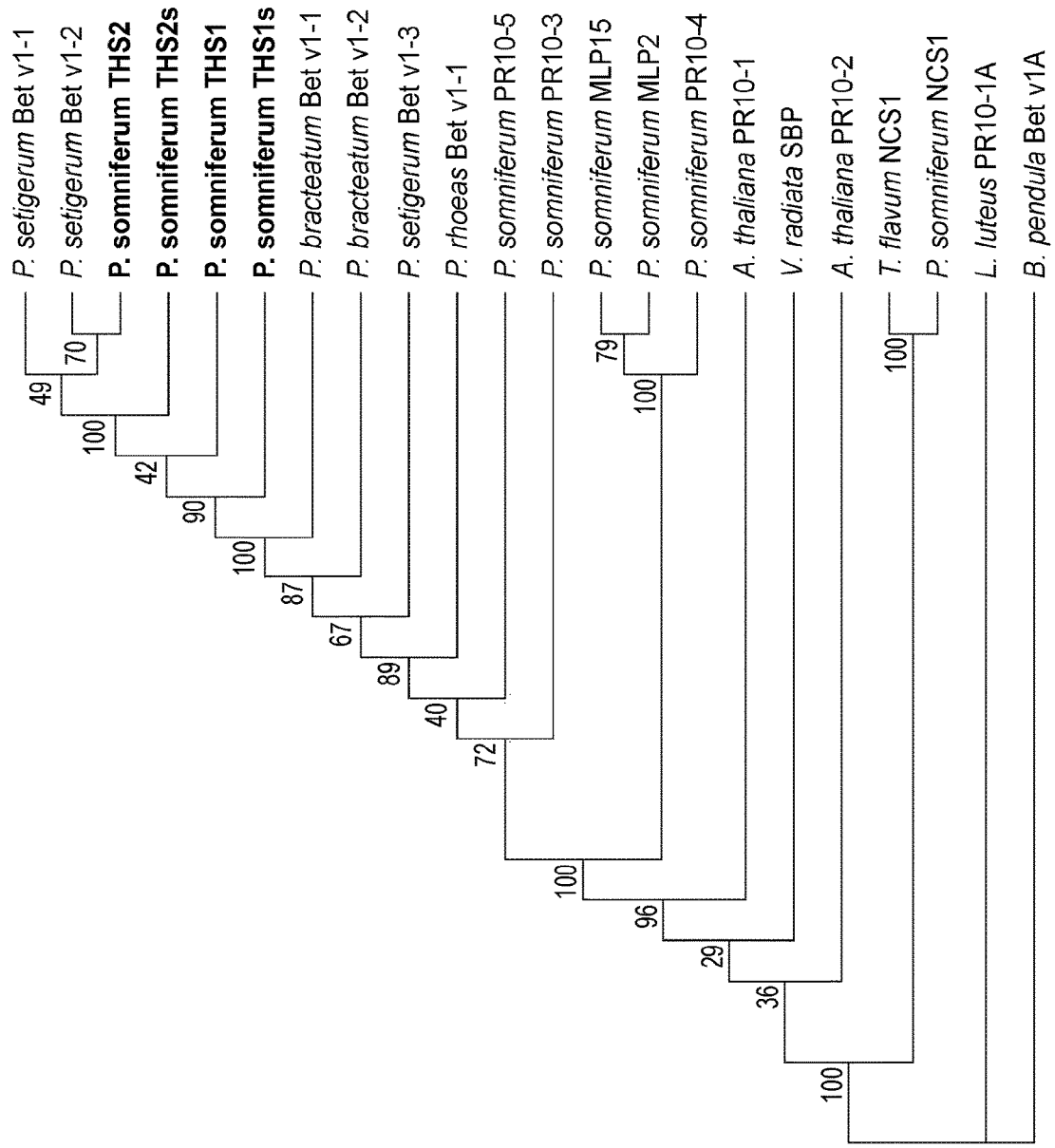
Figure 12A:
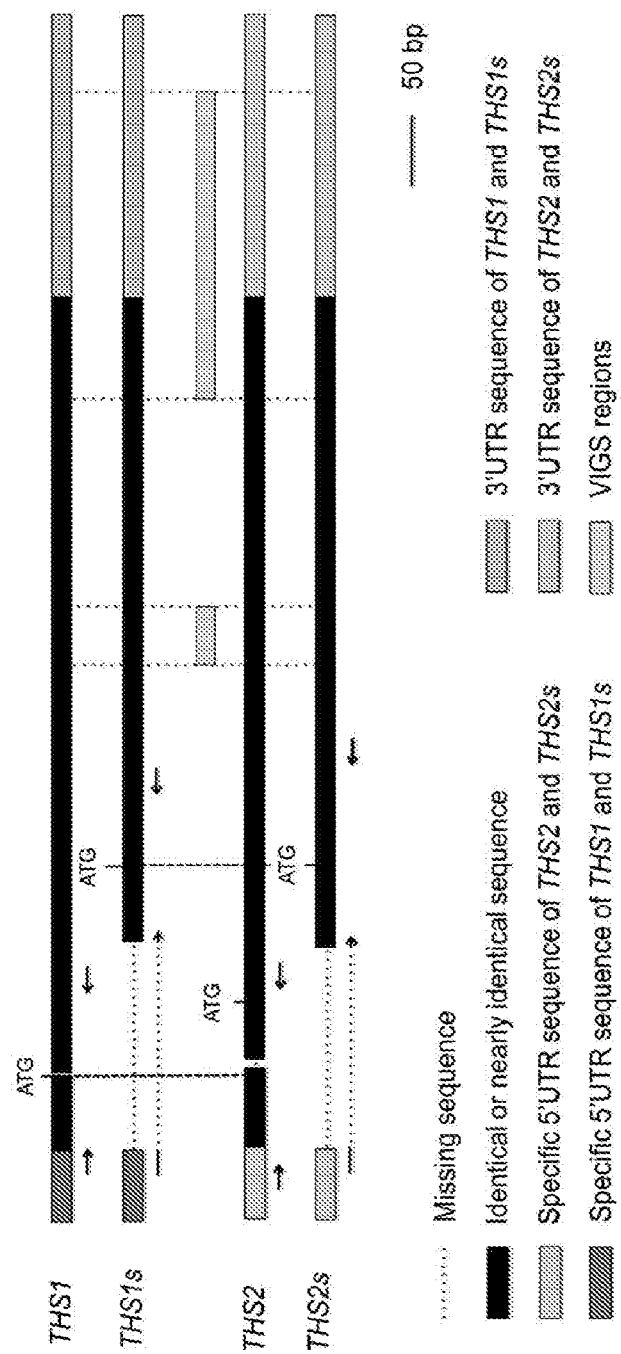
Figure 12C:
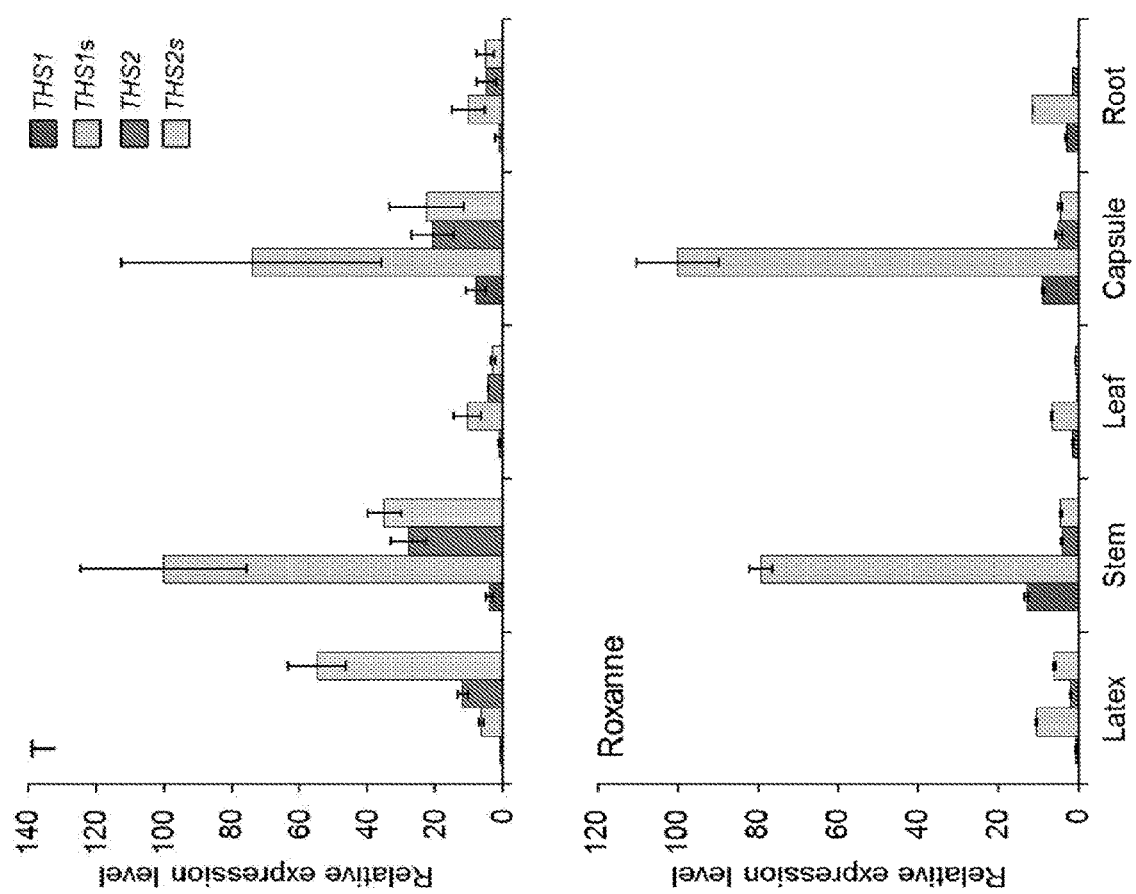

As a member of the PR10 family, opium poppy THS and orthologs from other thebaine-producing *Papaver* species are divergent from other plant PR10 proteins including norcoclaurine synthase (NCS), which catalyzes the first committed step of BIA biosynthesis (FIG. 11D). Tissue-specific expression analysis was performed by qRT-PCR using gene- and splice variant-specific primers (FIG. 12A and FIG. 12B) on two opium poppy chemotypes, T (a high-thebaine, high-oripavine and no-morphine, no-codeine variety) and Roxanne (a variety producing morphine, codeine, as well as noscapine and papaverine). Similar to the expression profile of genes encoding other late morphine pathway enzymes, THS transcripts were more abundant in latex, stem and capsule (FIG. 12C). In general, the truncated transcripts encoding THS1s (SEQ ID NO. 81) and THS2s (SEQ ID NO. 32) were expressed at higher level compared with the longer THS1 (SEQ ID NO. 80) and THS2 (SEQ ID NO. 6) versions.

Figure 13A:
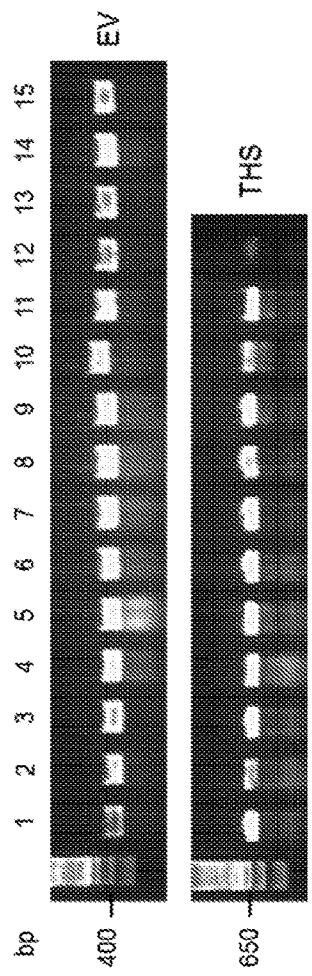
FIGS. 13A-13B.
Figure 13B:
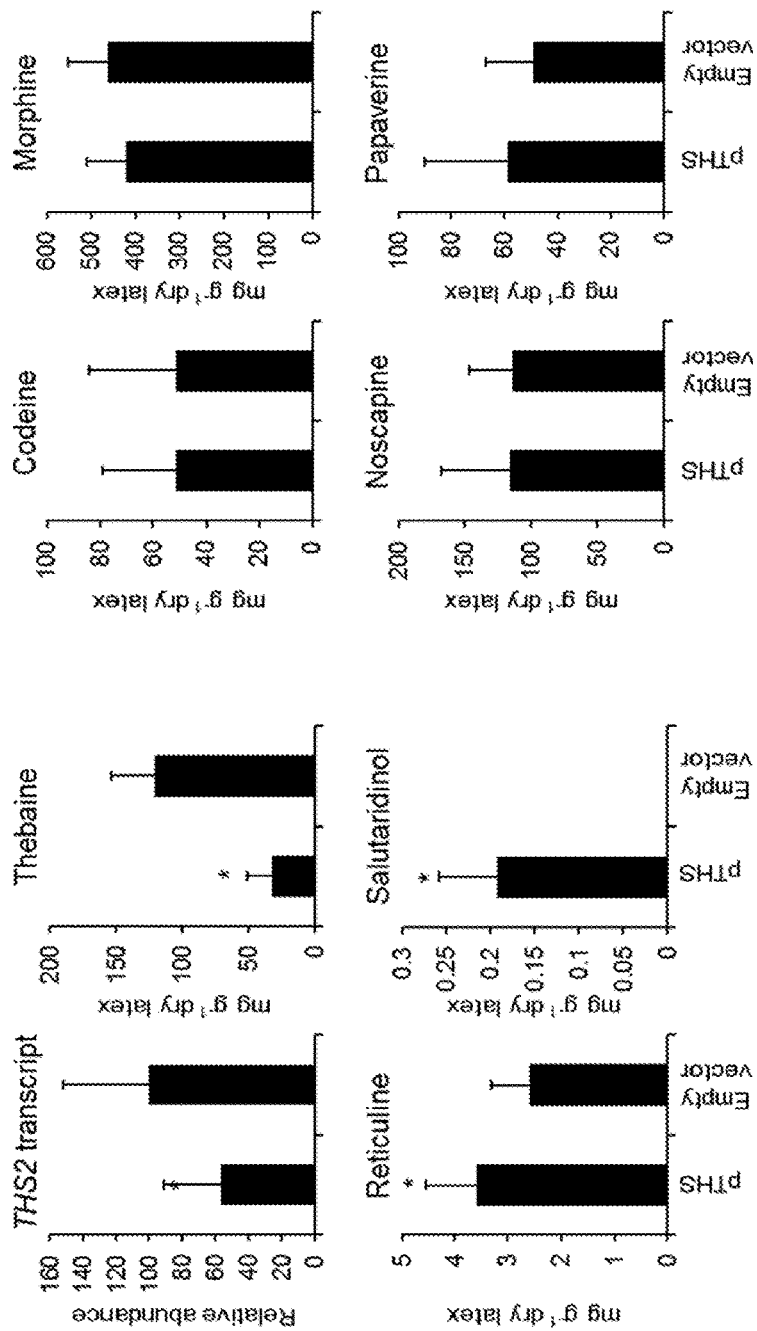

Suppression of THS transcript levels in opium poppy plants was performed using virus-induced gene silencing (VIGS). Conserved sequences of the THS1 and THS2 genes were used as the target region (FIG. 12A). THS transcript levels were significantly lower in THS-silenced plants compared with controls in plants infected with *Agrobacterium tumefaciens* harboring pTRV2-THS and pTRV2 empty-vector plasmids, respectively (FIG. 13A and FIG. 13B). Thebaine content in the THS-silenced plants was significantly reduced nearly two-fold compared with controls FIG. 13B). In contrast, accumulation of the upstream intermediates reticuline and salutaridinol increased significantly in THS-silenced compared with control plants. Interestingly, morphine and codeine levels were not significantly affected suggesting that the reduced THS activity was still able to support sufficient thebaine production to enable final product formation.

Figures 14A, 14B:
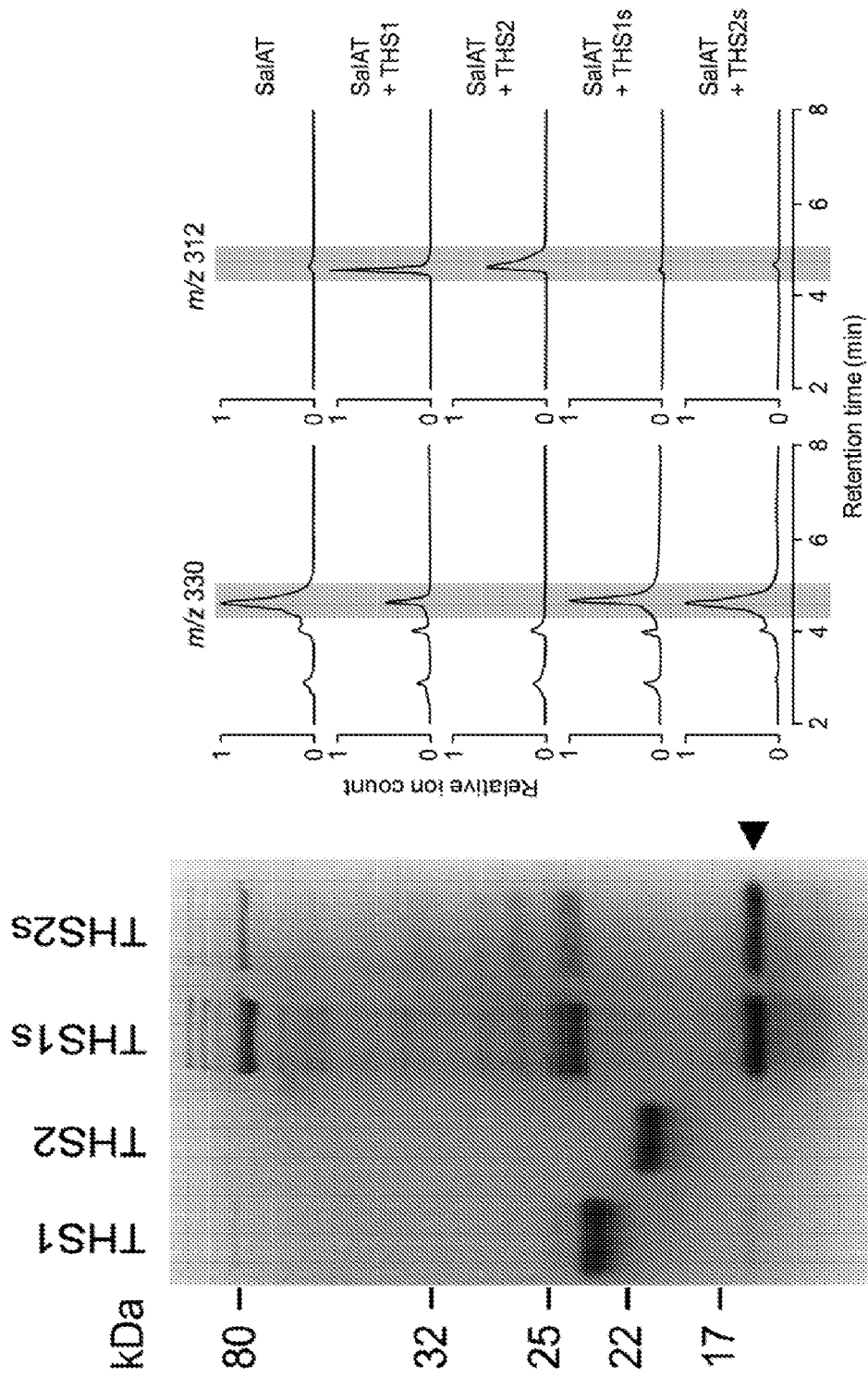
FIGS. 14A and 14B shows data from an in vitro enzyme assay of recombinant THS isoforms. THS1 is a thebaine synthesis polypeptide isoform represented by SEQ ID NO. 80; THS is a thebaine synthesis polypeptide isoform represented by SEQ ID NO. 81; THS2 is a thebaine synthesis polypeptide isoform represented by SEQ ID NO. 6, and THS2s is a thebaine synthesis polypeptide isoform represented by SEQ ID NO. 32.

All versions of THS1 and THS2 transcripts were codon-optimized and expressed in *E. coli*. Purified recombinant THS proteins were added to SalAT-coupled enzyme assays. Both THS1 and THS2 assays similarly increased thebaine formation, whereas the shorter versions did not show catalytic activity (FIG. 14B). Size exclusion chromatography (SEC) during the purification of THS from opium poppy latex revealed a molecular weight of ~40 kDa, suggesting that the native protein occurs as a homodimer. Chemical cross-linking with the purified, recombinant THS proteins was performed to confirm dimerization (FIGS. 15A and 15B). Both THS1 and THS2 can form homodimers, and also display the formation of higher molecular weight oligomers at lower abundance. In contrast, the shorter THS1s and THS2s versions exhibited considerably a lower ability to form dimers, but did yield higher molecular weight oligomers. Subjecting the native THS2 protein to SEC chromatography showed and a major peak of ~40 kDa with lesser quantities of higher molecular weight peaks (FIGS. 15A and 15B). To further investigate the relative abundance of THS isoforms in the plant, protein extracts derived from whole stem, latex-free stem, and latex isolated from the T chemotype were subjected to proteomics analysis (FIG. 11C). In detected peptides with at least one amino acid substitution spectral counts for THS2 were considerably higher than for THS1, consistent with the higher abundance of THS2, compared with THS1, transcripts (FIG. 12C).

Figure 16A:
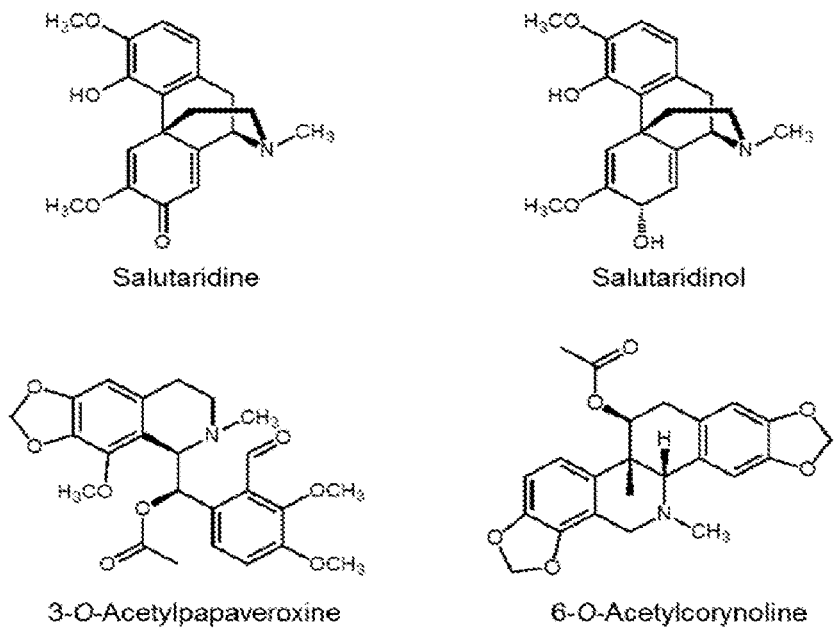
FIGS. 16A-16B shows substrate-competition assays for THS2 (a.k.a., thebaine synthesis polypeptide as encoded by SEQ ID NO. 6).
Figure 16B:
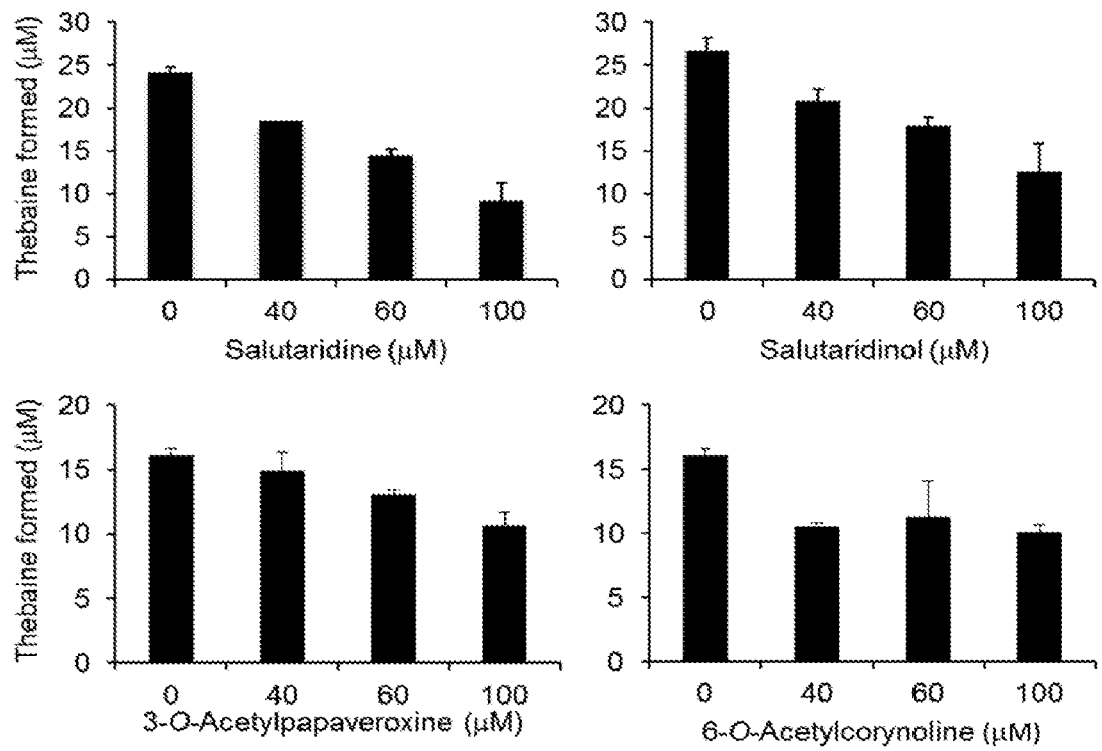

The catalytic function of THS1 and THS2 was investigated using salutaridinol 7-O-acetate as a direct enzymatic substrate. Salutaridinol 7-O-acetate is the immediate product of SalAT reaction and is normally not detectable because it spontaneously converts to a small amount of thebaine and a larger amount of m/z 330 compound(s). Approximately 70% of the salutaridinol 7-O-acetate used as a substrate for assays broke down within 2 min in aqueous solution; thus, THS assays using salutaridinol 7-O-acetate as the substrate were performed with an optimized quality of purified, recombinant THS2 for 30 sec, which was within the linear range of product formation. Boiled enzyme served as the control in all enzymatic assays to compensate for any spontaneous breakdown of salutaridinol 7-O-acetate. Chloroform was used as the storage solution for salutaridinol 7-O-acetate and quenching solution for the reaction, which prevented further degradation. THS2 showed no activity with other benzylisoquinoline alkaloids either sharing similar skeleton or containing an O-acetyl moiety (FIG. 16A). Competition assays using these compounds revealed marginal inhibition of THS activity associated with salutaridine and salutaridinol, but little if any effect of O-acetylated compounds (FIG. 16B).

Inclusion of THS2 in engineered yeast with chromosomally integrated biosynthetic genes facilitating the conversion of (R,S)-norlauranosoline to salutaridinol 7-O-acetate (Sc-3) substantially increased the yield of thebaine from (R,S)-norlauranosoline (FIGS. 18A-18C, FIGS. 21A-21C). A strain (Sc-2) capable only of salutaridine production, owing to the lack of genes encoding SalR and SalAT, was unable to produce thebaine. Episomal expression of THS2 in a strain (Sc-4) containing a chromosomally integrated THS2 gene further enhanced thebaine formation to ~750 µg/L. The m/z 330 by-product decreased as thebaine production increased.

Example 4—the Effect of HA Tag on Bet v1-1 Thebaine Synthesis Activity In Vivo

Figure 17:
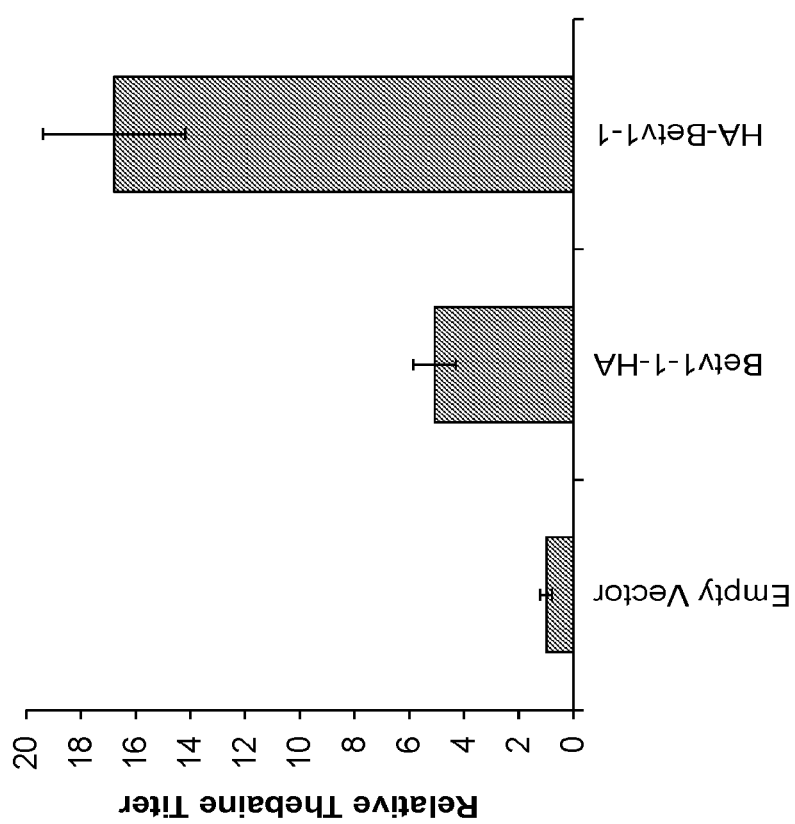
FIG. 17 shows relative thebaine titers produced from yeast. Bet v1 tested with HA epitope tag on C- or N-terminus (Bet v1-1-HA and HA-Bet v1-1, respectively) and expressed on a high copy plasmid. n=3. Bet v1 is also known as thebaine synthesis polypeptide or thebaine synthase.

In order to test whether the HA-tag had an effect on the Bet v1-1 (SEQ ID NO. 6) efficacy and efficiency, 2 constructs (N- and C-terminal HA-tagged Bet v1-1) were expressed on high copy plasmids and expressed in yeast. The transformed yeast were fed with 1 mM salutaridine for 48 hours and tested for its capability to make thebaine. As shown in FIG. 17, both the N- and C-terminal HA-tagged Bet v1-1 constructs had thebaine synthesis activity, however, the N-terminal tagged Bet v1-1 showed a significant increase in thebaine synthesis activity.

Example 5—Enzymatic Production of Thebaine in Yeast

Three separate yeast strains were generated having the genotype in Table 2:

TABLE 2

| Strain Name | Genotype |
|---|---|
| Sc2 | CEN.PK $T_{MET13}$::$T_{CBS1}$ $P_{GAL1}$-Pbra6OMT-$T_{ADH1}$ $T_{LYS2}$:: $T_{CST1}$ $P_{GAL10}$-Psom4OMT-$T_{PMA1}$ $P_{GAL1}$-CjapCNMT-$T_{PGK1}$ $T_{LYS4}$::$T_{CHS2}$ $P_{GAL10}$ -PsoREPI-2-$T_{ADH1}$ $T_{MET17}$::$T_{TUB1}$ $P_{GAL10}$-PbrSalSyn-$T_{ADE3}$ $P_{GAL1}$-PbrCPR1-$T_{PDR5}$ |
| Sc3 | Sc2 $T_{MET16}$::$T_{CHS2}$ $P_{GAL10}$-PsomSalR-$T_{HPC2}$ $P_{TEA1}$-PsomSalAT-$T_{ROX3}$ |
| Sc4 | Sc3 $T_{NCL1}$::$T_{STE5}$$P_{GAL1}$-PsomBetv1-1-$T_{ADH1}$ |

Figure 18A:
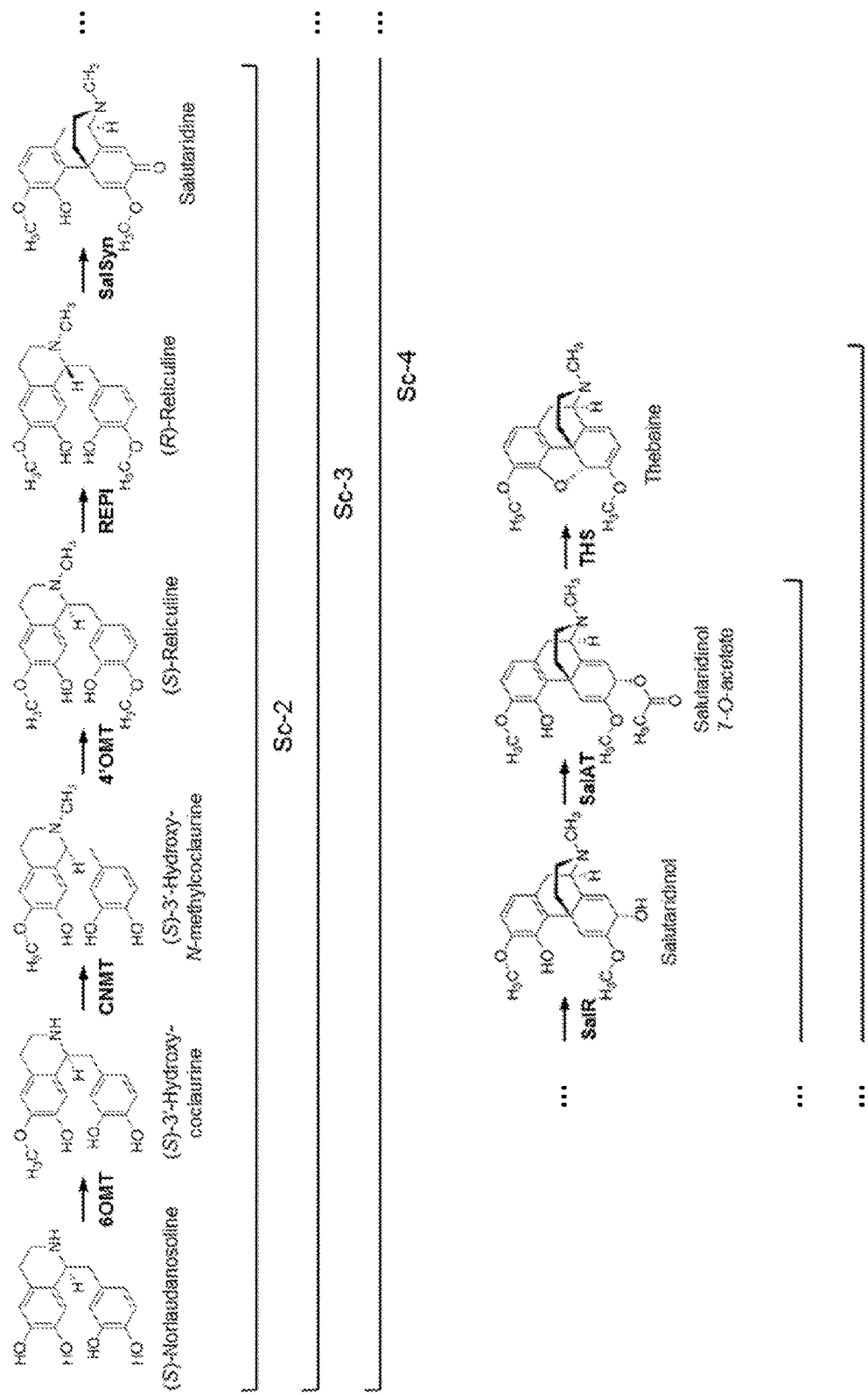
FIGS. 18A-18C.
Figure 18C:
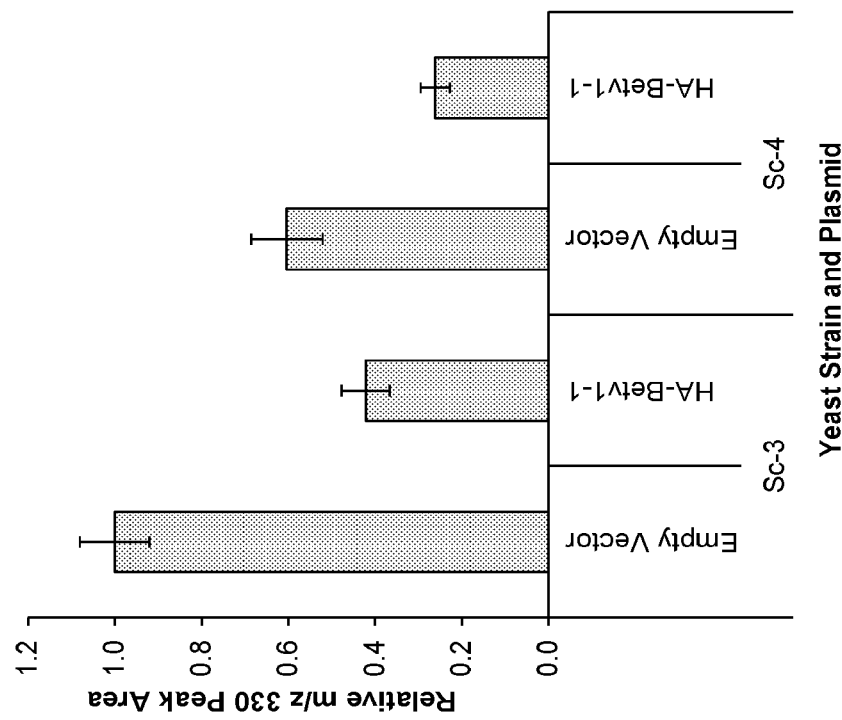
Figure 18B:
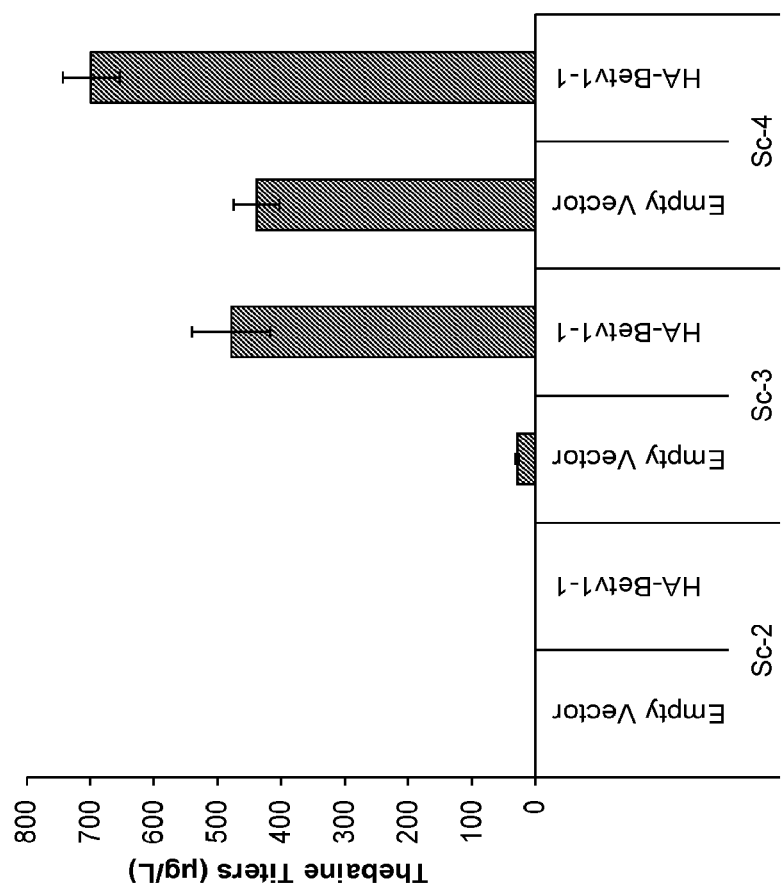

Yeast were grown in medium supplemented with 2.5 mM NLDS and 10 mM L-methionine for 96 hours. Thebaine titers of the supernatants of three engineered yeast strains (SC-2, SC-3 and SC-4) were measured. As seen in FIG. 18A, SC-2 produced no detectable levels of thebaine. Further, SC-3 produced increased amount of thebaine in the presence of integrated HA-BETv1-1 (N-terminal HA tagged version of SEQ ID NO. 6). SC-4 showed higher expression when both integrated copies and plasmid expressed HA-BETv1-1 were present. As shown in FIG. 18B, relative peak area of unknown side product (m/z 330) decreased in the supernatant in SC-3 and SC-4 strains in the presence of HA-BETv1-1. Error bars indicate standard deviations from four biological replicates.

Yeast expressing pGAL SalR and pTEA1 SalAT were also transformed with different thebaine synthesis polypeptide expression constructs. See Table 3. The thebaine synthesis polypeptide constructs were cloned into a high copy vector under pGAL. HA epitope tags were also present on both the N- and C-terminus.

TABLE 3

| Annotation | Accession number | Molecular weight (kDa) |
|---|---|---|
| PR10-3 | c25055_g1_i1 | 18 |
| Betv1-1 | c15408_g1_i1 | 18 |
| PR10-5 | c38417_g1_i1 | 17 |
| PR10-4 | c50593_g1_i1 | 18 |
| MLP15 | c27108_g1_i1 | 18 |
| PR10-7 | c33864_g1_i1 | 18 |
| MLP-2 | c37788_g2_i4 | 16 |
| MLP-3 | c1643_g1_i1 | 16 |

Figure 19A:
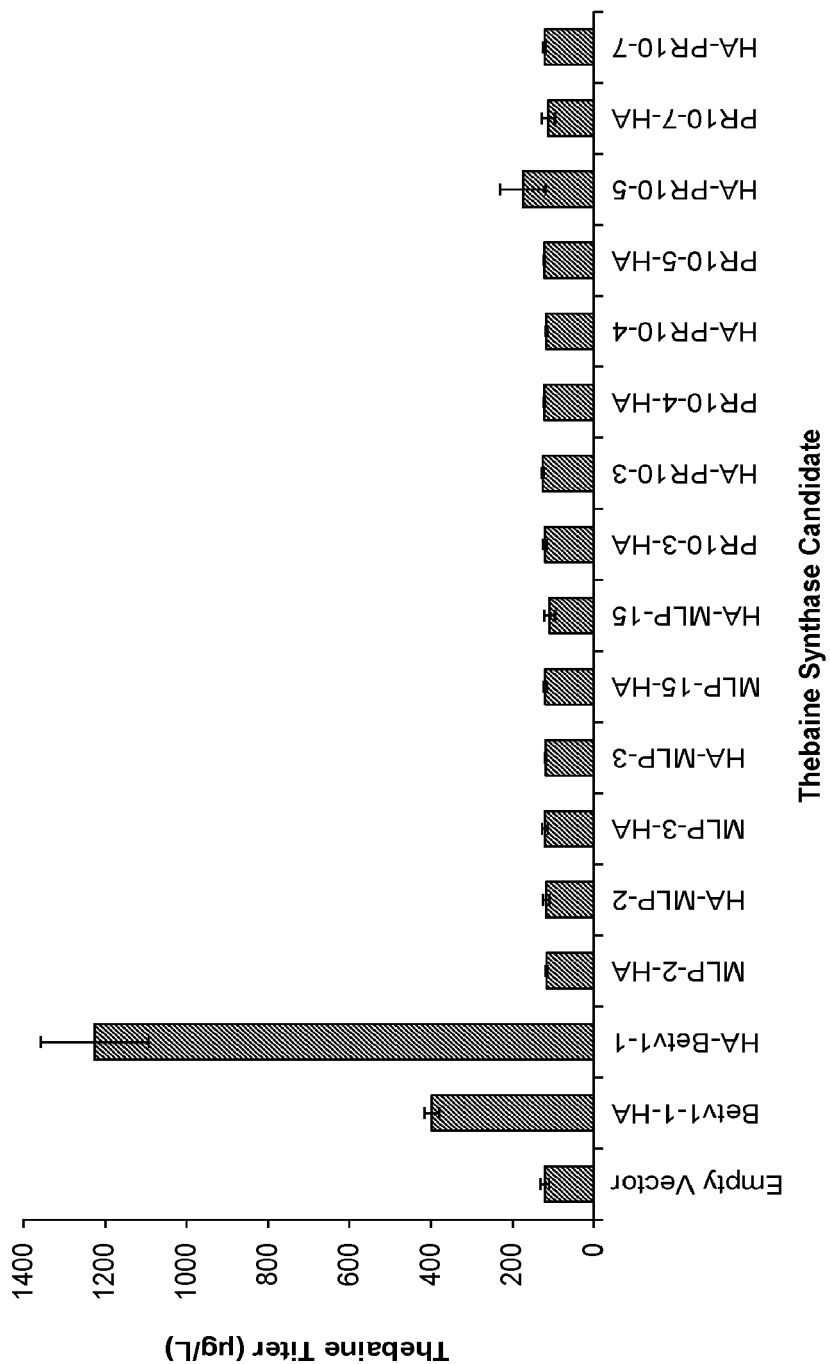
FIGS. 19A and 19B.
Figure 19B:
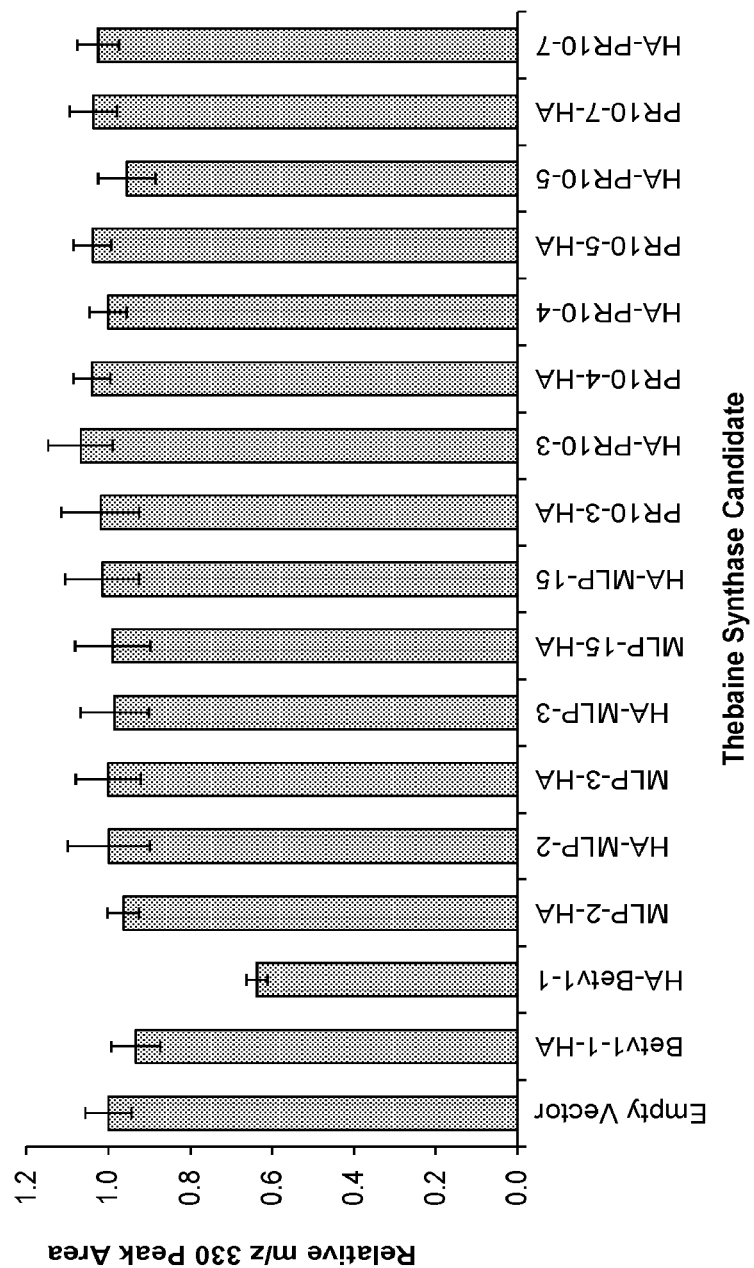

The cells were cultured in SC-Complete Media with 100 mM MES pH 7.5 (G418 selection) and were fed with 50 µM Salutaridine for 48 hours. After 48 hours, relative thebaine titers were measured. Relative titers for Bet v1-1 (SEQ ID NO. 6) were the highest (Data shown in FIG. 19A). N-terminal tagged Bet v1-1 exhibited an approximate 17-fold increase in thebaine titers (compared to empty vector controls) whereas C-terminal tagged Bet v1-1 produced an approximate 5-fold increase. Additionally, the unknown side product m/z 330 was also measured. As shown in FIG. 19B, the park area of m/z 300 is significantly lower in yeast expressing the N-terminal tagged Bet v1-1. Peak area is shown relative to the empty vector control. Error bars indicate standard deviations from three biological replicates.

Example 6—Effect of Integration on Thebaine Synthesis

Yeast expressing a stably integrated copy of Bet v1-1 (SEQ ID NO. 6) was created and tested for its ability to synthesize thebaine. The transformed yeast was cultured in media supplemented with 1 mM salutaridine for 48 hours. Integrated yeast showed an approximate 6-fold increase in thebaine synthesis activity. See FIG. 12A.

Yeast expressing stably integrated copies of Bet v1-1 splice variants (Bet v1-1S, and Bet v1-1L) were created and tested for its ability to synthesize thebaine. See Table 4 and FIG. 20C for sequences:

TABLE 4

| SEQ. ID. NO. | NAME | AMINO ACID SEQUENCE |
|---|---|---|
| 6 | BET V1-1 | MAPLGVSGLVGKLSTELEVDC EDAKYYNMYKHGEDVKKAVPH LCVDVKIISGDPTSSGCIKEW NVNIDGKTIRSVEETTHDDE TKTLRHRVFEGDVMKDFKKF DTIMVVNPKPDGNGCVVTRS IEYEKTNENSPTPFDYLQFG HQAIEDMNKYLRDSESN |
| 31 | BET V1-1L | MDSINSSIYFCAYFRELIIK LLMAPLGVSGLVGKLSTELE VDCDAEKYYNMYKHGEDVKK AVPHLCVDVKIISGDPTSSG CIKEWNVNIDGKTIRSVEET THDDETKTLRHRVFEGDVMK DFKKFDTIMVVNPKPDGNGC VVTRSIEYEKTNENSPTPFD YLQFGHQAIEDMNKYLRDSE |
| 32 | BET V1-1S | MYKHGEDVKKAVPHLCVDVK IISGDPTSSGCIKEWNVNID GKTIRSVEETTHDDETKTLR HRVFEGDVMKDFKKFDTIMV VNPKPDGNGCVVTRSIEYEK TNENSPTPFDYLQFGHQAIE DMNKYLRDSESN |

The transformed yeasts were cultured in media supplemented with 1 mM salutaridine for 48 hours. Yeast expressing the splice variant Bet v1-1S (SEQ ID NO. 32) did not exhibit any thebaine synthesis activity. See FIG. 20B. Yeast expressing the splice variant Bet v1-1L (SEQ ID NO. 31) exhibited similar, if not higher, thebaine synthesis activity.

Example 7—Thebaine, Reticuline and Salutaridine Titers

The strains described in Table 2 were tested for ability to produce thebaine, reticuline, and salutaridine. For each strain tested, at least three individual colonies were picked and placed into 0.8 mL of Synthetic Complete-Monosodium Glutamate (SC-MSG) media containing 2% glucose and 200 mg/L of G418 in 96-deep well plates (Axygen Scientific). Cultures were grown in a Multitron Pro shaker (Infors HT) at 30° C. with 80% humidity.

Figure 21A:
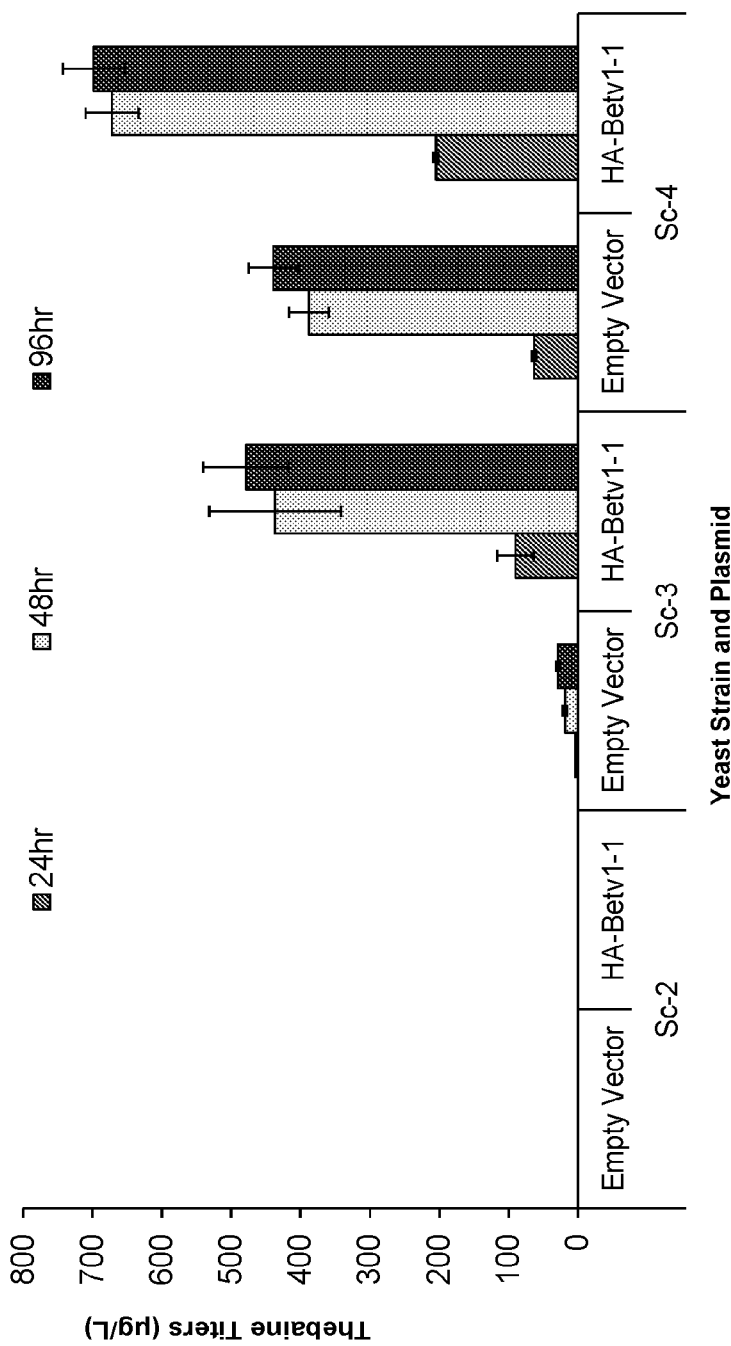
FIGS. 21A-21C.
Figure 21B:
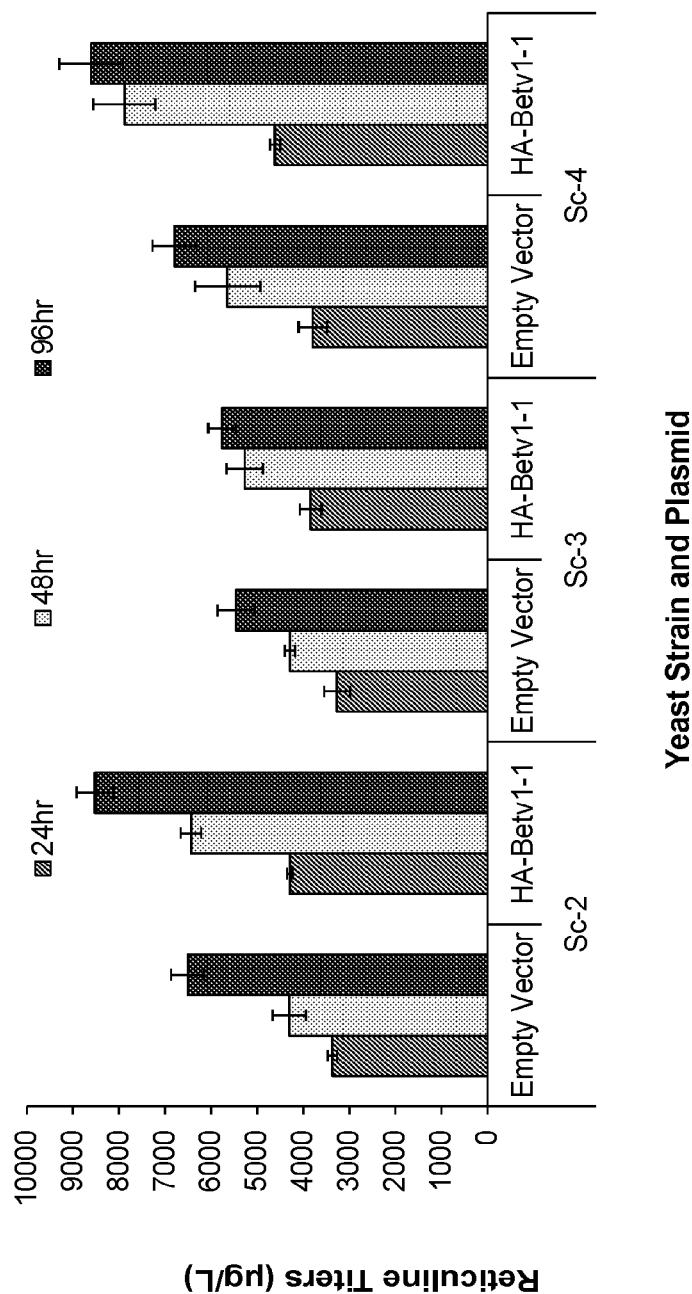

As shown in FIG. 21A, strain SC-2 did not produce any detectable levels of thebaine at 24, 38 or 96 hours. Strain SC-3 produced significantly increased amounts of thebaine between 24 and 48 hours. Strain SC-4 produced the highest thebaine titers of all strains tested and produced significantly increased amounts of thebaine between 24 and 48 hours.

All strains tested produced significant levels of reticuline titers. (See FIG. 21B) All strains also exhibited an increased production of reticuline between 24, 48 and 96 hours.

Figure 21C:
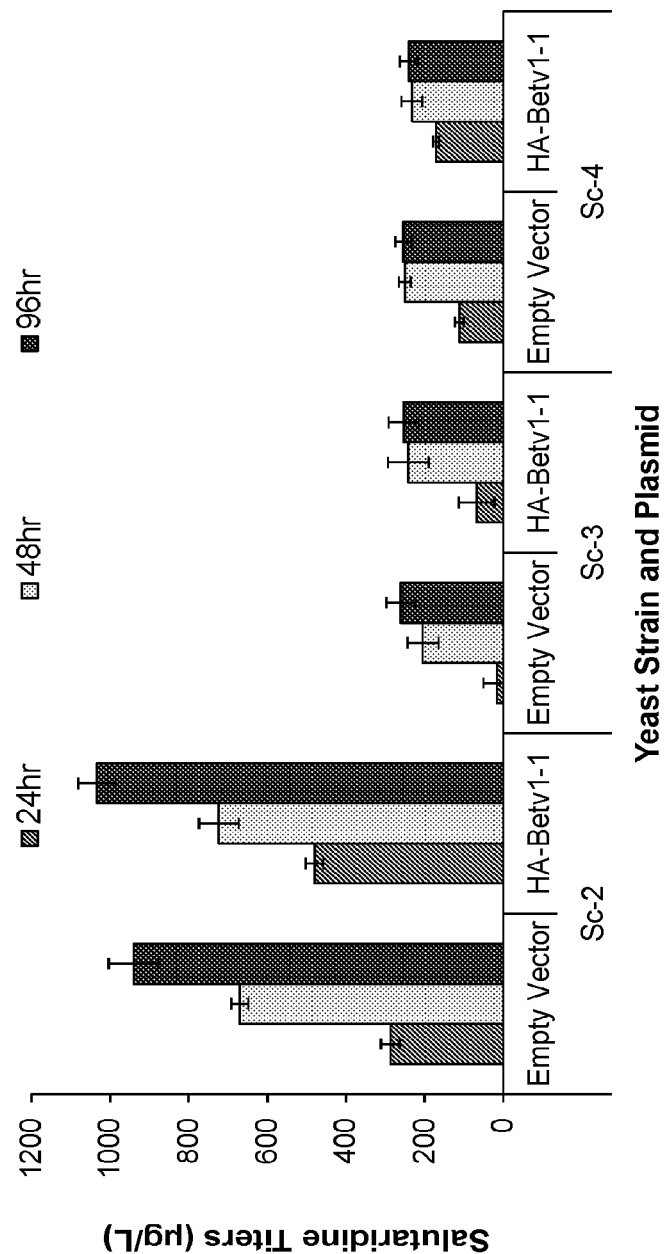
Figure 22A:
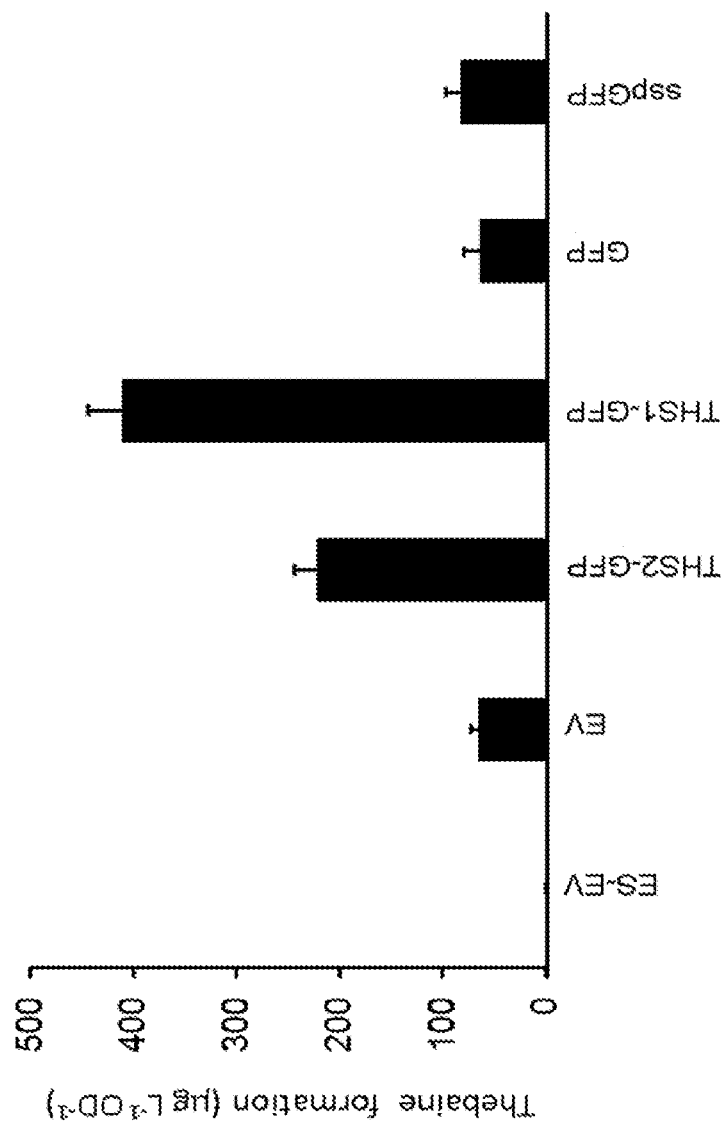
FIGS. 22A-22C is the characterization of the predicted THS1 secretion signal peptide. THS1 is a thebaine synthesis polypeptide isoform represented by SEQ ID NO. 80.
Figure 22B:
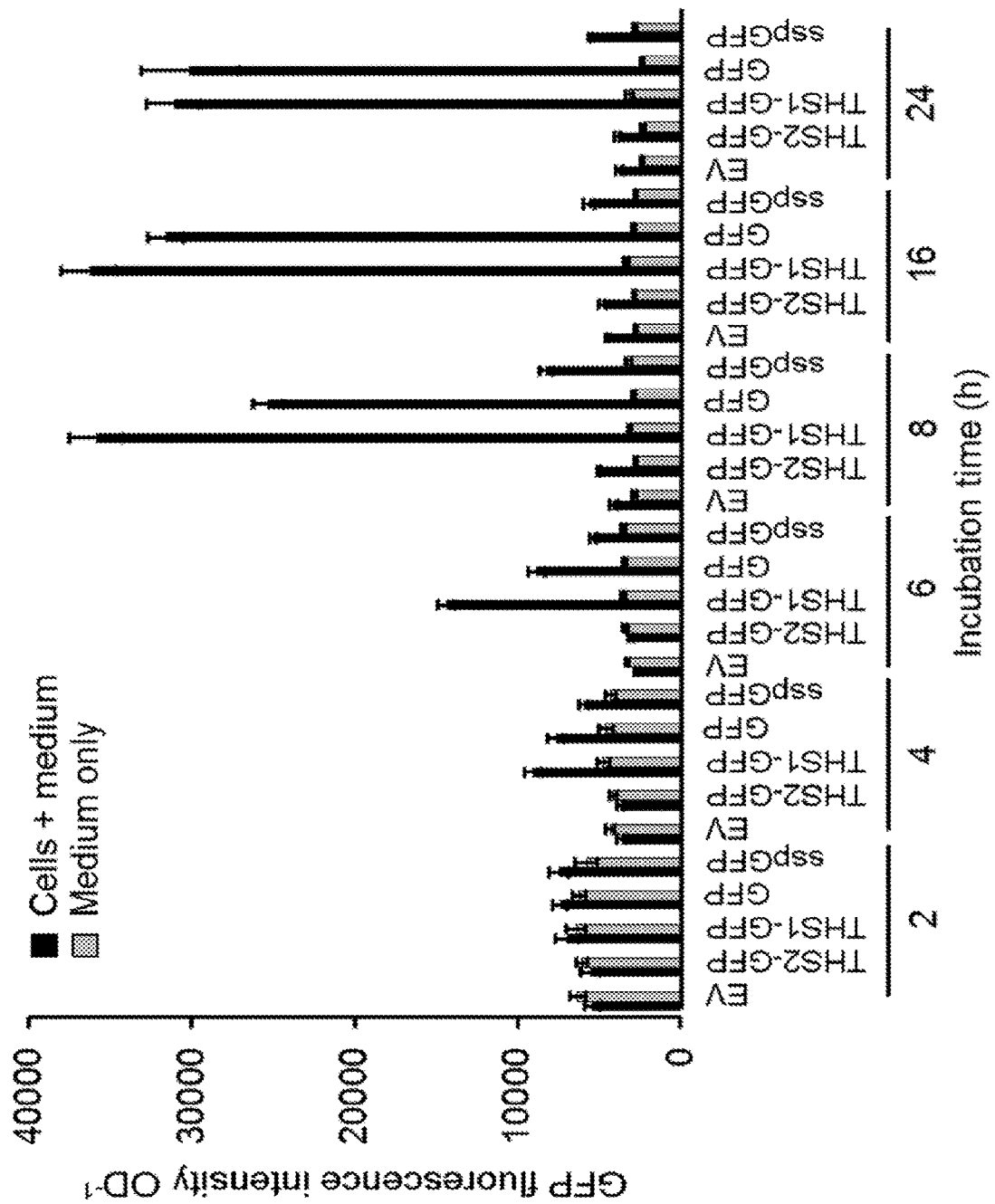
Figure 22C:
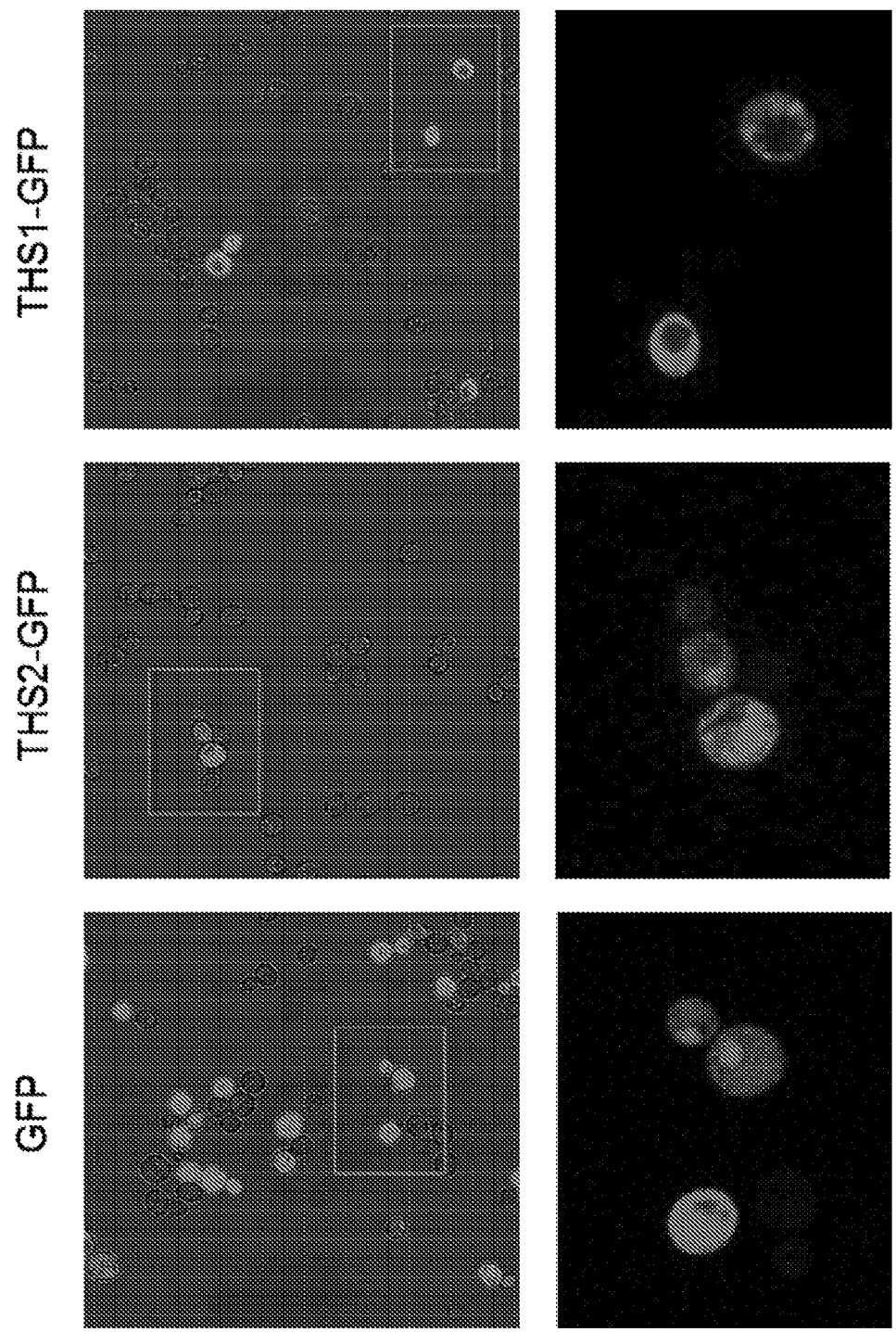

As shown in FIG. 21C, strain SC-2 produced the most amount of salutaridine comprised to strains SC-3 and SC-4. Generally, the strains also exhibited an increased production of salutaridine between 24, 48 and 96 hours.

Example 8—Purine Permeases Effect on Thebaine and Other BIA Intermediates

Figure 23A:
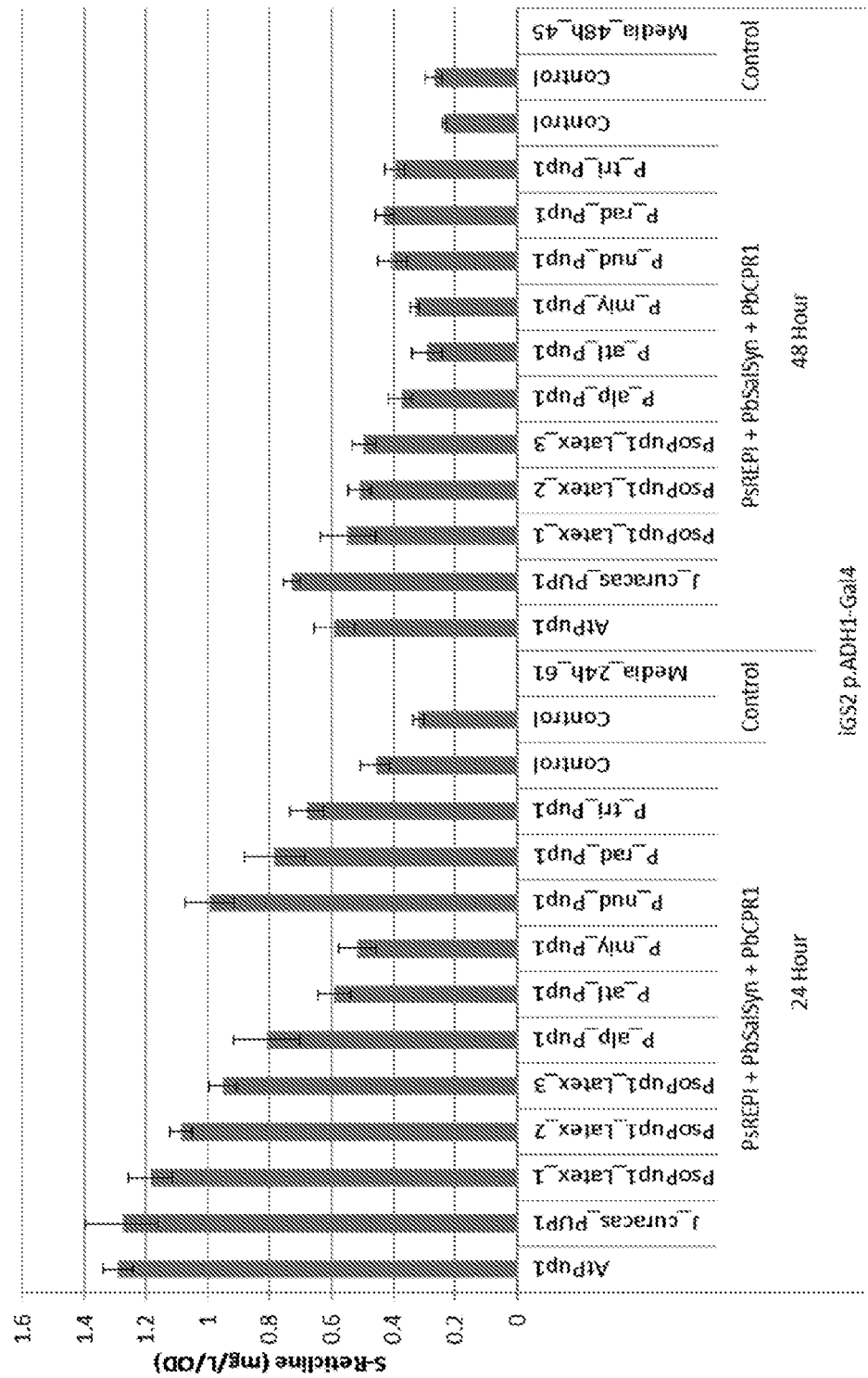
FIGS. 23A-23D.
Figure 23B:
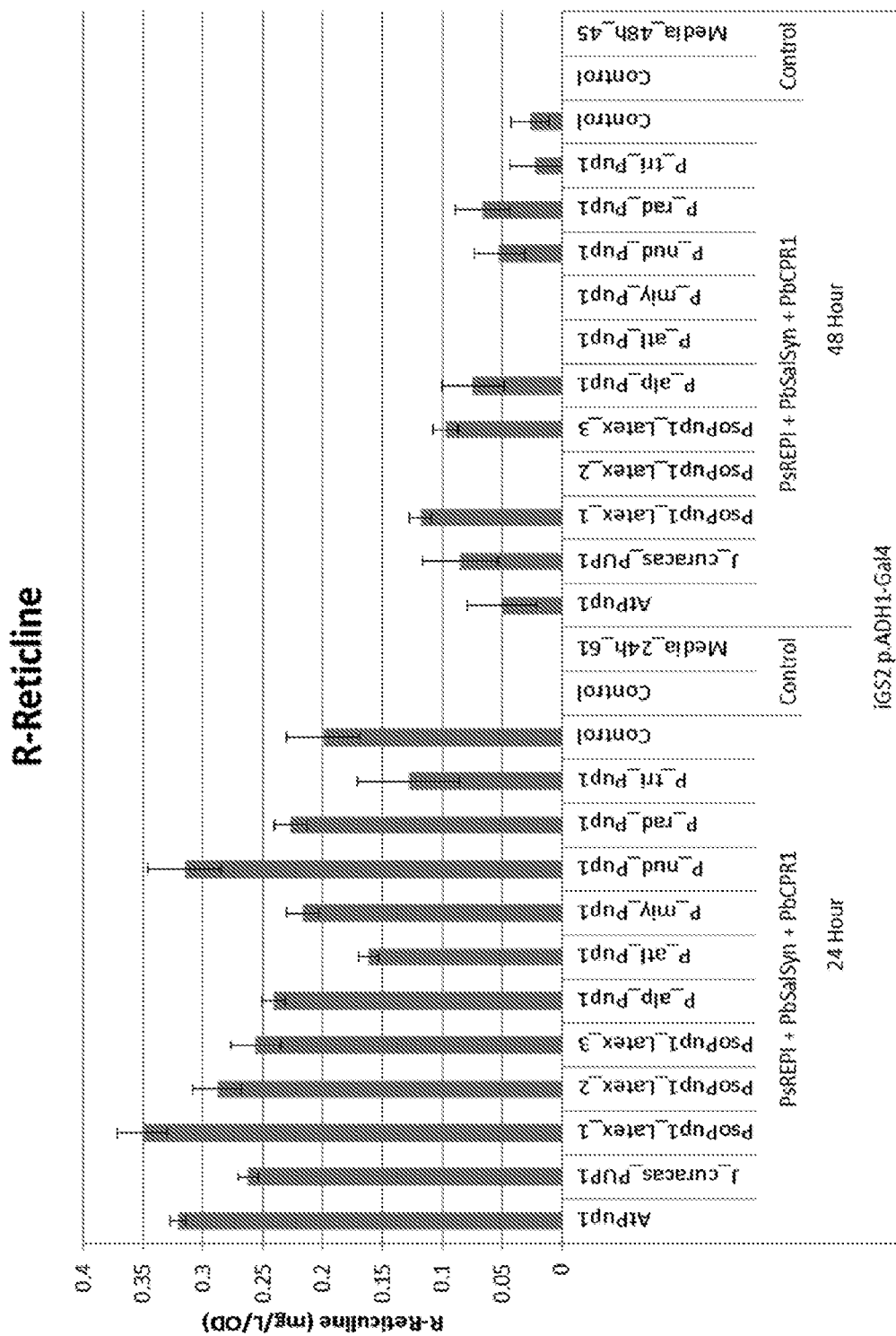
Figure 23C:
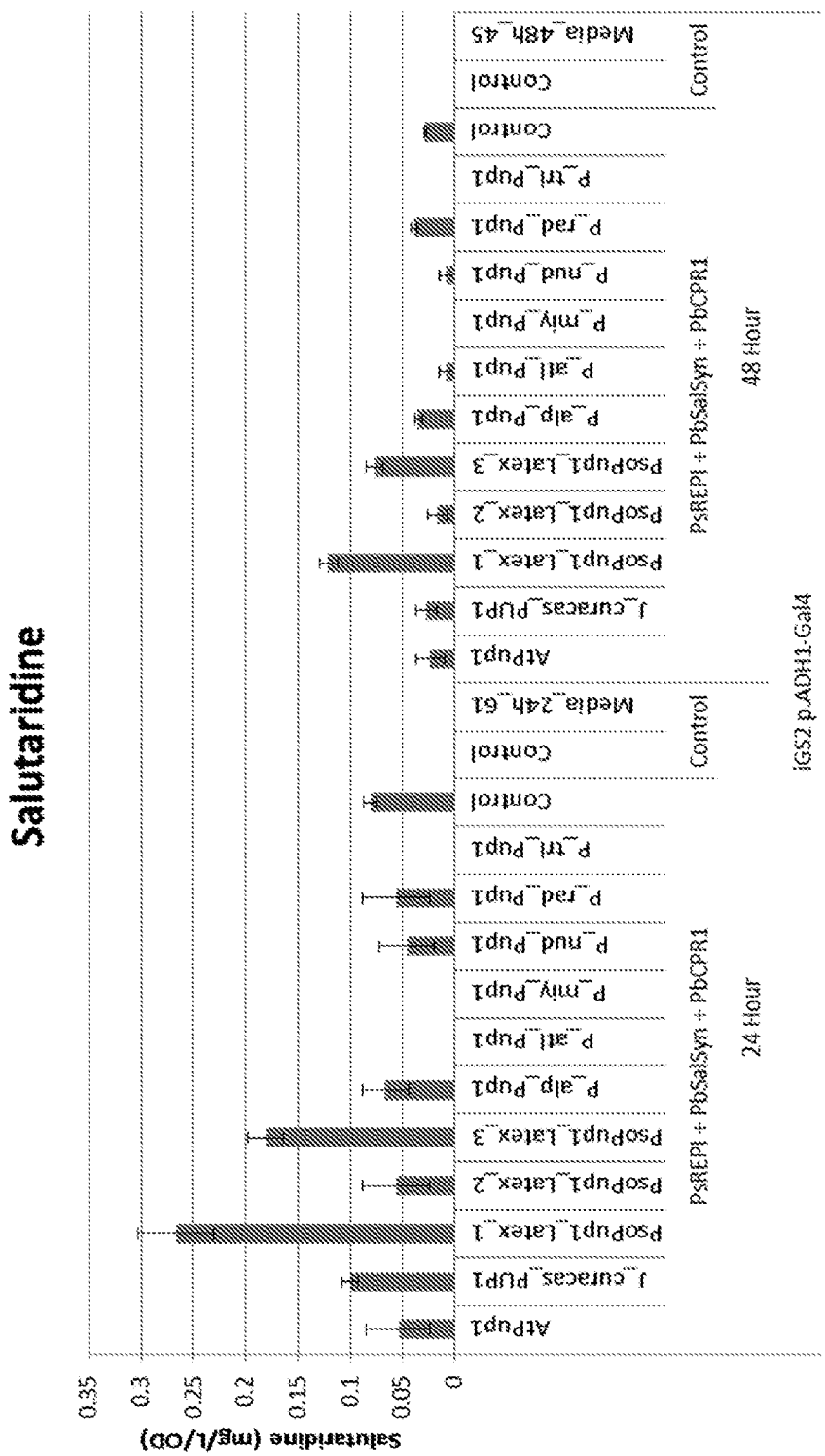
Figure 23D:
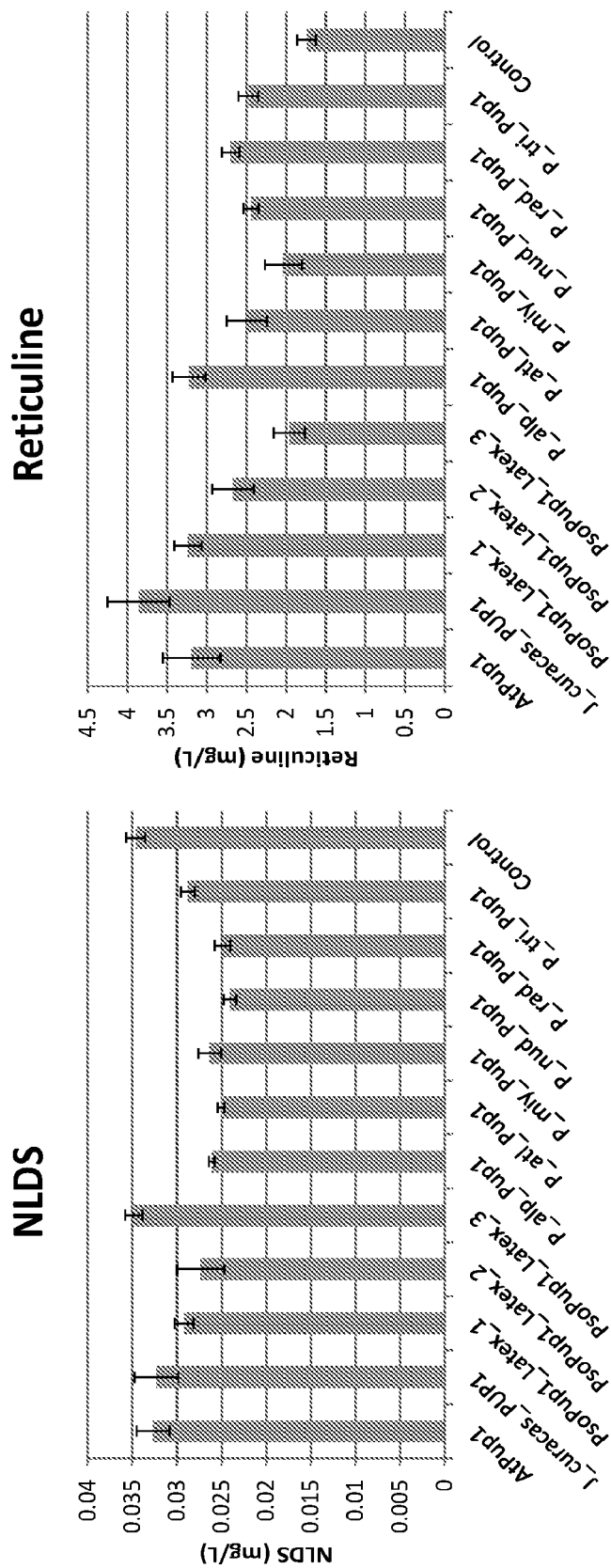

A *Saccharomyces cerevisiae* strain were transformed with one of the 11 different following purine permease homologs: 1)*Arabidopsis thalania* PUP 1 (AtPUP1; SEQ ID NO: 41 (amino acid) and 42 (nucleotide)); 2) *Jatropha curcas* PUP1 (JcurPUP1 (JC_PUP1; SEQ ID NO: 43 (amino acid) and 44 (nucleotide)); 3) *Papaver somniferum* PUP1-1 (PsoPUP1-1; SEQ ID NO: 45 (amino acid) and 46 (nucleotide)); 4) *Papaver somniferum* PUP1-2 (PsoPup1-2; SEQ ID NO: 47 (amino acid) and 48 (nucleotide)); 5) *Papaver somniferum* PUP1-3 (PsoPUP1-3; SEQ ID NO: 49 (amino acid) and 50 (nucleotide)); 6) *Papaver alpinum* PUP1 (PalpPUP1; SEQ ID NO: 53 (amino acid) and 54 (nucleotide)); 7) *Papaver atlanticum* PUP1 (PatlPUP1; SEQ ID NO: 55 (amino acid) and 56 (nucleotide)); 8) *Papaver miyabeanum* PUP1 (PmiyPUP1; SEQ ID NO: 57 (amino acid) and 58 (nucleotide)); 9) *Papaver nudicale* PUP1 (PnudPUP1; SEQ ID NO: 59 (amino acid) and 60 (nucleotide)); 10) *Papaver radicatum* PUP1 (PradPUP1; SEQ ID NO: 61 (amino acid) and 62 (nucleotide)); and 11) *Papaver trinifolium* PUP1 (PtriPUP1; SEQ ID NO: 63 (amino acid) and 64 (nucleotide)). The strains were grown in media supplemented with 2.5 nM NLDS and 1 mM methionine for 24 and 48 hours. Titers of respective end products were measured and OD adjusted. As seen in FIG. 23A, S-reticuline levels were generally higher across the board for those strains that expressed a purine permease. Similarly, as seen in FIG. 23B, R-reticuline levels were generally higher across the board for those strains that expressed a purine permease. As seen in FIG. 23C, salutaridine levels were increased in the presence of PsoPUP1-1 and PsoPUP1-3 purine permease. In the presence of an L-DOPA feed, as seen in FIG. 23D, NLDS levels remained largely unchanged whereas reticuline levels were generally increased in the presence of purine permeases.

Figure 24:
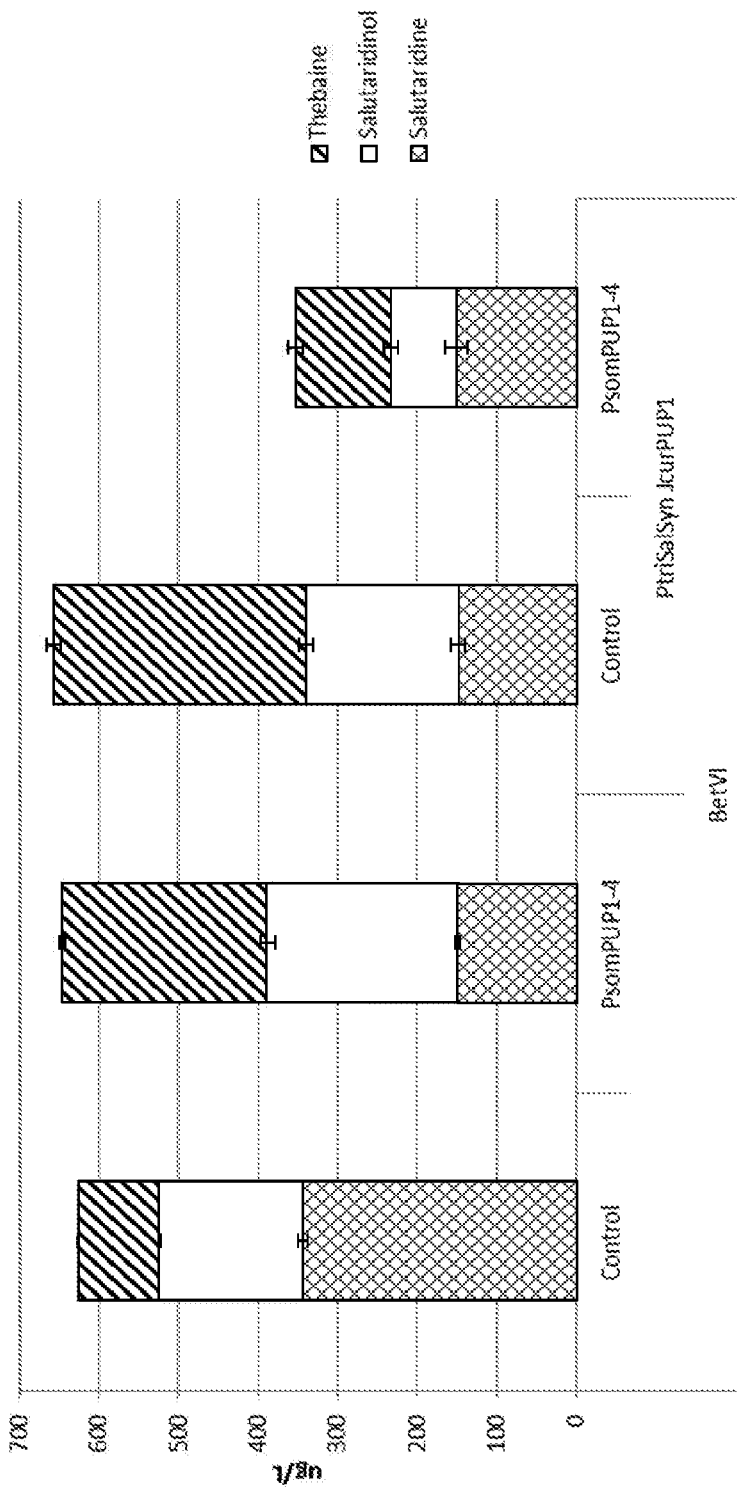
FIG. 24 shows thebaine, salutaridinol, and salutaridine titers in the presence of one or more copies of purine permeases and Betv-1 (represented by SEQ ID NO. 6) after 48 hours. A nucleotide sequence encoding for BetV1 was integrated into the genome of the yeast strain. Further, a purine permease (PUP-1—SEQ ID NO 46)) was integrated into the genome of the yeast strain (control—left side). A PsomPUP1-4 (SEQ ID NO. 51 (amino acid) and 52 (nucleotide)) was expressed via a high copy plasmid (second from left). Additionally, JcurPUP1 (SEQ ID NO: 43 (amino acid) and 44 (nucleotide)) was integrated into the control strain, thus expressing both integrated copies of JcurPUP1 and PsomPUP1 (control—third from the left). Finally, three copies of a purine permease were expressed, PsomPUP1 integrated, JcurPUP1 integrated, and high copy plasmid expressing PUP1-4 (far right).

Strains were transformed with one or more *Papaver somniferum* purine permeases and thebaine, salutaridinol, and salutaridine titers were measured. The strains were all transformed with BETV1 (SEQ ID NO. 6) in combination with one or more purine permeases for 48 hours. A nucleotide sequence encoding for BetV1 was integrated into the genome of the yeast strain. Further, a purine permease (PUP-1—SEQ ID NO 46)) was integrated into the genome of the yeast strain (control—left side). A PsomPUP1-4 (SEQ ID NO. 51 (amino acid) and 52 (nucleotide)) was expressed via a high copy plasmid (second from left). Additionally, JcurPUP1 (SEQ ID NO: 43 (amino acid) and 44 (nucleotide)) was integrated into the control strain, thus expressing both integrated copies of JcurPUP1 and PsomPUP1 (control—third from the left). Finally, three copies of a purine permease were expressed, PsomPUP1 integrated, JcurPUP1 integrated, and high copy plasmid expressing PUP-4 (far right). As seen in FIG. 24, yeast strains that expressed a plasmid copy of PsomPUP1-4 (SEQ ID NO. 52), plus an integrated copy of PsomPUP1-1 (SEQ ID NO. 46), and BetV1, produced significantly high levels of thebaine titers, compared to controls not expressing PsomPUP1-4. However, when PsomPUP1-1, PsomPUP1-4, and JcurPUP1 were all expressed in a yeast strain, thebaine production significantly decreased, and were similar to expressing a single PsomPUP1-1. Significantly, when three purine permeases were expressed, overall carbon flow to thebaine, salutaridinol, and salutaridine, decreased approximately 50%.

Example 9—Expression of Betv-1 in Yeast Expressing SalAT and SalR Genes, and Fed Salutaridine, and Co-Expression of Betv-1 and Purine Permease in Yeast Expressing SalAT and SalR Genes, and Fed Salutaridine A *Saccharomyces cerevisiae* strain CENPK102-5B expressing salutaridinol 7-O-acetyltransferase (SalAT) and salutaridine reductase (SalR) genes integrated into the yeast genome was transformed with a yeast expression vector pEV-1 harboring various polynucleotide constructs expressing Betv-1 (SEQ ID NO. 6) and purine permease polypeptides as follows: (i) a nucleic acid sequence encoding Betv-1 alone (SEQ. ID NO: 6) (HA_BetV1M); (ii) a nucleic acid sequence encoding Betv-1 alone (SEQ. ID NO: 31) (BETV1L_HA); a nucleic acid sequence expressing Betv-1 (SEQ. ID NO: 6) and purine permease (SEQ. ID NO: 35) (HA_BetV1M-pp); and (iv) a nucleic acid sequence expressing Betv-1 (SEQ. ID NO: 31) and purine permease (SEQ. ID NO: 35) (BetV1L_HA-pp). The strains, as well as a control strain with pEV-1 not comprising a nucleic acid sequences encoding Betv-1 or purine permease (EV) were separately cultivated in growth medium SD-Leu-His in the presence of 100 µM salutaridine for 24 hrs. An aliquot of 5 µL of culture medium was subjected to mass spectrometry analysis using an LTQ-Orbitrap XL high-resolution mass spectrometer. Thereafter the thebaine concentration in the medium of each strain was determined according to a thebaine standard curve. The results are shown in FIG. 25. As can be seen in FIG. 25, thebaine production increased 6-fold (to approximately 600 µg/L/OD) in the medium containing strains transformed with only a Betv-1 (HA_BetV1M and BETV1L_HA) compared with strains expressing only SalAT and SalR. However, and surprisingly, in excess of 9,000 µg/L/OD thebaine was detected in the medium containing strains transformed with both Betv_1 and purine permease (HA_BetV1M-pp and BetV1L_HA-pp), thus, generating an additional 16-fold increase compared with strains with only a Betv-1 (HA_BetV1M and BETV1L_HA). The production of thebaine increased approximately 100-fold in strains transformed with both Betv_1 and purine permease (HA_BetV1M-pp and BetV1L_HA-pp) compared with strains expressing only SalAT and SalR.

Example 10—Expression of Betv-1 in Yeast and Co-Expression of Betv-1 and Purine Permease in Yeast, Fed Salutaridine A *Saccharomyces cerevisiae* strain CENPK102-5B was transformed with a yeast expression vector pEV-1 harboring various polynucleotide constructs expressing Betv-1 and purine permease polypeptides as follows: (i) a nucleic acid sequence encoding Betv-1 alone (SEQ. ID NO: 6) (HA_BetV1M); (ii) a nucleic acid sequence encoding Betv-1 alone (SEQ. ID NO: 31) (BETV1L_HA); a nucleic acid sequence expressing Betv-1 (SEQ. ID NO: 6) and purine permease (SEQ. ID NO: 35) (HA_BetV1M-pp); and (iv) a nucleic acid sequence expressing Betv-1 (SEQ. ID NO: 31) and purine permease (SEQ. ID NO: 35) (BetV1L_HA-pp). The strains, as well as a control strain with pEV-1 not comprising a nucleic acid sequences encoding Betv-1 or purine permease (EV) were separately cultivated in growth medium SD-Leu-His in the presence of 100 µM salutaridine for 24 hrs. Yeast cells were collected by centrifugation, extracted in 500 µL of methanol, of which 5 µL was subjected to mass spectrometry analysis using an LTQ-Orbitrap XL high-resolution mass spectrometer. Thereafter the salutaridine concentration in the cells of each strain was determined according to a salutaridine standard curve. The results are shown in FIG. 26. As can be seen in FIG. 26, salutaridine accumulation increased 8-fold (to approximately 132 µg/L/OD) in the cells of strains transformed with a Betv-1 (HA_BetV1M and BETV1L_HA) and a purine permease (HA_BetV1M-pp and HA_BetV1L-pp). Compared with the empty vector (EV) control, salutaridine accumulation did not increase in cells transformed only with a Betv-1 (HA_BetV1M and BETV1L_HA).

Example 11—Expression of Purine Permeases (PUP-L) and (PUP-N) in Yeast Expressing DODC, MAO, NCS, 6OMT, CNMT and 4'OMT Genes, and Fed Either L-DOPA or Norlaudanosoline (NLDS), and Co-Expression of PUP-L and PUP-N with a Betv1 in Yeast Expressing DODC, MAO, NCS, 6OMT, CNMT and 4'OMT Genes, and Fed Either DOPA or Norlaudanosoline (NLDS)

A *Saccharomyces cerevisiae* strain CENPK102-5B expressing dopa decarboxylase (DODC), monoamine oxidase (MAO), norcoclaurine synthase (NCS), norcoclaurine 6-O-methyltransferase (6OMT), coclaurine N-methyltransferase (CNMT), and 3'hydroxy-N-methyltransferase 4'-O-methyltransferase (4'OMT) genes integrated into the yeast genome was transformed with a yeast expression vector pEV-1 harboring various polynucleotide constructs expressing purine permease and Betv1 polypeptides as follows: (i) a nucleic acid sequence encoding a purine permease containing a C-terminal extension absent in a purine permease linked to a cluster of 10 noscapine biosynthetic genes (Winzer, T., Gazda, V., He Z., Kaminski F., Kern M., Larson T. R., Li Y., Meade F., Teodor R., Vaistij F. E., Walker C., Bowser T. A., Graham, I. A. (2012) A *Papaver somniferum* 10-gene cluster for synthesis of the anticancer alkaloid noscapine. Science 336(6089): 1704-1708) alone (SEQ. ID NO: 35) (PUP-L); (ii) a nucleic acid sequence encoding a purine permease linked to a cluster of 10 noscapine biosynthetic genes (Winzer et al., 2012) alone (SEQ. ID NO: 37) (PUP-N) (nucleic acid sequence SEQ. ID NO: 38 was codon optimized and C-terminally myc-tagged to obtain nucleic acid sequence SEQ. ID NO: 39 (myc-tag sequence SEQ. ID NO: 40)); (iii) a nucleic acid sequence expressing PUP-L (SEQ. ID NO: 35) and a Betv1 (SEQ. ID NO: 6) (Betv1-PUP-L); and (iv) a nucleic acid sequence expressing PUP-N(SEQ. ID NO: 37) and a Betv1 (SEQ. ID NO: 6) (Betv1-PUP-N). The strains, as well as a control strain with pEV-1 not comprising a nucleic acid sequences encoding Betv-1 or purine permease (EV) were separately cultivated in growth medium SD-Leu-His in the presence of either 100 µL-DOPA or 100 µM norlaudanosoline (NLDS) for 24 hrs. An aliquot of 5 µL of culture medium was subjected to mass spectrometry analysis using an LTQ-Orbitrap XL high-resolution mass spectrometer. Thereafter the reticuline concentration in the medium of each strain was determined according to a reticuline standard curve. The results are shown in FIG. 27. As can be seen in FIG. 27, reticuline production was not affected in the medium of strains transformed with only a purine permease (PUP-L or PUP-N) or a purine permease and a Betv1 (Betv1 PUP-L and Betv1 PUP-N) compared with strains expressing only DODC, MAO, NCS, 6OMT, CNMT and 4'OMT. However, and surprisingly, reticuline production increased 25-fold to more than 1,000 µg/L/OD in the medium containing strains transformed with both PUP-L and PUP-L and Betv1. Neither PUP-N nor Betv1 alone affected the production of reticuline compared with empty vector controls.

Example 12—Expression of Purine Permeases (PUP-L) and (PUP-N) in Yeast Expressing REPI, CPR, and SalSyn Genes or REPI, CPR, SalSyn, SalR and SalAT Genes, and Fed (S)-Reticuline, and Co-Expression of PUP-L and PUP-N with a Betv1

A *Saccharomyces cerevisiae* strain CENPK102-5B expressing reticuline epimerase (REPI), cytochrome P450 reductase (CPR) and salutaridine synthase (SalSyn) genes integrated into the yeast genome was transformed with a yeast expression vector pEV-1 harboring various polynucleotide constructs expressing purine permease and Betv1 polypeptides as follows: (i) a nucleic acid sequence encoding a purine permease containing a C-terminal extension absent in a purine permease linked to a cluster of 10 noscapine biosynthetic genes (Winzer et al., 2012) alone (SEQ. ID NO: 35) (PUP-L); (ii) a nucleic acid sequence encoding a purine permease linked to a cluster of 10 noscapine biosynthetic genes (Winzer et al., 2012) alone (SEQ. ID NO: 37) (PUP-N); (iii) a nucleic acid sequence expressing PUP-L (SEQ. ID NO: 35) and a Betv1 (SEQ. ID NO: 6) (Betv1-PUP-L); and (iv) a nucleic acid sequence expressing PUP-N(SEQ. ID NO: 37) and a Betv1 (SEQ. ID NO: 6) (Betv1-PUP-N). The strains, as well as a control strain with pEV-1 not comprising a nucleic acid sequences encoding Betv-1 or purine permease (EV) were separately cultivated in growth medium SD-Leu-His in the presence of 100 µM (S)-reticuline for 24 hrs. An aliquot of 5 µL of culture medium was subjected to mass spectrometry analysis using an LTQ-Orbitrap XL high-resolution mass spectrometer. Thereafter the salutaridine and thebaine concentrations in the medium of each strain were determined according to salutaridine and thebaine standard curves, respectively. The results are shown in FIG. 28A. As can be seen in FIG. 28A, salutaridine production was not affected in the medium of strains transformed with PUP-N, or PUP-N and a Betv1 (Betv1 PUP-N) compared with strains expressing only REPI, CPR, and SalSyn. However, and surprisingly, salutaridine production increased 3-fold compared with the empty vector (EV) control to more than 150 µg/L/OD in the medium containing strains transformed with either PUP-L alone or PUP-L and a Betv1 (Betv1 PUP-L). B, A *Saccharomyces cerevisiae* strain CENPK102-5B expressing reticuline epimerase (REPI), cytochrome P450 reductase (CPR), salutaridine synthase (SalSyn), salutaridine reductase (SalR), and salutaridine acetyltransferase (SalAT) genes integrated into the yeast genome was transformed with a yeast expression vector pEV-1 harboring various polynucleotide constructs expressing purine permease and Betv1 polypeptides as follows: (i) a nucleic acid sequence encoding a purine permease containing a C-terminal extension absent in a purine permease linked to a cluster of 10 noscapine biosynthetic genes (Winzer et al., 2012) alone (SEQ. ID NO: 35) (PUP-L); (ii) a nucleic acid sequence encoding a purine permease linked to a cluster of 10 noscapine biosynthetic genes (Winzer et al., 2012) alone (SEQ. ID NO: 37) (PUP-N); (iii) a nucleic acid sequence expressing PUP-L (SEQ. ID NO: 35) and a Betv1 (SEQ. ID NO: 6) (Betv1-PUP-L); and (iv) a nucleic acid sequence expressing PUP-N(SEQ. ID NO: 37) and a Betv1 (SEQ. ID NO: 6) (Betv1-PUP-N). The strains, as well as a control strain with pEV-1 not comprising a nucleic acid sequences encoding Betv-1 or purine permease (EV) were separately cultivated in growth medium SD-Leu-His in the presence of 100 µM (S)-reticuline for 24 hrs. An aliquot of 5 µL of culture medium was subjected to mass spectrometry analysis using an LTQ-Orbitrap XL high-resolution mass spectrometer. Thereafter the salutaridine and thebaine concentrations in the medium of each strain were determined according to salutaridine and thebaine standard curves, respectively. The results are shown in FIG. 28B. As can be seen in FIG. 28B, salutaridine and thebaine production was not affected in the medium of strains transformed with PUP-N compared with strains expressing only REPI, CPR, SalSyn, SalR and SalAT. However, and surprisingly, salutaridine production increased 2-fold compared with the empty vector (EV) control to approximately 150 µg/L/OD in the medium containing strains transformed with either PUP-L alone or PUP-L and a Betv1 (Betv1 PUP-L). Thebaine production increased 4-fold compared with the empty vector (EV) control in the medium containing strains transformed with PUP-L alone. Thebaine production increased almost 20-fold compared with the empty vector (EV) control to approximately 95 µg/L/OD in the medium containing strains transformed with PUP-L and a Betv1 (Betv1 PUP-L). Thebaine production increased approximately 2-fold compared with the empty vector (EV) control to approximately 12 µg/L/OD in the medium containing strains transformed with PUP-N and a Betv1 (Betv1 PUP-L) owing to the thebaine-forming activity of Betv1.

Example 13—Expression of a Purine Permeases (PUP-L) and (PUP-N) in Yeast Expressing REPI, CPR, and SalSyn Genes or REPI, CPR, SalSyn, SalR and SalAT Genes, and Fed (R)-Reticuline, and Co-Expression of PUP-L and PUP-N with Betv1

A *Saccharomyces cerevisiae* strain CENPK102-5B expressing reticuline epimerase (REPI), cytochrome P450 reductase (CPR) and salutaridine synthase (SalSyn) genes integrated into the yeast genome was transformed with a yeast expression vector pEV-1 harboring various polynucleotide constructs expressing purine permease and Betv1 polypeptides as follows: (i) a nucleic acid sequence encoding a purine permease containing a C-terminal extension absent in a purine permease linked to a cluster of 10 noscapine biosynthetic genes (Winzer et al., 2012) alone (SEQ. ID NO: 35) (PUP-L); (ii) a nucleic acid sequence encoding a purine permease linked to a cluster of 10 noscapine biosynthetic genes (Winzer et al., 2012) alone (SEQ. ID NO: 37) (PUP-N); (iii) a nucleic acid sequence expressing PUP-L (SEQ. ID NO: 35) and a Betv1 (SEQ. ID NO: 6) (Betv1-PUP-L); and (iv) a nucleic acid sequence expressing PUP-N(SEQ. ID NO: 37) and a Betv1 (SEQ. ID NO: 6) (Betv1-PUP-N). The strains, as well as a control strain with pEV-1 not comprising a nucleic acid sequences encoding Betv-1 or purine permease (EV) were separately cultivated in growth medium SD-Leu-His in the presence of 100 µM (R)-reticuline for 24 hrs. An aliquot of 5 µL of culture medium was subjected to mass spectrometry analysis using an LTQ-Orbitrap XL high-resolution mass spectrometer. Thereafter the salutaridine and thebaine concentrations in the medium of each strain were determined according to salutaridine and thebaine standard curves, respectively. The results are shown in FIG. 29A. As can be seen in FIG. 29A, salutaridine production was not affected in the medium of strains transformed with PUP-N, or PUP-N and a Betv1 (Betv1 PUP-N) compared with strains expressing only REPI, CPR, and SalSyn. However, and surprisingly, salutaridine production increased 3-fold compared with the empty vector (EV) control to more than 150 µg/L/OD in the medium containing strains transformed with either PUP-L alone or PUP-L and a Betv1 (Betv1 PUP-L). B, A *Saccharomyces cerevisiae* strain CENPK102-5B expressing reticuline epimerase (REPI), cytochrome P450 reductase (CPR), salutaridine synthase (SalSyn), salutaridine reductase (SalR), and salutaridine acetyltransferase (SalAT) genes integrated into the yeast genome was transformed with a yeast expression vector pEV-1 harboring various polynucleotide constructs expressing purine permease and Betv1 polypeptides as follows: (i) a nucleic acid sequence encoding a purine permease containing a C-terminal extension absent in a purine permease linked to a cluster of 10 noscapine biosynthetic genes (Winzer et al., 2012) alone (SEQ. ID NO: 35) (PUP-L); (ii) a nucleic acid sequence encoding a purine permease linked to a cluster of 10 noscapine biosynthetic genes (Winzer et al., 2012) alone (SEQ. ID NO: 37) (PUP-N); (iii) a nucleic acid sequence expressing PUP-L (SEQ. ID NO: 35) and a Betv1 (SEQ. ID NO: 6) (Betv1-PUP-L); and (iv) a nucleic acid sequence expressing PUP-N(SEQ. ID NO: 37) and a Betv1 (SEQ. ID NO: 6) (Betv1-PUP-N). The strains, as well as a control strain with pEV-1 not comprising a nucleic acid sequences encoding Betv-1 or purine permease (EV) were separately cultivated in growth medium SD-Leu-His in the presence of 100 µM (R)-reticuline for 24 hrs. An aliquot of 5 µL of culture medium was subjected to mass spectrometry analysis using an LTQ-Orbitrap XL high-resolution mass spectrometer. Thereafter the salutaridine and thebaine concentrations in the medium of each strain were determined according to salutaridine and thebaine standard curves, respectively. The results are shown in FIG. 29B. As can be seen in FIG. 29B, salutaridine and thebaine production was not affected in the medium of strains transformed with PUP-N compared with strains expressing only REPI, CPR, SalSyn, SalR and SalAT. However, and surprisingly, salutaridine production increased 2-fold compared with the empty vector (EV) control to approximately 150 µg/L/OD in the medium containing strains transformed with either PUP-L alone or PUP-L and a Betv1 (Betv1 PUP-L). Thebaine production increased 4-fold compared with the empty vector (EV) control in the medium containing strains transformed with PUP-L alone. Thebaine production increased almost 20-fold compared with the empty vector (EV) control to approximately 95 µg/L/OD in the medium containing strains transformed with PUP-L and a Betv1 (Betv1 PUP-L). Thebaine production increased approximately 2-fold compared with the empty vector (EV) control to approximately 12 µg/L/OD in the medium containing strains transformed with PUP-N and a Betv1 (Betv1 PUP-N) owing to the thebaine-forming activity of Betv1.

Example 14—Expression of Purine Permeases (PUP-L) and (PUP-N) in Yeast Expressing SalAT and SalR Genes or REPI, CPR, SalSyn, SalR and SalAT Genes, and Fed Salutaridine and Co-Expression of PUP-L and PUP-N with a Betv1

A *Saccharomyces cerevisiae* strain CENPK102-5B expressing salutaridine reductase (SalR) and salutaridine acetyltransferase (SalAT) genes integrated into the yeast genome was transformed with a yeast expression vector pEV-1 harboring various polynucleotide constructs expressing purine permease and Betv1 polypeptides as follows: (i) a nucleic acid sequence encoding a purine permease containing a C-terminal extension absent in a purine permease linked to a cluster of 10 noscapine biosynthetic genes (Winzer et al., 2012) alone (SEQ. ID NO: 35) (PUP-L); (ii) a nucleic acid sequence encoding a purine permease linked to a cluster of 10 noscapine biosynthetic genes (Winzer et al., 2012) alone (SEQ. ID NO: 37) (PUP-N); (iii) a nucleic acid sequence expressing PUP-L (SEQ. ID NO: 35) and a Betv1 (SEQ. ID NO: 6) (Betv1-PUP-L); and (iv) a nucleic acid sequence expressing PUP-N(SEQ. ID NO: 37) and a Betv1 (SEQ. ID NO: 6) (Betv1-PUP-N). The strains, as well as a control strain with pEV-1 not comprising a nucleic acid sequences encoding Betv-1 or purine permease (EV) were separately cultivated in growth medium SD-Leu-His in the presence of 100 µM salutaridine for 24 hrs. An aliquot of 5 µL of culture medium was subjected to mass spectrometry analysis using an LTQ-Orbitrap XL high-resolution mass spectrometer. Thereafter the thebaine concentration in the medium of each strain was determined according to a thebaine standard curve. The results are shown in FIG. 30A. As can be seen in FIG. 30A, thebaine production was not affected in the medium of strains transformed with PUP-N compared with strains expressing only SalR and SalAT. However, and surprisingly, thebaine production increased 27-fold and 60-fold compared with the empty vector (EV) control to more than 1600 and 3500 µg/L/OD in the medium containing strains transformed with either PUP-L alone or PUP-L and a Betv1 (Betv1 PUP-L), respectively. Thebaine production increased approximately 4-fold compared with the empty vector (EV) control to approximately 250 µg/L/OD in the medium containing strains transformed with PUP-N and a Betv1 (Betv1 PUP-N) owing to the thebaine-forming activity of Betv1. B, A *Saccharomyces cerevisiae* strain CENPK102-5B expressing reticuline epimerase (REPO, cytochrome P450 reductase (CPR), salutaridine synthase (SalSyn), salutaridine reductase (SalR), and salutaridine acetyltransferase (SalAT) genes integrated into the yeast genome was transformed with a yeast expression vector pEV-1 harboring various polynucleotide constructs expressing purine permease and Betv1 polypeptides as follows: (i) a nucleic acid sequence encoding a purine permease containing a C-terminal extension absent in a purine permease linked to a cluster of 10 noscapine biosynthetic genes (Winzer et al., 2012) alone (SEQ. ID NO: 35) (PUP-L); (ii) a nucleic acid sequence encoding a purine permease linked to a cluster of 10 noscapine biosynthetic genes (Winzer et al., 2012) alone (SEQ. ID NO: 37) (PUP-N); (iii) a nucleic acid sequence expressing PUP-L (SEQ. ID NO: 35) and a Betv1 (SEQ. ID NO: 6) (Betv1-PUP-L); and (iv) a nucleic acid sequence expressing PUP-N(SEQ. ID NO: 37) and a Betv1 (SEQ. ID NO: 6) (Betv1-PUP-N). The strains, as well as a control strain with pEV-1 not comprising a nucleic acid sequences encoding Betv-1 or purine permease (EV) were separately cultivated in growth medium SD-Leu-His in the presence of 100 µM salutaridine for 24 hrs. An aliquot of 5 µL of culture medium was subjected to mass spectrometry analysis using an LTQ-Orbitrap XL high-resolution mass spectrometer. Thereafter the thebaine concentration in the medium of each strain was determined according to a thebaine standard curve. The results are shown in FIG. 30B. As can be seen in FIG. 30B, thebaine production was not affected in the medium of strains transformed with PUP-N compared with strains expressing only REPI, CPR, SalSyn, SalR and SalAT. However, and surprisingly, thebaine production increased 10-fold and 25-fold compared with the empty vector (EV) control to approximately 1000 and 2500 µg/L/OD in the medium containing strains transformed with either PUP-L alone or PUP-L and a Betv1 (Betv1 PUP-L), respectively. Thebaine production increased approximately 2-fold compared with the empty vector (EV) control to approximately 200 µg/L/OD in the medium containing strains transformed with PUP-N and a Betv1 (Betv1 PUP-N) owing to the thebaine-forming activity of Betv1.

Example 15—General Methods

The follow methods were used throughout the examples described above.

Recombinant protein expression in *Escherichia coli*. All genes expressed in *E. coli* were codon-optimized, a $His_6$-tag was added independently to the N-terminus and C-terminus, and the synthetic genes were cloned into the pACE vector. Expression vectors were transformed into *E. coli* stain Rosetta (DE3) pLysS (EMD Chemicals), which were subsequently induced overnight using 1 mM (w/v) isopropyl β-D-thiogalactoside (IPTG) at 16° C. Cells were harvested by centrifugation and sonicated in 50 mM sodium phosphate, pH 7.0, 300 mM NaCl and 10% (v/v) glycerol. After centrifugation at 20,000 g for 10 min, the supernatant was loaded onto Talon (Clontech) cobalt-affinity resin. Purification was performed according to the manufacturer's instructions. Purified, recombinant proteins were desalted using an Amicon (Millipore) centrifugal filter with a 30 kDa molecular weight cutoff, and stored in 50 mM sodium phosphate, pH 7.0, 50 mM NaCl and 10% (v/v) glycerol. Protein concentration was determined by the Bradford assay (Bio-Rad) using bovine serum albumin as the standard.

Cross-linking experiments. Bis[sulfosuccinimidyl] suberate (BS3) was used as cross-linking reagent and prepared in PBS buffer at a concentration of 10 mM, of which 2 µL was added to 20 µL of purified recombinant protein (1 µg/µL). After incubation on ice for 1 h, 5 µL of 5×SDS (10% w/v) was added to quench the reaction. Samples were then boiled for 5 min and subjected to SDS-PAGE and immunoblot analysis.

Enzyme assays. SalAT-coupled THS assays were performed in a 50-mL reaction containing latex protein or purified recombinant THS, 10 µM salutaridinol, 50 µM acetyl-CoA and 0.2 µg SalAT in 10 mM sodium phosphate, pH 7.0, at 30° C. for 30 min. The assay was quenched with 200 µL of acetonitrile and centrifuged at 17,000 g for 40 min. The supernatant was subjected to liquid chromatography-tandem mass spectrometry (LC-MS/MS) analysis. Direct THS assays were performed in a 50-mL reaction containing purified recombinant THS, phosphate buffer, pH 7.0, and salutaridinol-7-O-acetate at 30° C. for 30 sec. Chloroform (200 µL) was then added to stop the reaction and protect any residual salutaridinol-7-O-acetate from hydrolysis.

Liquid chromatography-tandem mass spectrometry (LC-MS/MS). Samples were analyzed using a 6410 Triple Quadrupole LC-MS (Agilent Technologies). Liquid chromatographic separation was performed using a Poroshell 120 SB-C18 HPLC column (Agilent Technologies) with a flow rate of 0.6 ml/min and a gradient of solvent A (0.05% [w/v] ammonium hydroxide, pH 6.5) and solvent B (100% acetonitrile) as follows: 0% solvent B from 1 min, 0-20% solvent B from 1 to 3 min, isocratic 99% solvent B from 6 to 8 min, 99-0% solvent B from 8 to 8.1 min, 0% solvent B from 8.1 to 11.1 min. Full scan mass analyses (m/z range 50-200) and collisional MS/MS experiments were performed as described previously (Nature Chemical Biology 11, 728-732, 2015).

Virus-induced Gene silencing (VIGS). Two regions conserved in THS genes, but distinct from similar Betv1 homologs were selected as the VIGS target. The first fragment was located in the middle of the coding region and the second fragment included the 3' end of the open reading frame and part of the 3' untranslated region (FIG. 12A). The two fragments were synthesized as a one DNA fragment and cloned into the pTRV2 vector. The pTRV2 and the pTRV2-THS vectors were independently mobilized in *Agrobacterium tumefaciens*, which were subsequently cultured and infiltrated into opium poppy seedlings as described previously (Nature Chemical Biology 11, 728-732, 2015). Latex and stem samples were collected from ~30 mature plants. To confirm infiltration with *A. tumefaciens*, PCR was performed with a TRV2-MSC (multiple-cloning site) primer pair (FIG. 12B) to detect the occurrence of a mobilized fragment of the pTRV2 vector using cDNA isolated from individual stem samples. Alkaloids were extracted in acetonitrile from lyophilized latex and analyzed by LC-MS/MS. Relative transcript abundance of THS2 (SEQ ID NO. 6) in VIGS plant was determined by qRT-PCR using gene-specific primers (FIG. 12B).

RNA extraction, cDNA synthesis and qRT-PCR. Total RNA was extracted using cetyl trimethyl ammonium bromide (CTAB) from frozen opium poppy tissue samples finely ground using a TissueLyser (Qiagen). cDNA synthesis was performed in a 10-μl reaction containing approximately 1 μg of total RNA using All-in-One RT mastermix (ABM) according to the manufacturer's instructions. SYBR-green qRT-PCR was used to quantify gene transcript levels. The 10-μl reactions contained 1× PowerUp SYBR Green master mix (Applied biosystems), 500 nM of each primer, and 2 μL of a 20-fold diluted cDNA sample. A thermal profile of 50° C. for 2 min, 95° C. for 2 min, 40 cycles of 95° C. for 1 sec, and 60° C. for 30 sec (with a dissociation curve at the end) was used to perform qRT-PCR on a QuantiStudio Real-Time PCR System 3 (Applied Biosystems). Gene-specific primers were used for all qRT-PCR experiments (FIG. 12B). All primer pairs used in qRT-PCR were tested using amplicon dissociation curve analysis (95° C. for 15 sec at a ramp rate of 1.6° C./sec, 60° C. for 1 min at a ramp rate of 1.6° C./sec, and 95° C. for 15 sec at a ramp rate of 0.15° C./sec) to confirm the amplification stringency.

Protein preparation for proteomics analysis. Soluble protein (~0.3 mg) was precipitated overnight using 3 volumes of ice-cold TCA/acetone (13.3:100, vol/vol) at −20° C. The protein pellet was collected by centrifugation at maximum speed for 20 min at 4° C. and washed three times with ice-cold 75% (v/v) acetone. Protein pellets or gel bands excised from SDS-PAGE were submitted to Southern Alberta Mass Spectrometry centre at the University of Calgary for proteomics analysis.

We claim:

1. A genetically modified cell comprising a recombinant polynucleotide encoding a heterologous thebaine synthase polypeptide wherein the thebaine synthase polypeptide comprises an amino acid sequence having at least 90% sequence identity to SEQ ID NO. 6, 31, 32, 80, or 81.

2. The genetically modified cell of claim 1, wherein the thebaine synthase polypeptide converts salutaridinol-7-O-acetate to thebaine.

3. The genetically modified cell of claim 1, wherein the thebaine synthase polypeptide comprises an amino acid sequence having at least 95% sequence identity to SEQ ID NO. 6, 31, 32, 80, or 81.

4. The genetically modified cell of claim 1, wherein the thebaine synthase polypeptide comprises the amino acid sequence of SEQ ID NO. 6, 31, 32, 80, or 81.

5. The genetically modified cell of claim 1, wherein the polynucleotide comprises the nucleotide sequence of SEQ ID NO. 19.

6. The genetically modified cell of claim 1, wherein the cell is a plant cell, fungus, yeast, or bacterium.

* * * * *